US011026887B2

(12) United States Patent
Meltzer et al.

(10) Patent No.: US 11,026,887 B2
(45) Date of Patent: *Jun. 8, 2021

(54) METHODS OF TREATING EOSINOPHILIC ESOPHAGITIS

(71) Applicant: ELLODI PHARMACEUTICALS, L.P., Lawrenceville, NJ (US)

(72) Inventors: Brian A. Meltzer, Wilton, CT (US); Gail M. Comer, Phoenixville, PA (US)

(73) Assignee: ELLODI PHARMACEUTICALS, L.P., Lawrenceville, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 16/131,812

(22) Filed: Sep. 14, 2018

(65) Prior Publication Data

US 2019/0008760 A1 Jan. 10, 2019

Related U.S. Application Data

(63) Continuation of application No. 15/680,301, filed on Aug. 18, 2017, now Pat. No. 10,105,315.

(60) Provisional application No. 62/489,292, filed on Apr. 24, 2017, provisional application No. 62/461,317, filed on Feb. 21, 2017, provisional application No. 62/376,703, filed on Aug. 18, 2016.

(51) Int. Cl.
*A61K 9/00* (2006.01)
*A61K 31/56* (2006.01)
*A61K 31/565* (2006.01)

(52) U.S. Cl.
CPC .......... *A61K 9/006* (2013.01); *A61K 31/56* (2013.01); *A61K 31/565* (2013.01)

(58) Field of Classification Search
None
See application file for complete search history.

(56) References Cited

U.S. PATENT DOCUMENTS

| | | | |
|---|---|---|---|
| 3,705,172 A | 12/1972 | Buchel et al. | |
| 3,929,768 A | 12/1975 | Brattsand et al. | |
| 4,080,448 A | 3/1978 | Mirsky | |
| 4,335,121 A | 6/1982 | Phillipps et al. | |
| 4,363,806 A | 12/1982 | Bergstrom et al. | |
| 4,472,393 A | 9/1984 | Shapiro | |
| 5,135,740 A | 8/1992 | Katz | |
| 5,278,175 A | 1/1994 | Ray et al. | |
| 5,403,893 A | 4/1995 | Tanaka et al. | |
| 5,446,070 A | 8/1995 | Mantelle | |
| 5,482,934 A | 1/1996 | Calatyud et al. | |
| 5,776,433 A | 7/1998 | Tzou et al. | |
| 6,171,617 B1 | 1/2001 | Gruber | |
| 6,316,027 B1 | 11/2001 | Johnson et al. | |
| 6,596,298 B2 | 7/2003 | Leung et al. | |
| 6,596,311 B1 | 7/2003 | Dobetti | |
| 6,740,332 B2 | 5/2004 | Zyck et al. | |
| 7,033,606 B1 | 4/2006 | Besse et al. | |
| 8,580,300 B2 | 11/2013 | Wilhelm et al. | |
| 8,679,545 B2 | 3/2014 | Dohil et al. | |
| 8,771,729 B2 | 7/2014 | Perrett et al. | |
| 9,387,167 B2 | 7/2016 | Perrett et al. | |
| 9,486,407 B2 | 11/2016 | Perrett et al. | |
| 9,782,347 B2 | 10/2017 | Dohil et al. | |
| 9,849,084 B2 | 12/2017 | Perrett et al. | |
| 9,867,780 B2 | 1/2018 | Greinwald et al. | |
| 10,105,315 B2 * | 10/2018 | Meltzer | A61K 9/006 |
| 10,176,301 B2 | 1/2019 | Hill et al. | |
| 10,272,037 B2 | 4/2019 | Dohil et al. | |
| 10,471,071 B2 | 11/2019 | Gosselin et al. | |
| 10,632,069 B2 | 4/2020 | Perrett et al. | |
| 2001/0006625 A1 | 7/2001 | Bohn et al. | |
| 2001/0014340 A1 | 8/2001 | Ohta et al. | |
| 2003/0054036 A1 | 3/2003 | Liggins et al. | |
| 2003/0099701 A1 | 5/2003 | Takaishi et al. | |
| 2003/0215500 A1 | 11/2003 | Ohta et al. | |
| 2004/0009212 A1 | 1/2004 | Tsai | |
| 2004/0053902 A1 | 3/2004 | Smith | |
| 2004/0106663 A1 | 6/2004 | Talley et al. | |
| 2004/0265375 A1 | 12/2004 | Platteeuw et al. | |
| 2005/0009848 A1 | 1/2005 | Brantl | |
| 2005/0112188 A1 | 5/2005 | Elias | |
| 2005/0232988 A1 | 10/2005 | Venkatesh et al. | |

(Continued)

FOREIGN PATENT DOCUMENTS

CA 2430481 A1 6/2002
CA 2776164 A1 4/2011
(Continued)

OTHER PUBLICATIONS

Ahmed and Shah, "Formulation of low dose medicines—theory and practice." Am. Pharm. Rev (2000), 3(3): 9-14.
Bower et al., "Manifestations and Treatment of Laryngeal Sarcoidosis". Am. Rev. Respir. Dis., 122(2): 325-332 (1980).
Brunner, et al., "Gastrointestinal transit, release and plasma pharmacokinetics of a new oral budesonide formulation." British Journal of Clinical Pharmacology (2005); 61(1): 31-38.
Buckton, G., "Water sorption and near IR spectroscopy to study the differences between microcrystalline cellulose and silicified microcrystalline cellulose before and after wet granulation." International Journal of Pharmaceutics (Apr. 1999); 181 (1): 41-47.
(Continued)

*Primary Examiner* — Jeffrey S Lundgren
*Assistant Examiner* — Michael J Schmitt
(74) *Attorney, Agent, or Firm* — Cooley LLP

(57) ABSTRACT

The present disclosure provides methods of treating inflammation of the upper gastrointestinal tract, especially the esophagus, by administering an oral corticosteroid. In some cases, the methods include treating eosinophilic esophagitis (EoE) by administering an oral corticosteroid in an induction phase and a maintenance phase to improve peak eosinophilic counts and symptoms. In embodiments, the methods include treating EoE by administering the oral corticosteroid at nighttime and/or while the patient is lying down.

30 Claims, 10 Drawing Sheets

(56) References Cited

U.S. PATENT DOCUMENTS

| | | |
|---|---|---|
| 2006/0051414 A1 | 3/2006 | Ramalho et al. |
| 2007/0020330 A1 | 1/2007 | Dang et al. |
| 2007/0059361 A1 | 3/2007 | Rawas-Qalaji et al. |
| 2007/0111978 A1 | 5/2007 | Dohil et al. |
| 2009/0074862 A1 | 3/2009 | Schioppi et al. |
| 2009/0123550 A1 | 5/2009 | Phillips et al. |
| 2009/0123551 A1 | 5/2009 | Phillips et al. |
| 2009/0131386 A1 | 5/2009 | Phillips |
| 2009/0149433 A1 | 6/2009 | Phillips |
| 2009/0155360 A1 | 6/2009 | Venkatesh et al. |
| 2009/0169620 A1 | 7/2009 | Venkatesh et al. |
| 2009/0181099 A1 | 7/2009 | Dohil et al. |
| 2010/0034894 A1 | 2/2010 | Szymczak et al. |
| 2010/0215753 A1 | 8/2010 | Sherwood et al. |
| 2010/0216754 A1 | 8/2010 | Phillips et al. |
| 2011/0081411 A1 | 4/2011 | Perrett et al. |
| 2011/0097401 A1 | 4/2011 | Phillips et al. |
| 2011/0123460 A1 | 5/2011 | Wilhelm et al. |
| 2012/0164080 A1 | 6/2012 | Hill et al. |
| 2012/0282335 A1 | 11/2012 | Venkatesh et al. |
| 2014/0187523 A1 | 7/2014 | Dohil et al. |
| 2014/0287051 A1 | 9/2014 | Perrett et al. |
| 2014/0303131 A1 | 10/2014 | Perrett et al. |
| 2014/0328861 A1 | 11/2014 | Payton et al. |
| 2015/0231156 A1 | 8/2015 | Santus et al. |
| 2016/0078186 A1 | 3/2016 | Hill et al. |
| 2016/0206627 A1 | 7/2016 | Gosselin et al. |
| 2016/0213681 A1 | 7/2016 | Phillips et al. |
| 2017/0071855 A1 | 3/2017 | Perrett et al. |
| 2017/0183719 A1 | 6/2017 | Rothenberg et al. |
| 2018/0071211 A1 | 3/2018 | Dohil et al. |
| 2018/0133145 A1 | 5/2018 | Meltzer et al. |
| 2018/0153802 A1 | 6/2018 | Perrett et al. |
| 2019/0201333 A1 | 7/2019 | Dohil et al. |
| 2020/0016171 A1 | 1/2020 | Gosselin et al. |
| 2020/0214979 A1 | 7/2020 | Perrett et al. |
| 2020/0368147 A1 | 11/2020 | Meltzer et al. |
| 2020/0381097 A1 | 12/2020 | Meltzer et al. |

FOREIGN PATENT DOCUMENTS

| | | |
|---|---|---|
| CA | 2704946 A1 | 5/2019 |
| CL | 3827-2008 | 12/2007 |
| DE | 2323215 A1 | 11/1973 |
| DE | 4129535 A1 | 3/1992 |
| DE | 60202794 T2 | 5/2006 |
| DE | 202010018594 U1 | 2/2018 |
| EP | 0057401 A1 | 8/1982 |
| EP | 0440372 A1 | 8/1991 |
| EP | 1 310 243 A1 | 5/2003 |
| EP | 1323417 A1 | 7/2003 |
| EP | 1595533 A1 | 11/2005 |
| EP | 2211896 B1 | 1/2018 |
| EP | 2214679 B1 | 3/2019 |
| EP | 3354276 B1 | 1/2020 |
| JP | S56-138200 A | 10/1981 |
| JP | 11-130679 A | 5/1999 |
| JP | H11-511162 A | 9/1999 |
| JP | 2001-524094 A | 11/2001 |
| JP | 2002-521321 A | 7/2002 |
| JP | 2003-509359 A | 3/2003 |
| JP | 2003-261439 A | 9/2003 |
| JP | 2003-292459 A | 10/2003 |
| JP | 2006-77018 A | 3/2006 |
| JP | 2006-516616 A | 7/2006 |
| JP | 2009-519793 | 5/2009 |
| JP | 2009-521523 A | 6/2009 |
| JP | 2009-173552 A | 8/2009 |
| JP | 2011-503073 A | 1/2011 |
| KR | 2006-0123160 A | 12/2006 |
| KR | 10-2012-0104975 | 9/2012 |
| WO | WO 1997/006786 A1 | 2/1997 |
| WO | WO 1998/047535 A1 | 10/1998 |
| WO | WO 2000/064450 A1 | 11/2000 |
| WO | WO 2001/019342 A2 | 3/2001 |
| WO | WO 2002/092057 A1 | 11/2002 |
| WO | WO 2003/039520 A1 | 5/2003 |
| WO | WO 2003/093344 A1 | 11/2003 |
| WO | WO 2004/064810 A1 | 8/2004 |
| WO | WO 2004/067004 A1 | 8/2004 |
| WO | WO 2004/069225 A1 | 8/2004 |
| WO | WO 2004/091585 A1 | 10/2004 |
| WO | WO 2005/087194 A1 | 9/2005 |
| WO | WO 2007/071179 A1 | 6/2007 |
| WO | WO 2007/074472 A2 | 7/2007 |
| WO | WO 2008/098634 A1 | 8/2008 |
| WO | WO 2009/064457 A2 | 5/2009 |
| WO | WO 2009/064458 A2 | 5/2009 |
| WO | WO 2009/064819 A2 | 5/2009 |
| WO | WO 2009/086046 A1 | 7/2009 |
| WO | WO 2009/098595 A2 | 8/2009 |
| WO | WO 2010/021636 A1 | 2/2010 |
| WO | WO 2010/144865 A2 | 12/2010 |
| WO | WO 2011/041509 A1 | 4/2011 |
| WO | WO 2015/034678 A2 | 3/2015 |
| WO | WO 2015/035114 A1 | 3/2015 |
| WO | WO 2018/035393 A1 | 2/2018 |
| WO | WO 2019/165138 A1 | 8/2019 |
| ZA | 6805392 | 6/1969 |

OTHER PUBLICATIONS

Campieria et al., "Oral budesonide is as effective as oral prednisolone in active Crohn's disease," Gut, 41: 209-214 (1997).

Dilger, K., et al. "Active eosinophilic esophagitis is associated with impaired elimination of budesonide by cytochrome P450 3A enzymes." Digestion. 2013; 87(2):110-117. doi: 10.1159/000346403. Epub Jan. 25, 2013.

Eurasian Application No. 201491358, Search Report (with English translation), dated Jan. 22, 2015, 4 pages.

European Application No. EP 10821232.5, Extended European Search Report dated Feb. 6, 2014, 10 pages.

European Application No. EP 14184844.0, Extended European Search Report dated Feb. 9, 2015, 7 pages.

European Application No. EP 14842811.3, Extended European Search Report dated Mar. 23, 2017, 6 pages.

European Application No. EP 18178891.0, Extended European Search Report dated Aug. 13, 2018, 3 pages.

Falcoz, et al., "Bioavailability of Orally Administered Micronised Fluticasone Propionate." Clinical Pharmacokinetics (2000); 39 Suppl. 1: 9-15.

Forum of the National Formulary of Japan, compilation, Drugs in Japan, 2009 edition, published 2008, p. 2161-2165 (and English translation/summary of pertinent paragraphs), 8 pages.

Georgia Application No. AP 2010012674, Search Report (with English translation) dated Nov. 28, 2013, 11 pages.

Ham, et al., "Quantitation of esophageal transit by means of $^{81m}$Kr." European Journal of Nuclear Medicine (1984); 9: 362-365.

International Search Report and Written Opinion for International Application No. PCT/US2017/047474, dated Dec. 26, 2017, 15 pages.

Kumari and Rajendran, "Effect of topical nasal steroid spray in the treatment of non-specific recurrent/chronic pharyngitis—a trial study." Indian Journal of Otolaryngology and Head & Neck Surgery, 60(3): 199-201 (2008).

Lipka, et al., "The natural history of steroid-naïve eosinophilic esophagitis in adults treated with endoscopic dilation and proton pump inhibitor therapy over a mean duration of nearly 14 years." Gastrointest Endosc. (2014); 80(4): 592-598.

Mahmoudi et al. "Effect of drug particle size on blend segregation and content uniformity". Contributed poster, AAPS Annual Meeting (USA) 2010, 1 page. (non-English).

Mahmoudi et al. "Influence of filler in blend uniformity of micronized drugs". Contributed poster, AAPS Annual Meeting (USA) 2010, 1 page.

Malaysian Application No. PI 2012001434, Search Report dated Jan. 29, 2016, 1 page.

(56) References Cited

OTHER PUBLICATIONS

McGinity, J. W., et al. "Dissolution and uniformity properties of ordered mixes of micronized griseofulvin and a directly compressible excipient." Drug Development and Industrial Pharmacy, 11(4): 891-900 (1985).
Merck Index, "Budesonide," 14th Edition, p. 240 (2006).
Merck Index, "Ciclesonide," 14th Edition, p. 376 (2006).
Merck Index, "Clotrimazole," 14th Edition, p. 407 (2006).
Merck Index, "Mometasone Furoate," 14th Edition, pp. 1077-1078 (2006).
Merck Index, "Voriconazole," 14$^{th}$ Edition, p. 1728 (2006).
Novopulmon E Novolizer®, Instructions for the medical use of the medicament, [Instrukciya po medicinskomu primeneniyu preparata Novopulmon E Novolizer (international nonproprietary name: budesonide), registracionniy nomer N LS-002405-231211, 23.12. 2011], MEDA Manufacturing, GmbH Registration No. LS-002405, Date of Registration Dec. 23, 2011 (with English summary of relevant portions), 9 pages.
PCT Application No. PCT/US2010/050860, International Preliminary Report on Patentability dated Apr. 3, 2012.
PCT Application No. PCT/US2010/050860, International Search Report dated Feb. 10, 2011.
PCT Application No. PCT/US2010/050860, Written Opinion of the International Search Authority dated Feb. 10, 2011.
PCT Application No. PCT/US2014/052073, International Preliminary Report on Patentability dated Mar. 8, 2016.
PCT Application No. PCT/US2014/052073, International Search Report dated Nov. 20, 2014.
PCT Application No. PCT/US2014/052073, Written Opinion of the International Searching Authority dated Nov. 20, 2014.
PCT Application No. PCT/US2014/054203, International Preliminary Report on Patentability dated Mar. 8, 2016.
PCT Application No. PCT/US2014/054203, International Search Report dated Dec. 23, 2014.
PCT Application No. PCT/US2014/054203, Written Opinion of the International Searching Authority dated Dec. 23, 2014.
Taiwanese Application No. TW 099133628, Search Report (English translation) dated Nov. 16, 2014, 9 pages.
Taiwanese Application No. TW 104107443, Search Report (English translation) dated May 29, 2015, 1 page.
Takaku, Fumimaro, et al. Manual of Therapeutic Agents 2007, Published 2007, p. 617-619 (and English translation/summary of pertinent paragraphs), 5 pages.
Teitelbaum et al. "Eosinophilic esophagitis in children: immunopathological analysis and response to fluticasone propionate." Gastroenterology (2002), 122(5): 1216-1225.
Vogt et al., "Biowaiver monographs for immediate release solid oral dosage forms: Prednisolone," Journal of Pharmaceutical Sciences, 96(1): 27-37 (2007).
Wei et al., "Efficacy of Single-Dose Dexamethasone as Adjuvant Therapy for Acute Pharyngitis" The Laryngoscope, 112(1):87-93 (2002).
Yalkowsky and Bolton. "Particle size and content uniformity." Pharmaceutical Research, 7(9): 962-966 (1990).
[Author Unknown] Definition of sustained-release (downloaded from Merriam-Webster online at https://www.merriam-webster.com/dictionary/sustainedrelease#medicalDictionary); accessed Jul. 31, 2019, 1 page.
[Author Unknown] Jorveza® package leaflet (downloaded from the European Medicines Agency at www.ema.europa.eu/en/medicines/human/EPAR/jorveza#product-informationsection); accessed Aug. 1, 2019, 8 pages.
[Author Unknown] Jorveza® package leaflet, Jorveza 1mg orodispersible tablets, Mat-No. 1147370 (Losan Pharma), Dated Mar. 15, 2018, Date Code Falk: GB-IE/03.18, 2 pagaes.
[Author Unknown] Jorveza® summary of product characteristics (downloaded from the European Medicines Agency at www.ema.europa.eu/en/medicines/human/EPAR/jorveza#product-informationsection); first published Jan. 18, 2018, accessed Aug. 1, 2019, 9 pages.
[Author Unknown] Solubility of budesonide (downloaded from https://pubchem.ncbi.nlm.nih.gov/compound/Budesonide#section=Solubility&fullscreen=true); information available as of Oct. 15, 2015, accessed Aug. 1, 2019, 1 page.
[Author Unknown] Definition of slow-release (downloaded from Merriam-Webster online at https://www.merriam-webster.com/medical/slow-release); accessed Jul. 31, 2019, 1 page.
[Author Unknown] Povidone (polyvinylpyrrolidone (PVP)) compound summary (downloaded from Wikipedia at https://en.wikipedia.org/wiki/Polyvinylpyrrolidone); accessed Jul. 31, 2019, 5 pages.
Bonnet, et al., "Formulation of a 3-months Stability Oral Viscous Budesonide Gel and Development of an Indicating Stability HPLC Method", Pharm Technol Hosp Pharm (2018); 3(2): 91-99.
Breuer, et al., "Glossary of Terms Related to Pharmaceutics (IUPAC Recommendations 2009)" Pure Appl. Chem. (2009); 81 (5): 971-999.
Certified Priority Document U.S. Appl. No. 61/186,777, filed Jun. 12, 2009, 104 pages.
European Application No. EP 19189185.2, Extended European Search Report dated Aug. 29, 2019, 9 pages.
German Cancellation Action filed by Dr. Falk Pharma GmbH on Mar. 1, 2019 with the German Patent Office, in connection with DE Pat. No. 202010018594 U1 in the name of Adare Pharmaceuticals, Inc., and English translation, 21 pages.
International Preliminary Report on Patentability for International Application No. PCT/US2017/047474, dated Feb. 19, 2019, 8 pages.
Khan and Orenstein, "Eosinophilic Gastroenteritis: Epidemiology, Diagnosis and Management." Paediatr Drugs. (2002); 4(9): 563-570.
Li, Xiaowei, et al., "Advances in Injectable Thermosensitive Polymers". Polymer Bulletin, No. 3, pp. 109-115, Jun. 30, 2015 (with English Abstract), 7 pages.
Miehlke, et al., "A randomised, double-blind trial comparing budesonide formulations and dosages for short-term treatment of eosinophilic oesophagitis", Gut (2016); 65: 390-399.
Opposition Proceedings in European Patent No. 2482822 (Appln. No. 1082123205), filed by Dr. Falk Pharma GmbH on Mar. 1, 2019, EPO Communication dated Mar. 8, 2019 regarding of notice of opposition, 1 page.
Opposition Proceedings in European Patent No. 2482822 (Appln. No. 1082123205), filed by Dr. Falk Pharma GmbH on Mar. 1, 2019, EPO Communication dated Nov. 5, 2019, enclosing Opponent's Further Written Submissions dated/filed on Oct. 29, 2019 (and English translation) including consolidated list of prior art, 29 pages.
Opposition Proceedings in European Patent No. 2482822 (Appln. No. 1082123205), filed by Dr. Falk Pharma GmbH on Mar. 1, 2019, Submission filed by Adare Development I, L.P., on Sep. 20, 2019, 29 pages.
Opposition Proceedings in European Patent No. 2482822 (Appln. No. 1082123205), filed by Dr. Falk Pharma GmbH on Mar. 1, 2019, Patentee, Adare Development I, L.P.'s Response dated Dec. 16, 2019 in response to further submissions filed by Dr. Falk Pharma GmbH on Oct. 29, 2019, 16 pages.
Opposition Proceedings in European Patent No. 2482822 (Appln. No. 1082123205), filed by Dr. Falk Pharma GmbH on Mar. 1, 2019, "Summons to attend oral proceedings pursuant to Rule 115(1) EPC", dated Feb. 13, 2020, 13 pages.
Opposition Proceedings in European Patent No. 2482822 (Appln. No. 1082123205), filed by Dr. Falk Pharma GmbH on Mar. 1, 2019, "Letter from Opponent" dated Jan. 14, 2020 (and English translation of letter), 36 pages.
Patent Complaint filed with Regional Court Mannheim, Germany, re *Adare Development I, L.P.* vs. *Dr. Falk Pharma GmbH*, dated Jul. 3, 2019, with English translation, 107 pages.
PCT Application No. PCT/US2019/019040, International Search Report and Written Opinion, dated Jun. 25, 2019, 12 pages.
PCT Application No. PCT/US2019/019040, Invitation to Pay Additional Fees, dated Apr. 25, 2019, 2 pages.
European Application No. EP 17842162.4, Extended European Search Report dated Apr. 1, 2020, 8 pages.

(56) References Cited

OTHER PUBLICATIONS

European Application No. EP 19207287.4, Extended European Search Report dated Apr. 6, 2020, 9 pages.
U.S. Appl. No. 16/821,464, filed Mar. 17, 2020, Pending.
Opposition Proceedings in European Patent No. EP 2482822 (Appln. No. 1082123205), filed by Dr. Falk Pharma GmbH on Mar. 1, 2019; EPO Communication in connection with Summons to attend oral proceedings, dated Nov. 20, 2020, 12 pages.
U.S. Appl. No. 12/896,005, dated Oct. 1, 2010, U.S. Pub. No. 2011-0081411 A1, Apr. 7, 2011, Registration No. 8,771,729, Registration date Jul. 8, 2014, Registered.
U.S. Appl. No. 14/294,660, dated Jun. 3, 2014, U.S. Pub. No. 2014-0287051 A1, Sep. 25, 2014, Registration No. 9,486,407, Registration date Nov. 8, 2016, Registered.
U.S. Appl. No. 14/311,732, dated Jun. 23, 2014, U.S. Pub. No. 2014-0303131 A1, Oct. 9, 2014, Registration No. 9,387,167, Registration date Jul. 12, 2016, Registered.
U.S. Appl. No. 15/205,390, dated Jul. 8, 2016, U.S. Pub. No. 2017-0071855 A1, Mar. 16, 2017, Registration No. 9,849,084, Registration date Dec. 26, 2017, Registered.
U.S. Appl. No. 14/917,125, dated Sep. 5, 2014, U.S. Pub. No. 2016-0206627 A1, Jul. 21, 2016, Registration No. 10,471,071, Registration date Nov. 12, 2019, Registered.
U.S. Appl. No. 15/680,301, dated Aug. 18, 2017, U.S. Pub. No. 2018-0133145 A1, May 17, 2018, Registration No. 10,105,315, Registration date Oct. 23, 2018, Registered.
U.S. Appl. No. 15/816,154, dated Nov. 17, 2017, U.S. Pub. No. 2018-0153802 A1, Jun. 7, 2018, Registration No. 10,632,069, Registration date Apr. 28, 2020, Registered.
U.S. Appl. No. 16/821,464, dated Mar. 17, 2020, U.S. Pub. No. 2020-0214979 A1, Jul. 9, 2020, Pending.
U.S. Appl. No. 16/992,671, dated Aug. 13, 2020, U.S. Pub. No. 2020-0368147 A1, Nov. 26, 2020, Pending.
U.S. Appl. No. 16/578,568, dated Sep. 5, 2014, U.S. Pub. No. 2020-0016171 A1, Jan. 16, 2020, Pending.
U.S. Appl. No. 16/968,711, dated Aug. 10, 2020, U.S. Pub. No. 2020-0381097 A1, Dec. 3, 2020, Pending.
Alexander, et al., "Review. Therapeutic Options for Eosinophilic Esophagitis". Gastroenterology & Hepatology (Jan. 1, 2011); 7(1): 59-61.
Beveridge, et al., "Novel Therapeutic Approaches to Eosinophilic Esophagitis". Gastroenterology & Hematology (Jun. 2020); 16(6): 294-301.
Dellon, et al., "Efficacy of Budesonide vs Fluticasone for Initial Treatment of Eosinophilic Esophagitis in a Randomized Controlled Trial". Gastroenterology (2019); 157: 65-73.
Furuta, et al., "Review article: the pathogenesis and management of eosinophilic oesophagitis". Alimentary Pharmacology & Therapeutics (2006); 24: 172-182.
Opposition Proceedings in European Patent No. EP 2482822 (Appln. No. 1082123205), filed by Dr. Falk Pharma GmbH on Mar. 1, 2019; Written Submissions of the Opponent in response to the Summons to attend Oral Proceedings, dated and filed Dec. 8, 2020, and English translation, 37 pages.
Opposition Proceedings in European Patent No. EP 3403654 (Appln. No. 18178891.0), filed by Dr. Falk Pharma GmbH; Consolidated List of References dated and filed Dec. 8, 2020, 1 page.
Opposition Proceedings in European Patent No. EP 3403654 (Appln. No. 18178891.0), filed by Dr. Falk Pharma GmbH; Opponent's Further Written Submissions dated and filed Dec. 8, 2020, and English translation, 30 pages.
Remedios, et al., "Eosinophilic esophagitis in adults: clinical, endoscopic, histologic findings, and response to treatment with fluticasone propionate". Gastrointestinal Endoscopy (2006); 63(1): 3-12.
Schaefer, et al., "Comparison of Oral Prednisone and Topical Fluticasone in the Treatment of Eosinophilic Esophagitis: A Randomized Trial in Children". Clinical Gastroenterology and Hepatology (2008); 6: 165-173.

Wen, Hong, (ed. Swarbick, James) "Adsorption at Solid Surfaces: Pharmaceutical Applications". Encyclopedia of Pharmaceutical Technology, Third Edition, vol. 1 (2007); pp. 34-38, 7 pages.
Patent Complaint Proceedings in the Regional Court, Mannheim, Germany, Adare Development I, L.P. vs. Dr. Falk Pharma GmbH, Reference No. 4c O Oct. 2019, Decision (and English translation) dated Oct. 26, 2020, pronounced in the oral hearing of Jul. 21, 2020, 45 pages.
Opposition Proceedings in European Patent No. Ep 3041476 (Appln. No. 14842811.3), filed by Dr. Falk Pharma GmbH on Jul. 22, 2020; EPO Communication dated Jul. 29, 2020 advising of and enclosing Notice of Opposition filed by Dr. Falk Pharma GmbH on Jul. 22, 2020, 82 pages.
Opposition Proceedings in European Patent No. EP 3041476 (Appln. No. 14842811.3), filed by Dr. Falk Pharma GmbH on Jul. 22, 2020; Notice of Opposition and Statement of Grounds of Opposition (with English translation of Statement of Grounds of Opposition), and Consolidated List of references relied upon, filed Jul. 22, 2020, 513 pages.
Moreton, R. Christian, "Disintegrants in Tableting". In book: Pharmaceutical Dosage Forms: Tablets, vol. 2, Herausgeber Augsburger & Hoag, CRC Press, Taylor and Francis Group (2008); Ch. 6, pp. 217-249.
Webb, Paul A., "Surface Area, Porosity, and Related Physical Characteristics". In book: Pharmaceutical Dosage Forms: Tablets, 3rd Edition, vol. 3, CRC Press, Taylor and Francis Group, Boca Raton, London, New York (2008); Chapter 11, pp. 277-302.
Dolo-Dobendan®, 1.4 mg/10 mg lozenges package insert, Reference ID 3030657, Revised: Jan. 2015, with English translation, 7 pages.
German Patent Complaint Proceedings in the Regional Court, Mannheim, Germany, *Adare Development I, L.P.* vs. *Dr. Falk Pharma GmbH*, Docket No. 7 O 75/19, Submission of Dr. Falk dated Feb. 10, 2020, 6 pages, in German and English.
German Patent Complaint Proceedings in the Regional Court, Mannheim, Germany, *Adare Development I, L.P.* vs. *Dr. Falk Pharma GmbH*, Docket No. 7 O 75/19, Writ as filed, dated Feb. 11, 2020, and English translation, 5 pages.
German Patent Complaint Proceedings in the Regional Court, Mannheim, Germany, *Adare Development I, L.P.* vs. *Dr. Falk Pharma GmbH*, Docket No. 7 O 75/19, Official Order dated Feb. 12, 2020, and English translation, 5 pages.
German Patent Complaint Proceedings in the Regional Court, Mannheim, Germany, *Adare Development I, L.P.* vs. *Dr. Falk Pharma GmbH*, Docket No. 7 O 75/19, Official Order dated Feb. 13, 2020, and English translation, 5 pages.
German Utility Model Cancellation Proceedings, *Dr. Falk Pharma GmbH*(Plaintiff) vs. *Adare Development I, L.P.*(Patentee), Utility model DE 20201 018594 U1, Auxiliary Request I-IV (marked-up) dated and as filed Jul. 1, 2020, and English translation, 17 pages.
Utility Model Cancellation Proceedings, *Dr. Falk Pharma GmbH*(Plaintiff) vs. *Adare Development I, L.P.*(Patentee), Utility model DE 202010018594 U1, Jul. 12, 2019 - Exhibit BB4—Letter from Lederer & Keller dated Sep. 27, 2018 regarding European Patent No. 2211896, and Machine English translation, 28 pages.
Supplementary European Search Report in European Patent Application No. EP 20192973.4, dated Nov. 18, 2020, 5 pages.
Jorveza (budesonide) Update by the Committee for Medicinal Products for Human Use (CHMP), Summary of opinion1 (post authorisation) dated Mar. 26, 2020, European Medicines Agency, 1 page.
Krishna, et al., "Treatment of Eosinophilic Esophagitis Is Oral Viscous Budesonide Superior to Swallowed Fluticasone Spray?" Gastroenterol Hepatol (Jan. 2011); 7(1): 55-59.
Langdon, BA and Mullamey, (2006) Handbook of Pharmaceutical Exclpients. (eds.) Rowe, R.C., Sheskey, PJ and Owen, S.C., London: Pharmaceutical Press and American Pharmacists Association (extract-pp. 53-55 and 742-743), 14 pages.
Opposition Proceedings in European Patent No. EP 3403654 (Appln. No. 18178891.0), filed Dr. Falk Pharma GmbH; EPO Communication of a notice of opposition dated Jun. 22, 2020, 1 page.

(56) References Cited

OTHER PUBLICATIONS

Opposition Proceedings in European Patent No. EP 3403654 (Appln. No. 18178891.0), filed Dr. Falk Pharma GmbH; EPO Communication of a notice of opposition dated May 8, 2020, 1 page.
Opposition Proceedings in European Patent No. EP 3403654 (Appln. No. 18178891.0), filed Dr. Falk Pharma GmbH; Statement of Grounds of Opposition filed Apr. 28, 2020, and English translation, 38 pages.
Opposition Proceedings in European Patent No. EP 2482822 (Appln. No. 1082123205), filed Dr. Falk Pharma GmbH on Mar. 1, 2019; Falk's Communication to the EPO re oral proceedings, dated Aug. 12, 2020, 3 pages.
Opposition Proceedings in European Patent No. EP 2482822 (Appln. No. 1082123205), filed Dr. Falk Pharma GmbH on Mar. 1, 2019; Adare's Communication to the EPO re oral proceedings, dated Aug. 11, 2020, 4 pages.
Opposition Proceedings in European Patent No. EP 2482822 (Appln. No. 1082123205), filed Dr. Falk Pharma GmbH on Mar. 1, 2019; EPO's Communication re oral proceedings, dated Aug. 5, 2020, 1 page.
Opposition Proceedings in European Patent No. EP 2482822 (Appln. No. 1082123205), filed Dr. Falk Pharma GmbH on Mar. 1, 2019; EPO Communication dated Jul. 23, 2020, with Written Submission from Adare (Proprietor) dated Jul. 17, 2020, 126 pages.
Declaration of Stephen Perrett, MBA, Ph.D. dated Jul. 16, 2020, 6 pages.
"Nurofen" tablet package insert (provided in German only), 1 page.
"Dolo-Dobendan" lozenge package insert (provided in German only), 1 page.
Pelle, et al., "Using defined daily doses to study the use of antibacterials in UK hospitals". Hosp Pharm (2006); 13: 133-136.
Lee, Geoffrey, Professor, Report of Professor Geoffrey Lee, Ph.D. on measurement of disintegration time of Jorveza® 1 mg orodispersible table dated Nov. 15, 2019, 16 pages.
Opposition Proceedings in European Patent No. EP 2482822 (Appln. No. 1082123205), filed by Dr. Falk Pharma GmbH on Mar. 1, 2019; EPO's consolidated list of cited opposition documents, Jul. 18, 2020, 1 page.
Opposition Proceedings in European Patent No. EP 2482822 (Appln. No. 1082123205), filed by Dr. Falk Pharma GmbH on Mar. 1, 2019; EPO Communication dated Jul. 13, 2020, 3 pages.
Katdare and Chaubal (eds)., Excipient Development for Pharmaceutical, Biotechnology and Drug Delivery Systems, Herausg. CRC Press, Taylor & Francis Group, Boca Raton, USA, 2006; dart: Excipients for Oral Liquid Formulations, S. 155-180, 28 pages.
Opposition Proceedings in European Patent No. EP 2482822 (Appln. No. 1082123205), filed by Dr. Falk Pharma GmbH on Mar. 1, 2019, Adare-Letter to EPO re Oral Proceedings dated Jul. 17, 2020, 5 pages.
Opposition Proceedings in European Patent No. EP 2482822 (Appln. No. 1082123205), filed by Dr. Falk Pharma GmbH on Mar. 1, 2019, Summons to Attend Oral Hearing and Preliminary Opinion in opposition dated Feb. 13, 2020, 15 pages.
Opposition Proceedings in European Patent No. 2482822 (Appln. No. 1082123205), filed by Dr. Falk Pharma GmbH on Mar. 1, 2019, EPO Communication dated Sep. 26, 2019, transmitting Adare's submission filed Sep. 20, 2019, 88 pages.
Opposition Proceedings in European Patent No. 2482822 (Appln. No. 1082123205), filed by Dr. Falk Pharma GmbH on Mar. 1, 2019, D18-Dr F's novelty table 2020, 2 pages.
Opposition Proceedings in European Patent No. 2482822 (Appln. No. 1082123205), filed by Dr. Falk Pharma GmbH on Mar. 1, 2019, Submission filed by Adare Development I, L.P., on Sep. 20, 2019, 91 pages.
Opposition Proceedings in European Patent No. 2482822 (Appln. No. 1082123205), filed by Dr. Falk Pharma GmbH on Mar. 1, 2019, EPO Communication-communication of notice of opposition dated May 13, 2019, 1 page.
Opposition Proceedings in European Patent No. 2482822 (Appln. No. 1082123205), filed by Dr. Falk Pharma GmbH on Mar. 1, 2019, Notice of Opposition dated Mar. 1, 2019, and English translation, 23 pages.
Opposition Proceedings in European Patent No. 3086782 (Appln. No. 14814872.9), filed by Adare Development, I, L.P. On Jun. 26, 2019, EPO Communication dated Jul. 22, 2020 regarding date of oral proceedings, 3 pages.
Opposition Proceedings in European Patent No. 3086782 (Appln. No. 14814872.9), filed by Adare Development, I, L.P. On Jun. 26, 2019, EPO Communication to Adare regarding oral proceedings dated Mar. 2, 2020, and English translation, 14 pages.
Opposition Proceedings in European Patent No. 3086782 (Appln. No. 14814872.9), filed by Adare Development, I, L.P. On Jun. 26, 2019, EPO Communication dated Jul. 2, 2019, transmitting Notice of Opposition filed Jun. 26, 2019, 43 pages.
Hahm and Augsburger, Orally Disintegrating Tablets and Related Tablet Formulations, Pharmaceutical Dosage Forms: Tablets, Third Edition, Ch. 9, vol. 2, Herausgeber: (eds) Larry L. Augsburger, Stephen W. Hoag, CRC Press (2008), 21 pages.
Opposition Proceedings in European Patent No. 2886108 (Appln. No. 13199278.6), filed by Adare Development, I, L.P. On Nov. 6, 2019, EPO Communication dated Jul. 24, 2020 regarding oral proceedings, 6 pages.
Opposition Proceedings in European Patent No. 2886108 (Appln. No. 13199278.6), filed by Adare Development, I, L.P. On Nov. 6, 2019, EPO Communication re Summons to Attend Oral Proceedings and Preliminary Opinion, dated Jul. 2, 2020, and English translation, 18 pages.
Opposition Proceedings in European Patent No. 2886108 (Appln. No. 13199278.6), filed by Adare Development, I, L.P. On Nov. 6, 2019, EPO Communication dated Mar. 25, 2020 transmitting communication from Dr. Falk Pharma GmbH dated Mar. 20, 2020, and English translation, 34 pages.
Opposition Proceedings in European Patent No. 2886108 (Appln. No. 13199278.6), filed by Adare Development, I, L.P. On Nov. 6, 2019, Consolidated List of Cited Opposition Documents, 1 page.
Auszug von European Pharmacopeia 6.0 (English language) <2.9. 8>; Jul. 23, 2007, 2 pages.
Auszug von European Pharmacopeia 8.0 (German language) <2.9. 8>; Jul. 15, 2013, 1 page.
Auszug von U.S. Pharmacopeia 35 <1217>; May 1, 2012, 3 pages.
Dr. Schleuniqer, "Key factors influencing measured tablet hardness"; Pharmatron; 2011, 5 pages.
Author Unknown, WHT 3ME brochure Version 2.0; Fully Automated 4 in 1 Tablet Testing Instrument' Pharma Test; publication date unknown.
Dohil, et al., "Oral Viscous Budesonide Is Effective in Children With Eosinophilic Esophagitis in a Randomized, Placebo-Controlled Trial". Gastroenterol. (Aug. 2010); 139(2): 418-429.
Tayebi and Mortazavi, "Formulation and Evaluation of a Novel Matrix-Type Orally Disintegrating Ibuprofen Tablet". Iran J Pharm Res. (2011 Summer); 10(3): 469-479.
German Patent Complaint Proceedings in the Regional Court, Mannheim, Germany, *Adare Development I, L.P.* vs. *Dr. Falk Pharma GmbH*, Docket No. 7 O 75/19, Submission of Dr. Falk-statement of defense, filed Oct. 7, 2019 (and English translation), 14 pages.
German Patent Complaint Proceedings in the Regional Court, Mannheim, Germany, *Adare Development I, L.P.* vs. *Dr. Falk Pharma GmbH*, Docket No. 7 O 75/19, submission by Dr. Falk Pharma GmbH dated May 27, 2020 (and English translation), 16 pages.
German Utility Model Cancellation Proceedings, *Dr. Falk Pharma GmbH*(Plaintiff) vs. *Adare Development I, L.P.*(Patentee), Utility model DE 202010018594 U1, Submission of Dr. Falk-response to Adare and summons, dated Jul. 8, 2020 (and English translation), 11 pages.
German Utility Model Cancellation Proceedings, *Dr. Falk Pharma GmbH*(Plaintiff) vs. *Adare Development I, L.P.*(Patentee), Utility model DE 202010018594 U1, submission/Response by Dr. Falk Pharma GmbH dated Apr. 8, 2020 (and English translation), 18 pages.

(56) References Cited

OTHER PUBLICATIONS

German Utility Model Cancellation Proceedings, *Dr. Falk Pharma GmbH*(Plaintiff) vs. *Adare Development I, L.P.*(Patentee), Utility model DE 20201 018594 U1, Official Communication Interlocutory Notice dated Jan. 22, 2020 (and English translation), 12 pages.
German Utility Model Cancellation Proceedings, *Dr. Falk Pharma GmbH*(Plaintiff) vs. *Adare Development I, L.P.*(Patentee), Utility model DE 20201 018594 U1, Submission of Dr. Falk-Pleadings dated Sep. 13, 2019 (and English translation), 27 pages.
Ponchel, Gilles, "Formulation of oral mucosal drug delivery systems for the systemic delivery of bioactive materials". Advanced Drug Delivery Reviews, vol. 13, Issues 1-2, Jan.-Feb. 1994, pp. 75-87.
Utility Model Cancellation Proceedings, *Dr. Falk Pharma GmbH*(Plaintiff) vs. *Adare Development I, L.P.*(Patentee), Utility model DE 202010018594 U1, Jul. 12, 2019-Exhibit BB2-Handbook of Pharmaceutical Excipients (2009); Sixth Edition, ISBN 978 1 58212 135 2, (eds.) Rowe, et al., Cover page, Print/Copyright and Preface pages, 4 pages.
New World Encyclopedia, "Gastrointestinal tract", https://www.newworldencyclopedia.org/entry/Gastrointestinal_tract, Jul. 8, 2019, 6 pages.
New World Encyclopedia, "Gastrointestinal tract", https://web.archive.org/web/20090917122455/https://www.newworldencyclopedia.or . . ., Jul. 8, 2019, 7 pages.
UM Complaint Proceedings in the Regional Court, Mannheim, Germany, *Adare Development I, L.P.* vs. *Dr. Falk Pharma GmbH*, Reference No. 4c O Oct. 2019, Submission of Dr. Falk-Rejoinder dated Sep. 13, 2019 (English translation), 8 pages.
UM Complaint Proceedings in the Regional Court, Mannheim, Germany, *Adare Development I, L.P.* vs. *Dr. Falk Pharma GmbH*, Reference No. 4c O Oct. 2019, Submission of Dr. Falk-statement of defense, dated May 24, 2019 (and English translation), 16 pages.
Opposition Proceedings in European Patent No. EP 3403654 (Appln. No. 18178891.0), filed by Dr. Falk Pharma GmbH; Adare's Response to the Grounds of Opposition, filed Nov. 2, 2020, 78 pages.
Opposition Proceedings in European Patent No. EP 2482822 (Appln. No. 1082123205), filed by Dr. Falk Pharma GmbH on Mar. 1, 2019; EPO Communication dated Jul. 23, 2020, with Adare's Written Submissions in Preparation for Oral Proceedings, Auxiliary Requests 1-7 (clean and marked-up), and supporting evidence, as filed Jul. 17, 2020, 126 pages.
"Nurofen" tablet package insert, 200 MG Tablets and Capsules, Date of revision: Feb. 2018, Reference ID 3039860, and English version, 2 pages.
Liacouras, et al., "Primary Eosinophilic Esophagitis in Children: Successful Treatment with Oral Corticosteroids". Journal of Pediatric Gastroenterology & Nutrition (1998); 26(4): 380-385.
Furuta, Glenn T., "Eosinophils in the Esophagus: Acid is Not the Only Cause". Journal of Pediatric Gastroenterology & Nutrition (Apr. 1998); 26(4): 468-471.
Opposition Proceedings in European Patent No. EP 2482822 (Appln. No. 1082123205), filed by Dr. Falk Pharma GmbH on Mar. 1, 2019, Opponent's response to Summons dated Jul. 17, 2020, and English translation, 15 pages.
Opposition Proceedings in European Patent No. 3086782 (Appln. No. 14814872.9), filed by Adare Development, I, L.P. On Jun. 26, 2019, Patentee, Dr. Falk's Written Submissions, Auxiliary Request I and Test Report Jorveza® 1 mg (dated Aug. 18, 2020, produced by Patentee, Dr. Falk Pharma), filed Sep. 10, 2020, and English translation, 22 pages.
Opposition Proceedings in European Patent No. 3086782 (Appln. No. 14814872.9), filed by Adare Development, I, L.P. On Jun. 26, 2019, EPO Communication dated Nov. 19, 2019, with Patentee's response to Opposition dated Nov. 8, 2019, and English translation, 22 pages.
PCT Application No. PCT/US2019/019040, International Preliminary Report on Patentability, dated Aug. 27, 2020, 8 pages.
UM Complaint Proceedings in the Regional Court, Mannheim, Germany, *Adare Development I, L.P.* vs. *Dr. Falk Pharma GmbH*, Reference No. 4c O Oct. 2019, submission by Dr. Falk Pharma GmbH dated May 24, 2020, and English translation, 16 pages.
German Utility Model Cancellation Proceedings, *Dr. Falk Pharma GmbH*(Plaintiff) vs. *Adare Development I, L.P.*(Patentee), Utility model DE 20201 018594 U1, Response to Dr. Falk and Summons dated Jul. 2, 2020, and English translation, 18 pages.
German Utility Model Cancellation Proceedings, *Dr. Falk Pharma GmbH*(Plaintiff) vs. *Adare Development I, L.P.*(Patentee), Utility model DE 202010018594 U1, Communication from Adare to German Patent Office, Auxiliary Requests 1 and 2 (clean, marked-up and English translations) as filed Apr. 6, 2020, 23 pages.
German Utility Model Cancellation Proceedings, *Dr. Falk Pharma GmbH*(Plaintiff) vs. *Adare Development I, L.P.*(Patentee), Utility model DE 202010018594 U1, Adare's Response dated Apr. 6, 2020 to Interlocutory Decision, and English translation, 29 pages.
German Utility Model Cancellation Proceedings, *Dr. Falk Pharma GmbH*(Plaintiff) vs. *Adare Development I, L.P.*(Patentee), Utility model DE 20201 018594 U1, Response to Pleadings as filed dated Oct. 17, 2019, and English translation, 25 pages.
Aceves, et al., "Topical viscous budesonide suspension for treatment of eosinophilic esophagitis". The Journal of Allergy and Clinical Immunology (Sep. 1, 2005); vol. 116, Issue 3, pp. 705-706. Epub Jul. 1, 2005.
Aceves, et al., "Oral viscous budesonide: a potential new therapy for eosinophilic esophagitis in children". Am J Gastroenterol. (Oct. 2007); 102(10): 1-9. Epub Jun. 20, 2007.
Thorburn and Ferguson, "Topical corticosteroids and lesions of the oral mucosa". Advanced Drug Delivery Reviews, vol. 13, Issues 1-2, Jan.-Feb. 1994, pp. 135-149.
Utility Model Cancellation Proceedings, *Dr. Falk Pharma GmbH*(Plaintiff) vs. *Adare Development I, L.P.*(Patentee), Utility model DE 202010018594 U1, Jul. 12, 2019-Exhibit BB1 "Breakdown of Features", and English translation, 2 pages
Wikipedia, "Retard", https://de.wikipedia.org/wiki/Retard, Jun. 13, 2019, and Google machine translation, 7 pages.
EPO Communication dated Apr. 25, 2019 in connection with Application No. EP 08848597.4, 13 pages.
Budesonid, https://www.chemie.de/lexikon/Budesonid.html, Jul. 12, 2019, and English version, Sep. 10, 2020, 3 pages.
UM Complaint Proceedings in the Regional Court, Mannheim, Germany, *Adare Development I, L.P.* vs. *Dr. Falk Pharma GmbH*, Reference No. 4c O Oct. 2019, Replica dated Jul. 19, 2019, and English translation, 25 pages.
UM Complaint Proceedings in the Regional Court, Mannheim, Germany, *Adare Development I, L.P.* vs. *Dr. Falk Pharma GmbH*, Complaint dated Jul. 3, 2019, and English translation, 34 pages.
U.S. Appl. No. 14/311,732, dated Jun. 23, 2014, U.S. Pub. No. 2014-0303131 A1, Oct. 9, 2014, Registration 9,387,167, Registration date Jul. 12, 2016, Registered.
U.S. Appl. No. 15/205,390, dated Jul. 8, 2016, U.S. Pub. No. 2017-0071855, Mar. 16, 2017, Registration No. 9,849,084, Registration date Dec. 26, 2017, Registered.
U.S. Appl. No. 15/816,154, dated Nov. 17, 2017, U.S. Pub. No. 2018-0153802 A1, Jun. 7, 2018, Registration 10,632,069, Registration date Apr. 28, 2020, Registered.
U.S. Appl. No. 16/821,464, dated Mar. 17, 2020, U.S. Pub. No. 2020-0214979 A1, Pub date Jul. 9, 2020, Pending.
U.S. Appl. No. 16/992,671, dated Aug. 13, 2020, Pending.
U.S. Appl. No. 16/578,568, dated Sep. 5, 2014, U.S. Pub. No. 2020-0016171 A1, Jan. 6, 2020, Pending.
Robertson, et al., "Oesophageal transit of small tablets", J. Pharm. Pharmacol. (1988); 40: 595-596.
Opposition Proceedings in European Patent No. EP 3041476 (Appln. No. 14842811.3), filed by Dr. Falk Pharma GmbH on Jul. 22, 2020; EPO Communication dated Feb. 22, 2021 enclosing Opponent's Submissions (and English translation), dated Feb. 16, 2021, 11 pages.
von Arnim and Malfertheiner, "Eosinophilic Esophagitis—Treatment of Eosinophilic Esophagitis with Drugs: Corticosteroids", Digestive Diseases (2014); 32: 126-129.

(56) References Cited

OTHER PUBLICATIONS

Opposition Proceedings in European Patent No. EP 3041476 (Appln. No. 14842811.3), filed by Dr. Falk Pharma GmbH on Jul. 22, 2020; Patentee Adare's Response to Opposition dated Jan. 11, 2021, 15 pages.

Opposition Proceedings in European Patent No. EP 2482822 (Appln. No. 10821232.05), filed by Dr. Falk Pharma GmbH on Mar. 1, 2019; Written Submissions of the Patentee in Preparation for Oral Proceedings on Mar. 8, 2021, dated Jan. 8, 2021, with Auxiliary Requests 1-14, 52 pages.

Opposition Proceedings in European Patent No. 2886108 (Appln. No. 13199278.6), filed by Ellodi Pharmaceuticals, L.P., on Nov. 6, 2019, Adare's Written Submissions in Preparation for Oral Proceedings on Apr. 23, 2021, dated Feb. 23, 2021, 25 pages.

German Utility Model Cancellation Proceedings DE 202010185945 U1, *Dr. Falk Pharma GmbH*(Plaintiff/Respondent) vs. *Adare Pharmaceuticals US*, L.P./Ellodi Pharmaceuticals L.P. (Patentee/Appellant), Statement of Grounds of Appeal dated Feb. 26, 2021 (and English translation), and Exhibit BB17-Current EPA register extract on D5 dated Nov. 27, 2020, 117 pages.

\* cited by examiner

METHODS OF TREATING EOSINOPHILIC ESOPHAGITIS

CROSS-REFERENCE TO RELATED APPLICATIONS

The present application is a continuation U.S. application Ser. No. 15/680,301, filed on Aug. 18, 2017, now U.S. Pat. No. 10,105,315, granted Oct. 23, 2018, which claims priority to U.S. Provisional Application No. 62/489,292, filed Apr. 24, 2017; U.S. Provisional Application No. 62/461,317, filed Feb. 21, 2017; and U.S. Provisional Application No. 62/376,703, filed Aug. 18, 2016, the entire contents of each of which are hereby incorporated by reference in its entirety for all purposes.

BACKGROUND

Esophageal inflammation disorders such as eosinophilic esophagitis (EoE), a disease characterized by high levels of eosinophils in the esophagus, as well as basal zonal hyperplasia, is increasingly being diagnosed in children and adults. Many aspects of the disease remain unclear including its etiology, natural history, and optimal therapy. EoE affects all age groups but most frequently individuals between 20 and 50 years of age. Symptoms of EoE often mimic those of gastroesophageal reflux disease (GERD) and include vomiting, dysphagia, pain and food impaction. The disease is painful, leads to difficulty swallowing, and predisposes patients to other complications. EoE is often misdiagnosed for GERD, causing delay in adequate treatment for EoE patients.

Currently, no topically administered anti-inflammatory medications are approved for the treatment of conditions associated with inflammation of the upper portion of the gastrointestinal tract, particularly the inflammatory conditions of the esophagus, such as EoE. Although systemic treatments with corticosteroids such as prednisolone are effective, these therapeutics are associated with significant adverse effects such as suppression of the hypothalamo-pituitary-adrenal (HPA) axis as reflected in salivary Cortisol levels, generalized suppression of immune function, and particularly in children, troubling side-effects from long term systemic exposure include growth retardation.

SUMMARY OF THE INVENTION

The present disclosure provides methods of administering pharmaceutical compositions comprising a low-dose topically active corticosteroid to treat, prevent, ameliorate, or delay the symptoms and/or inflammation associated with a gastrointestinal inflammatory disorder. In some embodiments, the gastrointestinal inflammatory disorder is in the esophagus. In some embodiments, the gastrointestinal inflammatory disorder is eosinophilic esophagitis.

In some embodiments, the present disclosure provides methods of treating eosinophilic esophagitis (EoE) in a patient in need thereof, comprising administrating an oral corticosteroid in an induction phase and a maintenance phase. In some embodiments, the induction phase results in improvement in Peak eosinophilic (Eos) counts in at least one esophageal biopsy, and the treatment (e.g. during the induction phase) results in no worsening of patient mean weekly scores in a patient-reported outcome assessment which includes the assessment of dysphagia-free days. In some embodiments, the patient exhibits substantial improvement in esophageal function and morphology, including lessening of esophageal furrows, lessening of esophageal focal narrowing, increased esophageal diameter, increased esophageal compliance, increased esophageal body distensibility, increased ease swallowing, reduced edema, improved vascularity, reduction of rings, decrease or absence of exudate, and/or absence of stricture.

In some embodiments, the present disclosure provides methods of treating eosinophilic esophagitis (EoE) in a patient in need thereof, comprising administrating an oral corticosteroid in an induction phase and a maintenance phase, wherein the induction phase does not result in substantial improvement in Peak eosinophilic counts in at least one esophageal biopsy. In some embodiments, the patient experiences at least one episode of food impaction in the induction phase. In some embodiments, the patient exhibits active symptoms of EoE during the induction phase. In some embodiments, the induction phase results in a histological response of ≥15 peak eosinophils per high power field (HPF). In some embodiments, the patient exhibits no substantial improvement in esophageal function and/or morphology during the induction phase. In some embodiments, following the ineffective induction phase, treatment is continued resulting in the patient exhibiting an improvement in Peak eosinophilic counts in at least one esophageal biopsy, and the continued treatment results in no worsening of patient mean weekly scores in a patient-reported outcome assessment, which includes the assessment of dysphagia-free days.

In some embodiments, the maintenance phase comprises a dose at least equal to, more than or less than the induction phase. In some embodiments the induction and maintenance doses are between about 1.5 mg and about 3 mg, e.g. administered once or twice daily.

In some embodiments, the induction phase comprises administration for at least about 6 weeks, for at least about 8 weeks, for at least about 10 weeks, or for at least about 12 weeks. In some embodiments, administration occurs twice per day. In some embodiments, the induction phase results in a histological response of <6 peak Eos per HPF. In some embodiments, the induction phase results in no episodes of food impaction.

In some embodiments, the patient in maintenance therapy does not relapse with active symptoms of EoE. In some embodiments, the maintenance does is substantially the same or less than the induction dose. In some embodiments, the maintenance dose is higher than the induction dose. In some embodiments, the patient in the withdrawal phase does not relapse with active symptoms of EoE. In some embodiments, the patient remains in withdrawal phase until active symptoms of EoE recur. In some embodiments, after recurrence of active symptoms of EoE, the patient receives an induction dose of an oral corticosteroid. In some embodiments, after recurrence of active symptoms of EoE, the patient receives a maintenance dose of an oral corticosteroid. In some embodiments, after recurrence of active symptoms of EoE, the patient receives an induction dose of an oral corticosteroid followed by a maintenance dose.

In some embodiments, the present disclosure provides for administering the oral corticosteroid composition to a patient while laying down. In some embodiments, the corticosteroid is administered to the patient while laying down and prior to going to sleep (e.g., about 1 minute, about 5 minutes, about 10 minutes, about 15 minutes, or about 30 minutes, inclusive of all values therein). In some embodiments, the pharmaceutical composition is administered to the patient at least about 2 hours after the evening meal. In some embodiments, the corticosteroid is administered to the patient at least about 4 hours after the evening meal.

In some embodiments, the corticosteroid is formulated in an orally dissolving dosage form. In some embodiments, the corticosteroid is selected from the group consisting of budesonide, fluticasone, flunisolide, ciclesonide, mometasone, beclomethasone, tixocortol and salts, or esters and mixtures thereof. In some embodiments, the orally dissolving dosage form is a tablet or wafer. In some embodiments, the corticosteroid is deposited topically in the upper gastrointestinal tract. In some embodiments, the patient has previously been administered proton pump inhibitor (PPI) therapy. In some embodiments, the patient has previously been administered PPI therapy for eight weeks. In some embodiments, the PPI therapy was not effective to substantially improve one or more symptoms of EoE. In some embodiments, the patient has previously not been administered PPI therapy.

In some embodiments, the present disclosure provides methods for assessing the suitability of subjects for a clinical trial to measure the effect of an oral corticosteroid on EoE after administration in both an induction phase and a maintenance phase, wherein the recruitment of subjects into the clinical trial is assessed based on (i) patients having Peak eosinophil counts per HPF of greater than 15, and (ii) prior treatment with a PPI over at least about 8 weeks had not been effective to substantially improve one or more symptoms of EoE.

In some embodiments, the present disclosure provides for a method of treating EoE in a patient in need thereof, comprising administering an oral corticosteroid to the patient, wherein the patient is lying down when the oral corticosteroid is administered or the patient lays down immediately after administration of the oral corticosteroid. In other embodiments, the present disclosure provides for a composition comprising an oral corticosteroid for use in the treatment of EoE in a patient in need thereof, wherein the patient is lying down when the composition is administered or the patient lays down after immediately after administration of the composition. In still other embodiments, the present disclosure provides for the use of composition comprising an oral corticosteroid for the manufacture of a medicament for the therapeutic application in EoE in a patient in need thereof, wherein the patient is lying down when the medicament is administered or the patient lays down immediately after administration of the medicament.

In various embodiments, the present disclosure provides for methods (or compositions for use in methods) for topically treating EoE in patient in need thereof with an oral corticosteroid, said methods comprising: (a) administering the oral corticosteroid while the patient is lying down or immediately prior to the patient lying down. In embodiments, a therapeutically effective amount of the oral corticosteroid contacts the esophagus, thereby topically treating EoE.

In embodiments, the lying down is in a supine, prone, or laterally recumbent position. In embodiments, the oral corticosteroid is administered about 30 minutes or less before target sleep time. In embodiments, the oral corticosteroid is administered at least about 30 minutes after a meal. In embodiments, the patient does not eat or drink for at least about 30 minutes after administration the oral corticosteroid.

In embodiments, the oral corticosteroid is administered: (i) once daily; or (ii) twice daily, wherein the first daily dose is administered while the subject remains upright. In embodiments, the corticosteroid has a systemic bioavailability of less than or equal to about 20% of its dose. In embodiments, the oral corticosteroid provides an average maximum blood plasma concentration (Cmax) of less than or equal to about 500 pg/mL after oral administration of about 0.01 mg to about 20 mg of the oral corticosteroid. In embodiments, the oral corticosteroid provides an average $AUC_{0-24}$ of less than or equal to about 3,000 pg*h/mL after oral administration of about 0.01 mg to about 20 mg of the oral corticosteroid. In embodiments, the oral corticosteroid is budesonide, fluticasone, flunisolide, ciclesonide, mometasone or beclomethasone, or a pharmaceutically acceptable salt, solvent, ester, polymorph or prodrug thereof. In embodiments, the oral corticosteroid is formulated: (i) as a liquid composition; (ii) as a solid composition; (iii) to form a solution or suspension prior to oral administration; or (iv) to form a solution, suspension or gel after oral administration, wherein (i)-(iv) delivers a therapeutically effective amount of the oral corticosteroid to the esophagus. In embodiments, (i) the liquid composition is in the form of a solution, suspension or slurry; and (ii) the solid composition is in the form of a gel, lozenge, lollipop, effervescent tablet, powder, granules or an orally disintegrating composition. In embodiments, the orally disintegrating composition is a tablet, wafer, film, or lyophilized matrix. In embodiments, the orally disintegrating composition is a tablet comprising: (a) the oral corticosteroid in an amount of from about 1.5 mg to about 7.5 mg; (b) a pharmaceutically acceptable carrier combined with the corticosteroid; and (c) rapidly dispersing microgranules, wherein the orally disintegrating tablet disintegrates within 60 seconds when tested using the USP <701> method for disintegration time.

In embodiments, the patient has a Cmax of the oral corticosteroid of less than or equal to about 200 pg/mL following oral administration 1.5 mg to about 7.5 mg of the oral corticosteroid. In embodiments, the oral corticosteroid is fluticasone propionate, and the lying down patient has a Cmax within the range of about 80% to about 125% of about 15 pg/mL to about 45 pg/mL following oral administration of 6 mg fluticasone propionate or 3 mg of fluticasone propionate to a lying down patient. In embodiments, the Cmax of the corticosteroid for the laying down patient is lower than the Cmax of the oral corticosteroid for a fed patient that is upright and does not lay down immediately after administration of the oral corticosteroid. In embodiments, the Cmax of the oral corticosteroid for the lying down patient is lowered by about 10% to about 30% compared to the Cmax of the oral corticosteroid for a fed patient that is upright and does not lay down immediately after administration of the oral corticosteroid.

In embodiments, the average time to reach a maximum blood plasma concentration (Tmax) is in the range of about 80% to about 125% of about 12 h to about 15 h. In embodiments, the Tmax of the corticosteroid for the lying down patient is delayed compared to the Tmax of the oral corticosteroid for a patient that is upright and does not lay down immediately after administration of the oral corticosteroid. In embodiments, the Tmax of the corticosteroid for the lying down patient is delayed by at least about 1 hour compared to the average Tmax of the oral corticosteroid for a patient that is upright and does not lay down immediately after administration of the oral corticosteroid. In embodiments, the Tmax of the corticosteroid for the lying down patient is delayed by an amount of time in the range of about 4 h to about 9 h compared to the Tmax of the oral corticosteroid for a patient that is upright and does not lay down immediately after administration of the oral corticosteroid.

In embodiments, after 12 weeks of daily administration of the oral corticosteroid, esophageal inflammation is reduced as measured by a reduction in eosinophil count, an increase in dysphagia-free days, a reduction in episodes of dysphagia, improvement in EREFS score, EndoFLIP documentation of improved esophageal compliance, evaluation of biomarkers, a decrease in episodes of food impaction, an improvement in EEsAI scores (patient, physician, endoscopy, pathology scores), EoE-QOL-A, Visual Dysphagia Questionnaire (VDQ), Avoidance Modification and Slow Eating (AMS) scores, or histology. In embodiments, the patient's eosinophil count is reduced by at least about 50%.

In embodiments, the patient has a lactose allergy or starch allergy.

DETAILED DESCRIPTION

Figure 1:
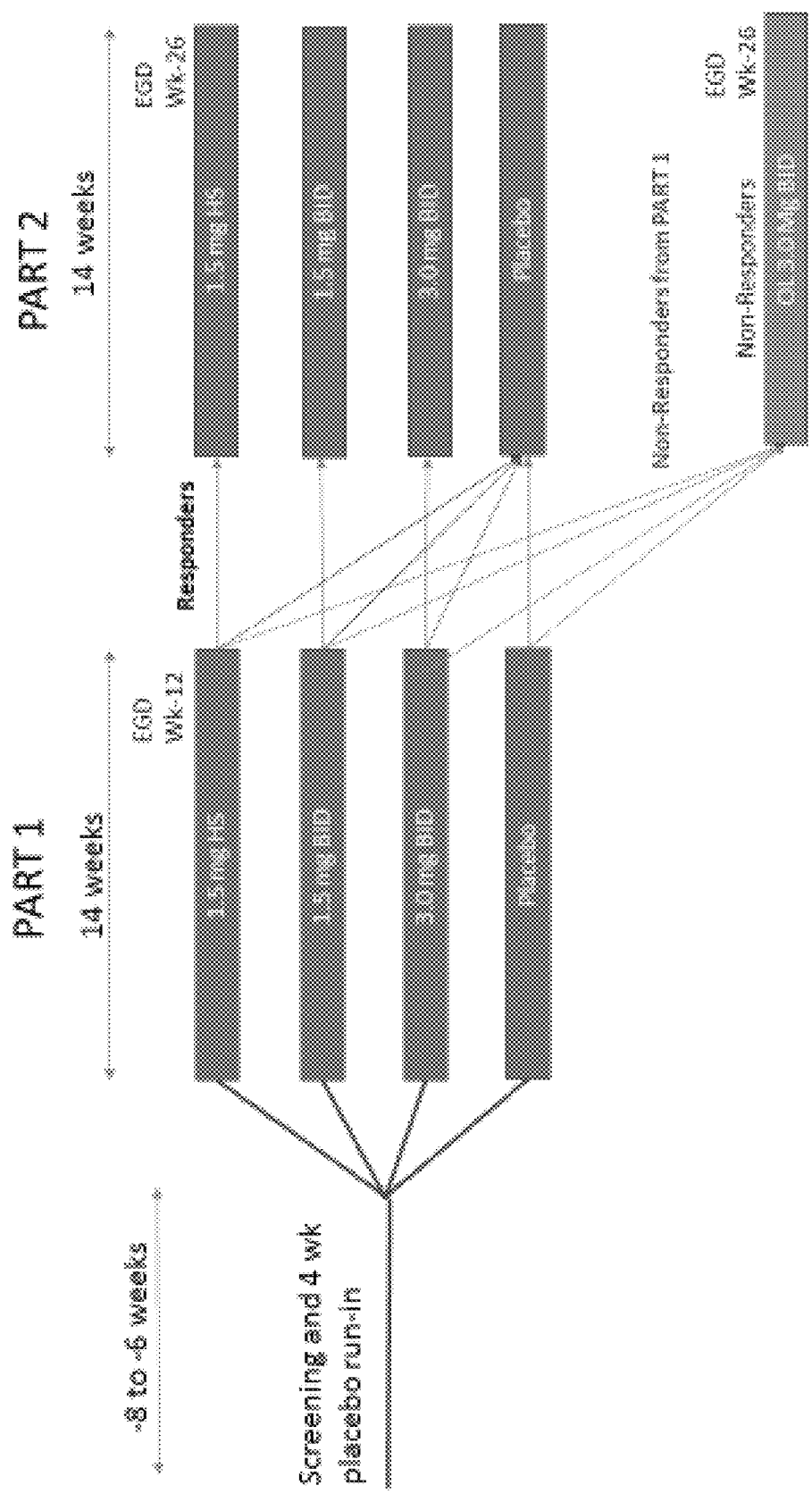
FIG. 1 shows an exemplary schematic overview of Parts 1 and 2 of a Phase 2b study design and depicts screening and run-in in Part 1 (induction stage), and randomized withdrawal in Part 2.

Gastrointestinal inflammatory disorders, such as Eosinophilic esophagitis (EoE), an allergic/immune condition where the subject suffers from inflammation and/or swelling of the esophagus, affect a patient's ability to swallow food and can consequently cause malnutrition and failure to thrive. Typically, eosinophils are not found in the esophagus, but in EoE these cells accumulate and produce swelling that reduces the interior diameter of the esophagus making swallowing and eating very difficult. Often patients experience episodes of food impaction where food becomes lodged in the patient's esophagus, which can require emergency treatment. Because of the difficulty swallowing, and fear of food impaction, many patients with EoE limit themselves to eating soft foods such as yogurt, soups, and smoothies. In severe cases of EoE patients receive parenteral nutrition (e.g. intravenous feeding), which can provide required sustenance but limits the patient's activities and can lead to increased infection at the site of the catheter.

EoE most commonly occurs in Caucasian males and can occur at any age, with the symptoms varying with age. Infants and toddlers suffering from EoE may refuse food, fail to thrive, or experience "reflux" and/or vomiting. Young children typically report heartburn/reflux, abdominal pain, vomiting, food avoidance, and/or poor growth. For adults, the hallmark symptom is dysphagia (trouble swallowing), and EoE is implicated in over 50% of food impactions. Adult patients less commonly exhibit heartburn or chest pain. Adults with EoE also exhibit altered eating behavior such as dietary modifications, slow eating, excessive chewing, and increased consumption of liquids with food.

While the causes of EoE are not known, many EoE patients have a family history of allergies, asthma, and/or symptoms of allergic disorders (e.g. asthma, allergic rhinitis, atopic dermatitis, and food allergy). Additionally, environmental allergens such as dust mites, animals, pollen, and molds may play a role in the development of EoE. Because of the link between EoE and allergies, especially food allergies, elimination of the allergen may help alleviate symptoms. However, these types of elimination can be difficult to achieve.

While there are no medications currently approved to treat EoE, some medications such as glucocorticosteroids, leukotriene antagonists, mast cell stabilizers, immunomodulators, biologics, and small molecules can help alleviate symptoms. Proton Pump Inhibitors (PPI) which control the amount of acid produced, have also been used to treat patients' symptoms, but may not reduce the amount of inflammation in the patient. Further, recent studies have linked long-term PPI use to dementia, making their use in EoE patients less desirable. Endoscopic therapy (dilation) may also be used to alleviate symptoms, but this too has no effect on the underlying inflammation causing the esophageal swelling.

While these therapies may help alleviate symptoms in some patients for a time, they often fall short of treatment of EoE. For example, current topical steroid medications are not optimal, with 5-50% of patients classified as non-responders. Similarly, diet elimination which requires significant endoscopic surveillance of the patient shows about 30% non-response rate.

New methods of not only alleviating the symptoms of esophageal inflammatory disorders such as EoE, but also addressing the inflammation causing the symptoms are required. The present disclosure provides methods of administering pharmaceutical compositions comprising a topically active corticosteroid to treat the symptoms and/or inflammation associated with a gastrointestinal inflammatory disorder. Pharmaceutical compositions comprising a topically active corticosteroid for use in such methods are also herein disclosed.

In various embodiments, the methods disclosed herein include at least two phases: an induction phase and a maintenance phase. During the induction phase, patients are administered a dosage of a pharmaceutical composition of the disclosure. Based upon patient response at the end of the induction phase (e.g. a histologic response and no worsening of symptoms or episodes of food impaction), the patient may enter the maintenance phase. The dose of the pharmaceutical composition may be the same or different during the maintenance and induction phases. Upon an amelioration or decrease of symptoms, the patient may also enter a withdrawal phase, and receive no doses of the pharmaceutical composition until symptoms recur.

The present disclosure provides methods of treating eosinophilic esophagitis (EoE) in a patient in need thereof, comprising administrating an oral corticosteroid in an induction phase and a maintenance phase, where the induction phase results in improvement in Peak eosinophilic counts in at least one esophageal biopsy and the treatment results in no worsening of patient mean weekly scores in a patient-reported outcome assessment which includes the assessment of dysphagia-free days.

Unless defined otherwise, all technical and scientific terms herein have the same meaning as commonly understood by one of ordinary skill in the art to which this disclosure belongs. Although any methods and materials, similar or equivalent to those described herein, can be used in the practice or testing of the present disclosure, the preferred methods and materials are described herein.

It should be understood that singular forms such as "a," "an," and "the" are used throughout this application for convenience, however, except where context or an explicit statement indicates otherwise, the singular forms are intended to include the plural. All numerical ranges should be understood to include each and every numerical point within the numerical range, and should be interpreted as reciting each and every numerical point individually. The endpoints of all ranges directed to the same component or property are inclusive, and intended to be independently combinable.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features. Although the open-ended term "comprising," as a synonym of terms such as including, containing, or having, is used herein to describe and claim the disclosure, the present technology, or embodiments thereof, may alternatively be described using more limiting terms such as "consisting of" or "consisting essentially of" the recited ingredients.

The term "drug", "active" or "active pharmaceutical ingredient" as used herein includes a pharmaceutically acceptable and topically acting corticosteroid, pharmaceutically acceptable salts, esters, solvates (including hydrates), polymorphs, stereoisomers, and/or prodrugs, and mixtures thereof. The terms "salts" refers to the product formed by the reaction of a suitable inorganic or organic acid with the "free base" form of the drug. Suitable acids include those having sufficient acidity to form a stable salt, for example acids with low toxicity such as the salt approved for use in humans or animals. Non-limiting examples of acids that may be used to form salts of an orally active drug, include inorganic acids, e.g., HCl, H3PO4 H2SO4. Non-limiting examples of organic acids include alkyl sulfonic acids and propionic acid.

The terms "pharmaceutical composition" and "pharmaceutical dosage form," are used interchangeably herein to refer to an oral dosage form (suspension, solution, powder, solid, etc.) which can be used to administer a corticosteroid. Non-limiting examples of dosage forms include an orally disintegrating composition, such as a tablet, a lyophilized matrix, a film, and a wafer, liquid composition, a gel, a slurry, a lozenge, a lollipop, sachet, an effervescent tablet, and the like.

The term "oral corticosteroid" and "corticosteroid" are used interchangeably to refer to a corticosteroid which is administered orally, e.g., in a pharmaceutical composition described herein.

The terms "orally disintegrating dosage form", "orally disintegrating tablet", "orally dispersing tablet", or "ODT" refer to a solid dosage form/tablet of the present disclosure, which disintegrates rapidly in the oral cavity of a patient after administration, without chewing, to form a suspension comprising the corticosteroid. The rate of oral disintegration can vary, but is significantly faster than the rate of oral disintegration of conventional solid dosage forms or chewable solid dosage forms (i.e., tablets or capsules) which are intended to be swallowed immediately after administration.

As used herein, the terms "treating," "treatment" and "treat" include (i) preventing a particular disease or disorder from occurring in a subject who may be predisposed to the disease or disorder but has not yet been diagnosed as having it; (ii) curing, treating, or inhibiting the disease, i.e., arresting its development; or (iii) ameliorating the disease by reducing or eliminating symptoms, conditions, and/or by causing regression of the disease. In some embodiments, "treating," "treatment" and "treat" may include administering a therapeutically effective regimen as defined herein.

The term "about", as used herein to refer to a numerical quantity, includes "exactly" plus or minus up to 10% of that referenced numeric indication. When the term "about" is used in reference to a range of values, the term "about" refers to both the minimum and maximum value of the range (e.g., "about 1-50 µm" means "about 1 µm to about 50 µm"). The term "intimately associated", as used herein to describe the spatial relationship between two or more components of a composition refers to components that are intimately mixed, such as, for example, in mixtures, coatings and matrices.

Unless indicated otherwise, all percentages and ratios are calculated by weight. Unless indicated otherwise, all percentages and ratios are calculated based on the total composition.

The term "having no significant systemic glucocorticoid or mineralocorticoid activity", as used herein refers to corticosteroid compositions which do not provide a generalized effect in the body through absorption into the circulation, but do provide local effects through topical contact with a diseased tissue. Examples include fluticasone, flunisolide, budesonide, circlesone, mometasone, tixocortol, and beclomethasone. Corticosteroids which have high systemic glucocorticoid potencies when administered orally include e.g., hydrocortisone, prednisone, prednisolone, methylprednisolone, dexamethasone, betamethasone, etc. or mineralocorticoid potencies (e.g., alsosterone). Corticosteroids which typically have systemic glucocorticoid or mineralocorticoid activity when administered orally can also be used in the diluted compositions of the present disclosure, wherein the systemic uptake of the corticosteroid is reduced or suppressed.

A "histologic responder" may be defined as a subject who achieves a histologic response of peak eosinophils/HPF number ≤6 (as primary determinant). HPF may be defined as a standard area of 0.237 square millimeters in a microscope with 40× lens and 22 mm ocular.

A "histologic non-responder" may be defined as a subject who does not have a histologic response (i.e., do not achieve a histologic response of peak eosinophils/HPF number ≤6).

Subjects who develop food impaction with or without esophageal dilatation anytime during a study may be considered "treatment failures".

Pharmaceutical Compositions and Administration

The pharmaceutical compositions used in (or for use in) the methods described herein can be any dosage form which can be used to topically administer a therapeutic agent (e.g., corticosteroid) to the esophagus. Suitable dosage forms include liquid compositions (e.g., solutions, suspensions, and slurries), gels, and solid compositions which form a liquid or gel after oral administration. For example, orally disintegrating compositions (e.g., ODT, film, lyophilize matrix, or wafer), lozenges, and lollipops can from a solution, suspension, or gel comprising the therapeutic agent in the oral cavity of the patient, and after the solution or suspension is swallowed, the corticosteroid dissolved or suspended therein contacts the esophagus as the liquid traverses the esophageal tract. In a preferred embodiment, the pharmaceutical composition is in the form of an ODT.

In some embodiments, the present disclosure provides an oral solid pharmaceutical composition comprising a corticosteroid (e.g., about 10 mg or less, including 7.5 mg, 6.0 mg, 4.5 mg, 3.0 mg, 1.5 mg, or 0.75 mg) and at least one pharmaceutically acceptable carrier, wherein the corticosteroid is combined with (e.g., adsorbed onto or suspended in) the pharmaceutically acceptable carrier. In some embodiments, the drug is present in an amount of less than about 5% (weight of drug/weight of composition), particularly less than 3% by weight. The pharmaceutical compositions disclosed herein can be formulated as an orally disintegrating tablet (hereafter referred to as an ODT) that disintegrates within 60 seconds (e.g., within 30 seconds) when tested using the USP <701> Disintegration Test, and/or disintegrates within 60 seconds when placed in the oral cavity of a human.

In some embodiments, the corticosteroid used in the compositions and methods described herein is a topically acting corticosteroid. In some embodiments, the corticosteroid has low or substantially no systemic effect. In some embodiments, corticosteroids that have low or no systemic effects are those which have no significant systemic glucocorticoid or mineralocorticoid activity after oral administration in humans. Corticosteroid with "no significant systemic glucocorticoid or mineralocorticoid activity after oral administration in humans" refer to corticosteroids, or pharmaceutical compositions comprising corticosteroids, which have less than about 20% systemic glucocorticoid or mineralocorticoid activity after oral administration, e.g., less than about 15%, less than about 10%, less than about 5%, less than about 5%, less than about 4%, less than about 3%, less than about 2%, or less than about 1%. Systemic glucocorticoid or mineralocorticoid activity can be determined using methods known in the art, such as by measuring morning cortisol levels.

In some embodiments, corticosteroids for use in the methods and compositions described herein have a systemic bioavailability of less than or equal to about 20% of the administered dose. Non-limiting examples of oral corticosteroids that have a bioavailability of less than or equal to about 20% include fluticasone, flunisolide, budesonide, ciclesone, mometasone, tixocortol, and beclomethasone, and pharmaceutically acceptable salts, solvates, esters, polymorphs or prodrugs thereof. In preferred embodiments, the oral corticosteroid used in the methods and compositions described herein is fluticasone propionate.

In some embodiments, the oral corticosteroids for use in the methods and compositions described herein are formulated to provide a pharmacokinetic profile which reduces the likelihood that a patient will experience side effects associated with systemic corticosteroid administration, including, but not limited to, osteoporosis, weight gain, immune system suppression (i.e., increased incidence of infections), high blood pressure, hyperglycaemia, muscle weakness, skin problems (e.g., poor healing of injuries, thinning of skin, easy bruising, stretchmarks, etc.) mood and behavioral changes, increased risk of developing cataracts, and increased risk of duodenal ulcers. That is, the pharmacokinetic profile of a corticosteroid can be modified to provide an average maximum plasma concentration (Cmax), an average time to reach the maximum plasma concentration (Tmax), and/or AUC that reduces systemic side effects. Pharmacokinetic profile can be measured by methods known in the art, for example the methods described in Example 5.

In some embodiments, oral corticosteroids for use in the methods and compositions described herein are formulated to provide an average maximum blood plasma concentration (Cmax) of less than or equal to about 10,000 pg/mL after oral administration of about 0.01 mg to about 20 mg of the oral corticosteroid, e.g., about 9,000 pg/mL, about 8,000 pg/mL, about 7,000 pg/mL, about 6,000 pg/mL, about 5,000 pg/mL, about 4,000 pg/mL, about 3,000 pg/mL, about 2,000 pg/mL, about 1,000 pg/mL, about 900 pg/mL, about 800 pg/mL, about 700 pg/mL, about 600 pg/mL, or about 500 pg/mL, inclusive of all values and subranges therebetween. In preferred embodiments, the oral corticosteroid is formulated to provide a Cmax of less than or equal to about 500 pg/mL after oral administration of about 0.01 mg to about 20 mg of the oral corticosteroid.

In some embodiments, oral corticosteroids for use in the methods and compositions described herein are formulated to provide an average $AUC_{0-24}$ of less than or equal to about 15,000 pg*h/mL after oral administration of about 0.01 mg to about 20 mg of the oral corticosteroid, e.g., about 14,000 pg*h/mL, about 13,000 pg*h/mL, about 12,000 pg*h/mL, about 11,000 pg*h/mL, about 10,000 pg*h/mL, about 9,000 pg*h/mL, about 8,000 pg*h/mL, about 7,000 pg*h/mL, about 6,000 pg*h/mL, about 5,000 pg*h/mL, about 4,000 pg*h/mL, about 3,000 pg*h/mL, about 2,000 pg*h/mL, about 1,000 pg*h/mL, inclusive of all values and subranges therebetween. In preferred embodiments, oral corticosteroids for use in the methods and compositions described herein are formulated to provide an average $AUC_{0-24}$ of less than or equal to about 3,000 pg*h/mL after oral administration of about 0.01 mg to about 20 mg of the oral corticosteroid.

In some embodiments, the pharmaceutical compositions described herein can be formulated to reduce systemic bioavailability, glucocorticoid activity, and/or mineralocorticoid activity (or combinations thereof) of the oral corticosteroid following oral administration. Reducing systemic bioavailability may allow the corticosteroid to exhibit local therapeutic effects, rather than being absorbed systemically. For example, a corticosteroid which otherwise has high systemic bioavailability (systemic bioavailability of e.g., >20%) can be formulated in an ion-exchange resin to reduce systemic bioavailability while increasing local therapeutic effects.

Salts, solvates, polymorphs, and prodrugs can be used to modify corticosteroids that otherwise have a systemic bioavailability of greater than about 20% to provide a "topically activating corticosteroid" having less than about 20% systemic activity and greater than about 80% local effect by decreasing the systemic bioavailability of the corticosteroid.

Non-limiting examples of corticosteroids which can be modified (e.g., by forming a salt or prodrug, or formulating the oral corticosteroid in an ion-exchange resin) to reduce systemic bioavailability and increase local effects, include hydrocortisone, prednisone, prednisolone. methylprednisolone, dexamethasone, betamethasone, alsosterone, and the like.

The compositions of the present disclosure may include a water soluble or water-swellable pharmaceutically acceptable excipient, such as bio-gelling or bioadhesive polymer that will enhance bioadherence of the corticosteroid to the inflamed esophageal mucosa.

Suitable topically acting corticosteroids which may be included in the pharmaceutical composition of the present disclosure include budesonide, fluticasone, flunisolide, ciclesonide, mometasone, beclomethasone, tixocortol and salts, esters, solvates, polymorphs, or prodrugs, and mixtures thereof.

In preferred embodiments, the composition of the present disclosure comprises fluticasone (e.g. fluticasone propionate). In preferred embodiments, the pharmaceutical composition is an ODT comprising fluticasone or a pharmaceutically acceptable salt thereof (e.g., fluticasone propionate). In other embodiments, the composition of the present disclosure comprises budesonide. In certain other embodiments, the composition of the present disclosure comprises ciclesonide.

In some embodiments, the corticosteroid may be in the form of crystals having a mean particle size of about 100 μm or less, about 75 μm or less, about 50 μm or less, more particularly about 25 μm or less, or about 15 μm or less. Particular embodiments of the disclosure provide the corticosteroid is micronized in order to achieve a mean particle size of less than about 10 less than about 8 μm or less, less than about 6 or particularly, less than about 4 μm.

Alternatively, such crystals may have an average size in the sub-micron range (e.g., average particle size of about <1 μm), i.e., may be as nanoparticles (e.g., average particle size in the range of about 1-100 nm). In some embodiments, the corticosteroid may be present in an amorphous form, for example in association with a stabilizing agent which limits drug recrystallization, e.g., polyvinylpyrrolidone (PVP), hydroxypropyl methylcellulose (HPMC), hydroxypropyl cellulose, hydroxyethylcellulose; Soluplus®, Kollidon® VA64, sodium lauryl sulphate, Tween surfactants, Eudragit® EPO polymer, and mixtures thereof.

The amount of corticosteroid present in the pharmaceutical compositions of the present disclosure is selected so as to maximize the therapeutic benefit from topical administration while minimizing side effects from systemic absorption. In the case of solid pharmaceutical compositions of the present disclosure, the amount of corticosteroid in the composition is less than about 5% w/w (weight of drug/weight of composition). In some embodiments the amount of corticosteroid in the pharmaceutical composition is less than about 4%. In another embodiment it is less than about 3%. In some embodiments it is less than about 2%, less than about 1.5%, less than about 1%, less than about 0.5% by weight or less. In some embodiments the amount of corticosteroid in the pharmaceutical composition is between about 0.50 mg and about 18 mg. In some embodiments the amount of corticosteroid in the pharmaceutical composition is between about 0.75 mg and about 12 mg. In some embodiments the amount of corticosteroid in the pharmaceutical composition is between about 1.5 mg and about 9 mg. In still other embodiments, the amount of corticosteroid is about 0.01 mg, about 0.05 mg, about 0.1 mg, about 0.15 mg, about 0.1 mg, about 0.2 mg, about 0.25 mg, about 0.3 mg, about 0.35 mg, about 0.4 mg, about 0.45 mg, about 0.5 mg, about 0.6 mg, about 0.7 mg, about 0.75 mg, about 0.8 mg, about 1 mg, about 1.5 mg, about 2 mg, about 3 mg, about 4 mg, about 4.5 mg, about 5 mg, about 6 mg, about 7 mg, about 8 mg, about 9 mg, about 10 mg, about 12 mg, about 18 mg, inclusive of all ranges and sub-ranges there between.

In preferred embodiments, the amount of corticosteroid in the pharmaceutical composition disclosed herein (e.g., ODT) is the range of from about 1.5 mg to about 7.5 mg, including about 3.0 mg, about 4.5 mg, and about 6.0 mg. In preferred embodiments, the pharmaceutical composition is an ODT and the corticosteroid is present in an amount of about 1.5 mg. In other preferred embodiments, the pharmaceutical composition is an ODT and the corticosteroid is present in an amount of about 3.0 mg. In still other preferred embodiments, the pharmaceutical composition is an ODT and the corticosteroid is present in an amount of about 4.5 mg. In yet other preferred embodiments, the pharmaceutical composition is an ODT and the corticosteroid is present in an amount of about 6.0 mg. In some other preferred embodiments, the pharmaceutical composition is an ODT and the corticosteroid is present in an amount of about 7.5 mg.

In some embodiments, the rapidly disintegrating composition of the disclosure may comprise pharmaceutically acceptable excipients which swell, dissolve or otherwise facilitate disintegration of the orally disintegrating dosage form (e.g. an ODT, film, lyophilized matrix, or wafer) providing a smooth viscous suspension containing micronized corticosteroid particles to coat inflammatory esophageal mucosa to treat eosinophilic esophagitis. Examples of such pharmaceutically acceptable excipients include disintegrants or rapidly dispersing microgranules as described herein. As used herein, the term "rapidly dispersing microgranules" refers to granules comprising particles of at least one sugar alcohol and/or saccharide in combination with particles of at least one disintegrant, which are formed in a granulator. In embodiments, the corticosteroid (e.g., micronized corticosteroid particles) may be granulated with the alcohol and/or saccharide particles. Alternatively, in some embodiments, the corticosteroid (e.g., micronized corticosteroid particles) can be combined with the pharmaceutically acceptable carrier, and then blended with the rapidly dispersing microgranules comprising particles of at least one sugar alcohol and/or saccharide in combination with particles of at least one disintegrant.

In certain embodiments of the present disclosure the total weight of the dosage form is kept in the range of from 300 to 900 mg to incorporate as much rapidly dispersing microgranules comprising at least one sugar alcohol and/or saccharide in combination with at least one disintegrant, as possible to maximize eosinophilic esophagitis surface coating with micronized corticosteroid. In some embodiments, the rapidly dispersing microgranules comprise at least one disintegrant in combination with a sugar alcohol and/or a saccharide. The amount of sugar alcohol and/or saccharide in the rapidly dispersing granules ranges from about 99%-90%, or about 95%-90% of the total weight of the disintegrant-containing granules, including all ranges and sub-ranges there between. In some embodiments, the average particle size of a sugar alcohol and/or saccharide is about 30 μm or less, for example about 1-30 μm, about 5-30 μm, about 5-25 μm, about 5-20 μm, about 5-15 μm, about 5-10 μm, about 10-30 μm, about 10-25 μm, about 10-20 μm, about 10-15 μm, about 15-30 μm, about 15-25 μm, about 15-20 μm, about 20-30 μm, about 20-25 μm, or about 25-30 μm.

In some embodiments, the dosage form has total weight of 300 mg and contain about 0.05 mg (0.16%), about 0.75 mg (0.25% w/w), about 1.5 mg (0.5% w/w), about 3 mg (1% w/w), about 4.5 mg (1.5%), about 6 mg (2% w/w), about 7.5 mg (2.5% w/w), about 9 mg (3% w/w), about 12 mg (4% w/w), about 16 mg (5%) of the corticosteroid.

In some embodiments, the dosage forms has total weight of 600 mg and contain about 0.75 mg (0.125% w/w), about 1.5 mg (0.25% w/w), about 3 mg (0.5% w/w), about 4.5 mg (0.75%), about 6 mg (0.1% w/w), about 7.5 mg (1.25% w/w), about 9 mg (1.5% w/w), about 12 mg (2% w/w), about 18 mg (3% w/w) of the corticosteroid. In some embodiments, the topically acting corticosteroid is fluticasone propionate and it is in the range of about 0.05 to about 15 mg in the pharmaceutical composition at a drug content of from about 0.16% to 5% by weight of the composition.

In some embodiments, the fluticasone propionate is in the range of about 0.75 to about 7.5 mg in the composition at a drug content of from about 0.25% to 2.5% by weight in the composition.

In some embodiments, the fluticasone propionate is in the range of 0.05 to about 18 mg in the composition at a drug content of from about 0.125% to 5% by weight in the composition.

The pharmaceutically acceptable carrier used in the mixture of the present disclosure is suitable for combining with the drug (e.g., adsorption of the drug, or dissolution of suspension of the drug in the pharmaceutically acceptable carrier), it should have the properties of an excellent carrier for dry blends providing blend flowability and workability and preventing the segregation. It may concur in providing corticosteroid content uniformity. Suitable pharmaceutically acceptable carriers include, but are not limited to, microcrystalline cellulose, silicified microcrystalline cellulose, pregelatinized starch, corn starch, colloidal silica, or amorphous magnesium aluminum silicate (commercially available as VEEGUM™ or NEUSILIN™). In preferred embodiments, the pharmaceutical carrier for the adsorption of the corticosteroid is silicified microcrystalline cellulose. It is preferably silicified microcrystalline cellulose which is composed of intimately associated microcrystalline cellulose and colloidal silicon dioxide particles, (PROSOLV® SMCC: MCC, 98% and CSD, 2%). The use of this ingredient in the composition of the disclosure improves the flow and blending properties of the corticosteroid mixture; improved blend uniformity/homogeneity and physical stability of the formulations during storage until their final processing into finished dosage forms such as tablets or capsules, i.e., to avoid or minimize potential de-mixing and segregation of corticosteroid microparticles is also achieved. The presence of this carrier in admixture with the active also ensures reproducibility of preparations of the composition of the disclosure (in particular with the applied technology of direct tableting). In some embodiments, a low-dose corticosteroid blend with the carrier showing high blend uniformity, low-segregation potential and excellent flowability is disclosed. This blend is particularly suitable for producing a rapidly disintegrating diluted corticosteroid composition. In some embodiments, of the disclosure the blend comprises fluticasone propionate adsorbed on silicified microcrystalline cellulose, and rapidly dispersing microgranules.

In embodiments, the pharmaceutically acceptable carrier for absorption of the corticosteroid is micronized. In some embodiments, the micronized pharmaceutically acceptable carrier has a diameter of less than about 20 microns, e.g., less than about 15 microns, less than about 10 microns, less than about 9 microns, less than about 8 microns, less than about 7 microns, less than about 6 microns, less than about 5 microns, less than about 4 microns, less than about 3 microns, less than about 2 microns, or less than about 1 micron. In particular embodiments, the micronized pharmaceutically acceptable carrier has a diameter of less about 5 microns.

In some embodiments, the pharmaceutically acceptable carrier is present in the pharmaceutical composition (e.g., ODT) an amount in the range of about 1% w/w to about 20% w/w, e.g., about 2%, about 3%, about 4%, about 5%, about 6%, about 7%, about 8%, about 9%, about 10%, about 11%, about 12%, about 13%, about 14%, about 15%, about 16%, about 17%, about 18%, or about 19%, inclusive of all values and subranges therein. In preferred embodiments, the pharmaceutically carrier is present in the pharmaceutical composition (e.g., ODT) an amount in the range of about 10% w/w.

In some embodiments, combining the corticosteroid with the pharmaceutically acceptable carrier provides a batch of orally disintegrating compositions having a corticosteroid content uniformity within the range of about 85% to about 115% of the corticosteroid dosage on the label (e.g., 1.5-7.5 mg, including 1.5 mg, 3.0 mg, 4.5 mg, 6.0 mg, and 7.0 mg). In some embodiments, the batch has a corticosteroid content uniformity within the range of about 90% to about 110% of the corticosteroid dosage on the label, or within the range of about 95% to about 105%, or about 96% to about 104%, or about 97% to about 103%, or about 98% to about 102%, or about 99% to about 101%.

In some embodiments, the rate of disintegration of the disintegrating compositions of the present disclosure (e.g., ODT, wafer, lyophilized matrix, film, etc) in the oral cavity of an individual can be on the order of about 60 seconds or less, about 50 seconds or less, about 40 seconds or less, about 30 seconds or less, about 20 seconds or less, or about 10 seconds or less.

In some embodiments, the rate of disintegration of the disintegrating compositions of the present disclosure (e.g., ODT, wafer, lyophilized matrix, film, etc) measured using the USP <701> Disintegration Test is about 60 seconds or less, about 45 seconds or less, about 30 seconds or less, about 20 seconds or less, or about 10 seconds or less.

In addition to the corticosteroid and the carrier, the blend of the compositions or the oral dosage forms of the present disclosure may contain further pharmaceutically acceptable ingredients which swell, dissolve or otherwise facilitate disintegration. Such ingredients can include, but are not limited to, a disintegrant, a sugar alcohol, a saccharide, or a mixture thereof, a water-soluble polymeric binder, a bio-gelling or a bioadhesive polymer, which can retain the corticosteroid particle adhered onto the inflamed esophageal tissues longer than in its absence.

In some embodiments, the present disclosure provides a solid pharmaceutical composition comprising a corticosteroid and a pharmaceutically acceptable bio-gelling polymer which enables longer retention of the corticosteroid at the inflamed esophageal tissues. The ingredient herein called "bio-gelling polymer" or "bio-adhesive agent" is an agent which promote adhesion of the corticosteroid to biological surfaces, especially the inflamed mucosa through gelling under GI tract physiological conditions, for example, upon contact with physiological fluids and/or at physiological temperature, and includes, but is not limited to, the bio-gelling polymers listed below.

The bio-gelling polymer may be a thermosensitive polymer. Suitable thermosensitive polymers include polyacrylamides, such as poly(N-isopropylacrylamide), as well as poly(ether-ester) copolymers, such as poly(ethylene glycol-(DL-lactic acid-co-glycolic acid)-ethylene glycol). Such thermosensitive polymers can partially or fully cover the inflamed esophageal tissues while keeping the corticosteroid particle(s) close or in intimate contact with the inflamed tissues, thereby increasing the topical contact of the corticosteroid with the inflamed tissues.

In some embodiments, the compositions of the present disclosure include a bioadhesive agent such as a lipid or a polymer. Examples of such lipids are glycerphospholipids such as phosphatidyl choline, and diacyl glycerols such as glycerol dioleate. Examples of bioadhesive polymers include chitosan, polyorthoesters, and copolymers, terpolymers and mixtures thereof.

In some embodiments, the solid pharmaceutical compositions of the present disclosure include an adhesive agent. Suitable adhesive agents include, but are not limited to, sucrose aluminum sulfate complex, chitosan and derivatives such as trimethylchitosan, polyvinylpyrrolidone, methylcellulose, hydroxypropyl cellulose, cross-linked polyacrylic acid copolymers, polyvinylpyrrolidone, vinylpyrrolidone-polyvinyl acetate copolymer (e.g., Kollidon® VA 64 from BASF), Soluplus®, poly(ethylene glycol 6000-vinylcaprolactam-vinyl acetate) (13:57:30) copolymer from BASF), polyvinyl alcohol, polyethylene oxide, polyamide, alginic acid and its salts, carrageenan, xanthan gum, ammoniomethacrylate copolymers, CARBOPOL polymers, maltodextrins, pectins, sucralose, and combinations thereof. In certain embodiments of the solid pharmaceutical compositions of the present disclosure, the corticosteroid and the adhesive agent are intimately associated. In some embodiments, the solid pharmaceutical composition comprises corticosteroid surrounded or encapsulated by the adhesive agent. In some embodiments, the solid pharmaceutical composition comprises corticosteroid disposed on the surface of the adhesive agent. In still other embodiments, the solid pharmaceutical composition comprises corticosteroid mixed or granulated with the adhesive agent.

In certain embodiments, the solid pharmaceutical composition includes any solid dosage form which disintegrates rapidly in the mouth to form a suspension of powdered corticosteroid, which is hypothesized to coat or adhere onto the inflamed esophageal mucosa when swallowed.

In some embodiments, the composition of the present disclosure is in the form of an ODT. The ODT comprises the drug in an amount less than about 5% (weight of drug/weight of composition) and a pharmaceutically acceptable carrier, wherein the composition has no significant systemic glucocorticoid or mineralocorticoid activity after oral administration in humans. The drug particles, (e.g., a corticosteroid as described herein optionally coated or optionally combined with an adhesive agent as described herein) are combined with rapidly dispersing microgranules. Rapidly dispersing microgranules comprise a sugar alcohol, a saccharide, or a mixture thereof and a disintegrant alone or a disintegrant in combination with a pharmaceutically acceptable additive with multi-functional activity (e.g., pregelatinized starch, hydroxypropylcellulose or the like).

A non-limiting list of suitable disintegrants for the rapidly dispersing microgranules includes crospovidone (cross-linked PVP), sodium starch glycolate, cross-linked sodium carboxymethylcellulose, calcium silicate, and low substituted hydroxypropyl cellulose.

The amount of disintegrant in the ODT is typically in the range of about 1% to about 10% by weight.

Sugar alcohols are hydrogenated forms of carbohydrates in which the carbonyl group (i.e., aldehyde or ketone) has been reduced to a primary or secondary hydroxyl group. Non-limiting examples of suitable sugar alcohols for the rapidly dispersing granules of the pharmaceutical compositions of the present disclosure include e.g., arabitol, isomalt, erythritol, glycerol, lactitol, mannitol, sorbitol, xylitol, maltitol, and mixtures thereof.

The term "saccharide" is synonymous with the term "sugars", and includes but is not limited to, monosaccharides such as glucose, fructose and ribose, and disaccharides such as sucrose, lactose, maltose, trehalose, and cellobiose. Non-limiting examples of suitable saccharides for use in the compositions of the present disclosure include e.g., lactose, sucrose, maltose, and mixtures thereof. In preferred embodiments, the composition does not include lactose. In some embodiments, the rapidly dispersing granules comprise at least one disintegrant in combination with a sugar alcohol. In some embodiments, the rapidly dispersing granules comprise at least one disintegrant in combination with a saccharide. In some embodiments, the disintegrant-containing granules comprise at least one disintegrant in combination with a sugar alcohol and a saccharide.

The amount of sugar alcohol and/or saccharide in the rapidly dispersing granules ranges from about 99%-90%, or about 95%-90% of the total weight of the disintegrant-containing granules, including all ranges and sub-ranges there between.

The amount of sugar alcohol and/or saccharide in the ODT ranges from about 30% to about 70% by weight.

In some embodiments, the average particle size of a sugar alcohol and/or saccharide is 30 µm or less, for example about 1-30 µm, about 5-30 µm, about 5-25 µm, about 5-20 µm, about 5-15 µm, about 5-10 µm, about 10-30 µm, about 10-25 µm, about 10-20 µm, about 10-15 µm 15-30 µm, about 15-25 µm, about 15-20 µm, about 20-30 µm, about 20-25 or about 25-30 µm.

The ratio of the disintegrant to the sugar alcohol, saccharide, or mixture thereof in the rapidly dispersing microgranules ranges from about 90/10 to about 99/01, for example about 90/10, about 91/9, about 92/8, about 93/7, about 94/6, about 95/5, about 96/4, about 97/3, about 98/2, about 99/1, inclusive of all values, ranges, and sub-ranges there between.

The rapidly dispersing microgranules present in the ODT help rapid disintegration of the tablet when placed in the oral cavity, creating a smooth suspension containing the corticosteroid drug particles. It is desirable to incorporate sufficient amount of rapidly dispersing microgranules to coat extensively the esophageal mucosa. This creates a content uniformity problem in these low-dose ODTs (for example, 300 mg ODT containing 12 mg or less of a corticosteroid). Typically, this problem is overcome by granulation, which involves spraying a dilute solution of the corticosteroid on to an excipient powder bed. The drug particles are embedded in the granules and consequently may not become exposed to the inflamed mucosa, resulting in being poorly efficacious. It has been surprisingly observed that it is possible not only to achieve desired content uniformity but also to enhance the probability of largely keeping the corticosteroid drug particles exposed to the inflamed mucosa by adsorbing micronized topically acting corticosteroid drug particles onto the pharmaceutically acceptable carrier (such as silicified microcrystalline cellulose) prior to blending with rapidly dispersing microgranules and other excipients and compressing into ODTs.

The dosage form as described herein may also include pharmaceutically acceptable excipients typically used in disintegrating tablet formulations such as fillers, diluents, glidants, disintegrants, binders and lubricants.

Examples of suitable fillers, diluents and/or binders include, but are not limited to, lactose (e.g. spray-dried lactose, such as FAST-FLO®), microcrystalline cellulose (various grades of Avicel®, CEOLUS®), hydroxypropylcellulose, L-hydroxypropylcellulose (low substituted), low molecular weight hydroxypropyl methylcellulose (HPMC) (e.g., Methocel™ E, F and K from Dow Chemical, MethoIoseE SH from Shin-Etsu, Ltd), hydroxyethylcellulose, sodium carboxymethylcellulose, carboxymethylhydroxyethylcellulose and other cellulose derivatives, sucrose, agarose, sorbitol, mannitol, dextrins, maltodextrins, starches or modified starches (including potato starch, maize starch and rice starch), calcium phosphate (e.g., basic calcium phosphate, calcium hydrogen phosphate, dicalcium phosphate hydrate), calcium sulfate, calcium carbonate, sodium alginate and collagen. The preferred filler for the composition of the disclosure is mannitol such as spray dried mannitol.

Examples of suitable disintegrants include, but are not limited to, crospovidone (cross-linked PVP), sodium starch glycolate, cross-linked sodium carboxymethylcellulose, calcium silicate, and low substituted hydroxypropyl cellulose. The preferred disintegrant for the composition of the disclosure is crospovidone.

Specific examples of glidants and lubricants include stearic acid, magnesium stearate, calcium stearate or other metallic stearates, talc, glyceryl behenate, colloidal silica, corn starch, and optionally magnesium stearate or sodium stearyl fumarate (lubricant intragranularly mixed or used externally to lubricate die and punch surfaces). The preferred glidant for the composition of the disclosure is colloidal silica and preferred lubricant is sodium stearyl fumarate.

In some embodiments, the methods and compositions described herein can be used to treat a patient suffering from EoE who also has a lactose allergy and/or a starch allergy. Pharmaceutical formulations comprising lactose can aggravate a lactose allergy in a patient suffering from such, and this can cause increased discomfort in patients also suffering from EoE. In certain embodiments, the pharmaceutical compositions described herein do not include lactose. Similarly, pharmaceutical formulations comprising starch can aggravate a starch allergy in a patient suffering from such, and this can cause increased discomfort in patients also suffering from EoE. In certain embodiments, the pharmaceutical compositions described herein do not include starch. In further preferred embodiments, the pharmaceutical compositions described herein do not include lactose and sucrose.

The solid pharmaceutical compositions of the present disclosure can include other dosage forms besides an ODT, a wafer, a film, or other solid dosage form which disintegrates rapidly in the mouth to form a suspension or dispersion of a corticosteroid, which can readily be swallowed to coat the mucosal surface of eosinophilic esophagitis.

For example, wafers can include dried or lyophilized compositions such as orally disintegrating or dissolving dosage forms prepared using Zydis® lyophilization technology (e.g., as described in U.S. Pat. No. 6,316,027), containing a corticosteroid as the active pharmaceutical ingredient. Film dosage forms can include edible films such as those described in U.S. Pat. No. 6,596,298 or 6,740,332, containing a corticosteroid as the active pharmaceutical ingredient. In some embodiments, the solid composition comprises a lyophilized matrix, wherein the lyophilized matrix comprises corticosteroid, the carrier and excipient. Suitable excipients include, but are not limited to, mannitol, xylitol, sorbitol, maltol, maltitol, lactose, sucrose, maltose, and combinations thereof.

Topical administration of a corticosteroid to the oral cavity of individuals has been associated with candidiasis infection and oral thrush. While the disclosure is designed so as to be less prone to promoting such infections, in some embodiments of the disclosure, the pharmaceutical composition may include an antifungal agent. Suitable antifungal agents include, but are not limited, to mitotic inhibitor antifungals, pyrimidine analog antifungals, polyene antifungals, benzimidazole antifungals, imidazole antifungals, polyene antifungals, triazole antifungals, thiazole antifungals, allylamine antifungals, echinocandin antifungals, and other "uncategorized" antifungals recognized in the art that do not fall within any of the above categories (e.g., tolnaflate and ciclopirox). For example, suitable antifungal agents which may be included in the solid pharmaceutical compositions of the present disclosure include, but are not limited to, abafungin, amorolfine, anidulafungin, bifonazole, butenafine, butoconazole, candicin, caspofungin, ciclopirox, clotrimazole, econazole, fenticonazole, filipin, fluconazole, flucytosine, griseofulvin, isavuconizole, isoconazole, itraconazole, ketoconazole, micafungin, miconazole, miconazole nitrate, naftifine, natamycin, nystatin, oxiconazole, posaconazole, pramiconazole, ravuconazole, rimocidin, setaconizole, sulconazole, terbafine, terconazole, tioconazole, tolnaftate, undecylenic acid, and voriconazole.

In some embodiments, pharmaceutical compositions of the present disclosure include an antiviral agent. Antiviral agents which may be included in the solid pharmaceutical compositions of the present disclosure include interferons, nucleoside and nucleotide reverse transcriptase inhibitors, non-nucleoside reverse transcriptase inhibitors, protease inhibitors, integrase inhibitors, fusion inhibitors, maturation inhibitors, guanosine analogs, puridine analogs, pyrimidine analogs, and other "uncategorized" antiviral drugs recognized in the art which do not fall within any of the above classes (e.g., foscarnet and miltefosine). For example, suitable antiviral agents which may be included in the solid pharmaceutical compositions of the present disclosure include, but are not limited to, abacavir, aciclovir (also known as acyclovir), adefovir, amantadine, amdoxovir, amprenavir, aplaviroc, apricitabine, arbidol, atazanavir, beviritmat, BMS-488043, boceprevir, brivudine, cidofovir, DCM205, docosanol, delavirdine, didanosine, durunavir, efavirenz, elvitegravir, elvucitabine, emtricitabine, enfuvirtide, epigallocatechin gallate, etravirine, famciclovir, fosamprenavir, ganciclocvir, globoidnan A, griffithsin, ibalizumab, idoxuridine, indinavir, lamivudine, lopinavir, loviride, maraviroc, nelfinavir, nevirapine, oseltamivir, pegylated interferon alpha-2a, pegylated interferon alpha-2b, penciclovir, peramivir, plerixafor, PRO 140, racivir, raltegrvir, ritonavir, ribavirin, rimantadine, rlipivirine, saquinavir, stampidine, stavudine, tenofovir, tipranavir, TNX-355, trifluridine, tromantadine, valaciclovir, valganciclovir, vicriviroc, vidarabione, viramidine, vivecon, zalcitabine, zanamivir, and zidovudine.

Tablet dosage forms, including ODT dosage forms, comprising the low dosage strength of a topically acting corticosteroid (e.g., corticosteroids having systemic bioavailability of less or equal to about 20% of the dose, or corticosteroids which are formulated to reduce systemic bioavailability, each of which are described above) and a pharmaceutically acceptable carrier, wherein the drug is in amount less than about 5% (weight drug/weight of composition), disintegrate in less than about 30 sec (USP method), and have a low friability in order to have sufficient durability to withstand handling, shipping, and/or packaging in push-through blister packaging. In some embodiments, friability of the ODT dosage form described herein is less than about 1%, e.g., less than about 0.9%, less than about 0.8%, less than about 0.7%, less than about 0.6%, less than about 0.5%, less than about 0.4%, less than about 0.3%, etc., inclusive of all ranges and sub-ranges there between).

In preferred embodiments, the ODT used in (or for use in) in the methods described herein comprises: a corticosteroid in an amount of from about 0.25% to about 2.5% w/w (or about 0.75 mg to about 7.5 mg); a pharmaceutically acceptable carrier in an amount of from about 5% to about 15% w/w (or about 20 mg to about 40 mg); and rapidly dispersing microgranules in an amount of from about 40% to about 60% w/w (or about 125 mg to about 175 mg), wherein the rapidly dispersing microgranules comprise a ratio of sugar alcohol/saccharide to disintegrant of about 90:10 to about 99:1. In embodiments, the ODT optionally further comprises: a disintegrant in an amount of about 5% to about 10% w/w (or about 5 mg to 20 mg to about 30 mg); a sugar alcohol or saccharide in an amount of about 20% to about 40% w/w (or about 80 mg to about 100 mg); and optional excipients.

Preferred embodiments of the pharmaceutical formulation disclosed herein are described in Table 1 or Table 2.

TABLE 1

Compositions of compressible blends of Fluticasone ODTs, 1.5 and 3 mg

| Ingredients | Fluticasone ODTs ODT | | | |
|---|---|---|---|---|
| | 1.5 mg | | 3 mg | |
| | (%/tablet) | (mg/tablet) | (%/tablet) | (mg/tablet) |
| Micronized Fluticasone Propionate USP | 0.50 | 1.50 | 1.0 | 3.00 |
| Colloidal Silicon Dioxide NF | 0.30 | 0.90 | 0.30 | 0.90 |
| Silicified Microcrystalline Cellulose NF | 10.00 | 30.00 | 10.00 | 30.00 |
| Crospovidone NF | 7.50 | 22.50 | 7.50 | 22.50 |
| Sucralose NF | 0.40 | 1.20 | 0.40 | 1.20 |
| Spray-dried Mannitol USP | 30.30 | 90.90 | 29.80 | 89.40 |
| Rapidly Dispersing Granules | 50.00 | 150.00 | 50.00 | 150.0 |
| Sodium Stearyl Fumarate NF | 1.00 | 3.00 | 1.00 | 3.00 |
| Total | 100.00 | 300.0 | 100.00 | 300.0 |

TABLE 2

Compositions of compressible blends of Fluticasone ODTs, 0.75 mg, 4.5 mg, 6 mg

| Ingredients | Fluticasone ODTs ODT | | | |
|---|---|---|---|---|
| | 0.75 mg | | 4.5 mg | 6.0 mg |
| | (%/tablet) | (mg/tablet) | (mg/tablet) | (mg/tablet) |
| Micronized Fluticasone Propionate USP | 0.25 | 0.75 | 4.50 | 6.00 |
| Colloidal Silicon Dioxide NF | 0.30 | 0.90 | 0.90 | 0.90 |
| Silicified Microcrystalline Cellulose NF | 10.00 | 30.0 | 30.00 | 30.00 |
| Crospovidone NF | 7.50 | 22.50 | 22.50 | 22.50 |
| Sucralose NF | 0.40 | 1.20 | 1.20 | 1.20 |
| Spray-dried Mannitol USP | 30.05 | 90.15 | 86.40 | 84.90 |
| Rapidly Dispersing Granules | 50.00 | 150.00 | 150.00 | 150.0 |
| Sodium Stearyl Fumarate NF | 1.50 | 4.50 | 4.50 | 4.50 |
| Total | 100.00 | 300.0 | 300.0 | 300.0 |

Gastrointestinal Inflammation and Methods of Treatment

Treatment with topically acting corticosteroid (e.g., fluticasone propionate) results in fewer side-effects than other treatments, for example a highly systemically acting corticosteroid. Upon administration of a pharmaceutical composition of the present disclosure to a patient, the composition disintegrates in the patient's oral cavity, and contacts the esophagus without being absorbed systemically, thus limiting systemic effects.

In some embodiments, the present disclosure provides methods of treating the symptoms associated with an inflammatory disorder of the intestinal tract. In some embodiments, the present disclosure provides methods of treating inflammation associated with an inflammatory gastrointestinal disorder. In some embodiments the present disclosure provides methods of treating both symptoms and inflammation associated an inflammatory gastrointestinal disorder. In some embodiments, the inflammatory gastrointestinal disorder affects the upper gastrointestinal tract. In some embodiments, the upper gastrointestinal tract is the esophagus.

In some embodiments, the oral corticosteroid contacts and/or is deposited in the upper part of the gastrointestinal tract. In some embodiments, the oral corticosteroid contacts and/or is deposited in the esophagus. In some embodiments, the oral corticosteroid contacts and/or is deposited in the distal portion of the esophagus. In some embodiments, the pharmaceutical composition contacts and/or is deposited in the proximal portion of the esophagus. In some embodiments, the oral corticosteroid contacts and/or is deposited in a substantially equivalent amount in the distal and proximal portion of the esophagus.

Inflammatory gastrointestinal disorders which may be treated according to the present disclosure include, but are not limited to, inflammation of the esophagus, inflammation of the glottis, inflammation of the epiglottis, inflammation of the tonsils, inflammation of the oropharynx, eosinophilic esophagitis (EoE), gastroesophageal reflux disease (GERD), non-erosive reflux disease (NERD), erosive esophagitis, Barrett's esophagus, eosinophilic gastroenteritis, hypereosinophilic syndrome, corrosive (caustic) chemical esophagitis, radiation-induced esophagitis, chemotherapy-induced esophagitis, transient drug-induced esophagitis (also known as medication esophagitis), persistent drug-induced esophagitis, Crohn's disease of the esophagus, and pseudomembranous esophagitis. In some embodiments, the present disclosure includes a method for treating a food allergy with an identified allergen, e.g., "atopic IBS", and "atopic bowel". In some embodiments, the present disclosure includes a method for treating a patient having one or more of the above gastrointestinal disorders, wherein the patient also has a lactose allergy and/or a starch allergy. In some embodiments, the inflammatory gastrointestinal disorder is eosinophilic esophagitis (EoE). In some embodiments, the present disclosure includes a method for treating a patient EoE, wherein the patient also a lactose allergy and/or a starch allergy.

In some embodiments, the pharmaceutical compositions disclosed herein are administered until symptoms and/or inflammation associated with gastrointestinal inflammation are treated. In some embodiments, the pharmaceutical compositions disclosed herein continue to be administered after symptoms and/or inflammation associated with gastrointestinal inflammation are treated. In some embodiments, the symptom is dysphagia, episodes of food impaction, feelings of having a lump in one's throat, and/or increased eosinophil count in the esophagus.

The treatment of gastrointestinal inflammation may be measured by any means known in the art. For example, tests used to evaluate patients with esophageal inflammation such as EoE include, but are not limited to, biopsies, evaluation of symptoms (e.g. through patient reported outcome (PRO) or physician questionnaire), quality of life measurements, determination of Dysphagia-Free-Days in a patient, endoscopy (e.g. EREFS), esophageal compliance and/or improvement in esophageal remodeling (e.g. using a suitable diagnostic test such as EndoFLIP (available from Crospon Inc.), evaluation of biomarkers, decrease in peak eosinophil count, decrease in food impaction, EEsAI, Strong Dysphagia Index (DSQ), MDQ-30, EoE-QOL-A, VDQ (Visual Dysphagia Questionnaire), Avoidance Modification and Slow Eating (AMS) scores, and/or histology.

In some embodiments, patient response to treatment is determined by measuring changes in one or more questionnaire scores with a biological response such as histology score (e.g. eosinophil count). Reliance on patient reported symptoms may yield false positive results as patients may modify their behavior to reduce incidents of dysphagia (e.g. avoiding problematic foods or other behavior modifications such as increased chewing or liquid consumption) which can alter questionnaire score regardless of whether biological symptoms have improved.

In some embodiments, patient response is evaluated by assessing histology scores in a patient. In some embodiments the histology score is assessed by one or more different histologic features, including but not limited to, eosinophil inflammation, basal zone hyperplasia, dilated intercellular spaces, lamina propria fibrosis, eosinophil abscess, surface layering, surface epithelial alteration, and dyskeratotic epithelial cells.

In some embodiments, administration of the oral corticosteroid according to the methods disclosed herein reduces a histology score in a treated patient compared to an untreated patient or the same patient before treatment. In some embodiments, the histology score is measured in a treated patient between week 1 and year 10. In some embodiments, administration of the pharmaceutical compositions disclosed herein reduces a histology score at about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with the histology score in an untreated patient or the same patient before treatment. In some embodiments, administration of the pharmaceutical compositions disclosed herein reduces a histology score for about 1 week, about 1 month, about 2 months, about 3 months, about 4 months, about 5 months, about 6 months, about 1 year, about 2 years, about 5 years, or about 10 years, or more compared with the histology score in an untreated patient or the same patient before treatment.

In some embodiments, a histology score is reduced by about 1%, about 5%, about 10%, about 20%, about 30%, about 40%, about 50%, about 60%, about 70%, about 80%, about 90%, or about 100% compared with the histology score in an untreated patient or the same patient before treatment. In some embodiments, administration of the pharmaceutical compositions disclosed herein reduces the histology score by about 1%, about 5%, about 10%, about 20%, about 30%, about 40%, about 50%, about 60%, about 70%, about 80%, about 90%, or about 100% at about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with the histology score in an untreated patient or the same patient before treatment. In some embodiments, administration of the pharmaceutical compositions disclosed herein reduces the histology score by about 1%, about 5%, about 10%, about 20%, about 30%, about 40%, about 50%, about 60%, about 70%, about 80%, about 90%, or about 100% for about 1 week, about 1 month, about 2 months, about 3 months, about 4 months, about 5 months, about 6 months, about 1 year, about 2 years, about 5 years, or about 10 years or more compared with the histology score in an untreated patient or the same patient before treatment.

In some embodiments, administration of the oral corticosteroid according to the methods disclosed herein reduces peak eosinophil (per high power field (HPF), e.g., as described in Example 2) in at least one biopsy in a treated patient compared to peak eosinophil per HPF in an untreated patient or the same patient before treatment. In some embodiments, administration of the pharmaceutical compositions disclosed herein reduces peak eosinophil in at least one biopsy to less than 15/HPF. In some embodiments, administration of the pharmaceutical compositions disclosed herein reduces peak eosinophil in at least one biopsy in a treated patient to less than about 14/HPF, less than about 13/HPF, less than about 12/HPF, less than about 11/HPF, less than about 10/HPF, less than about 9/HPF, less than about 8/HPF, less than about 7/HPF, less than about 6/HPF, less than about 5/HPF, less than about 4/HPF, less than about 3/HPF, less than about 2/HPF, less than about 1/HPF, or less (e.g. 0) in the patient. In some embodiments, administration of the pharmaceutical compositions disclosed herein reduce peak eosinophil in at least one biopsy to less than 1 HPF in the patient. In some embodiments, the reduction of peak eosinophil in at least one biopsy in a treated patient is measured between about week 1 and about year 10. In some embodiments, the reduction of peak eosinophil is measured at about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3. In some embodiments, administration of the pharmaceutical compositions disclosed herein reduces peak eosinophil in at least one biopsy to less than about 14/HPF, less than about 13/HPF, less than about 12/HPF, less than about 11/HPF, less than about 10/HPF, less than about 9/HPF, less than about 8/HPF, less than about 7/HPF, less than about 6/HPF, less than about 5/HPF, less than about 4/HPF, less than about 3/HPF, less than about 2/HPF, less than about 1/HPF or less (e.g. 0) in the patient at about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3. In some embodiments, administration of the pharmaceutical compositions disclosed herein reduces peak eosinophil in at least one biopsy to less than about 14/HPF, less than about 13/HPF, less than about 12/HPF, less than about 11/HPF, less than about 10/HPF, less than about 9/HPF, less than about 8/HPF, less than about 7/HPF, less than about 6/HPF, less than about 5/HPF, less than about 4/HPF, less than about 3/HPF, less than about 2/HPF, less than about 1/HPF or less (e.g. 0) in the patient for about 1 week, about 1 month, about 2 months, about 3 months, about 4 months, about 5 months, about 6 months, about 1 year, about 2 years, about 5 years, or about 10 years, or more In some embodiments, administration of the oral corticosteroid according to the methods disclosed herein reduces peak eosinophil (per high power field (HPF), e.g., as described in Example 2) in at least one biopsy in a treated patient compared to peak eosinophil per HPF in an untreated patient or the same patient before treatment by at least about 10%, e.g., about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99%, inclusive of all values and subranges therebetween. In particular embodiments, the peak eosinophil count is reduced by an amount in the range of about 50% to about 99%, e.g., about 55%, about 60%, about 65%, about 70%, about 75%, about 80%, about 85%, about 90%, about 91%, about 92%, about 93%, about 94%, about 95%, about 96%, about 97%, about 98%, inclusive of all values and subranges therebetween.

In some embodiments, administration of the pharmaceutical compositions disclosed herein reduces peak eosinophil in at least one biopsy from a treated patient at week 12, week 26, or week 52. In some embodiments, administration of the pharmaceutical compositions disclosed herein reduces peak eosinophil in at least one biopsy from a treated patient to less than about 6/HPF at week 12, week 26, or week 52. In some embodiments, administration of the pharmaceutical compositions disclosed herein reduces peak eosinophil in all tested biopsies from a treated patient at week 12, week 26, or week 52. In some embodiments, administration of the pharmaceutical compositions disclosed herein reduces peak eosinophil in all tested biopsies from a treated patient to less than about 6/HPF at week 12, week 26, or week 52.

In some embodiments, administration of the pharmaceutical compositions disclosed herein reduce mean score in a patient questionnaire completed by the patient or a physician. In some embodiments, the questionnaire is Eosinophilic Esophagitis Activity Index (EEsAI), which can use either a 7-day recall period or a daily recall period to monitor the severity and frequency of dysphagia and any dietary modifications. In some embodiments, the questionnaire is Dysphagia Symptom Questionnaire (DSQ), which is a daily symptom diary used to monitor dysphagia frequency. In some embodiments, the questionnaire is a customized patient-reported outcome assessment which includes the assessment of dysphagia-free days. In some embodiments, the total score of a questionnaire such as the EEsAI or PROSE are used in combination with other patient assessments to measure patient response to treatment. In some embodiments, the correlation of questionnaire score with improvement in histological measurements (e.g. eosinophil count) indicates patient response to treatment.

In some embodiments, the mean questionnaire score is measured in a treated patient between week 1 and year 10. In some embodiments, administration of the pharmaceutical compositions disclosed herein reduces the mean questionnaire score at about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with the mean questionnaire score in an untreated patient or the same patient before treatment. In some embodiments, administration of the pharmaceutical compositions disclosed herein reduces the mean questionnaire score for about 1 week, about 1 month, about 2 months, about 3 months, about 4 months, about 5 months, about 6 months, about 1 year, about 2 years, about 5 years, or about 10 years or more compared with the mean questionnaire score in an untreated patient or the same patient before treatment. In some embodiments, the mean questionnaire score is reduced by about 1%, about 5%, about 10%, about 20%, about 30%, about 40%, about 50%, about 60%, about 70%, about 80%, about 90%, or about 100% compared with the mean questionnaire score in an untreated patient or the same patient before treatment. In some embodiments, administration of the pharmaceutical compositions disclosed herein reduces the mean questionnaire score by about 1%, about 5%, about 10%, about 20%, about 30%, about 40%, about 50%, about 60%, about 70%, about 80%, about 90%, or about 100% at about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with the mean questionnaire score in an untreated patient or the same patient before treatment. In some embodiments, administration of the pharmaceutical compositions disclosed herein reduces the mean questionnaire score by about 1%, about 5%, about 10%, about 20%, about 30%, about 40%, about 50%, about 60%, about 70%, about 80%, about 90%, or about 100% for about 1 week, about 1 month, about 2 months, about 3 months, about 4 months, about 5 months, about 6 months, about 1 year, about 2 years, about 5 years, or about 10 years or more compared with the mean questionnaire score in an untreated patient or the same patient before treatment.

In some embodiments, the patient questionnaire is EEsAI. In some embodiments, administration of the pharmaceutical compositions disclosed herein reduces mean EEsAI score to less than 20. In some embodiments, administration of the pharmaceutical compositions disclosed herein reduces mean EEsAI score of a treated patient to less than about 19, less than about 18, less than about 17, less than about 16, less than about 15 less than about 14, less than about 13, less than about 12, less than about 11, less than about 10, less than about 9, less than about 8, less than about 7, less than about 6, less than about 5, less than about 4, less than about 3, less than about 2, less than about 1, or about 0. In some embodiments, the reduction of mean EEsAI score in a treated patient is measured between about week 1 and about year 10. In some embodiments, the reduction of mean EEsAI score is measured at about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3. In some embodiments, administration of the pharmaceutical compositions disclosed herein reduces mean EEsAI score to less than about 20, less than about 19, less than about 18, less than about 17, less than about 16, less than about 15, less than about 14, less than about 13, less than about 12, less than about 11, less than about 10, less than about 9, less than about 8, less than about 7, less than about 6, less than about 5, less than about 4, less than about 3, less than about 2, less than about 1, or less (e.g. 0) at about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3. In some embodiments, administration of the pharmaceutical compositions disclosed herein reduces mean EEsAI score to less than about 20, less than about 19, less than about 18, less than about 17, less than about 16, less than about 15, less than about 14, less than about 13, less than about 12, less than about 11, less than about 10, less than about 9, less than about 8, less than about 7, less than about 6, less than about 5, less than about 4, less than about 3, less than about 2, less than about 1, or less (e.g. 0) for about 1 week, about 1 month, about 2 months, about 3 months, about 4 months, about 5 months, about 6 months, about 1 year, about 2 years, about 5 years, or about 10 years, or more.

In some embodiments, administration of the pharmaceutical compositions disclosed herein reduces mean EEsAI score in a treated patient at week 12, week 26, or week 52. In some embodiments, administration of the pharmaceutical compositions disclosed herein reduces mean EEsAI score in a treated patient to less than about 20 at week 12, week 26, or week 52.

In some embodiments, administration of the pharmaceutical compositions disclosed herein reduce mean EoE Endoscopic Reference Score (EREFS) in a treated patient, which measures edema (e.g. decreased vascularity or pallot), rings present, exudates (e.g. white plaques), furrows, and/or stricture in the esophagus according to Table 3. In some embodiments, the EREFS score in a patient correlates with histologic response (e.g. eosinophil count) and EREFS score can be used in conjunction with histologic response to measure patient response to treatment.

TABLE 3

| EREFS Score Assessment | | | | |
|---|---|---|---|---|
| Characteristic | Grade 0 | Grade 1 | Grade 2 | Grade 3 |
| Edema (loss vascular markings) | Distinct vascularity | Decreased | Absent | |
| Rings (trachealization) | None | Mild (ridges) | Moderate (distinct rings) | Severe (cannot pass endoscope) |
| Exudate (white plaques) | None | Mild ($\leq$10% surface area) | Severe ($\geq$10% surface area) | |
| Furrows (vertical lines) | None | Mild | Severe (depth) | |
| Stricture | Absent | Present | | |

In some embodiments, the compositions and methods disclosed herein reduce the EREFS score for edema to 1 or 0. In some embodiments, the compositions and methods disclosed herein reduce the EREFS score for rings to 2, 1, or 0. In some embodiments, the compositions and methods disclosed herein reduce the EREFS score for exudates to 1, or 0. In some embodiments, the compositions and methods disclosed herein reduce the EREFS score for exudates to 1, or 0. In some embodiments, the compositions and methods disclosed herein reduce the EREFS score for furrows to 1, or 0. In some embodiments, the compositions and methods disclosed herein substantially remove strictures.

In some embodiments, administration of the pharmaceutical compositions disclosed herein reduces the mean EREFS score to less than about 10, about 9, about 8, about 7, about 6, about 5, about 4, about 3, about 2, about 1, or about zero in a treated patient. In some embodiments, the mean EREFS score is measured in a treated patient between week 1 and year 10. In some embodiments, administration of the pharmaceutical compositions disclosed herein reduces the EREFS score at about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3. In some embodiments, administration of the pharmaceutical compositions disclosed herein reduces the mean EREFS score for about 1 week, about 1 month, about 2 months, about 3 months, about 4 months, about 5 months, about 6 months, about 1 year, about 2 years, about 5 years, or about 10 years or more in a treated patient. In some embodiments, administration of the pharmaceutical compositions disclosed herein reduces the mean EREFS score to less than about 10, about 9, about 8, about 7, about 6, about 5, about 4, about 3, about 2, about 1, or about zero at about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3. In some embodiments, administration of the pharmaceutical compositions disclosed herein reduces the mean EREFS score to less than about 10, about 9, about 8, about 7, about 6, about 5, about 4, about 3, about 2, about 1, or about zero for about 1 week, about 1 month, about 2 months, about 3 months, about 4 months, about 5 months, about 6 months, about 1 year, about 2 years, about 5 years, or about 10 years or more in a treated patient.

In some embodiments, administration of the pharmaceutical compositions disclosed herein reduces mean EREFS score in a treated patient at about week 12, about week 26, or about week 52.

In some embodiments, administration of the pharmaceutical compositions disclosed herein reduces episodes of dysphagia in a treated patient. In some embodiments, reduction of episodes of dysphagia in a treated patient is measured by determining Dysphagia-Free-Days in the patient. In some embodiments, improvement in Dysphagia-Free-Days in a patient is measured in conjunction with other patient measurements such as improved histologic scores (e.g. eosinophil counts) to measure patient response to treatment. In some embodiments, administration of the pharmaceutical compositions disclosed herein reduce dysphagia in a treated patient compared with episodes of dysphagia in an untreated subject or in the same patient before treatment. In some embodiments, administration of the pharmaceutical compositions disclosed herein reduce episodes of dysphagia to fewer than about 6 per week. In some embodiments, administration of the pharmaceutical compositions disclosed herein reduces episodes of dysphagia to fewer than 6 per week over a time period of two weeks. In some embodiments, administration of the pharmaceutical compositions disclosed herein reduces episodes of dysphagia to fewer than about 6 per week, about 5 per week, about 4 per week, about 3 per week, about 2 per week, about one per week, or none per week. In some embodiments, administration of the pharmaceutical compositions disclosed herein reduces episodes of dysphagia to fewer than about 6 per week, about 5 per week, about 4 per week, about 3 per week, about 2 per week, about one per week, or none per week over a time period of two weeks.

In some embodiments, episodes of dysphagia are reduced by up to about 100%. In some embodiments, episodes of dysphagia are reduced by up to about 1%, about 5%, about 10%, about 20%, about 30%, about 40%, about 50%, about 60%, about 70%, about 80%, about 90%, or about 100% compared with episodes of dysphagia in an untreated patient or the same patient before treatment. In some embodiments, dysphagia is eliminated. In some embodiments, dysphagia is assessed in a treated patient between week 1 and year 10. In some embodiments, administration of the pharmaceutical compositions disclosed herein reduces episodes of dysphagia at about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3. In some embodiments, administration of the pharmaceutical compositions disclosed herein reduces dysphagia for about 1 week, about 1 month, about 2 months, about 3 months, about 4 months, about 5 months, about 6 months, about 1 year, about 2 years, about 5 years, or about 10 years or more compared with the number of episodes of dysphagia in an untreated patient or the patient before treatment. In some embodiments, episodes of dysphagia are reduced by up to about 1%, about 5%, about 10%, about 20%, about 30%, about 40%, about 50%, about 60%, about 70%, about 80%, about 90%, or about 100% compared with episodes of dysphagia in an untreated patient or the same patient before treatment at about week 1, week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3. In some embodiments, episodes of dysphagia are reduced by up to about 1%, about 5%, about 10%, about 20%, about 30%, about 40%, about 50%, about 60%, about 70%, about 80%, about 90%, or about 100% compared with episodes of dysphagia in an untreated patient or the same patient before treatment for about 1 week, about 1 month, about 2 months, about 3 months, about 4 months, about 5 months, about 6 months, about 1 year, about 2 years, about 5 years, or about 10 years or more compared with the number of episodes of dysphagia in an untreated patient or the patient before treatment.

In some embodiments, administration of the pharmaceutical compositions disclosed herein reduces episodes of dysphagia in a treated patient at week 12, week 26, or week 52 compared with episodes of dysphagia in an untreated patient or the same patient before treatment.

In some embodiments, administration of the pharmaceutical compositions disclosed herein reduces food impaction in a treated patient compared with episodes of food impaction in an untreated patient or in the same patient before treatment. In some embodiments, administration of the pharmaceutical compositions disclosed herein reduces episodes of food impaction to fewer than 4 per week. In some embodiments, administration of the pharmaceutical compositions disclosed herein reduces episodes of food impaction to fewer than 4 per week over a time period of two weeks. In some embodiments, administration of the pharmaceutical compositions disclosed herein reduces episodes of food impaction to fewer than about 4 per week, about 3 per week, about 2 per week, about one per week, or none per week. In some embodiments, administration of the pharmaceutical compositions disclosed herein reduces episodes of food impaction to fewer than about 4 per week, about 3 per week, about 2 per week, about one per week, or none per week over a time period of two weeks.

In some embodiments, episodes of food impaction are reduced by up to about 100%. In some embodiments, episodes of food impaction are reduced by up to about 1%, about 5%, about 10%, about 20%, about 30%, about 40%, about 50%, about 60%, about 70%, about 80%, about 90%, or about 100% compared with episodes of food impaction in an untreated patient or the same patient before treatment. In some embodiments, food impaction is eliminated. In some embodiments, episodes of food impaction are assessed in a treated patient between week 1 and year 10. In some embodiments, administration of the pharmaceutical compositions disclosed herein reduces episodes of food impaction at about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3. In some embodiments, administration of the pharmaceutical compositions disclosed herein reduces episodes of food impaction for about 1 week, about 1 month, about 2 months, about 3 months, about 4 months, about 5 months, about 6 months, about 1 year, about 2 years, about 5 years, or about 10 years or more compared with the number of episodes of food impaction in an untreated patient or the same patient before treatment. In some embodiments, episodes of food impaction are reduced by up to about 1%, about 5%, about 10%, about 20%, about 30%, about 40%, about 50%, about 60%, about 70%, about 80%, about 90%, or about 100% compared with episodes of food impaction in an untreated patient or the same patient before treatment at about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3. In some embodiments, episodes of food impaction are reduced by up to about 1%, about 5%, about 10%, about 20%, about 30%, about 40%, about 50%, about 60%, about 70%, about 80%, about 90%, or about 100% compared with episodes of food impaction in an untreated patient or the same patient before treatment for about 1 week, about 1 month, about 2 months, about 3 months, about 4 months, about 5 months, about 6 months, about 1 year, about 2 years, about 5 years, or about 10 years or more compared with the number of episodes of food impaction in an untreated patient or the same patient before treatment.

In some embodiments, administration of the pharmaceutical compositions disclosed herein reduces episodes of food impaction in a treated patient at week 12, week 26, or week 52 compared with food impaction in an untreated patient or the same patient before treatment.

In some embodiments, administration of the pharmaceutical compositions disclosed herein reduces Global EoE score in a treated patient compared with Global EoE score in an untreated patient or in the same patient before treatment.

In some embodiments, the reduction of Global EoE score in a treated patient is measured between about week 1 and about year 10. In some embodiments, administration of the pharmaceutical compositions disclosed herein reduces Global EoE score at about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with an untreated patient or the same patient before treatment. In some embodiments, administration of the pharmaceutical compositions disclosed herein reduces Global EoE score for about 1 week, about 1 month, about 2 months, about 3 months, about 4 months, about 5 months, about 6 months, about 1 year, about 2 years, about 5 years, or about 10 years compared with the Global EoE score in an untreated patient or the patient before treatment. In some embodiments, Global EoE score is reduced by up to about 1%, about 5%, about 10%, about 20%, about 30%, about 40%, about 50%, about 60%, about 70%, about 80%, about 90%, or about 100% compared with Global EoE score in an untreated patient or the same patient before treatment commenced.

In some embodiments, administration of the pharmaceutical compositions disclosed herein reduces Global EoE score by up to about 1%, about 5%, about 10%, about 20%, about 30%, about 40%, about 50%, about 60%, about 70%, about 80%, about 90%, or about 100% compared with Global EoE score in an untreated patient or the same patient before treatment at about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3. In some embodiments, administration of the pharmaceutical compositions disclosed herein reduces Global EoE score by up to about 1%, about 5%, about 10%, about 20%, about 30%, about 40%, about 50%, about 60%, about 70%, about 80%, about 90%, or about 100% compared with Global EoE score in an untreated patient or the same patient before treatment for about 1 week, about 1 month, about 2 months, about 3 months, about 4 months, about 5 months, about 6 months, about 1 year, about 2 years, about 5 years, or about 10 years, or more.

Global EoE is scored on a scale of 0 to 10, with 0 representing no EoE symptoms, and 10 representing most severe EoE symptoms. In some embodiments, administration of the pharmaceutical compositions disclosed herein reduces Global EoE score in a treated subject to less than about 5. In some embodiments, administration of the pharmaceutical compositions disclosed herein reduces Global EoE score to less than about 10, less than about 9, less than about 8, less than about 7, less than about 6, less than about 5, less than about 4, less than about 3, less than about 2, less than about 1, or about 0. In some embodiments, administration of the pharmaceutical compositions disclosed herein reduces Global EoE score in a treated subject to less than about 10, less than about 9, less than about 8, less than about 7, less than about 6, less than about 5, less than about 4, less than about 3, less than about 2, less than about 1, or about 0 at about week 1, week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3. In some embodiments, administration of the pharmaceutical compositions disclosed herein reduces Global EoE score in a treated subject to less than about 10, less than about 9, less than about 8, less than about 7, less than about 6, less than about 5, less than about 4, less than about 3, less than about 2, less than about 1, or about 0 for about 1 week, about 1 month, about 2 months, about 3 months, about 4 months, about 5 months, about 6 months, about 1 year, about 2 years, about 5 years, or about 10 years, or more.

In some embodiments, administration of the pharmaceutical compositions disclosed herein reduces Global EoE score in a treated patient at about week 12, about week 26, or about week 52 compared with Global EoE score in an untreated patient or the same patient before treatment.

In some embodiments, administration of the pharmaceutical compositions disclosed herein improves characteristics as measured by endoscopy (e.g. EndoFlip) in a treated patient compared with an untreated patient or the same patient before treatment commenced. These characteristics include, but are not limited to esophagus diameter, esophageal compliance, focal narrowing of the esophagus, esophageal body distensibility, esophageal body cross-sectional areas (CSA), and intra-luminal diameter.

In some embodiments, the characteristics as measured by endoscopy are assessed in a treated patient between week 1 and year 10. In some embodiments, administration of the pharmaceutical compositions disclosed herein improves characteristics as measured by endoscopy at about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3 compared with an untreated patient or the same patient before treatment. In some embodiments, administration of the pharmaceutical compositions disclosed herein improves characteristics as measured by endoscopy for about 1 week, about 1 month, about 2 months, about 3 months, about 4 months, about 5 months, about 6 months, about 1 year, about 2 years, about 5 years, or about 10 years or more compared with an untreated patient or the same patient before treatment. In some embodiments, characteristics as measured by endoscopy are improved by up to about 100%. In some embodiments, characteristics as measured by endoscopy are improved by up to about 1%, about 5%, about 10%, about 20%, about 30%, about 40%, about 50%, about 60%, about 70%, about 80%, about 90%, or about 100% compared with an untreated patient or the same patient before treatment. In some embodiments, administration of the pharmaceutical compositions disclosed herein improves characteristics as measured by endoscopy by up by about 1%, about 5%, about 10%, about 20%, about 30%, about 40%, about 50%, about 60%, about 70%, about 80%, about 90%, or about 100% compared with an untreated patient or the same patient before treatment at about week 1, about week 2, about week 3, about week 4, about week 5, about week 6, about week 7, about week 8, about week 9, about week 10, about week 20, about week 30, about week 40, about week 50, about week 60, about week 70, about week 80, about week 90, about week 100, about year 1, about year 2, or about year 3. In some embodiments, administration of the pharmaceutical compositions disclosed herein improves characteristics as measured by endoscopy by up by about 1%, about 5%, about 10%, about 20%, about 30%, about 40%, about 50%, about 60%, about 70%, about 80%, about 90%, or about 100% compared with EndoFlip score in an untreated patient or the same patient before treatment for about 1 week, about 1 month, about 2 months, about 3 months, about 4 months, about 5 months, about 6 months, about 1 year, about 2 years, about 5 years, or about 10 years or more.

In some embodiments, administration of the pharmaceutical compositions disclosed herein improves characteristics as measured by endoscopy in a treated patient at week 12, week 26, or week 52 compared with an untreated patient or the same patient before treatment.

In some embodiments, administration of the pharmaceutical compositions disclosed reduces the number of episodes associated with EoE experienced by a patient over a period of time. Non-limiting examples of such episodes include difficulty swallowing a pill or food. The occurrence of such episodes may be reported by the patient as a feeling of discomfort after swallowing a pill or food, and may be measured after each instance of swallowing a pill or food or over a 24 hour period or more. Any method can be used to assess or report patient discomfort, including PROSE.

In some embodiments, the number of episodes occurring over said period of time is reduced by at least 1 episode, at least 2 episodes, at least 3 episodes, at least 4 episodes, at least 5 episodes, at least 6 episodes, at least 7 episodes, at least 8 episodes, at least 9 episodes, at least 10 episodes, at least 11 episodes, at least 12 episodes, at least 13 episodes, at least 14 episodes, at least 15 episodes, at least 16 episodes, at least 17 episodes, at least 18 episodes, at least 19 episodes, or at least 20 episodes, least 21 episodes, at least 22 episodes, at least 23 episodes, at least 24 episodes, at least 25 episodes, at least 26 episodes, at least 27 episodes, at least 28 episodes, at least 29 episodes, or at least 30 episodes, least 31 episodes, at least 32 episodes, at least 33 episodes, at least 34 episodes, at least 35 episodes, at least 36 episodes, at least 37 episodes, at least 38 episodes, at least 39 episodes, or at least 40 episodes, least 41 episodes, at least 42 episodes, at least 43 episodes, at least 44 episodes, at least 45 episodes, at least 46 episodes, at least 47 episodes, at least 48 episodes, at least 49 episodes, or at least 50 episodes. In some embodiments, the time period is about 1 week, about 2 weeks, about 3 weeks, about 4 weeks, about 5 weeks, about 6 weeks, about 7 weeks, about 8 weeks, about 9, weeks about 10 weeks, about 20 weeks, about 30 weeks, about 40 weeks, about 50 weeks, about 60 weeks, about 70 weeks, about 80 weeks, about 90 weeks, about 100 weeks, about 1 year, about 2 years, or about 3 years.

Dosing and Administration

The oral corticosteroids disclosed herein may be administered in any appropriate dose and using any suitable pharmaceutical composition. While one of skill in the art can determine the desirable dose in each case, a suitable dose of the therapeutic agent for achievement of therapeutic benefit, may, for example, be in a range of about 1 microgram (m) to about 100 milligrams (mg) per kilogram body weight of the recipient per day, preferably in a range of about 10 µg to about 50 mg per kilogram body weight per day and most preferably in a range of about 10 µg to about 50 mg per kilogram body weight per day. In some embodiments, the pharmaceutical composition is administered at a low dose, e.g., about 20 mg or less. In some embodiments, the oral corticosteroid is administered at about 1 mg per kilogram body weight per day, about 3 mg per kilogram body weight per day, and/or about 9 mg per kilogram body weight per day. The desired dose may be presented as one dose or two or more sub-doses administered at appropriate intervals throughout the day. These sub-doses can be administered in unit dosage forms, for example, containing from about 10 µg to about 1000 mg, preferably from about 0.05 mg to about 20 mg, and most preferably from about 0.5 mg to about 7.5 mg. In some embodiments, the pharmaceutical composition is administered in a unit dosage form of 0.75 mg, 1.5 mg, 3.0 mg, 4.5 mg, 6.0 mg, or 7.5.

In some embodiments, the pharmaceutical composition described herein (e.g., a liquid or solid composition comprising an oral corticosteroid) is administered to a patient once a day at bedtime (HS). In some embodiments, the pharmaceutical composition is administered to a patient twice a day (BID). In some embodiments, the pharmaceutical composition is administered to a patient once in the morning and once in the evening. In some embodiments, the pharmaceutical composition is administered on an empty stomach (e.g. at least 2 hours after eating or at least 1 hour before eating; or at least 30 minutes before or after eating). In some embodiments, the pharmaceutical composition is administered to a patient 30 minutes before breakfast and 30 minutes before bedtime. In some embodiments, administering the pharmaceutical composition before bedtime decreases systemic adsorption of the oral corticosteroid compared to systemic adsorption observed after daytime dosing.

Thus, in some embodiments, the pharmaceutical composition is administered during the evening between about 7 pm and about 10 pm, e.g., at about 7 pm, 7:30 pm, about 8 pm, about 8:30 pm, about 9 pm, or about 9:30 pm, inclusive of all values and subranges therebetween. In some embodiments, the pharmaceutical composition is administered about 30 minutes before the target sleep time. The term "target sleep time" can mean the time of day that the patient anticipates going to bed.

Preliminary investigations of therapeutic efficacy in treating EoE following conventional oral administration of the oral corticosteroid (i.e., while the patient is upright) revealed higher eosinophil clearance in the proximal portion esophagus (e.g., closer to the oral cavity) and lower eosinophil clearance in the distal portion of the esophagus (e.g., closer to the stomach). Without being bound by theory, these results suggested increased contact of the corticosteroid with the proximal esophageal tissue, and decreased contact of the corticosteroid with the distal esophageal tissue. Various experiments were performed in an attempt to improve contact of the corticosteroid with the distal esophagus. It was surprisingly discovered that administering the oral corticosteroid while the patient is lying down increases eosinophil clearance in the distal esophagus while maintaining high eosinophil clearance in the proximal esophagus. Without being bound by theory, contact of the corticosteroid with the distal esophagus is increased when the corticosteroid is administered while the patient is lying down, because drug transit through the esophagus is driven primarily by peristalsis, whereas adopting an upright position decreases contact of the oral corticosteroid with the distal esophagus because drug transit is driven primarily by gravity and the continuous flow of fluids down the esophagus.

Contact of the corticosteroid with the esophagus can be observed directly by conducting a scintigraphy study as described in Example 6. Alternatively, contact of the corticosteroid with the esophagus can be determined indirectly by measuring eosinophil clearance in the proximal and distal portions of the esophagus. For example, eosinophil clearance can be determined by measuring the eosinophil count in the proximal and distal esophagus before treatment (cells/mm² of the high power field) to establish a baseline and comparing said baseline to the eosinophil count in the proximal and distal esophagus measured after 8-weeks of treatment, as described in Example 2.

Accordingly, in particular embodiments, the oral corticosteroid is administered once daily, at nighttime while the patient is lying down (or wherein the patient lays down immediately after oral administration). In other particular embodiments, the oral corticosteroid is administered twice daily, wherein the patient may remain upright during the first daily dose and the patient is lying down for the second daily dose (or the patient lays down immediately after oral administration). In further embodiments, the patient is lying down for both daily doses.

In certain embodiments, the pharmaceutical composition is administered to a patient while the patient is lying down or immediately prior to the patient lying down, e.g., within about 1 second, about 2 seconds, about 3 seconds, about 4 seconds, about 5 seconds, about 6 seconds, about 7 seconds, about 8 seconds, about 9 seconds, about 10 seconds, about 15 seconds, about 20 seconds, about 25 seconds, about 30 seconds, about 35 seconds, about 40 seconds, about 45 seconds, about 50 seconds, about 60 seconds, about 1.1 minutes, about 1.2 minutes, about 1.3 minutes, about 1.4 minutes, about 1.5 minutes, about 1.6 minutes, about 1.7 minutes, about 1.8 minutes, about 1.9 minutes, about 2.0 minutes, about 2.5 minutes, about 3 minutes, about 4 minutes, or about 5 minutes prior to the patient lying down, inclusive of all values and ranges therebetween.

In various embodiments, the pharmaceutical composition is administered HS while the patient is lying down (or the patient lays down immediately following administration). In other embodiments, the pharmaceutical composition is administrated during daytime (e.g., BID or QD administration), while the patient is lying down (or the patient lays down immediately following administration). In various embodiments, the patient remains lying down following administration for an amount of time sufficient for topical deposition and/or contact of the corticosteroid onto the esophagus to treat inflammation thereof (e.g., a time sufficient to result in improvement of EoE using the measurements described herein, such as a reduction in episodes of dysphagia). In some such embodiments, the patient remains lying down following administration for an amount of time in the range of from about 1 minute to about 8 hours, including about 5 minutes, about 10 minutes, about 15 minutes, about 20 minutes, about 25 minutes, about 30 minutes, about 35 minutes, about 40 minutes, about 45 minutes, about 50 minutes, about 55 minutes, about 1 hr, about 1.1 hr, about 1.2 hr, about 1.3 hr, about 1.4 hr, about 1.5 hr, about 1.6 hr, about 1.7 hr, about 1.8 hr, or about 1.9 hr, about 2 hrs, about 2.1 hr, about 2.2 hr, about 2.3 hr, about 2.4 hr, about 2.5 hr, about 2.6 hr, about 2.7 hr, about 2.8 hr, or about 2.9 hr, about 3 hrs, about 3.1 hr, about 3.2 hr, about 3.3 hr, about 3.4 hr, about 3.5 hr, about 3.6 hr, about 3.7 hr, about 3.8 hr, or about 3.9 hr, about 4 hrs, about 4.1 hr, about 4.2 hr, about 4.3 hr, about 4.4 hr, about 4.5 hr, about 4.6 hr, about 4.7 hr, about 4.8 hr, about 4.9 hr, about 5 hrs, about 5.1 hr, about 5.2 hr, about 5.3 hr, about 5.4 hr, about 5.5 hr, about 5.6 hr, about 5.7 hr, about 5.8 hr, about 5.9 hr about 6 hrs, about 6.1 hr, about 6.2 hr, about 6.3 hr, about 6.4 hr, about 6.5 hr, about 6.6 hr, about 6.7 hr, about 6.8 hr, or about 6.9 hr, about 7 hrs, about 7.1 hr, about 7.2 hr, about 7.3 hr, about 7.4 hr, about 7.5 hr, about 7.6 hr, about 7.7 hr, about 7.8 hr, or about 7.9 hr, inclusive of all values and subranges therebetween. In embodiments in which the pharmaceutical composition is administered during daytime, the patient remains lying down for an amount of time in the range of from about 1 minute to about 60 minutes, including about 5 minutes, about 10 minutes, about 15 minutes, about 20 minutes, about 25 minutes, about 30 minutes, about 35 minutes, about 40 minutes, about 45 minutes, about 50 minutes, about 55 minutes, inclusive of all values and subranges therebetween. In certain embodiments, the patient remains lying down for about 5 to about 10 minutes.

As used herein, "lying down," "lays down," and derivations and variants thereof, refer to a patient adopting a supine, prone, or laterally recumbent position, as on a bed or on the ground, or a substantially horizontal body position, whereby the corticosteroid (upon swallowing) contacts the esophagus and topically deposits the corticosteroid on esophagus, e.g., at the site of inflammation. As used herein, "substantially horizontal" refers to a body position which at least 10° less than vertical, e.g., less than about 15°, less than about 20°, less than about 25°, less than about 30°, less than about 35°, less than about 40°, less than about 45°, less than about 50°, less than about 55°, less than about 65°, less than about 70°, less than about 75°, less than about 80°, less than about 85°, or about 90° from vertical, inclusive of all values and ranges therebetween. For example, when the composition is formulated as an ODT, the ODT rapidly disintegrates in the mouth of the supine patient to form a suspension comprising the corticosteroid which is swallowed. The suspension then traverses the esophagus of the patient, providing topical contact of the corticosteroid on the esophagus to topically treat inflammation thereof. As used herein, "upright" refers to a patient adopting essentially any other position, including, but not limited to, standing or sitting.

In some embodiments, the pharmaceutical composition is administered to a patient at bedtime. In some embodiments, the pharmaceutical composition is administered to a patient at bedtime while the patient is lying down. In some embodiments, the pharmaceutical composition is administered to the patient while lying down and prior to sleep (e.g., about 1 minute to about 1 hour before going to sleep, e.g., about 1 minute, about 5 minutes, about 10 minutes, about 15 minutes, about 20 minutes, about 25 minutes, about 30 minutes, about 35 minutes, about 40 minute, about 45 minutes, about 50 minutes, about 55 minutes, inclusive of all values therein). In preferred embodiments, the pharmaceutical composition is administered to a lying down patient about 30 minutes before bedtime. In some embodiments, the pharmaceutical composition is administered to a patient after the evening meal, e.g., from about 1 minute to about 5 hours after the evening meal (e.g., about 5 minutes, about 10 minutes, about 15 minutes, about 20 minutes, about 25 minutes, about 30 minutes, about 35 minutes, about 40 minute, about 45 minutes, about 50 minutes, about 55 minutes, about 1 hour, about 1.5 hours, about 2 hours, about 2.5 hours, about 3 hours, about 3.5 hours, about 4 hours, about 4.5 hours, inclusive of all values and subranges therebetween. In preferred embodiments, the pharmaceutical composition is administered at least about 30 minutes after the evening meal.

In some embodiments, administering the pharmaceutical composition comprising a corticosteroid while the patient is lying down increases contact of the corticosteroid with the upper gastrointestinal tract (e.g., the esophagus), while also decreasing systemic absorption of the corticosteroid. Thus, in embodiments, administering the pharmaceutical composition while the patient is lying improves efficacy, and (in further embodiments) reduces side effects associated with systemic administration of corticosteroids.

Transit time of a liquid pharmaceutical composition in the esophagus is generally in the range of about 1 to about 5 seconds. Without being limited by theory, administration of a pharmaceutical composition described herein while the patient is lying down increases the residence time (also referred to as dwell time) of the corticosteroid in the esophagus, which increases the time required for the corticosteroid to reach the stomach, and decreases the amount of the corticosteroid that reaches the stomach and is absorbed systemically. In some embodiments, increased residence time of the corticosteroid in the esophagus increases contact of the corticosteroid with the esophagus. In some embodiments, residence time of the corticosteroid on the esophagus and/or contact of the corticosteroid with the esophagus is increased in a lying down patient compared to the residence time of the corticosteroid when administering in a similar composition while the patient is upright.

In some embodiments, the residence time of the corticosteroid on the esophagus following administration while the patient is lying down is in the range of from about 1 second to about 5 minutes, e.g., about 2 seconds, about 3 seconds, about 5 seconds, about 6 seconds, about 7 seconds, about 8 seconds, about 9 seconds, about 10 seconds, about 15 seconds, about 20 seconds, about 25 seconds, about 30 seconds, about 35 seconds, about 40 seconds, about 45 seconds, about 50 seconds, about 55 seconds, about 60 seconds, about 65 seconds, about 70 seconds, about 75 seconds, about 80 seconds, about 85 seconds, about 90 seconds about 95 seconds, about 100 seconds, about 105 seconds, about 110 seconds, about 115 seconds, about 120 seconds, about 125 seconds, about 130 seconds, about 135 seconds, about 140 seconds, about 145 seconds, about 150 seconds, about 155 seconds, about 160 seconds, about 165 seconds, about 170 seconds, about 175 seconds, about 180 seconds, about 185 seconds, about 190 seconds about 195 seconds, about 200 seconds, 205 seconds, about 210 seconds, about 215 seconds, about 220 seconds, about 225 seconds, about 230 seconds, about 235 seconds, about 240 seconds, about 245 seconds, about 250 seconds, about 255 seconds, about 260 seconds, about 265 seconds, about 270 seconds, about 275 seconds, about 280 seconds, about 285 seconds, about 290 seconds, or about 295 seconds, inclusive of all values and subranges therebetween. In particular embodiments, the traverse time of the corticosteroid on the esophagus following administration while the patient is lying down is in the range of about 5 seconds to about 60 seconds.

In some embodiments, administering the pharmaceutical composition while the patient is lying down increases the residence time of the corticosteroid in the esophagus (compared to the residence time of the corticosteroid in the esophagus when the patient is upright) by about 5 seconds, about 10 seconds, about 15 seconds, about 20 seconds, about 25 seconds, about 30 seconds, about 35 seconds, about 40 seconds, about 45 seconds, about 50 seconds, about 55 seconds, about 60 seconds, about 65 seconds, about 70 seconds, about 75 seconds, about 80 seconds, about 85 seconds, about 90 seconds about 95 seconds, about 100 seconds, about 105 seconds, about 110 seconds, about 115 seconds, about 120 seconds, about 125 seconds, about 130 seconds, about 135 seconds, about 140 seconds, about 145 seconds, about 150 seconds, about 155 seconds, about 160 seconds, about 165 seconds, about 170 seconds, about 175 seconds, about 180 seconds, about 185 seconds, about 190 seconds about 195 seconds, about 200 seconds, 205 seconds, about 210 seconds, about 215 seconds, about 220 seconds, about 225 seconds, about 230 seconds, about 235 seconds, about 240 seconds, about 245 seconds, about 250 seconds, about 255 seconds, about 260 seconds, about 265 seconds, about 270 seconds, about 275 seconds, about 280 seconds, about 285 seconds, about 290 seconds, about 295 seconds, or about 300 seconds. In particular embodiments, the residence time of the corticosteroid on the esophagus following administration while the patient is lying down is increased by an amount of time in the range of from about 5 seconds to about 60 seconds.

In some embodiments, the average time to reach the maximum blood plasma concentration of the corticosteroid ($T_{max}$) for the lying down patient is the range of about 80% to about 125% of about 8 hr to about 20 hr, e.g., about 4.0 hr, about 4.5 hr, about 5 hr, about 5.5 hr, about 6 hr, about 6.6 hr, about 7 hr, about 7.5 hr, about 8 hr, about 8.5 hr, about 9.0 hr, about 9.5 hr, about 10.0 hr, about 10.5 hr, about 11 hr, about 11.5 hr, about 12 hr, about 12.5 hr, about 13 hr, about 13.5 hr, about 14 hr, about 14.5 hr, about 15 hr, about 15.5 hr, about 16 hr, about 16.5 hr, about 17 hr, about 17.5 hr, about 18 hr, about 18.5 hr, about 19 hr, about 19.5 hr, about 20 hr, about 20.5 hr, about 21 hr, about 21.5 hr, or about 22 hr, about 22.5 hr, about 23 hr, or about 23.5 hr, about 24 hr, about 24.5 hr, about 25 hr, about 25.5 hr, or about 26 hr, inclusive of all values and subranges therebetween. In preferred embodiments, the $T_{max}$ of the oral corticosteroid for the lying down patient is the range of about 80% to about 125% of about 14 hr±6 hr, inclusive of all values and subranges therebetween.

In some embodiments, the lying down patient's $T_{max}$ of the oral corticosteroid is increased by an amount of time in the range of from about 1 hr to about 15 hr compared to the $T_{max}$ of an upright patent (e.g., AM fed or fasted conditions), e.g., about 1.5 hr, about 2.5 hr, about 3 hr, about 3.5 hr, about 4 hr, about 4.5 hr, about 5 hr, about 5.5 hr, about 6 hr, about 6.5 hr, about 7 hr, about 7.5 hr, about 8 hr, about 8.5 hr, about 9 hr, about 9.5 hr, about 10 hr, about 10.5 hr, about 11 hr, about 11.5 hr, about 12 hr, about 12.5 hr, about 13 hr, about 13.5 hr, about 14 hr, about 14.5 hr, inclusive of all values and subranges therebetween.

In some embodiments, the $T_{max}$ of the oral corticosteroid when administered to an upright patient in a fed state (and the patient does not lay down immediately thereafter) is in the range of about 80% to about 125% of about 1 hr to about 10 hr, e.g., about 1.5 hr, about 2.5 hr, about 3 hr, about 3.5 hr, about 4 hr, about 4.5 hr, about 5 hr, about 5.5 hr, about 6 hr, about 6.5 hr, about 7 hr, about 7.5 hr, about 8 hr, about 8.5 hr, about 9 hr, about 9.5 hr, about 10 hr, about 10.5 hr, about 11 hr, about 11.5 hr, about 12 hr, about 12.5 hr, about 13 hr, inclusive of all values and subranges therebetween.

In some embodiments, the $T_{max}$ of the oral corticosteroid when administered to an upright patient in a fasted state (and the patient does not lay down immediately thereafter) is in the range of about 80% to about 125% of about 2 hr to about 30 hr, e.g., about 1 hr, about 1.5 hr, about 2.5 hr, about 3 hr, about 3.5 hr, about 4 hr, about 4.5 hr, about 5 hr, about 5.5 hr, about 6 hr, about 6.5 hr, about 7 hr, about 7.5 hr, about 8 hr, about 8.5 hr, about 9 hr, about 9.5 hr, about 10 hr, about 10.5 hr, about 11 hr, about 11.5 hr, about 12 hr, about 12.5 hr, about 13 hr, about 13.5 hr, about 14 hr, about 14.5 hr, about 15 hr, about 15.5 hr, about 16 hr, about 16.5 hr, about 17 hr, about 17.5 hr, about 18 hr, about 18.5 hr, about 19 hr, about 19.5 hr, about 20 hr, about 20.5 hr, about 21 hr, about 21.5 hr, about 22 hr, about 22.5 hr, about 23 hr, about 23.5 hr, about 24 hr, about 24.5 hr, about 25 hr, about 25.5 hr, about 26 hr, about 26.5 hr, about 27 hr, about 27.5 hr, about 28 hr, about 28.5 hr, about 29 hr, about 29.5 hr, about 30 hr, about 30.5 hr, about 31 hr, about 31.5 hr, about 32 hr, about 32.5 hr, about 33 hr, inclusive of all values and subranges therebetween.

Conventionally, food usually delays $T_{max}$, and therefore $T_{max}$ for the fed state are usually larger than fasted state $T_{max}$. However, the pharmacokinetic studies revealed that fasted state $T_{max}$ values are larger than fed state $T_{max}$. Thus, in some embodiments, fasted state $T_{max}$ are larger than fed state $T_{max}$ by about 1 hr, about 1.5 hr, about 2 hr, about 2.5 hr, about 3 hr, about 3.5 hr, about 4 hr, about 4.5 hr, about 5 hr, about 5.5 hr, about 6 hr, about 6.5 hr, about 7 hr, about 7.5 hr, about 8 hr, about 8.5 hr, about 9 hr, about 9.5 hr, about 10 hr, about 10.5 hr, about 11 hr, about 11.5 hr, about 12 hr, about 12.5 hr, about 13 hr, about 13.5 hr, about 14 hr, about 14.5 hr, about 15 hr, about 15.5 hr, about 16 hr, about 16.5 hr, about 17 hr, about 17.5 hr, about 18 hr, about 18.5 hr, about 19 hr, about 19.5 hr, about 20 hr, or more.

Due to the topical contact of the oral corticosteroid with the esophagus, and the use of corticosteroids having low (or modified to have low) systemic bioavailability, the methods and compositions described herein are able to treat EoE with blood plasma levels of the corticosteroid that are surprisingly low. A benefit of low blood plasma levels of the corticosteroid is a reduction or avoidance of side effects associated with systemic administration of corticosteroids. Thus, in some embodiments, the methods and compositions described herein topically administer a corticosteroid to the upper gastrointestinal tract (e.g., the esophagus) in an effective amount of the corticosteroid to topically treat inflammation thereof (e.g., EoE). In some embodiments, the oral corticosteroid provides an average maximum blood plasma concentration (Cmax) of less than or equal to about 1000 pg/mL after oral administration of about 0.01 mg to about 20 mg of the oral corticosteroid, e.g., less than or equal to about 950 pg/mL, about 900 pg/mL, about 850 pg/mL, about 800 pg/mL, about 750 pg/mL, about 700 pg/mL, about 650 pg/mL, about 600 pg/mL, about 550 pg/mL, about 500 pg/mL, about 450 pg/mL, about 400 pg/mL, about 350 pg/mL, about 300 pg/mL, about 250 pg/mL, about 200 pg/mL, about 150 pg/mL, about 100 pg/mL, or about 50 pg/mL. In preferred embodiments, the oral corticosteroid provides a Cmax of less than or equal to about 500 pg/mL after oral administration of about 0.01 mg to about 20 mg of the oral corticosteroid.

In preferred embodiments, the lying down patient's Cmax is within the range of about 80% to about 125% of about 15 pg/mL to about 40 pg/mL following administration of 6 mg of fluticasone propionate while the patient is lying down, e.g., about 10 pg/mL, about 11 pg/mL, about 12 pg/mL, about 13 pg/mL, about 14 pg/mL, about 15 mg/mL, about 16 pg/mL, about 17 pg/mL, about 18 pg/mL, about 19 pg/mL, about 20 pg/mL, about 21 pg/mL, about 22 pg/mL, about 23 pg/mL, about 24 pg/mL, about 25 pg/mL, about 26 pg/mL, about 27 pg/mL, about 28 pg/mL, about 29 pg/mL, about 30 pg/mL, about 31 pg/mL, about 32 pg/mL, about 33 pg/mL, about 34 pg/mL, about 35 pg/mL, about 36 pg/mL, about 37 pg/mL, about 38 pg/mL, about 39 pg/mL, about 40 pg/mL, about 41 pg/mL, about 42 pg/mL, about 43 pg/mL, about 44 pg/mL, about 45 pg/mL, about 46 pg/mL, about 47 pg/mL, about 48 pg/mL, about 49 pg/mL, about 50 pg/mL, about 51 pg/mL, about 52 pg/mL, about 53 pg/mL, about 54 pg/mL, or about 55 pg/mL, inclusive of all values and subranges therebetween. In some embodiments, the low blood plasma levels achieved to treat EoE also reduces side effects associated with systemic administration of corticosteroids. For example, in embodiments involving HS administration, topical delivery of the corticosteroid decreases systemic administration and associated side effect even though HS administration is generally known to increase systemic absorption.

In some embodiments, a lying down patient's Cmax of the oral corticosteroid is at least about 1% lower compared to the fed patient's Cmax of the oral corticosteroid for a fed patient that is upright and does not lay down immediately after administration of the oral corticosteroid, e.g., at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 25%, at least about 30%, at least about 35%, at least about 40%, at least about 45%, or at least about 50%, inclusive of all values and subranges therebetween.

In some embodiments, the oral corticosteroid provides and an average $AUC_{0-24}$ of less than or equal to about 10,000 pg*h/mL after oral administration of about 0.01 mg to about 20 mg of the oral corticosteroid, e.g., about 9,000 pg*h/mL, about 8,000 pg*h/mL, about 7,000 pg*h/mL, about 6,000 pg*h/mL, about 5,000 pg*h/mL, about 4,000 pg*h/mL, about 3,000 pg*h/mL, about 2,000 pg*h/mL, about 1,000 pg*h/mL, about 900 pg*h/mL, about 800 pg*h/mL, about 700 pg*h/mL, about 600 pg*h/mL, about 500 pg*h/mL, about 400 pg*h/mL, about 300 pg*h/mL, about 200 pg*h/mL, or about 100 pg*h/mL. In particular embodiments, the oral corticosteroid provides and an average $AUC_{0-24}$ of less than or equal to about 3,000 pg*h/mL after oral administration of about 0.01 mg to about 20 mg of the oral corticosteroid.

In some embodiments, the patient's $AUC_{0-24}$ (pg*h/mL) is within the range of about 80% to about 125% of about 50 pg·h/mL to about 1,000 pg·h/mL following administration of 1.5, 3.0, 4.5, 6.0 or 7.5 mg of fluticasone propionate while the patient is lying down, e.g., about 10 pg·h/mL, about 20 pg·h/mL, about 30 pg·h/mL, about 40 pg·h/mL, about 50 pg·h/mL, about 60 pg·h/mL, about 70 pg·h/mL, about 80 pg·h/mL, about 90 pg·h/mL, about 100 pg·h/mL, about 110 pg·h/mL, about 120 pg·h/mL, about 130 pg·h/mL, about 140 pg·h/mL, about 150 pg·h/mL, about 160 pg·h/mL, about 170 pg·h/mL, about 180 pg·h/mL, about 190 pg·h/mL, about 200 pg·h/mL, about 210 pg·h/mL, about 220 pg·h/mL, about 230 pg·h/mL, about 240 pg·h/mL, about 250 pg·h/mL, about 260 pg·h/mL, about 270 pg·h/mL, about 280 pg·h/mL, about 290 pg·h/mL, about 300 pg·h/mL, about 310 pg·h/mL, about 320 pg·h/mL, about 330 pg·h/mL, about 340 pg·h/mL, about 350 pg·h/mL, about 360 pg·h/mL, about 370 pg·h/mL, about 380 pg·h/mL, about 390 pg·h/mL, about 400 pg·h/mL, about 410 pg·h/mL, about 420 pg·h/mL, about 430 pg·h/mL, about 440 pg·h/mL, about 450 pg·h/mL, about 460 pg·h/mL, about 470 pg·h/mL, about 480 pg·h/mL, about 490 pg·h/mL, about 500 pg·h/mL, about 510 pg·h/mL, about 520 pg·h/mL, about 530 pg·h/mL, about 540 pg·h/mL, about 550 pg·h/mL, about 560 pg·h/mL, about 570 pg·h/mL, about 580 pg·h/mL, about 590 pg·h/mL, about 600 pg·h/mL, about 610 pg·h/mL, about 620 pg·h/mL, about 630 pg·h/mL, about 640 pg·h/mL, about 650 pg·h/mL, about 660 pg·h/mL, about 670 pg·h/mL, about 680 pg·h/mL, about 690 pg·h/mL, about 700 pg·h/mL, about 710 pg·h/mL, about 720 pg·h/mL, about 730 pg·h/mL, about 740 pg·h/mL, about 750 pg·h/mL, about 760 pg·h/mL, about 770 pg·h/mL, about 780 pg·h/mL, about 790 pg·h/mL, about 800 pg·h/mL, about 810 pg·h/mL, about 820 pg·h/mL, about 830 pg·h/mL, about 840 pg·h/mL, about 850 pg·h/mL, about 860 pg·h/mL, about 870 pg·h/mL, about 880 pg·h/mL, about 890 pg·h/mL, about 900 pg·h/mL, about 910 pg·h/mL, about 920 pg·h/mL, about 930 pg·h/mL, about 940 pg·h/mL, about 950 pg·h/mL, about 960 pg·h/mL, about 970 pg·h/mL, about 980 pg·h/mL, about 990 pg·h/mL, about 1000 pg·h/mL, about 1010 pg·h/mL, about 1020 pg·h/mL, about 1030 pg·h/mL, about 1040 pg·h/mL, about 1050 pg·h/mL, about 1060 pg·h/mL, about 1070 pg·h/mL, about 1080 pg·h/mL, about 1090 pg·h/mL, about 1100 pg·h/mL, about 1110 pg·h/mL, about 1120 pg·h/mL, about 1130 pg·h/mL, about 1140 pg·h/mL, about 1150 pg·h/mL, about 1160 pg·h/mL, about 1170 pg·h/mL, about 1180 pg·h/mL, about 1190 pg·h/mL, about 1200 pg·h/mL, about 1210 pg·h/mL, about 1220 pg·h/mL, about 1230 pg·h/mL, about 1240 pg·h/mL, about 1250 pg·h/mL, about 1260 pg·h/mL, about 1270 pg·h/mL, about 1280 pg·h/mL, about 1290 pg·h/mL, about 1300 pg·h/mL, inclusive of all values and subranges therebetween.

In some embodiments, the patient's $AUC_{0-24}$ (pg*h/mL) is within the range of about 80% to about 125% of about 50 pg·h/mL to about 1,000 pg·h/mL following administration of 1.5, 3.0, 4.5, 6.0 or 7.5 mg of fluticasone propionate while the patient is upright (AM dosing in the fed or fasted state), e.g., about 10 pg·h/mL, about 20 pg·h/mL, about 30 pg·h/mL, about 40 pg·h/mL, about 50 pg·h/mL, about 60 pg·h/mL, about 70 pg·h/mL, about 80 pg·h/mL, about 90 pg·h/mL, about 100 pg·h/mL, about 110 pg·h/mL, about 120 pg·h/mL, about 130 pg·h/mL, about 140 pg·h/mL, about 150 pg·h/mL, about 160 pg·h/mL, about 170 pg·h/mL, about 180 pg·h/mL, about 190 pg·h/mL, about 200 pg·h/mL, about 210 pg·h/mL, about 220 pg·h/mL, about 230 pg·h/mL, about 240 pg·h/mL, about 250 pg·h/mL, about 260 pg·h/mL, about 270 pg·h/mL, about 280 pg·h/mL, about 290 pg·h/mL, about 300 pg·h/mL, about 310 pg·h/mL, about 320 pg·h/mL, about 330 pg·h/mL, about 340 pg·h/mL, about 350 pg·h/mL, about 360 pg·h/mL, about 370 pg·h/mL, about 380 pg·h/mL, about 390 pg·h/mL, about 400 pg·h/mL, about 410 pg·h/mL, about 420 pg·h/mL, about 430 pg·h/mL, about 440 pg·h/mL, about 450 pg·h/mL, about 460 pg·h/mL, about 470 pg·h/mL, about 480 pg·h/mL, about 490 pg·h/mL, about 500 pg·h/mL, about 510 pg·h/mL, about 520 pg·h/mL, about 530 pg·h/mL, about 540 pg·h/mL, about 550 pg·h/mL, about 560 pg·h/mL, about 570 pg·h/mL, about 580 pg·h/mL, about 590 pg·h/mL, about 600 pg·h/mL, about 610 pg·h/mL, about 620 pg·h/mL, about 630 pg·h/mL, about 640 pg·h/mL, about 650 pg·h/mL, about 660 pg·h/mL, about 670 pg·h/mL, about 680 pg·h/mL, about 690 pg·h/mL, about 700 pg·h/mL, about 710 pg·h/mL, about 720 pg·h/mL, about 730 pg·h/mL, about 740 pg·h/mL, about 750 pg·h/mL, about 760 pg·h/mL, about 770 pg·h/mL, about 780 pg·h/mL, about 790 pg·h/mL, about 800 pg·h/mL, about 810 pg·h/mL, about 820 pg·h/mL, about 830 pg·h/mL, about 840 pg·h/mL, about 850 pg·h/mL, about 860 pg·h/mL, about 870 pg·h/mL, about 880 pg·h/mL, about 890 pg·h/mL, about 900 pg·h/mL, about 910 pg·h/mL, about 920 pg·h/mL, about 930 pg·h/mL, about 940 pg·h/mL, about 950 pg·h/mL, about 960 pg·h/mL, about 970 pg·h/mL, about 980 pg·h/mL, about 990 pg·h/mL, about 1000 pg·h/mL, about 1010 pg·h/mL, about 1020 pg·h/mL, about 1030 pg·h/mL, about 1040 pg·h/mL, about 1050 pg·h/mL, about 1060 pg·h/mL, about 1070 pg·h/mL, about 1080 pg·h/mL, about 1090 pg·h/mL, about 1100 pg·h/mL, about 1110 pg·h/mL, about 1120 pg·h/mL, about 1130 pg·h/mL, about 1140 pg·h/mL, about 1150 pg·h/mL, about 1160 pg·h/mL, about 1170 pg·h/mL, about 1180 pg·h/mL, about 1190 pg·h/mL, about 1200 pg·h/mL, about 1210 pg·h/mL, about 1220 pg·h/mL, about 1230 pg·h/mL, about 1240 pg·h/mL, about 1250 pg·h/mL, about 1260 pg·h/mL, about 1270 pg·h/mL, about 1280 pg·h/mL, about 1290 pg·h/mL, about 1300 pg·h/mL, inclusive of all values and subranges therebetween.

In some embodiments, the patient's $AUC_{0-24}$ (pg*h/mL) is within the range of about 80% to about 125% of about 250 pg·h/mL to about 475 pg·h/mL following administration of 6 mg of fluticasone propionate while the patient is lying down, e.g., about 150 pg·h/mL, about 160 pg·h/mL, about 170 pg·h/mL, about 180 pg·h/mL, about 190 pg·h/mL, about 200 pg·h/mL, about 210 pg·h/mL, about 220 pg·h/mL, about 230 pg·h/mL, about 240 pg·h/mL, about 250 pg·h/mL, about 260 pg·h/mL, about 270 pg·h/mL, about 280 pg·h/mL, about 290 pg·h/mL, about 300 pg·h/mL, about 310 pg·h/mL, about 320 pg·h/mL, about 330 pg·h/mL, about 340 pg·h/mL, about 350 pg·h/mL, about 360 pg·h/mL, about 370 pg·h/mL, about 380 pg·h/mL, about 390 pg·h/mL, about 400 pg·h/mL, about 410 pg·h/mL, about 420 pg·h/mL, about 430 pg·h/mL, about 440 pg·h/mL, about 450 pg·h/mL, about 460 pg·h/mL, about 470 pg·h/mL, about 480 pg·h/mL, about 490 pg·h/mL, about 500 pg·h/mL, about 510 pg·h/mL, about 520 pg·h/mL, about 530 pg·h/mL, about 540 pg·h/mL, about 550 pg·h/mL, about 560 pg·h/mL, about 570 pg·h/mL, about 580 pg·h/mL, about 590 pg·h/mL, about 600 pg·h/mL inclusive of all values and subranges therebetween.

In some embodiments, the patient's $AUC_{0-24}$ (pg*h/mL) is within the range of about 80% to about 125% of about 250 pg·h/mL to about 475 pg·h/mL following administration of 6 mg of fluticasone propionate while the patient is upright, e.g., about 150 pg·h/mL, about 160 pg·h/mL, about 170 pg·h/mL, about 180 pg·h/mL, about 190 pg·h/mL, about 200 pg·h/mL, about 210 pg·h/mL, about 220 pg·h/mL, about 230 pg·h/mL, about 240 pg·h/mL, about 250 pg·h/mL, about 260 pg·h/mL, about 270 pg·h/mL, about 280 pg·h/mL, about 290 pg·h/mL, about 300 pg·h/mL, about 310 pg·h/mL, about 320 pg·h/mL, about 330 pg·h/mL, about 340 pg·h/mL, about 350 pg·h/mL, about 360 pg·h/mL, about 370 pg·h/mL, about 380 pg·h/mL, about 390 pg·h/mL, about 400 pg·h/mL, about 410 pg·h/mL, about 420 pg·h/mL, about 430 pg·h/mL, about 440 pg·h/mL, about 450 pg·h/mL, about 460 pg·h/mL, about 470 pg·h/mL, about 480 pg·h/mL, about 490 pg·h/mL, about 500 pg·h/mL, about 510 pg·h/mL, about 520 pg·h/mL, about 530 pg·h/mL, about 540 pg·h/mL, about 550 pg·h/mL, about 560 pg·h/mL, about 570 pg·h/mL, about 580 pg·h/mL, about 590 pg·h/mL, about 600 pg·h/mL inclusive of all values and subranges therebetween.

In some embodiments, the pharmaceutical composition is administered to a patient at least about 2 hours after the evening meal (with no snacks) while the patient is lying down. In some embodiments, the pharmaceutical composition is administered to a patient at least about 4 hours after the evening meal (with no snacks) while the patient is lying down. In some embodiments, the pharmaceutical composition is administered to a patient within about 2 hours after the evening meal (with no snacks) while the patient is lying down. In some embodiments, the pharmaceutical composition is administered to a patient within about 4 hours after the evening meal (with no snacks) while the patient is lying down. In some embodiments, after administration of the pharmaceutical composition while the patient is lying down, the patient goes to sleep. In some embodiments, after administration of the pharmaceutical composition while the patient is lying down, the patient does not rise for at least one hour.

In some embodiments, the patient holds the pharmaceutical composition in the oral cavity for a length of time sufficient to swallow the composition (e.g., about 1 second, about 2 seconds, about 3 seconds, about 4 seconds, about 5 seconds, about 6 seconds, about 7 seconds, about 8 seconds, about 9 seconds, or about 10 seconds). In other embodiments, the patient holds the pharmaceutical composition in the oral cavity for a length of time sufficient to allow the pharmaceutical composition to dissolve in the saliva. One skilled in the art will appreciate that the length of time necessary for the pharmaceutical composition depends, in part, on the dosage form. For example, orally disintegrating compositions disintegrate in saliva within about 60 seconds (e.g., about 50 seconds, about 40 seconds, about 30 seconds, about 20 seconds, or about 10 seconds) to form a suspension which is then swallowed. In embodiments in which the pharmaceutical composition is a lozenge or lollipop, the lozenge or lollipop may remain in the patient's oral cavity for about 1 minute, about 2 minute, about 3 minutes, about 4 minutes, about 5 minutes, about 6 minutes, about 7 minutes, about 8 minutes, about 9 minutes, or about 10 minutes.

In some embodiments, the pharmaceutical composition is administered to a patient from one to five times a day. In some embodiments, the pharmaceutical composition is administered to a patient at least once a day, at least twice a day, at least three times a day, at least 4 times a day, or at least five times a day. In some embodiments, the pharmaceutical composition is administered to a patient at least one to five times a day for one week to 10 years or more. In some embodiments, the pharmaceutical composition is administered to a patient at least once a day, at least twice a day, at least three times a day, at least 4 times a day, or at least five times a day for at least one week, at least two weeks, at least three weeks, at least four weeks, at least five weeks, at least six weeks, at least seven weeks, at least eight weeks, at least nine weeks, at least ten weeks, at least fifteen weeks, at least twenty weeks, at least thirty weeks, at least forty weeks, at least fifty weeks, at least fifty-two weeks, at least sixty weeks, at least seventy weeks, at least eighty weeks, at least ninety weeks, or at least one hundred weeks or more. In some embodiments, the pharmaceutical composition is administered to a patient indefinitely. In some embodiments, the pharmaceutical composition is administered twice a day for at least about 6 weeks, at least about 8 weeks, at least about 10 weeks, or at least about 12 weeks. In some embodiments, the pharmaceutical composition is administered twice a day during the induction and/or maintenance phase. In some embodiments, the pharmaceutical composition is administered twice a day for at least about 6 weeks, at least about 8 weeks, at least about 10 weeks, or at least about 12 weeks during the induction phase.

In some embodiments, the pharmaceutical composition is administered to a patient at 0.75 mg, 1.5 mg, 3.0 mg, 4.5 mg, or 6.0 mg at least once a day, at least twice a day, at least three times a day, at least four times a day, or at least five times a day. In some embodiments, the pharmaceutical composition is administered to a patient at the same dose multiple times a day. In some embodiments, the pharmaceutical composition is administered to a patient at the same dose at least twice a day, at least three times a day, at least 4 times a day, or at least five times a day. In some embodiments, the pharmaceutical composition is administered to a patient at the same dose two to five times a day for one week to 10 years or more. In some embodiments, the pharmaceutical composition is administered to a patient at least at the same dose at least twice a day, at least three times a day, at least 4 times a day, or at least five times a day for at least one week, at least two weeks, at least three weeks, at least four weeks, at least five weeks, at least six weeks, at least seven weeks, at least eight weeks, at least nine weeks, at least ten weeks, at least fifteen weeks, at least twenty weeks, at least thirty weeks, at least forty weeks, at least fifty weeks, at least fifty-two weeks, at least sixty weeks, at least seventy weeks, at least eighty weeks, at least ninety weeks, or at least one hundred weeks or more or indefinitely.

In some embodiments, the pharmaceutical composition is administered twice a day at different doses. In some embodiments, the pharmaceutical composition is administered twice a day, with the morning dose being greater than the evening dose. In some embodiments, the pharmaceutical composition is administered twice a day, with the morning dose being less than the evening dose.

In some embodiments, the patient is administered different doses of the pharmaceutical composition depending on the phase of the regimen. For example, the regimen may be divided into at least induction, treatment, withdrawal, or maintenance phase. In some embodiments, the regimen includes at least one of these phases. In some embodiments, the regimen includes a combination of one or more of these phases. In some embodiments, the regimen includes all of these phases.

In some embodiments, the regimen includes induction and withdrawal. In some embodiments, the regimen includes multiple cycles of induction and withdrawal as needed. In some embodiments, the regimen includes multiple cycles of induction and withdrawal repeated indefinitely. In some embodiments, the induction period does not result in a recurrence of symptoms.

The regimen phases may be any appropriate duration. In some embodiments, the induction phase lasts between about 1 and about 10 weeks, about 12 weeks, about 15 weeks, about 20 weeks, about 30 weeks, about 40 weeks, or about 50 weeks. In some embodiments, the induction phase lasts about 14 weeks. In some embodiments, the withdrawal phase lasts between about 1 and about 10 weeks, about 15 weeks, about 20 weeks, about 30 weeks, about 40 weeks, about 50 weeks, about 1 year, about 2 years, about 5 years, about 10 years or indefinitely. In some embodiments, the withdrawal phase lasts until symptoms recur. In some embodiments, the withdrawal phase lasts about 14 weeks. In some embodiments, the maintenance phase lasts between about 1 and about 15 weeks, about 20 weeks, about 30 weeks, about 40 weeks, about 50 weeks, about 1 year, about 2 years, about 5 years, about 10 years or more. In some embodiments, the maintenance phase lasts about 28 weeks. In some embodiments, the maintenance phase is an indefinite duration.

In some embodiments, the patient is administered a greater dose in one or more regimen phases compared to the others. In some embodiments, the patient is administered the same dose in one or more regimen phases. In some embodiments, the patient is administered the same dose in every regimen phases. In some embodiments, the patient is administered no dose during one or more phases.

In some embodiments, the patient is administered a greater dose during the induction stage compared to the maintenance stage. In some embodiments, the patient is administered a smaller dose during the induction stage compared to the maintenance stage. In some embodiments, the patient is administered no dose during either the induction or maintenance stage. In some embodiments, the patient is administered no dose during both the induction and maintenance stages. In some embodiments, the patient is administered the same dose during the induction and maintenance stages. In some embodiments, the patient is administered substantially the same dose during the induction and maintenance stages. In some embodiments, the patient is administered 3.0 mg BID during the induction stage, and 1.5 mg BID during the maintenance stage. In some embodiments, the patient is administered 3.0 mg BID during the induction stage, and 1.5 mg HS during the maintenance stage. In some embodiments, the patient is administered 1.5 mg BID during the induction stage, and 3.0 mg BID during the maintenance stage. In some embodiments, the patient is administered 1.5 mg HS during the induction stage, and 3.0 mg BID during the maintenance stage. In some embodiments, the patient is administered 1.5 mg BID during both the induction and maintenance stages. In some embodiments, the patient is administered 1.5 mg HS during the induction and maintenance stages. In some embodiments, the patient is administered 3.0 mg BID during the induction and maintenance stages. In some embodiments, the patient is administered 6.0 mg BID during the induction stage, and 3.0 or 1.5 mg BID during the maintenance stage. In some embodiments, the patient is administered 6.0 mg BID during the induction stage, and 3.0 or 1.5 mg HS during the maintenance stage. In some embodiments, the patient is administered 1.5 or 3.0 mg BID during the induction stage, and 6.0 mg BID during the maintenance stage. In some embodiments, the patient is administered 1.5 or 3.0 mg HS during the induction stage, and 6.0 mg BID during the maintenance stage. In some embodiments, the patient is administered 6.0 or 3.0 mg BID during both the induction and maintenance stages. In some embodiments, the patient is administered 6.0 or 3.0 mg HS during the induction and maintenance stages. In some embodiments, the patient is administered 6.0 mg BID during the induction and maintenance stages.

In some embodiments, the patient is not co-administered a strong cytochrome P4503A4 inhibitor. In some embodiments, the patient is not co-administered ritonavir or ketoconazole.

In certain embodiments, the patient is a human, but in other embodiments may be a non-human mammal, such as a domesticated pet (e.g., dog or cat), or livestock or farm animal (e.g., horse, cow, sheep, or pig).

Patient Populations

Any patient diagnosed with, or presumed to be suffering from an inflammatory gastrointestinal disorder, may be administered the pharmaceutical compositions of the present disclosure. In some embodiments, the patient is an adult. In some embodiments, the patient is an adolescent. In some embodiments, the patient is a child. In some embodiments, the patient is an infant.

In some embodiments, the inflammatory gastrointestinal disorder is EoE. The patient may be diagnosed using any appropriate measures in the art. In some embodiments, the patient is diagnosed with EoE based on symptoms, histology, and/or failed documentation on proton pump inhibitors. In some embodiments, the patient received PPI therapy prior to administration of a pharmaceutical composition of the present disclosure. In some embodiments, the patient did not receive PPI therapy prior to administration of a pharmaceutical composition of the present disclosure. In some embodiments, the patient failed to improve after 8 weeks of high-dose (e.g. 40 mg) PPI. A lack of response to PPI therapy may be defined as Peak eosinophil count ≥15/HPF in at least one biopsied location after 8 weeks of treatment with a high dose PPI. In some embodiments, the failure of PPI therapy is documented before administration of a pharmaceutical composition of the present disclosure. In some embodiments, the failure of PPI therapy is documented subsequently to administration of a pharmaceutical composition of the present disclosure. In some embodiments, patients which did not respond to previous PPI therapy are administered a high dose of the oral corticosteroid according to (or for use in) the methods disclosed herein, such as 6.0 mg, 7.5 mg, or more (e.g., about 9.0 mg to about 20 mg, including about 9 mg, about 10 mg, about 11 mg, about 12 mg, about 13 mg, about 14 mg, about 15 mg, about 16 mg, about 17 mg, about 18 mg, and about 19 mg, inclusive of all values and subranges therebetween).

In some embodiments, the patient diagnosed with EoE has an esophageal stricture. In some embodiments, said patient is administered a high dose of the oral corticosteroid according to (or for use in) the methods disclosed herein, such as 6.0 mg, 7.5 mg, or more (e.g., about 9.0 mg to about 20 mg, including about 9 mg, about 10 mg, about 11 mg, about 12 mg, about 13 mg, about 14 mg, about 15 mg, about 16 mg, about 17 mg, about 18 mg, and about 19 mg, inclusive of all values and subranges therebetween).

In some embodiments, the patient diagnosed with EoE has a severe food allergy (e.g., a lactose or starch allergy). In some embodiments, said patient is administered a high dose of the oral corticosteroid according to (or for use in) the methods disclosed herein, such as 6.0 mg, 7.5 mg, or more (e.g., about 9.0 mg to about 20 mg, including about 9 mg, about 10 mg, about 11 mg, about 12 mg, about 13 mg, about 14 mg, about 15 mg, about 16 mg, about 17 mg, about 18 mg, and about 19 mg, inclusive of all values and subranges therebetween).

In some embodiments, the patient has been diagnosed with EoE by histological analysis. In some embodiments, the patient is diagnosed as having ≥15 peak eosinophil count per HPF (400× magnification) in at least one biopsy. In some embodiments, there are at minimum of 6 biopsies taken from the patient. In some embodiments, at least 3 biopsies are taken from each of the proximal and the distal esophagus.

In some embodiments, the patient is diagnosed as having EoE by their EEsAI, Global EoE, EREFS, PROSE, and/or measurement of esophageal characteristics via endoscopy (e.g. EndoFlip). In some embodiments, the patient is diagnosed as having EoE based on a 7-day recall EEsAI score of >30. In some embodiments, the patient is diagnosed as having EoE based on a 7-day recall Global EoE score of ≥5. In some embodiments, the patient is diagnosed has having EoE based on the EREFS score which scores endoscopic characteristics (see Table 3). In some embodiments EoE is diagnosed in a patient scoring above Grade 0 in any of the five characteristics disclosed in Table 3.

In some embodiments, the patient is diagnosed as having EoE based on symptoms, including but not limited to episodes of food impaction, episodes of food impaction requiring endoscopy, food avoidance, vomiting, reflux, and/or dysphagia. In some embodiments, the patient is diagnosed as having EoE based on dysphagia (difficulty swallowing). In some embodiments, the patient is diagnosed as having EoE based on experiencing dysphagia at least 3 times per week within 2 weeks.

Patient outcome and response to administration with a pharmaceutical composition of the present disclosure may be monitored or measured using any appropriate means in the art (e.g. endoscopy, histology, questionnaires).

Patients who exhibit an improvement of symptoms and/or histologic response after treatment commences are categorized as Responders. In some embodiments, patients who exhibit <15 peak eosinophils/HPF are categorized as Responders. In some embodiments, patients who exhibit <6 peak eosinophils/HPF are categorized as Responders. In some embodiments, patients who exhibit <6 peak eosinophils/HPF and no worsening of symptoms (e.g. no increase in weekly EEsAI score compared to baseline; stricture requiring dilation) are categorized as Responders. In some embodiments, patients who exhibit <6 peak eosinophils/HPF and no episodes of food impaction are categorized as Responders. In some embodiments, Responders exhibit evidence of inflammatory endoscopic remission such as an absence of white exudate and/or furrows. In some embodiments, Responders exhibit evidence of fibrotic remission including an absence of strictures and rings or moderate to severe rings. In some embodiments, Responders exhibit improved vascularity. In some embodiments, Responders exhibit improved biomarkers (e.g. IL-5, IgE levels).

In some embodiments, patients who are categorized as Responders enter the maintenance stage of the regimen. In some embodiments, patients who are categorized as Responders are administered a different dose of a pharmaceutical composition of the present disclosure after categorization. In some embodiments, Responders receive a greater dose after categorization after categorization. In some embodiments, Responders receive a smaller dose after categorization. In some embodiments, Responders receive the same dose after categorization. In some embodiments, Responders receive substantially the same dose after categorization.

In some embodiments, the patient is classified as a responder if the pharmaceutical compositions disclosed herein are administered in an induction phase and a maintenance phase, and during the induction phase improvement in Peak eosinophilic counts in at least one esophageal biopsy and/or at least no worsening of patient mean weekly EESAI scores are observed, and where the maintenance phase comprises a dose at least equal to, more than or less than the induction phase.

Patients who do not meet the definition of Responder as disclosed above are categorized as Non-Responders. Patients whose histologic score and/or symptoms worsen are categorized as Relapse. In some embodiments, patients whose histologic score and/or symptoms worsen at any point during treatment are categorized as Relapse. In some embodiments, patients who experience food impaction requiring endoscopy and/or clinically-significant worsening of symptoms are categorized as Relapse. In some embodiments, patients who are categorized as Non-Responders or Relapsers are administered a different dose of a pharmaceutical composition of the present disclosure after categorization. In some embodiments, Non-Responders and/or Relapsers receive a greater dose after categorization. In some embodiments, Non-Responders and/or Relapsers receive a smaller dose after categorization. In some embodiments, Non-Responders and/or Relapsers receive the same dose after categorization. In some embodiments, Non-Responders and/or Relapsers receive substantially the same dose after categorization.

In some embodiments, the patient is classified as a responder if the pharmaceutical compositions disclosed herein are administered in an induction phase and a maintenance phase, and during the induction phase no improvement in Peak eosinophilic counts in at least one esophageal biopsy and/or worsening of patient mean weekly EESAI scores are observed, and where the maintenance phase comprises a dose at least equal to, more than or less than the induction phase.

In some embodiments, the present disclosure provides methods for assessing the suitability of subjects for a clinical trial to measure the effect of an oral corticosteroid on EoE, after administration in both an induction phase and a maintenance phase. In some embodiments, the recruitment of subjects into the clinical trial is assessed on patient's eosinophil count and prior treatment. In some embodiments, the patients selected for the clinical trial have Peak eosinophil counts per HPF of greater than about 6, greater than about 10, greater than about 15, or greater than about 20. In some embodiments, the patients selected for the clinical trial have Peak eosinophil counts per HPF of greater than about 15. In some embodiments, the patients selected for the clinical trial have failed prior treatment. In some embodiments, the prior treatment was administration of a PPI over at least about 8 weeks that had not been effective to substantially improve one or more symptoms of EoE.

Purpose Bound Products

In keeping with the foregoing, the present disclosure provides an oral corticosteroid for use in a method of treating EoE in a patient, wherein the oral corticosteroid is administered immediately prior to the patient lying down or whilst the patient is lying down. In embodiments, a therapeutically effective amount of the oral corticosteroid contacts the patient's esophagus. The term "therapeutically effective amount" can mean an amount capable of eliciting beneficial biological activity in vivo and, in an embodiment, capable of treating EoE as measured using any of the metrics disclosed herein. The doses of oral corticosteroid disclosed herein suitably deliver a therapeutically effective amount of the oral corticosteroid to a patient.

The oral corticosteroid, method of treating and patient can all be as described herein. Indeed, any and all of the features as described herein for the disclosed compositions, methods of treatment, dosing, administration and patient populations can be employed in connection with the disclosed purpose-bound products. Any and all combinations of such features are explicitly encompassed by the disclosed invention, except combinations where at least some of such features are mutually exclusive.

Thus, in embodiments, the lying down may be in a supine, prone or laterally recumbent position.

The oral corticosteroid may be administered about 30 minutes or less before target sleep time. The oral corticosteroid may be administered at least about 30 minutes after a meal. In an embodiment, the patient may not eat or drink for at least about 30 minutes after administration of the oral corticosteroid.

The oral corticosteroid may be administered once daily. It may be administered twice daily, the first daily dose being administered whilst the patient remains upright.

The oral corticosteroid may be administered in a dose of from about 0.01 mg to about 20 mg. The oral corticosteroid may be fluticasone propionate, administered in a dose of from about 1.5 mg to about 7.5 mg, and preferably about 1.5, 3.0, 4.5, 6.0 or 7.5 mg.

In an embodiment, the patient may have a lactose allergy or a starch allergy.

The oral corticosteroid may have a systemic bioavailability of less than or equal to about 20%, less than about 15%, less than about 10%, less than about 5% or less than about 1% of its dose.

The oral corticosteroid may provide an average maximum blood plasma concentration (Cmax) of less than or equal to about 500 pg/mL after oral administration of from about 0.01 mg to about 20 mg of the oral corticosteroid.

The oral corticosteroid may provide an average $AUC_{0-24}$ of less than or equal to about 3,000 pg*h/mL of after oral administration of from about 0.01 mg to about 20 mg of the oral corticosteroid.

In embodiments the oral corticosteroid may be budesonide, fluticasone, flunisolide, ciclesonide, mometasone, tixocortol or beclomethasone, or a pharmaceutically acceptable salt, solvate, ester, polymorph or prodrug thereof.

In an embodiment, the oral corticosteroid may be formulated as a liquid composition. In another embodiment, it may be formulated as a solid composition. It may be formulated to form a solution or suspension prior to oral administration. It may be formulated to form a solution, suspension or gel upon oral administration. If formulated as a liquid composition, the oral corticosteroid may be in the form of a solution, suspension or slurry. If formulated as a solid composition, the oral corticosteroid may be in the form of a gel, lozenge, lollipop, effervescent tablet, powder, granules or an orally disintegrating composition. The orally disintegrating composition may be in the form of a tablet, wafer, film or lyophilized matrix.

In an embodiment, the oral corticosteroid is formulated as an orally disintegrating tablet comprising the oral corticosteroid in an amount of from about 1.5 mg to about 7.5 mg, a pharmaceutically acceptable carrier combined with the corticosteroid, and rapidly dispersing microgranules, wherein the orally disintegrating tablet disintegrates within 60 seconds when tested using the USP <701> Disintegration Test.

In an embodiment, the patient may have a Cmax of the oral corticosteroid of less than or equal to about 200 pg/mL following oral administration of from about 1.5 mg to about 7.5 mg of the oral corticosteroid.

The average time to reach a maximum blood plasma concentration (Tmax) of the oral corticosteroid may be in the range of from about 80% to about 125% of from about 12 h to about 15 h.

In an embodiment, the oral corticosteroid may be fluticasone propionate and the Cmax may be within the range of from about 80% to about 125% of from about 15 pg/mL to about 40 pg/mL following administration of 6 mg of fluticasone propionate or 3 mg of fluticasone propionate.

In embodiments, after 12 weeks of daily administration of the oral corticosteroid, esophageal inflammation may be reduced as measured by a reduction in eosinophil count, an increase in dysphagia-free days, a reduction in episodes of dysphagia, improvement in EREFS score, EndoFLIP documentation of improved esophageal compliance, evaluation of biomarkers, a decrease in episodes of food impaction, an improvement in EEsAI scores (patient, physician, endoscopy, pathology scores), EoE-QOL-A, Visual Dysphagia Questionnaire (VDQ), Avoidance Modification and Slow Eating (AMS) scores, or histology.

In an embodiment, the patient's eosinophil count may be reduced by at least about 50%.

Combination Therapies

The one or more therapeutic agents may be "co-administered", i.e., administered together in a coordinated fashion to a subject, either as separate pharmaceutical compositions or admixed in a single pharmaceutical composition. By "co-administered", the one or more therapeutic agents may also be administered simultaneously with the present pharmaceutical compositions, or be administered separately, including at different times and with different frequencies. The one or more therapeutic agents may be administered by any known route, such as orally, intravenously, intramuscularly, nasally, subcutaneously, intra-vaginally, intra-rectally, and the like; and the therapeutic agent may also be administered by any conventional route.

When two or more medicines are used in combination, dosage of each medicine is commonly identical to the dosage of the medicine when used independently, but when a medicine interferes with metabolism of other medicines, the dosage of each medicine is properly adjusted. Each medicine may be administered simultaneously or separately in an appropriate time interval.

The pharmaceutical compositions disclosed herein may be co-administered with various therapies used to treat, prevent, delay, and/or ameliorate inflammatory conditions of the gastrointestinal tract, including but not limited to inflammation of the esophagus, inflammation of the glottis, inflammation of the epiglottis, inflammation of the tonsils, inflammation of the oropharynx, eosinophilic esophagitis (EoE), gastroesophageal reflux disease (GERD), non-erosive reflux disease (NERD), erosive esophagitis, Barrett's esophagus, eosinophilic gastroenteritis, hypereosinophilic syndrome, corrosive (caustic) chemical esophagitis, radiation-induced esophagitis, chemotherapy-induced esophagitis, transient drug-induced esophagitis (also known as medication esophagitis), persistent drug-induced esophagitis, Crohn's disease of the esophagus, and pseudomembranous esophagitis.

The one or more therapeutic agents may be any compound, molecule, or substance that exerts therapeutic effect to a subject in need thereof.

In some embodiments, the pharmaceutical compositions disclosed herein are co-administered with one or more corticosteroids. Suitable corticosteroids include, but are not limited to hydrocortisone, prednisone, prednisolone, methylprednisolone, dexamethasone, betamethasone, etc. or mineralocorticoid potencies (e.g., alsosterone), budesonide, fluticasone, flunisolide, ciclesonide, mometasone, beclomethasone, tixocortol and salts, or esters and mixtures thereof.

In some embodiments, the pharmaceutical compositions disclosed herein are co-administered with one or more proton pump inhibitors (PPI). Suitable PPIs include, but are not limited to, omeprazole, lansoprazole, dexlansoprazole, rabeprazole, pantoprazole, and esomeprazole. In some embodiments the PPI is administered at high doses.

In some embodiments, the pharmaceutical compositions disclosed herein are co-administered with an antifungal agent. Suitable antifungal agents include, but are not limited to mitotic inhibitor antifungals, pyrimidine analog antifungals, polyene antifungals, benzimidazole antifungals, imidazole antifungals, polyene antifungals, triazole antifungals, thiazole antifungals, allylamine antifungals, echinocandin antifungals, and other "uncategorized" antifungals recognized in the art that do not fall within any of the above categories (e.g., tolnaflate and ciclopirox). For example, suitable antifungal agents which may be included in the solid pharmaceutical compositions of the present disclosure include abafungin, amorolfine, anidulafungin, bifonazole, butenafine, butoconazole, candicin, caspofungin, ciclopirox, clotrimazole, econazole, fenticonazole, filipin, fluconazole, flucytosine, griseofulvin, isavuconizole, isoconazole, itraconazole, ketoconazole, micafungin, miconazole, miconazole nitrate, naftifine, natamycin, nystatin, oxiconazole, posaconazole, pramiconazole, ravuconazole, rimocidin, setaconizole, sulconazole, terbafine, terconazole, tioconazole, tolnaftate, undecylenic acid, and voriconazole.

In other embodiments, pharmaceutical compositions disclosed herein are co-administered with an antiviral agent. Antiviral agents which may be used in the present disclosure include, but are not limited to, interferons, nucleoside and nucleotide reverse transcriptase inhibitors, non-nucleoside reverse transcriptase inhibitors, protease inhibitors, integrase inhibitors, fusion inhibitors, maturation inhibitors, guanosine analogs, puridine analogs, pyrimidine analogs, and other "uncategorized" antiviral drugs recognized in the art which do not fall within any of the above classes (e.g., foscarnet and miltefosine). For example, suitable antifungal agents which may be included in the solid pharmaceutical compositions of the present disclosure include abacavir, aciclovir (also known as acyclovir), adefovir, amantadine, amdoxovir, amprenavir, aplaviroc, apricitabine, arbidol, atazanavir, bevirimat, BMS-488043, boceprevir, brivudine, cidofo vir, DCM205, docosanol, delavirdine, didanosine, durunavir, efavirenz, elvitegravir, elvucitabine, emtricitabine, enfuvirtide, epigallocatechin gallate, etravirine, famciclovir, fosamprenavir, ganciclocvir, globoidnan A, griffithsin, ibalizumab, idoxuridine, indinavir, lamivudine, lopinavir, loviride, maraviroc, nelfinavir, nevirapine, oseltamivir, pegylated interferon alpha-2a, pegylated interferon alpha-2b, penciclovir, peramivir, plerixafor, PRO 140, racivir, raltegrvir, ritonavir, ribavirin, rimantadine, rlipivirine, saquinavir, stampidine, stavudine, tenofovir, tipranavir, TNX-355, trifluridine, tromantadine, valaciclovir, valganciclovir, vicriviroc, vidarabione, viramidine, vivecon, zalcitabine, zanamivir, and zidovudine.

In some embodiments, the pharmaceutical compositions disclosed herein are co-administered with one or more immunosuppressants. Suitable immunosuppressants include, but are not limited to, cyclosporine, tacrolimus, prednisolone, hydrocortisone, sirolimus, everolimus, azathioprine, mycophenolic acid, methotrexate, basiliximab, daclizumab, rituximab, anti-thymocyte globulin, and anti-lymphocyte globulin.

Kits

The disclosure also provides kits for the treatment of gastrointestinal inflammatory disorders. In some embodiments, the kits include a pharmaceutical composition of the present disclosure (fluticasone propionate, ODT) in unit dosage form. In some embodiments, the kits include 1.5 mg or 3.0 mg of a pharmaceutical composition of the present disclosure. In some embodiments, the kits include a maintenance dosage of a pharmaceutical composition of the present disclosure. In some embodiments, the kits include an induction dosage of a pharmaceutical composition of the present disclosure. In some embodiments, the kits include both an induction and a maintenance dosage of a pharmaceutical composition of the present disclosure. The kit can further include a label or printed instructions instructing the use of described reagents. The kit can further include a treatment to be tested.

INCORPORATION BY REFERENCE

All publications, patents, and patent publications cited are incorporated by reference herein in their entirety for all purposes.

This application incorporates by reference the following publications and applications in their entireties for all purposes: U.S. Pat. No. 8,771,729 filed Oct. 1, 2010; US 2016/0206627 filed Sep. 5, 2014, U.S. 61/874,450 filed Sep. 6, 2013, WO 2015/034678 filed Aug. 21, 2014, and WO 2015/035114 filed Sep. 5, 2014.

This disclosure is further illustrated by the following non-limiting examples.

EXAMPLES

Example 1—A Randomized, Double Blind Dose-Ranging Study of Fluticasone Propionate Oral Dissolving Tablet This Phase 2b study will enroll 320 patients with eosinophilic esophagitis (EoE) between the ages of 14-75. To be eligible for the study, patients must have a diagnosis of EoE (>15 peak eosinophil per HPF) after proven failure of 8 weeks or more of high-dose (i.e. 40 mg BID esomeprazole) proton pump inhibitor (PPI). PPI therapy may be continued during the study only if the subject was on PPI therapy at the time of enrolling in the study. No new initiation of, nor alteration of PPI therapy is allowed during the study. Subjects must also be symptomatic and have a 7-day recall Global EoE symptom score of ≥5 and a 7-day recall EEsAI score of >20 to enter the placebo run-in, and an increased EEsAI score based upon a daily diary.

Primary Objectives:

To evaluate the efficacy of fluticasone propionate oral disintegrating tablet (APT-1011) in adolescents and adults with eosinophilic esophagitis (EoE).

Secondary Objectives:

To evaluate the safety of APT-1011 (fluticasone propionate, ODT) in adolescents and adults with EoE. To define the dose-response of APT-1011. To evaluate the pharmacokinetics (PK) of APT-1011 in patients with EoE. To evaluate the effect of Treatment-Withdrawal, including time to relapse and effect of re-treatment. To evaluate maintenance of efficacy of treatment and long-term safety. To evaluate the effects on endoscopic appearance using the EoE Endoscopic Reference Score (ERES).

Study Rationale and Design:

Doses from 1.5 mg HS to 3.0 BID will be explored to define the exposure-response of APT-1011 and the minimum effective dose. This is a randomized, double-blind, placebo-controlled dose-ranging study of three daily doses (1.5 mg, 3 mg, and 6 mg) of APT-1011 administered as 1.5 mg HS, 1.5 mg BID, or 3.0 mg BID compared to matching placebo. The impact of treatment withdrawal, re-treatment, and long-term maintenance will also be evaluated.

The formulations of APT-1011 (fluticasone propionate, ODT) used in the clinical trials are listed in the following tables.

| | Fluticasone ODTs ODT | | | |
|---|---|---|---|---|
| | 1.5 mg | | 3 mg | |
| Ingredients | (%/tablet) | (mg/tablet) | (%/tablet) | (mg/tablet) |
| Micronized Fluticasone Propionate USP | 0.50 | 1.50 | 1.0 | 3.00 |
| Colloidal Silicon Dioxide NF | 0.30 | 0.90 | 0.30 | 0.90 |

-continued

| | 10.00 | 30.00 | 10.00 | 30.00 |
|---|---|---|---|---|
| Silicified Microcrystalline Cellulose NF | | | | |
| Crospovidone NF | 7.50 | 22.50 | 7.50 | 22.50 |
| Sucralose NF | 0.40 | 1.20 | 0.40 | 1.20 |
| Spray-dried Mannitol USP | 30.30 | 90.90 | 29.80 | 89.40 |
| Rapidly Dispersing Granules | 50.00 | 150.00 | 50.00 | 150.0 |
| Sodium Stearyl Fumarate NF | 1.00 | 3.00 | 1.00 | 3.00 |
| Total | 100.00 | 300.0 | 100.00 | 300.0 |

| | Fluticasone ODTs ODT | | | |
|---|---|---|---|---|
| | 0.75 mg | | 4.5 mg | 6.0 mg |
| Ingredients | (%/tablet) | (mg/tablet) | (mg/tablet) | (mg/tablet) |
| Micronized Fluticasone Propionate USP | 0.25 | 0.75 | 4.50 | 6.00 |
| Colloidal Silicon Dioxide NF | 0.30 | 0.90 | 0.90 | 0.90 |
| Silicified Microcrystalline Cellulose NF | 10.00 | 30.0 | 30.00 | 30.00 |
| Crospovidone NF | 7.50 | 22.50 | 22.50 | 22.50 |
| Sucralose NF | 0.40 | 1.20 | 1.20 | 1.20 |
| Spray-dried Mannitol USP | 30.05 | 90.15 | 86.40 | 84.90 |
| Rapidly Dispersing Granules | 50.00 | 150.00 | 150.00 | 150.0 |
| Sodium Stearyl Fumarate NF | 1.50 | 4.50 | 4.50 | 4.50 |
| Total | 100.00 | 300.0 | 300.0 | 300.0 |

Dosing:

For 3 dosing groups, APT-1011 will be provided as blinded tablets in dose strengths of 1.5 mg and 3.0 mg. For the fourth dosing group there will be a matching placebo. Tablets will be administered BID—30 minutes before breakfast and HS (at bedtime). Note that in the 1.5 mg dosing group, subjects will receive placebo tablets 30 minutes before breakfast, and 1.5 mg APT-1011 HS (at bedtime). To maintain the blind, all tablets will be labeled for "before breakfast" and "bedtime" administration.

Screening:

Subjects will be screened with upper endoscopy (EGD) at 2-4 weeks. Subjects who meet other inclusion criteria and have ≥15 peak eosinophil per HPF and have a global symptom score of >5 and a 7-day recall EEsAI score of >20 may enter the placebo run-in. Subjects who have an increased EEsAI score based upon a daily diary, >80% compliance daily diary, and >90% compliance with study drug and meet all the other inclusion criteria will be randomized. Subjects will be randomized 1:1:1:1 to 3 active doses and placebo.

Figure 2:
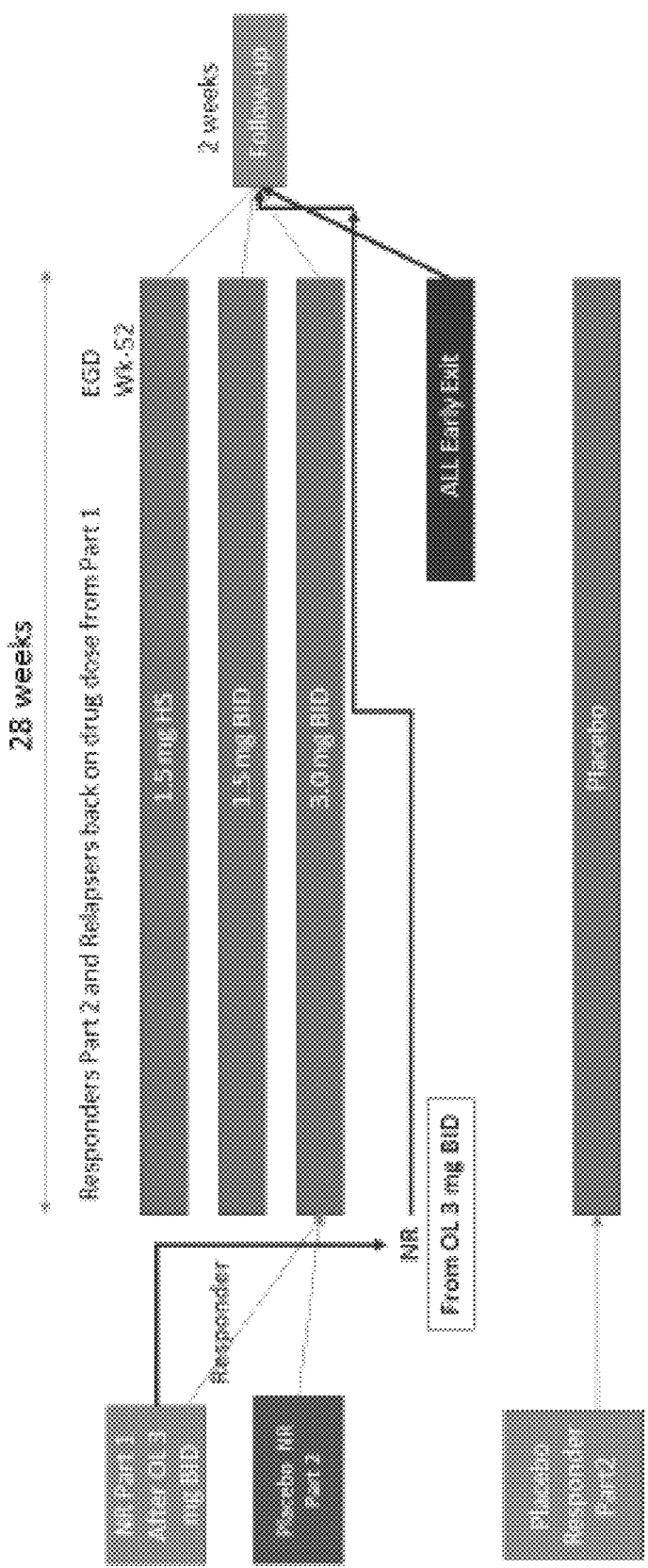
FIG. 2 shows an exemplary schematic overview of Part 3 (maintenance) and follow-up of a Phase 2b study.

The study will be conducted in three parts as shown in FIGS. 1 and 2. Part 1 and Part 2 represent a Treatment-Withdrawal Design. In Part 1, treatment efficacy is assessed. In Part 2, the effect of withdrawal is assessed including Time to Relapse and difference in relapse rates between active treatment and placebo.

Part 1: Treatment (Day 1 to Week 14).

Subjects will be stratified by age (<18 and ≥18 years) and by concomitant PPI use during the study ("yes" or "no"); then randomly assigned to 1 of the 4 dosing groups (ratio: 1:1:1:1).

All subjects will come in monthly for routine visits, and for unscheduled visits should symptoms worsen between visits. Subjects will be treated for 12 weeks and undergo an EGD to assess histologic and endoscopic improvement. Symptom improvement will be assessed on an ongoing basis. EoE Responders, defined as subjects who achieve a histologic response of <6 Peak Eos per HPF, and no worsening of symptoms (e.g. an increase in weekly EEsAI score compared to baseline) or episodes of food impaction will be re-randomized to Part 2 at week 14. Non-Responders, defined as subjects who do not meet the definition of Response, will receive open-label (OL) 3 mg BID until week 28 with an EGD at week 28. EoE Responders at the end of the OL period will be eligible to enter Part 3. Non-responders to OL treatment will enter a 2-week follow-up period.

Part 2: Treatment-Withdrawal (Week 14 to Week 28).

EoE Responders from Part 1 will be randomized to either continue their dose or receive placebo in a 3:1 randomization. Placebo responders, which are expected to be few, will remain on placebo. Subjects who experience a worsening of symptoms (e.g. return to baseline weekly EEsAI score or complain of symptoms worsening) or food impaction will undergo endoscopy at an unscheduled visit. Subjects with food impaction requiring endoscopy or a stricture requiring dilation will enter the 2-week follow-up period and exit the study. Subjects deemed to be a relapse will be returned to their previous dose, except those previously on placebo who will receive 3 mg BID. Subjects who relapse on Study Drug will also receive 3 mg BID to avoid unblinding the study. The relapsers will enter Part 3. All subjects in the study at weeks 12, 26 and 52 will undergo endoscopy. EoE Responders at week 28 will continue to Part 3. Non-responders at the end of Part 2 will receive 3 mg BID when they enter Part 3.

Part 3: Maintenance (Week 28 to Week 54).

Non-Responders from Part 1 who respond to open-label 3 mg BID will continue on this dose in Part 3. Note that this group will not participate in Part 2. EoE responders from Part 2 will continue on the same dose. Relapsers and non-responders from Part 2 will receive 3 mg BID in Part 3. Subjects who relapse (e.g. experience food impaction requiring endoscopy or clinically-significant worsening of symptoms) in Part 3 will undergo an unscheduled endoscopy, enter the 2-week follow-up, and exit the study. All continuing subjects will undergo endoscopy at week 52 and complete their final on treatment visit at week 54.

Follow-Up: (2-Weeks after Last Dose).

All subjects must have a final endoscopy within 3 weeks prior to entering follow-up. Exceptions include withdrawal of consent or contra-indication to endoscopy. Reasons for entering follow-up include completing week 54, adverse event requiring early withdrawal including food impaction requiring endoscopy, failed to respond to open-label 3 mg BID, or relapsed in Part 3.

Pharmacokinetics:

All doses of APT-1011 will be administered twice daily 30 minutes before breakfast and bedtime with the exception of the 1.5 mg dose, which will be administered HS at bedtime or 30 minutes before breakfast. A population PK analysis will be performed based on a combination of serial and sparse plasma concentration data.

Population PK: Sparse PK samples will be collected from all subjects (excluding subject +/−3 days) of repeat dosing. On Week 4, Day 1 (+/−3 days) of the repeat-dose period, PK samples will be collected no more than 15 minutes prior to the morning dose, and at 0.5, 1.5, and 3 hours following the morning dose. The time of the night-time dosing (e.g. bedtime) along with actual PK sampling time will be documented.

Intensive PK Subset to be Performed in Part 1:

At selected sites, 24 evaluable subjects (6 subjects per dose group) will undergo intensive serial PK sampling following a single dose on Week 1, Day 1 and following repeat-dose administration on Week 4, Day 1 (+/−3 days). On the morning of Week 1, Day 1, subjects will receive a single dose of APT-1011 and PK samples will be collected no more than 15 minutes prior to the AM dose and at 0.5, 1, 2, 4, 8, 24, and 48 hours following dose administration. NOTE: the 48-hour sample should be collected following the single dose and prior to the start of the repeat-dose period. This sample would be collected on the visit when subjects return to receive medication for the repeat-dose outpatient period.

The repeat-dose period will start following collection of the 48-hour PK sample on Week 1 Day 3. On Week 4, Day 1 (+/−3 days) of the repeat-dose period PK samples will be collected no more than 15 minutes prior to AM dose and at 0.5, 1, 2, 4, 8 and 12 hours post AM dose, immediately prior to PM dose. NOTE: the 12-hour post AM dose PK sample is 'Optional'. The 12-hour PK sample should be collected immediately prior to the PM dose. Time of dosing (bedtime the preceding night and following morning) along with actual PK sampling times will be documented).

Study Duration:

This study has an anticipated recruitment period of 12 months.

Subjects who enter and complete the study (Part 1, Part 2 and Part 3) will be in the study for up to 15 months.

Study Population:

The study will enroll approximately 320 adolescent and adult subjects diagnosed with EoE who meet the entry criteria and will randomize subjects into 1 of 4 dosing groups (including placebo) of 80 subjects per dosing group.

Inclusion Criteria:

Male and female subjects between the ages of 14 and 75 inclusive. Patients must have a diagnosis or presumptive diagnosis of EoE, including those patients with relapse, must be confirmed by symptoms and histology; by historical documentation of failed treatment on 8 weeks or more of high-dose (e.g. 40 mg BID) proton pump inhibitor (PPI) either prior to initial diagnosis or documented subsequently. A lack of response to PPI therapy is defined as a peak eosinophil count ≥15 per HPF in at least one biopsied location after the 8 weeks of high dose treatment. PPI therapy may be continued during the study only if the subject was on PPI therapy at the time of biopsies from the screening endoscopy. No new initiation of, nor alteration of PPI therapy is allowed during the study.

Subjects must have evidence of eosinophilic esophagitis defined by the PEAK esophageal mucosal eosinophil count ≥15 per high-powered field (HPF, 400× magnification) in at least 1 of the esophageal sites biopsied (≥3 biopsies from each the proximal and the distal esophagus; a minimum of 6 total biopsies). Biopsies are to be obtained no more than 30 days prior to the Screening Visit, and slides must be received by the central pathologist within 30 days after the Screening Visit or 2 weeks prior to randomization. Eligibility will be based solely on the central pathologist's assessment.

The subjects must have a 7-day recall Global EoE score ≥5, as measured on a scale from 0 to 10 (0 representing no symptoms and 10 representing most severe symptoms).

Subjects must have 7-day recall EEsAI score >20 to enter the placebo run-in. For randomization, an increased EEsAI score based upon a daily diary is required and clinical symptoms of dysphagia (difficulty swallowing) at least 3 times per week within 2 weeks.

Exclusion Criteria:

Known contraindication, hypersensitivity or intolerance to corticosteroids; any physical, mental, or social condition, history of illness or laboratory abnormality that in the investigator's judgment might interfere with study procedures or the ability of the subject to adhere to and complete the study; presence of oral or esophageal mucosal infection of any type; any condition affecting the esophageal mucosa or altering esophageal motility other than EoE including erosive esophagitis, hiatus hernia longer than 3 cm, and Barrett's esophagus; use of systemic, oral or parenteral corticosteroids within 30 days, or inhaled or extended use of high-potency dermal topical corticosteroids within 30 days prior to: the esophageal biopsy required for entrance to this study or EGD if done during the pre-screening period; morning (0700 to 0800 hours, or as close to that window as possible) serum cortisol level ≤5 µg/dL (138 nmol/L); a plasma cortisol level of <18 µg/mL (497 nmol/L) at 60 minutes with adrenocorticotropic hormone (ACTH) stimulation test using 250 µg cosyntropin, consumption of grapefruit juice during the treatment is prohibited; use of biologic immunomodulators within the past 6 months; use of calcineurin inhibitors, purine analogues (azathioprine, 6-mercaptopurine) within the past 3 months; contraindication to EGD or esophageal biopsy or narrowing of the esophagus precluding EGD with a standard 9 mm endoscope; gastrointestinal bleeding within 1 month prior to the Screening Visit or between the Screening Visit and the Randomization Visit; current chronic infection, immunosuppression, or immunodeficiency; history or presence of Crohn's disease, celiac disease, or other inflammatory disease of the gastrointestinal tract including eosinophilic gastroenteritis; current alcohol or drug abuse; female subjects who are pregnant or breastfeeding; sexually active females of child-bearing potential who do not agree to follow highly effective contraceptive methods during the study including the follow-up period. (abstinence is acceptable for adolescents); female subjects with surgical menopause or menopause confirmed by FSH do not require contraception or pregnancy testing during the study; participation in a clinical study involving an investigational drug within 30 days of the Screening Visit.

Methodology/Study Procedures are shown in Tables 4-7.

Primary Efficacy Endpoints:

There are 2 co-primary efficacy endpoints for EoE Response

The percentage of subjects with a PEAK eosinophil count <6/HPF at all biopsied esophageal locations at Week 12 and change from baseline in mean weekly EEsAI score. EoE Endoscopic Response and no worsening of the mean weekly EEsAI score will be the basis for entering Part 2.

Secondary Efficacy Endpoints:

EoE Response will be assessed also at week 26 with comparisons to placebo to assess the impact of treatment-withdrawal. EoE Response will also be assessed at week 52 by dose and subgroup. EoE Remission and Response will also be assessed after 12 weeks of OL treatment in non-responders to Part 1.

Sustained EoE Response will be assessed at Weeks 24 and 52 for subjects remaining on the same dose: Assessment of Relapse and Treatment Failure; non-Response at each endoscopic endpoint; relapse on Placebo in Part 2; percentage of subjects requiring emergency endoscopic food disimpaction by dose and part of the study; percentage of subjects requiring esophageal dilation.

The effect of re-treatment will be assessed by assessing EoE Response in Part 2 Relapsers at week 52 by treatment group.

The percent of subjects with PEAK Eos per HPF <1 and <15 at all major time points where EoE Response is assessed The percent of subjects with mean weekly EEsAI score <20 at all major time points where EoE Response is assessed Endoscopic changes will be based upon the EREFS score based on 5 endoscopic features: edema, furrowing, exudates, rings, strictures and physician assessment of overall disease activity (absent, mild, moderate, severe): the percentage of subjects with overall assessment of 'improved', 'no change' and 'worsened' from baseline (Screening Visit) at Week 12, 26 and 52 as well as at the end of OL treatment of non-responders from Part 1; the change from baseline in 7-day Global EoE Score which will be assessed before run-in, baseline, week 12, week 26 and week 52.

Pharmacokinetic Endpoints:

Steady-state Population PK (sparse PK and intensive PK) analyses; single-dose PK analyses.

Exploratory Endpoints:

Collin's Histologic Score for EoE for all biopsies performed, the change from baseline will be assessed; evaluation of quality of life based on the EoE-QOL-A at week 12, 26, 52 and week 12 of OL treatment by dose and subgroup; patient's assessment of symptoms compared to the previous visit. This Question will be assessed at weeks 8, 12, 18, 26, 30 and 52.

Safety:

Safety will be assessed by monitoring and recording all treatment-emergent adverse events (TEAEs), TEAEs leading to withdrawal and serious adverse events (SAEs). All TEAEs will be coded based upon the MedDRA version 14.0 classification of adverse events (AEs) and classified by severity (mild, moderate, severe) and relatedness to study drug (related or not related) by the Investigator. TEAEs occurring within 2 days of a dose change will be attributed to the previous dose. This time of attribution may be altered based on the half-life of the dose. Physical examinations will be performed to document the baseline condition of the subject and to highlight changes related. to AEs. Vital signs will also be assessed at all visits and clinically significant deviations will be reported.

Routine laboratory tests will be performed throughout the study including hematology, blood chemistry, urinalysis, electrocardiograms (ECGs) as indicated in the Schedules of Assessments. Clinically significant changes in laboratory tests or ECGs will be summarized.

Cortisol Issues:

Abnormal AM cortisol, urinary glucose or serum glucose would necessitate following the subject to resolution. CRFs should capture presence or absence of known glucocorticoid AEs such as moon facies, acne, hirsutism, mood swings, insomnia or depression. ICF should highlight that stress steroids may be required during significant medical illnesses. ACTH stimulation test (cosyntropin 250 mcg) should be performed at baseline and Week 12, early withdrawal and at week 52 for all subjects. ACTH test should be performed in all subjects with plasma cortisol >5 mcg/dL (138 mmol/L). All subjects with positive tests should be excluded. Any positive results at the end of treatment should be followed to recovery of adrenal function. The number of subjects discontinuing for HPA suppression or positive ACTH stimulation tests will be summarized. The Sponsor will provide each site and investigator with guidelines for safety follow-up and document restoration of adrenal function in all subjects demonstrating evidence of hypercorticism or HPA axis suppression during the course of the study. Subjects under age 18 will be evaluated for growth parameters such as height, weight, body mass index (BMI) and corresponding z-scores. The safety endpoints of interest are: frequency of treatment emergent adverse events (TEAEs), TEAEs leading to withdrawal and treatment-emergent serious adverse events (SAEs), as well as the percentage of subjects with serum cortisol level ≤5 µg/dL (138 nmol/L) or positive ACTH stimulation test (serum cortisol <18 µg/mL (497 nmol/L) at 60 minutes). The number of subjects discontinuing for HPA axis suppression will be recorded.

Statistical Methods: Sample Size Determination:

For Part 1, sample size determination is based on the planned comparisons between each dosing group with respect to EOE Response: 1) the percentage of subjects with a peak eosinophil count <6 Eosinophil/HPF at all biopsied esophageal locations at Week 12; and 2) Change from baseline in EEsAI score. If for the present study, after 12 weeks of treatment, the percentage of placebo treated subjects with a peak eosinophil count <6/HPF at all biopsied esophageal locations is assumed to be 15% for placebo and 60% for active arms with an expected delta of 45. For the mean weekly EEsAI score, the EoE Response for symptoms at week 12, we assume a placebo rate of 35% with an expected efficacy of 65% in the active arms with an expected delta of 30%. Based upon an equal randomization, approximately 60% of subjects will enter Part 2 of the study. In order to ensure that the sample size is sufficient to detect a delta of 30% in Part 1 and to ensure sufficient subjects enter PART 2 for analysis assuming 20% of active and 80% of placebo develop a symptomatic relapse, a minimum of 320 subjects will be enrolled (80 per arm). With 320 per arm, assuming and overall dropout rate of 20%, we assume that approximately 35 subjects per active arm will be evaluable for assessment of sustained remission at week 52.

The primary analysis population for efficacy is the intent-to-treat (ITT) population, defined as all randomized subjects. The analysis population for safety is the safety population, defined as all subjects who receive at least one dose of study drug. The single-dose PK population will be defined as all subjects in the ITT population of PART 1 who are randomized to one of the three APT-1011 dosing groups, take their first dose of APT-1011, and have at least one PK sample included in the final single-dose population PK analysis. The steady-state PK population will be defined as all subjects in the ITT population of PART 1 who are randomized to one of the three APT-1011 arms, take their dose of APT-1011 that corresponds to the steady-state PK sampling period, and have at least one PK sample included in the final steady-state population PK analysis. Additional per protocol analysis populations who complete Parts 1, 2, and 3 and OL treatment may be defined in the Statistical Analysis Plan (SAP). Baseline and demographic information will be summarized using descriptive statistics for continuous and ordinal variables (e.g., age, weight, height) and counts and percentages for categorical variables (e.g., sex, race).

Primary Efficacy for Part 1

There are two co-primary efficacy endpoints for PART 1: the percentage of subjects with a peak eosinophil count <6/HPF at all biopsied esophageal locations at Week 12; and the change from baseline in mean weekly EEsAI score at week 12. To preserve the overall level of significance at 0.05 for the study, each of the two co-primary efficacy endpoints will be assessed at the 0.05 level.

For each co-primary endpoint, the primary treatment comparisons of interest are the comparisons of each APT-1011 dosing group versus placebo. The efficacy hypotheses of APT-1011 versus placebo will be tested in the following order:

$H_0$: µ of APT-1011 3.0 mg BID=µ of placebo
$H_0$: µ of APT-1011 1.5 mg BID=µ of placebo
$H_0$: µ of APT-1011 1.5 mg HS=µ of placebo where µ denotes the proportion of subjects with a peak eosinophil count <15/HPF at all biopsied esophageal locations at Week 12 for one co-primary efficacy end-point and µ denotes the change from baseline in mean weekly EEsAI score at Week 12 for the other co-primary efficacy endpoint.

The statistical testing will begin with the comparison of APT-1011 3.0 mg BID vs. placebo with respect to each of the two co-primary efficacy endpoints. If both comparisons are statistically significant at the 0.05 level, the next lower dose will be tested vs. placebo for both co-primary efficacy endpoints. The procedure stops after the first pair-wise comparison yields a non-statistically significant result for one or both of the co-primary efficacy endpoints. Since statistical testing of treatment differences between APT-1011 and placebo is to be performed by means of a priori ordered hypotheses, no adjustment of the significance level for multiplicity is required.

The pair-wise comparisons between each APT-1011 arm and placebo with respect to the proportion of subjects with a peak eosinophil count <6/HPF at all biopsied esophageal locations at Week 12 will be performed using the Cochran-Mantel-Haenszel (CMH) test adjusting for the two randomization stratification factors: age group and PPI use; and also geographic region (North America; non-North America). The pair-wise comparisons between each APT-1011 arm and placebo with respect to the change from baseline in mean weekly EEsAI score at week 12 will be performed by comparing the corresponding least squares means from an analysis of covariance (ANCOVA) with treatment, the two randomization stratification factors, and the geographic region in the model as fixed effects and the baseline SQ score as a covariate. The method will be used to adjust for multiple comparisons. The sample size has been increased accordingly.

If superiority of at least one of the APT-1011 dose groups over placebo is demonstrated for the two co-primary endpoints, the dose-response relationship will be assessed for the two co-primary endpoints with total daily dose among the explanatory variables in the appropriate statistical models.

Efficacy for OL Treatment

A similar approach will be taken as in Part 1 for non-responders from Part 1 who receive OL treatment with 3.0 mg BID.

Efficacy for Part 2

There is one primary efficacy endpoint for PART 2, the percentage of subjects who relapse on or before the end of the double-blind treatment in PART 2, defined as a return to baseline in EEsAI score or a verbal complaint that "My symptoms have worsened and are about the same as when I entered the study") and a peak eosinophil count ≥15/HPF in at least one biopsied esophageal location on or before the end of the assessment at week 26 Part 2. To preserve the overall level of significance at 0.05 for the study, the statistical testing for the efficacy endpoint in PART 2 will be performed only if statistical significance in favor of at least one APT-1011 dosing group over placebo is demonstrated for the two PART 1 co-primary efficacy endpoints. The efficacy hypothesis of APT-1011 3.0 mg QD versus placebo is as follows:

$H_0$: µ of APT-1011 3.0 mg QD=µ of placebo where µ denotes the proportion of subjects who relapse on or before the end of the 12-week double-blind treatment in PART 2. The test will be conducted at the 0.05 level of significance using the CMH test adjusting for the two randomization stratification factors (from Part 1), geographic region, and the prior treatment the subject was on before being randomized into double-blind treatment in PART 2. The prior treatments are placebo, APT-1011 1.5 mg QD, 1.5 mg BID, and 3.0 mg BID for randomized subjects in Part 1.

Efficacy for Part 3

Sustained EoE Response will be assessed in the subgroup of subjects who achieved EoE Response in Part 1 and Part 2 and who complete the week 52 evaluations.

Secondary and Exploratory Efficacy

Statistical tests to compare each APT-1011 dosing group to placebo will be performed for the secondary efficacy endpoints, but the corresponding p-values will be considered as descriptive rather than inferential. The secondary endpoints will be analyzed in the same manner as described above for the primary efficacy endpoints, namely, using CMH test for categorical endpoints and ANCOVA for change or percentage change from baseline endpoints, except for the endpoint of time to relapse after initiation of double-blind treatment in PART 2, which will be analyzed using Kaplan-Meier methods. No statistical testing of exploratory efficacy endpoints will be performed.

Safety

The incidence of TEAEs will be summarized by system organ class and preferred term. Separate summaries by maximum severity and relationship to study drug will be provided. The incidence of TEAEs leading to withdrawal from the study and treatment-emergent SAEs will also be summarized. In subjects who change dose groups, the TEAEs will be attributed to the previous dose, if they occur within 2 days of the change. The attribution period may be altered depending on the half-life of the dose. Clinically significant changes of potential clinical interest in clinical tests will be summarized including hematology, chemistry, urinalysis, ECG, cortisol, vital signs, growth-related assessments for adolescents, and bone mineral density. No statistical testing of safety endpoints will be performed. Shift tables may be performed, if needed.

Pharmacokinetics and Pharmacodynamics Analysis

In this study, all doses of APT-1011 will be administered twice daily (before breakfast and at bedtime) with the exception of 1.5 mg daily, which will be administered QD at bedtime with placebo administered after breakfast. A population PK analysis will be performed based on a combination of serial and sparse plasma concentration data. Previous serial PK data for APT-1011 may be included in this analysis to facilitate development of a base PK model.

Population PK analysis will be performed using the nonlinear mixed-effects software, NONMEM, Version 7.2.0 or later (ICON Development Solutions, Ellicott City, Md.) or other appropriate nonlinear mixed-effects modeling software. The structural PK model will include CL/F and V/F as fixed-effect parameters. In addition, the between-subject (intersubject) variability in the parameter estimates and the random residual error in the data will be estimated with appropriate error models. The optimal base model will be selected according to the standard criteria such as minimum objective function value and diagnostic plots. Given the relatively small number of subjects in this study, a covariate analysis is not planned. The relevant information from bioanalytical and clinical databases (e.g., dosing times and sampling times) will be extracted and integrated for generation of the population PK input file(s). All possible efforts will be made to capture any missing information. Any additional information obtained regarding missing data and the procedures followed to handle any missing data will be documented and discussed in the clinical study report. After the final model is constructed, secondary parameters such as AUC and Cmax will be calculated to characterize the extent of FP systemic exposure. Additional simulations may be performed, as necessary, to inform decision making for future studies. In general, the simulation step will include creation of data files using dummy subjects with desired sampling times and dosing regimens, running simulation with desired number of replicates using the final model output parameters in the control file. The output from the final population models including appropriate diagnostic plots, listings, and summaries of PK parameters will be generated. In addition, graphical and tabular presentations of any PK simulations will be produced.

As data permit, exploratory analyses assessing the relationship between systemic exposure to FP and changes in cortisol levels also may be performed as described above. Potential exploratory PK/PD analyses will be used to facilitate selection of safe and effective doses for future studies.

TABLE 4

Schedule of Assessments: Screening through PART 1

| Assessments and Procedures | VISIT | | | | | | | | |
|---|---|---|---|---|---|---|---|---|---|
| | Screening | Run-In | Randomization | Week 4 | Week 8 | Week 12 | Week 14 | Unscheduled Visit[c] | Early Withdrawal[b] |
| | | | | DAY | | | | | |
| | −56 to −29 | −28 to −1 | 1 | 28 ± 3 | 56 ± 3 | 84 ± 3 | 98 ± 3 | | |
| Informed consent signed | X | | | | | | | | |
| Inclusion/exclusion criteria | X | | X[d] | | | | | | |
| Demographics, medical, surgical history, medication history | X | | | | | | | | |
| Concomitant medication(s) | X | X | X | X | X | X | | X | X |
| Physical examination | X | | X | X | X | X | | X | X |
| Vital signs | X | X | X | X | X | X | | X | X |
| Chemistry; Hematology; LFTs | X | | X | X | X | X | | X | X |
| Serum cortisol (AM fasting)[e] | X | | X | X | X | X | Results[f] | optional | X |
| Urinalysis | X | | X | X | X | X | | X | X |
| Electrocardiogram - Standard 12-lead | X | | X | | | X | | | X |
| Population Pharmacokinetics | | | X[g] Pre-Dose | X[g] | X[g] | X[g] | X[g] | | |
| Intensive PK | | | X[h] Pre-Dose | X[h] | | | | | |
| EGD with multiple esophageal biopsies[a,i] | X | | | | | X | | | X[m] |
| EndoFlip will be performed at selected sites at the time of endoscopy as part of a substudy | | | | | | | | | |
| Urine pregnancy test for women of CBP Menopausal women FSH at screening only | X | | X | X | X | X | | | X |
| ACTH stimulation test (250 μg)[k] | X | | | | | X | | Optional[k] | X |

TABLE 4-continued

Schedule of Assessments: Screening through PART 1

| Assessments and Procedures | Screening | Run-In | Randomization | Week 4 | Week 8 | Week 12 | Week 14 | Unscheduled Visit[c] | Early Withdrawal[b] |
|---|---|---|---|---|---|---|---|---|---|
| | | | | DAY | | | | | |
| | −56 to −29 | −28 to −1 | 1 | 28 ± 3 | 56 ± 3 | 84 ± 3 | 98 ± 3 | | |
| Adverse events | X | X | X | X | X | X | X | X | X |
| Global EoE Score | X | | X | | | | X | | |
| 7-day EEsAI | X | | X | X | X | X | X | | X |
| EEsAI Daily | | X | X | X | X | X | X | | X |
| EoE-QOL-A and Global EoE Symptoms | X | | X | | | X | X | | X |
| Bone Age[m] | X | | | | | | | | |
| Study Drug Dispensed | | X All placebo BID | X | X | X | X | | | |
| Drug return and accountability (Study Drug compliance assessment) | | | X | X | X | X | X | | X |
| Daily Diary Compliance Assessment | | | X | | | | | | |

[a] Endoscopy may be performed at a separate visit. Results of histology will be required at randomization and week 14.

[b] Patient should be seen in the office within 7 days of determination of the need to withdraw the patient. If this is not possible due to an SAE or other unforeseen circumstance, visit may be completed with a phone visit with the patient or family member. Documentation of why the patient could not come in should be placed in the patient record.

[c] The reason for an unscheduled visit will guide procedures, at the discretion of the PI.

[d] Confirmation that the patient still meets inclusion/exclusion criteria based upon Daily EEsAI in addition to other criteria

[e] To be drawn as close as possible to 0800 hours. Patients must be fasting for an eight (8)-hour period prior to the serum cortisol assessments. Blood may be drawn for AM Serum Cortisol +/− 2 days of scheduled visit to accommodate accurate timing. Other blood draws scheduled for the visit may be done at the same time.

[f] If abnormal serum cortisol level is reported at Final on treatment Visit; additional monitoring and ACTH test may be required.

[g] A sample will be obtained at Week 4 in all subjects excluding those in the intensive PK subset, no more than 15 minutes prior to the AM dose and at 0.5, 1.5 and 3 hours following the AM dose. The time of the PM dose (bedtime preceding) and AM dose along with actual PK sampling will be documented.

[h] Approximately 6 subjects per dose group will undergo intensive PK at selected sites between Weeks 2 and 4: PK samples will be collected no more than 15 minutes prior to AM dose and at 0.5, 1, 2, 4, 8 and 12 hours post AM dose, immediately prior to PM dose. NOTE: the 12-hour post AM dose PK sample is 'Optional'. The 12-hour PK sample should be collected immediately prior to the PM dose. The time of the PM dose (bedtime preceding) and AM dose along with actual PK sampling will be documented.

[i] Can be done up to 30 days prior to Screening Visit (in absence of systemic or inhaled, intranasal or high-potency dermal topical corticosteroids within these 30 days prior to the Screening Visit). If a previous histology is considered not acceptable, an additional Screening Visit must be scheduled to perform EGD and biopsies during the Screening Period. The results from the central pathologist must be available before randomization. EREFS must be available or able to be performed from an endoscopy report for any standard of care endoscopies as well.

[j] If the patient is withdrawing from the study due to lack of efficacy or other reasons, the Investigator may perform an EGD, if clinically indicated.

[k] All subjects undergo a 250 μg ACTH stimulation test at baseline and EOT or at early withdrawal. An ACTH simulation test will also be performed during the study at an optional visit for subjects whose serum cortisol level is confirmed by two blood draws as ≤5 μg/dL (138 nmol/L) or if they have signs and symptoms of hypercortism to assess for hypophyseal-pituitary-adrenal (HPA) axis suppression of potential clinical concern.

[l] Bone age to be performed on all adolescents (<18 years of age at randomization); exceptions include female subjects who have completed their linear growth or male subject who have not completed their liner growth by 18 years of age, at the discretion of the PI.

TABLE 5

Schedule of Assessments: PART 2

| Assessments and Procedures | Week 14 Randomization | Week 18 | Week 22 | Week 26 | Week 28 | Unscheduled Visit[c] | Early Withdrawal[b] |
|---|---|---|---|---|---|---|---|
| | | | | DAY | | | |
| | 98 + 3 | 126 ± 3 | 154 ± 3 | 192 ± 3 | 220 ± 3 | | |
| EoE Responder in PART 1 No contra-indications to continue >80% compliant with diary | X | | | | | | |

TABLE 5-continued

Schedule of Assessments: PART 2

| Assessments and Procedures | Week 14 Randomization 98 + 3 | Week 18 126 ± 3 | Week 22 154 ± 3 | Week 26 192 ± 3 | Week 28 220 ± 3 | Unscheduled Visit[c] | Early Withdrawal[b] |
|---|---|---|---|---|---|---|---|
| >90% compliant with drug | | | | | | | |
| Concomitant medication(s) | TR Week 12 | X | X | X | X | X | X |
| Physical examination | TR Week 12 | X | | X | | X | X |
| Vital signs | TR week 12 | X | X | X | X | X | X |
| Chemistry; Hematology; LFTs | TR week 12 | X | X | X | | X | X |
| Serum cortisol (AM fasting)[e] | TR week 12 | X | X | X | Results[f] | optional | X |
| Urinalysis | TR week 12 | X | X | X | | X | X |
| Electrocardiogram - Standard 12-lead | TR week 12 | | | X | | | X |
| Population Pharmacokinetics (Needed?) | | | | | | | |
| EGD with multiple esophageal biopsies[a,i] | TR Week 12 | | | | Results | X | |
| EndoFlip at selected sites as part of a substudy | | | | | | | |
| ACTH stimulation test (250 µg)[k] | TR Week 12 | | | X | Results | Optional[k] | X |
| Adverse events | X | X | X | X | X | X | X |
| 7-day EEsAI | X | X | X | X | X | X | X |
| EEsAI Daily | X | X | X | X | | | X |
| Global EoE Score | X | | | X | | | X |
| EoE-QOL-A and Global EoE Symptoms | X | | | X | | | X |
| Study Drug Dispensed | X | X | X | X | | | |
| Drug return and accountability (Study Drug compliance assessment) | | X | X | X | X | | X |

TABLE 6

Schedule of Assessments: OL Treatment

| Assessments and Procedures | Week 14 98 + 3 | Week 18 126 ± 3 | Week 22 154 ± 3 | Week 26 192 ± 3 | Week 28 220 ± 3 | Unscheduled Visit[c] | Early Withdrawal[b] |
|---|---|---|---|---|---|---|---|
| EoE NON-Responder in PART 1 | X | | | | | | |
| >80% compliant with diary | | | | | | | |
| >90% compliant with study drug | | | | | | | |
| Concomitant medication(s) | TR from Part 1 | X | X | X | | X | X |
| Physical examination | TR from Part 1 | X | X | X | | X | X |
| Vital signs | TR from Part 1 | X | X | X | | X | X |

TABLE 6-continued

Schedule of Assessments: OL Treatment

| Assessments and Procedures | Week 14 / 98 + 3 | Week 18 / 126 ± 3 | Week 22 / 154 ± 3 | Week 26 / 192 ± 3 | Week 28 / 220 ± 3 | Unscheduled Visit[c] | Early Withdrawal[b] |
|---|---|---|---|---|---|---|---|
| Chemistry; Hematology; LFTs | TR from Part 1 | X | X | X | | X | X |
| Serum cortisol (AM fasting)[e] | TR from Part 1 | X | X | X | Results[f] | optional | X |
| Urinalysis | TR from Part 1 | X | X | X | | X | X |
| Electrocardiogram - Standard 12-lead | TR from Part 1 | | | X | | | X |
| Population Pharmacokinetics (Needed?) | | | | | | | |
| Intensive PK (Needed?) | | | | | | | |
| EGD with multiple esophageal biopsies[a,j] | TR from Part 1 | | | | | X | |
| EndoFlip at selected sites as part of substudy | | | | | | | |
| Urine pregnancy test for women of CBP | X | X | X | X | | | X |
| ACTH stimulation test (250 μg)[k] | | | | X | | Optional[k] | X |
| Adverse events | X | X | X | X | X | X | X |
| 7-day EEsAI | X | X | X | X | X | X | X |
| EEsAI Daily | X | X | X | X | | | X |
| Global EoE Score | X | | | X | | | X |
| EoE-QOL-A and Global EoE Symptoms | X | | | X | | | X |
| Study Drug Dispensed | X | X | X | X | | | |
| Drug return and accountability (Study Drug compliance assessment) | | X | X | X | X | | X |

TABLE 7

Schedule of Assessment: PART 3

| Assessments and Procedures | Week 28 Randomization Or assigned dose / 220 + 3 | Week 32 / 126 ± 3 | Week 36, 40, 44, 48 / 154 ± 3 | Week 52 / 192 ± 3 | Week 54 / 220 ± 3 | Unscheduled Visit[c] | Early Withdrawal[b] | Follow-up Any subject with Early Withdrawal / 2 weeks after last dose |
|---|---|---|---|---|---|---|---|---|
| Inclusion Criteria for PART 3[o] | X | | | | | | | |
| Concomitant medication(s) | TR week 26 | X | X | X | | X | X | X |
| Physical examination | TR week 26 | X | X | X | | X | X | X |
| Vital signs | TR week 26 | X | X | X | | X | X | X |
| Chemistry; Hematology; LFTs | TR week 26 | X | X | X | | X | X | X |
| Serum cortisol (AM fasting)[e] | TR week 26 | X | X | X | Results[f] | optional | X | X |

TABLE 7-continued

Schedule of Assessment: PART 3

| | VISIT | | | | | | | |
|---|---|---|---|---|---|---|---|---|
| Assessments and Procedures | Week 28 Randomization Or assigned dose<br>DAY<br>220 + 3 | Week 32<br><br>126 ± 3 | Week 36, 40, 44, 48<br><br>154 ± 3 | Week 52<br><br>192 ± 3 | Week 54<br><br>220 ± 3 | Unscheduled Visit[c] | Early Withdrawal[b] | Follow-up Any subject with Early Withdrawal<br><br>2 weeks after last dose |
| Urinalysis | TR week 26 | X | X | X | | X | X | X |
| Electrocardiogram - Standard 12-lead | TR week 26 | | | X | | | X | X |
| Population Pharmacokinetics (Needed?) | | | | | | | | |
| EGD with multiple esophageal biopsies[a,i] | TR week 26 | | | X | Results | X | | |
| Urine pregnancy test for women of CBP | X | X | X | X | | | X | X |
| ACTH stimulation test (250 µg)[k] | | | | X | Results | Optional[k] | X | |
| Adverse events | X | X | X | X | X | X | X | |
| 7-day EEsAI | X | X | X | X | X | X | X | |
| EEsAI Daily | X | X | X | X | X | X | X | |
| Global EoE Score | X | | | X | | | X | |
| EoE-QOL-A and Global EoE Symptoms | X | | | X | | | X | |
| Study Drug Dispensed | X | X | X | X | | | | |
| Drug return and accountability (compliance assessment) | | X | X | X | X | | X | X | a-m see previous footnotes
[o]Subjects meet Inclusion Criteria for PART 3
Complete PART 2 as a Responder - continue on same dose
Complete PART 2 as a Non-Responder - Assigned to 3 mg BID
Relapse on Placebo - return to prior dose in PART 3
Relapse in PART 2 on placebo - Assigned to 3 mg BID in PART 3
Complete OL Treatment as a Responder - Continue 3 mg BID
Complete OL Treatment as a Non-Responder - Exit Study and enter Follow-up Period Example 2—A Randomized, Double-Blind, Placebo-Controlled Trial of a Fluticasone Propionate Orally Disintegrating Tablet in Adult and Adolescent Patients with Eosinophilic Esophagitis: A Phase 1/2a Safety and Tolerability Study Background & Aims:

Eosinophilic esophagitis (EoE) is a chronic immune-mediated disease characterized by presence of tissue eosinophilia and symptoms of esophageal dysfunction. This was the first clinical study of APT-1011, fluticasone propionate (FP) a novel orally disintegrating tablet (ODT), that evaluated the tolerability and safety of 2 dosing regimens of APT-1011 compared to placebo (PBO) in adolescent and adult EoE patients.

Methods:

Subjects were randomized 1:1:1 to receive either APT-1011 1.5 mg BID [BID] (n=8), APT-1011 3.0 mg QD [QD] (n=8), or PBO (n=8). Patients underwent esophago-gastro-duodenoscopy (EGD) with esophageal biopsy at baseline (BL) and end of treatment [EOT] (week 8) to assess change in median eosinophil count. Secondary endpoints included improvement in endoscopic features as measured by the EoE Endoscopic Reference Score (EREFS), and Patient Global Assessment of Disease Severity (PatGA). Safety was also assessed.

Results:

Twenty four subjects (including 9 adolescent patients, 3 in each treatment arm) completed the 8-week double-blind period. Baseline and EOT median esophageal eosinophil counts (cells/mm² of the high power field), median EREFS score, as well as median PatGA for PBO, BID and QD groups are shown (Table 8). At EOT, the median esophageal eosinophil counts were significantly decreased from BL in biopsies of patients given APT-1011 (both regimens) but not in those of patients given placebo. There was a significant reduction in the 1 median EREFS (when compared to BL) in both groups of patients given APT-1011, but not placebo. There was a significant improvement in Patient Global Assessment of Disease Severity in patients given APT-1011 BID (trend in group given QD), but not placebo. Table 8 shows the median (and IQR) esophageal eosinophil counts as well as median EREFS score. P-value of <0.05 is considered to be significant.

TABLE 8

|  | Eosinophil counts | EREFS score | PatGA |
| --- | --- | --- | --- |
| PBO BL | 459 (286-609) | 6.5 (4.5-7.5) | 4.0 (4.0-6.5) |
| APT-1011 1.5 mg BID BL | 379 (289-563) | 6.0 (2.5-9.0) | 3.0 (2.0-6.0) |
| APT-1011 3.0 mg QD BL | 378 (224-458) | 6.0 (4.5-7.5) | 4.5 (2.0-6.5) |
| PBO EOT | 323 (200-523) | 5.0 (3.0-7.0) | 3.5 (3.0-5.0) |
| APT-1011 1.5 mg BID EOT | 0 (0-60) | 2.0 (0.5-3.0) | 0.5 (0-2.5) |
| APT-1011 3.0 mg QD EOT | 23 (0-109) | 2.5 (2.0-3.5) | 2.0 (1.0-3.0) |
| p-values PBO (BL vs EOT) | 0.3261 | 0.5347 | 0.1167 |
| p-values BID (BL vs EOT) | 0.0002 | 0.0088 | 0.0104 |
| p-values QD (BL vs EOT) | 0.0111 | 0.0019 | 0.0563 |

The rates of treatment emergent adverse events (TEAEs) were 75% (PBO), 75% (APT-1011) (QD). All TEAEs were of mild intensity except for 1 each of moderate fatigue and moderate depression by 1 subject in the placebo group.

Conclusions:

Eight-week treatment with APT-1011 is well tolerated. Use of APT-1011 in adult and adolescent EoE patients led to significant reduction in esophageal eosinophilia and improvements in the severity of EoE-associated endoscopic findings.

Example 3—A Randomized, Double-Blind, Placebo-Controlled, Dose-Ranging, and Maintenance Study of APT-1011 in Adolescents and Adults with Eosinophilic Esophagitis (EoE)

Primary Objective:

Evaluate the efficacy of APT-1011 in adolescents and adults with eosinophilic esophagitis (EoE).

Secondary Objectives:

To evaluate the safety of APT-1011 in adolescents and adults with EoE; To define the dose-response of APT-1011; To select a dose(s) for Phase 3; To evaluate individual pharmacokinetics of APT-1011 in a subset of adults and adolescents with EoE; To evaluate the population pharmacokinetics (PopPK) of APT-1011 in patients with EoE; Evaluate maintenance of efficacy and long-term safety; To evaluate the effects on endoscopic appearance using the EoE Endoscopic Reference Score (EREFs) (Hirano 2015; van Rhijn 2014); Evaluate change from baseline of the 7-day EEsAI and Global EoE Symptom Score.

Safety Objectives:

To determine the safety profile of acute and chronic administration of FP and its effects on the HP axis.

Exploratory Objectives:

Evaluate the change from baseline in the EoE Histology Scoring System (EoEHSS) score (Collins 2016); To evaluate Quality of Life via the Adult Eosinophilic Esophagitis Quality of Life Questionnaire (EoE-QoL-A). (Taft 2011); Evaluate Symptoms compared to prior visit(s) (7 scale); To evaluate PK/PD (cortisol) and exposure-response (efficacy) relationships.

Study Rationale:

Doses from 1.5 mg HS to 3.0 mg BID will be explored to define the exposure-response of APT-1011 and the minimum effective dose while remaining below any clinically significant hypothalamic-pituitary-adrenal (HPA) axis effects.

Study Design

This is a randomized, double-blind, placebo-controlled dose-ranging study of 3 total daily doses (1.5, 3 and 6 mg) of APT-1011 administered as 1.5 mg HS, 1.5 mg BID, and 3.0 mg BID compared to matching placebo in 320 adult and adolescent subjects with EoE. Maintenance of efficacy and long-term safety will also be evaluated.

Eligible subjects will be 14-75 years of age (inclusive) and have a diagnosis of EoE (≥15 Peak Eos per HPF) after proven failure of 8 weeks or more of high-dose (i.e. twice daily dosing) proton pump inhibitor (PPI). Subjects who have not had an adequate trial of PPI therapy should have this performed BEFORE screening for this study. PPI therapy may be continued during the study only if the subject was on PPI therapy at the time of signing an informed consent. No new initiation of, nor alteration of PPI therapy is allowed during the study. Subjects must also be symptomatic with dysphagia and have a 7-day recall Global EoE symptom score of >3 AND report at least 3 episodes of dysphagia in the past 7 days AND no exclusions for the study to enter the 2-week baseline symptom assessment. The subjects must report dysphagia at least 3 episodes per week for each of the two weeks of the baseline symptom assessment in the daily diary to be eligible for randomization.

In PART 1, subjects will be stratified by age (<18 and ≥18 years) and by concomitant PPI use during the study ("yes" or "no"); then randomly assigned to 1 of the 4 dosing groups (ratio: (1.7):1:1:1).

All subjects will come in monthly for routine visits, and for unscheduled visits should symptoms worsen between visits.

The study will be conducted in several parts:

Screening:

1-4 Weeks Including Upper Endoscopy (EGD)

Baseline Symptom Assessment: 2 Weeks have a Global EoE symptom score of >3 AND report at least 3 dysphagia episodes in the past 7 days AND have no exclusions for the study may enter the baseline symptom assessment Randomization:

Subjects must report at least 3 dysphagia episodes per week for each of the two weeks of the baseline symptom assessment in the daily diary, have >75% compliance with daily diary and have ≥15 Peak Eos per HPF and meet all the other inclusion and exclusion criteria will be randomized. Subjects will be randomized 1.7:3 for placebo to active doses. Response adaptive randomization will be used among the active doses which will be updated at each interim analysis.

Subjects will be stratified by age and current PPI use.

Figure 3:
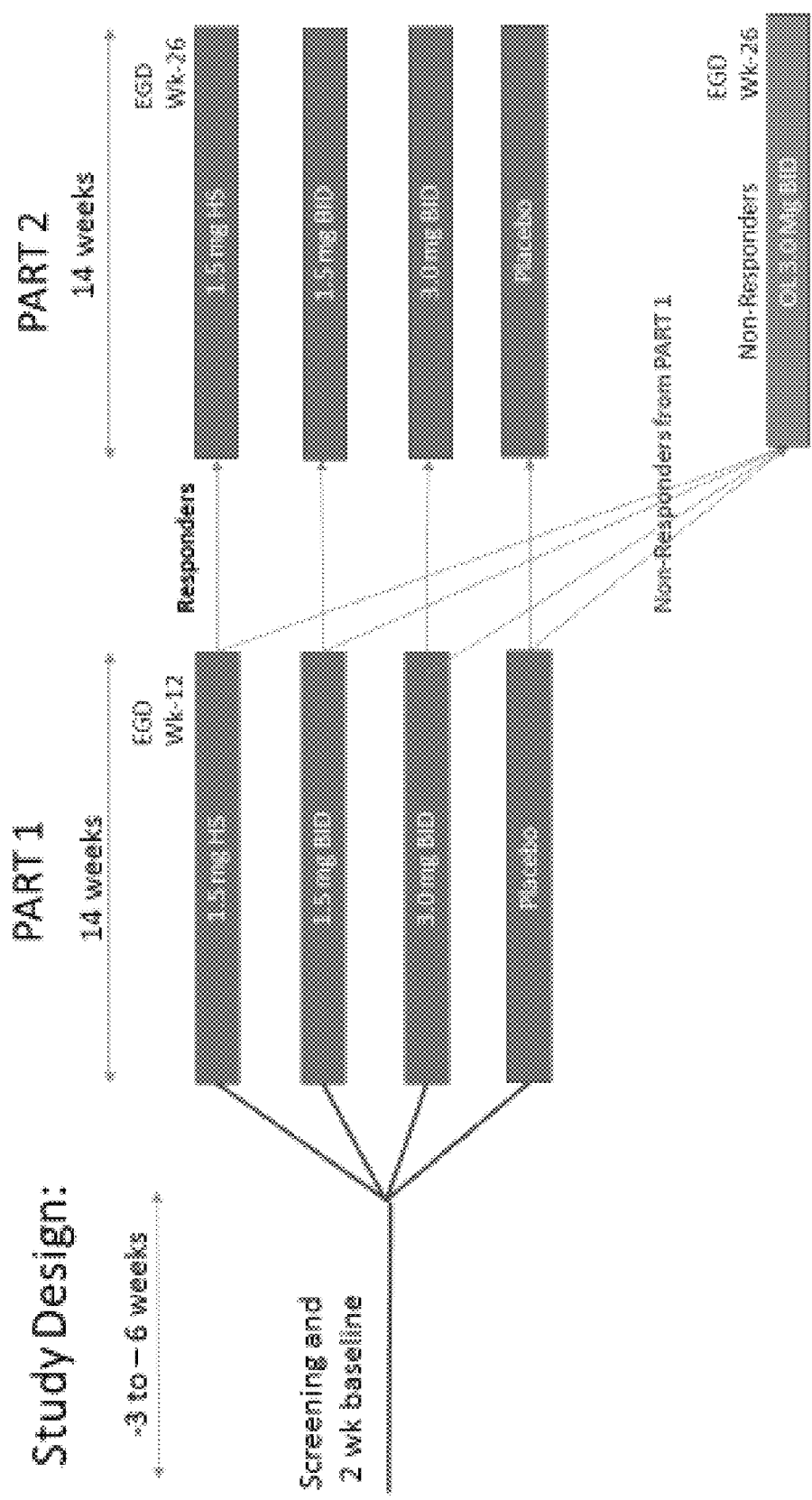
FIG. 3 shows another an exemplary schematic overview of Parts 1 and 2 of a Phase 2b study design and depicts screening and run-in in Part 1 (induction stage), and randomized withdrawal in Part 2.
Figure 4:
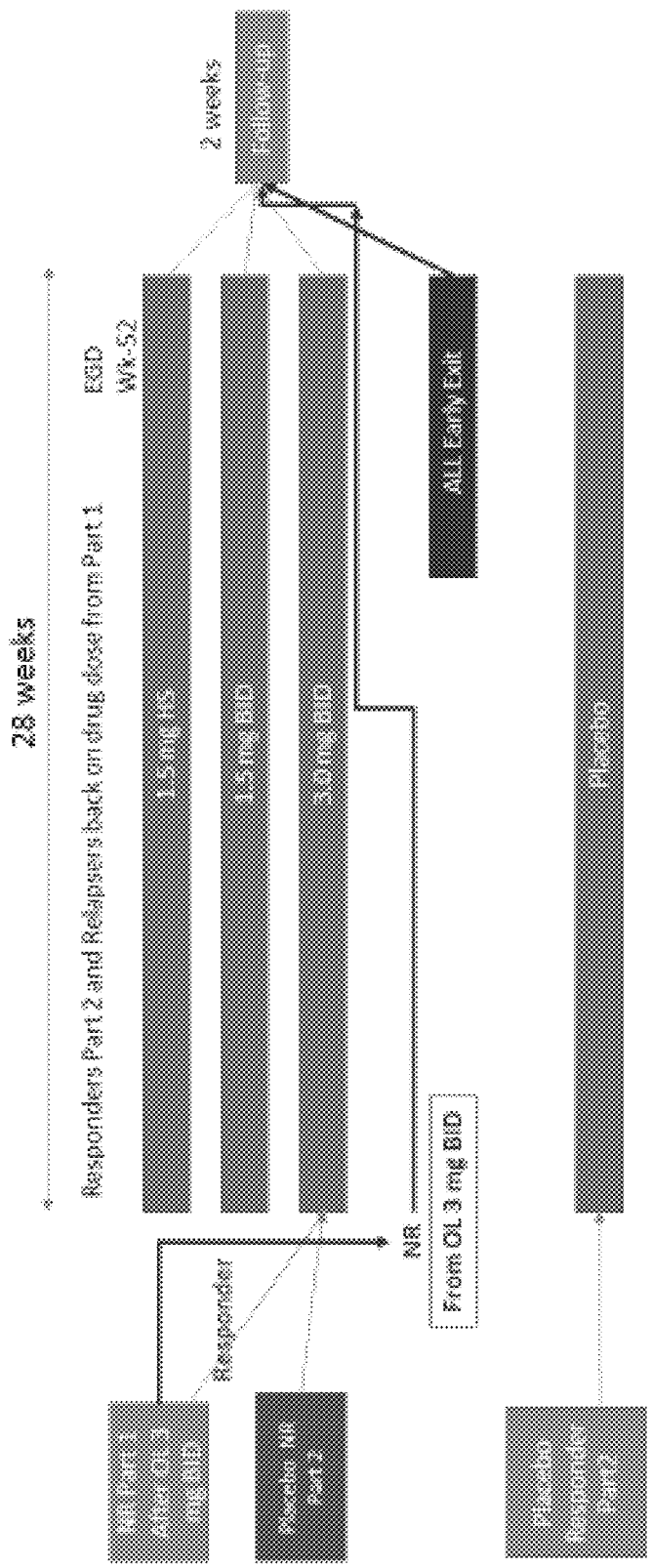
FIG. 4 shows another shows an exemplary schematic overview of Part 3 (maintenance) and follow-up of a Phase 2b study.

The overall protocol is shown in FIGS. 3 and 4. PART 1 represents induction of EoE response and PARTS 2 and 3 will assess maintenance.

Open-label treatment will be offered to non-responders in PART 1.

PART 1: Treatment (Day 1 to Week 14)

Subjects will be treated for 12 weeks and undergo an EGD to assess histologic and endoscopic improvement. Symptom improvement will be assessed on an ongoing basis. EoE Responders, defined as subjects who achieve a histologic response of =<6 Peak Eos per HPF and no worsening of symptoms (i.e. no increase in dysphagia based upon the daily diary compared to baseline) or episode of food impaction, will enter the PART 2 maintenance at week 14. This part will incorporate an adaptive sample size and response adaptive randomization within active arms. Interim analyses will be conducted frequently after 160 subjects are randomized, in which randomization probabilities are modified and early stopping criteria evaluated.

Open-Label (OL) Treatment (Weeks 14 to 28)

Non-responders (subjects who do not have a histologic response and/or have worsening of their dysphagia) at week 14 will receive open-label (OL) 3 mg BID until week 28 with an EGD at week 28, and then if they are responders at the end of the OL period (same definition as above), they will be eligible to enter PART 3. Non-responders to OL treatment will enter a 2-week follow-up period and then exit the study.

PART 2: Maintenance (Week 14 to Week 28)

EoE Responders (histologic response and no worsening of dysphagia) from PART 1 will continue on their same dose as in PART 1. Placebo responders, which are expected to be few, will remain on placebo. Either worsening of dysphagia or food impaction will prompt an endoscopy at an unscheduled visit. After the endoscopy, all "relapsers" will immediately enter PART 3 except those with food impaction requiring endoscopy or stricture requiring dilation. Subjects with food impaction requiring endoscopy or a stricture requiring dilatation will enter the 2-week follow-up period and exit the study. All subjects in the study at week 26 will undergo endoscopy. EoE Responders at week 28 will continue to PART 3. Non-responders at the end of PART 2 or early relapsers will receive 3 mg BID when they enter PART 3.

PART 3: Maintenance (Week 28 to Week 54)

Non-Responders from PART 1 who respond to open-label 3 mg BID will continue on this dose in PART 3. Note that this group will not participate in PART 2.

EoE Responders from PART 2 will continue on the same dose.

Non-responders and early relapsers from PART 2 will receive open-label 3 mg BID in PART 3.

Subjects who relapse (food impaction requiring endoscopy or clinically-significant recurrent symptoms) in PART 3 will undergo an unscheduled endoscopy and enter the 2-week follow-up and exit the study.

All continuing subjects will undergo endoscopy at week 52 and complete their final on treatment visit at week 54.

Follow-Up (2 Weeks after Last Dose)

All subjects must have a final endoscopy within 3 weeks prior to entering follow-up. Exceptions include: withdrawal of consent or contra-indication to endoscopy. Reasons for entering follow-up: Completed week 54; Adverse event requiring early withdrawal including food impaction requiring endoscopy; Failed to respond to open-label 3 mg BID; Relapsed in PART 3.

Pharmacokinetics:

In this study, the 1.5 mg BID and 3.0 mg BID doses of APT-1011 will be administered at least 30 minutes AFTER breakfast and at bedtime, (at least 2 hours after the evening meal). The 1.5 mg dose will be administered at bedtime (at least 2 hours after the evening meal). Subjects receiving the 1.5 mg dose will receive placebo in the morning at least 30 minutes AFTER breakfast. No food or drink will be permitted for at least 1 hour after dosing.

A combination of intensive PK sampling from a subset of subjects and sparse PK sampling from the remaining subjects will be collected to characterize FP exposure in the patient population. Non compartmental analysis (NCA) will be performed on the intensive PK data and a population PK analysis will be performed based on a combination of intensive serial and sparse plasma concentration data.

Intensive PK:

Intensive PK serial sampling will be performed at baseline and at Steady-State in a subset of adult subjects (8 per dose group) and in a subset of adolescent subjects (approximately 5 per dose group) at pre-specified PK sites. These subjects will take the daily dose (both tablets) on Day 1. Blood samples for determination of fluticasone plasma concentrations will be collected pre-dose and at 0.5, 1, 2, 4, 8, and 12 hours following the morning dose on Day 1 and Week 4. Steady-state samples may be collected at the Week 8 or 12 visit if the subject cannot stay for 12 hours on Week 4. Collection of intensive PK samples over a 12-hour period is related to the BID dosing schedule and the need to avoid an in-patient stay for these EoE patients.

Sparse PK:

Sparse PK samples will be collected from all adult and adolescent subjects (excluding subjects in the intensive PK Subset). A baseline pre-dose sample will be taken prior to dosing on Day 1. At Weeks 4, 8 and 12 of repeat dosing the subjects will take their AM dose at home and will have two samples taken during their scheduled visit. One sample will be taken upon arrival to the site and another sample taken 1 to 1.5 hours later immediately prior to leaving the site. The time of dosing the prior evening (bedtime of preceding night) and the time of the morning dosing (the day of planned visit) will be recorded. The actual PK sampling times also will be documented. Sites will be encouraged to vary site visits throughout the day. Due to the variability of site visits, the sparse PK samples will be taken to typically cover a large portion of the 12-hour post-dosing period.

Study Duration:

This study has an anticipated recruitment period of approximately 12-18 months. Subjects who enter and complete the study (PART 1, PART 2 and PART 3) will be in the study for up to 14 months.

Study Population:

The study uses an adaptive sample size, with a range of 160 to 320 adult subjects diagnosed with EoE who meet the entry criteria. The study is expected to enroll approximately 25% females and 5% elderly subjects.

Inclusion Criteria:

Male and female subjects ≥14 and ≤75 years of age at the time of informed consent.

Have signed the informed consent form (ICF) (parent or guardian must sign when applicable) and assent form (required for adolescents under 18 or legal age of majority per local law) and willing and able to adhere to all study procedures.

Diagnosis or presumptive diagnosis of EoE, must be confirmed by symptoms, and histology; and by historical documentation of failed treatment on 8 weeks or more of high-dose) proton pump inhibitor (PPI). (i.e. 20 mg BID omeprazole or 20-40 mg BID of an approved prescription PPI. Maintenance or OTC doses are too low) Documentation of PPI failure prior to initial diagnosis OR by documentation of PPI failure at the time of screening. A lack of response to PPI therapy is defined as a peak eosinophil count ≥15/HPF in at least one biopsied location AFTER the 8 weeks of high dose treatment. PPI therapy may be continued during the study only if the subject was on PPI therapy at the time of biopsies from the screening endoscopy. Subjects on PPI's may either stop them after the endoscopy or reduce the dose as long as this is BEFORE the baseline run in period. After this dose change the subjects must remain on a stable dose after that. Once a PPI is stopped it may not be restarted. No new initiation of PPI therapy is allowed during the study.

Have evidence of eosinophilic esophagitis defined by the PEAK esophageal mucosal eosinophil count ≥15 per high-powered field (HPF, 400× magnification (0.3 mm$^2$) in at least 1 of the esophageal sites biopsied (≥3 biopsies from each the proximal and the distal esophagus; a minimum of 6 total biopsies). Additional mid esophageal biopsies may be taken at the investigator's discretion. Biopsies are to be obtained and must be received by the central pathologist within 30 days AFTER the Screening Visit or 2 weeks prior to randomization and before starting the baseline period. Eligibility will be based solely on the central pathologist's assessment. Optional biopsies may be taken and processed locally for local use if specified in the local ICF. The subjects must have a 7-day recall Global EoE score >3; Subjects must report at least 3 dysphagia episodes per week for each week of the Baseline Symptom Assessment; Willing and able to adhere to study related treatment regimens, procedures and visit schedule.

Exclusion Criteria:

Known contraindication, hypersensitivity or intolerance to corticosteroids. Any physical, mental, or social condition, history of illness or laboratory abnormality that in the investigator's judgment might interfere with study procedures or the ability of the subject to adhere to and complete the study. Presence of oral or esophageal mucosal infection of any type. Any mouth or dental condition that prevents normal eating. Any condition affecting the esophageal mucosa or altering esophageal motility other than EoE including erosive esophagitis (LA grade B or higher), hiatus hernia longer than 3 cm, Barrett's esophagus, and achalasia. Use of systemic, oral or parenteral corticosteroids within 30 days, or inhaled or extended use of high-potency dermal topical corticosteroids within 30 days prior to: The esophageal biopsy required for entrance to this study; EGD if done during the pre-screening period. Use of swallowed/topical steroids within 30 days. Initiation of an elimination diet or elemental diet within 30 days of screening. No dietary therapy may be started during the study. Morning (0700 to 0800 hours, or as close to that window as possible) serum cortisol level ≤5 µg/dL (138 nmol/L). A serum cortisol level of <18 ug/mL (497 nmol/L) at 60 minutes with adrenocorticotropic hormone (ACTH) stimulation test using 250 µg cosyntropin. Consumption of grapefruit juice during the treatment is prohibited. Use of biologic immunomodulators within the past 6 months. Use of calcineurin inhibitors, purine analogues (azathioprine, 6-mercaptopurine) within the past 3 months. Contraindication to esophagogastroduoendoscopy (EGD) or esophageal biopsy or narrowing of the esophagus precluding EGD with a standard 9 mm endoscope. Overt gastrointestinal bleeding within 1 month prior to the Screening Visit or between the Screening Visit and the Randomization Visit. Current chronic infection, immunosuppression, or immunodeficiency. History or presence of Crohn's disease, celiac disease, or other inflammatory disease of the gastrointestinal tract including eosinophilic gastroenteritis. Current alcohol or drug abuse. Female subjects who are pregnant or breastfeeding. Sexually active females of child-bearing potential who do not agree to follow highly effective contraceptive methods during the study including the follow-up period. Abstinence is acceptable for adolescents. Female subjects with surgical menopause or menopause confirmed by FSH do not require contraception or pregnancy testing during the study. Participation in a clinical study involving an investigational drug within 30 days of the Screening Visit.

Study Drug Administration:

For 3 dosing groups, APT-1011 (fluticasone propionate, ODT) will be provided as blinded tablets in dose strengths of 1.5 mg and 3.0 mg. For the fourth dosing group there will be a matching placebo. Tablets will be administered BID—30 minutes AFTER breakfast and HS (at bedtime) at least 2 hours after the evening meal. Note that in the 1.5 mg dosing group, subjects will receive placebo tablets 30 minutes AFTER breakfast, and 1.5 mg APT-1011 HS. To maintain the blind, all tablets will be labeled for "AFTER breakfast" and "BEDTIME" administration. The subjects should not eat or drink for 1 hour after study drug administration. The BEDTIME dose should be administered after all drinks and snacks and tooth brushing and immediately before going to bed.

Primary Efficacy Endpoints at Week 12:

There are two co-primary efficacy endpoints for EOE RESPONSE: PEAK eosinophil count=<6/HPF at all biopsied esophageal locations and change from baseline in dysphagia episodes over the prior 14 days Secondary Efficacy Endpoints:

Change from baseline in Dysphagia-Free Days over the previous 14 days; EoE Sustained Response will be assessed at Weeks 26 and 52 with the Co-Primary Endpoint; Change from baseline in 7-day Global EoE Score will be assessed before the baseline symptom assessment, baseline, Week 12, Week 26 and Week 52. 7-day Global EoE symptom score will be assessed at each visit. Change from baseline in EREFS score at Weeks 12, 26 and 52. Endoscopic changes will be based upon the EREFS score based on 5 endoscopic features: edema, furrowing, exudates, rings, strictures. Percent of subjects with PEAK Eos per HPF <1 and <15 at all major time points where EoE Response is assessed Change from baseline in 7-day EEsAI score and percent of subjects with mean weekly EEsAI score <20 and change from baseline in sub scores will be assessed at Weeks 12, 26 and 52. 7-day EEsAI will be assessed at each visit.

Assessment of Relapse and Treatment Failure (a) Non-Response at each endoscopic time point (b) Percentage of subjects requiring emergency endoscopic food disimpaction by dose and part of the study.

(c) Percentage of subjects requiring esophageal dilation.

OL Treatment:

EoE Response (Co-Primary above) will also be assessed after 12 weeks of OL treatment in non-responders to PART 1.

Pharmacokinetic Endpoints

The following PK parameters will be calculated for the intensively-sampled PK subjects using noncompartmental methods, as data permit: Cmax, Tmax, $AUC_{0-12}$, CLss/F and Accumulation Ratio.

Population pharmacokinetic parameters including oral clearance (CL/F) and volume of distribution (V/F) will be estimated, as data permit. Additional parameters will be estimated, as appropriate, based on the final structural pharmacokinetic model.

Exploratory Endpoints:

EoE Histology Scoring System for all biopsies performed. Change from baseline will be assessed. Evaluation of quality of life based on the EoE-QoL-A at Week 12, 26, 52 and Week 12 of OL treatment by dose and subgroup. Patient's assessment of symptoms compared to the previous visit. This question will be assessed at Weeks 8, 12, 18, 26, 36 and 52. Evaluation of PK/PD (cortisol) and exposure-response (efficacy) relationships.

Safety Endpoints:

Safety will be assessed by monitoring and recording all treatment-emergent adverse events (TEAEs), TEAEs leading to withdrawal and Serious adverse events (SAEs). All TEAEs will be coded based upon the MedDRA version 14.0 classification of adverse events (AEs) and classified by severity (mild, moderate, severe) and relatedness to study drug (related or not related) by the Investigator. TEAEs occurring within 3 days of a dose change will be attributed to the previous dose. Physical examinations will be performed to document the baseline condition of the subject and to highlight changes related. to AEs. Vital signs will also be assessed at all visits and clinically significant deviations will be reported.

Routine laboratory tests will be performed throughout the study including hematology, blood chemistry, urinalysis, electrocardiograms (ECGs) as indicated in the Schedules of Assessments. Clinically significant changes in laboratory tests or ECGs will be summarized.

Cortisol Issues:

Abnormal AM cortisol, urinary glucose or serum glucose would necessitate following the subject to resolution CRFs should capture presence or absence of known glucocorticoid AEs such as moon facies, acne, hirsutism, mood swings, insomnia or depression. ICF should highlight that stress steroids may be required during significant medical illnesses. ACTH stimulation test (cosyntropin 250 mcg) should be performed at baseline and Week 12, early withdrawal and at Week 52 for all subjects. ACTH test should be performed in all subjects with AM serum cortisol >5 mcg/dL (138 mmol/L). All subjects with positive tests should be excluded. Any positive results at the end of treatment should be followed to recovery of adrenal function. The number of subjects discontinuing for HPA suppression or positive ACTH stimulation tests will be summarized. Subjects under age 18 will be evaluated for growth parameters such as height, weight, body mass index (BMI) and corresponding z-scores. Tanner stage and bone age will also be determined in adolescents less than 18 who have not completed their linear growth.

The safety endpoints of interest are: frequency of treatment emergent adverse events (TEAEs), TEAEs leading to withdrawal and treatment-emergent serious adverse events (SAEs), as well as the percentage of subjects with serum cortisol level ≤5 µg/dL (≤138 nmol/L) or positive ACTH stimulation test (serum cortisol <18 ug/mL (497 nmol/L) at 60 minutes). The number of subjects discontinuing for HPA axis suppression will be recorded.

Statistical Methods

Sample Size Determination

PART 1 incorporates an adaptive sample size that ranges between 160 and 320 adult patients. Frequent interim analyses will be conducted after at least 160 subjects are randomized in which success and futility criteria are evaluated. If evidence of treatment efficacy with respect to co-primary outcomes is sufficiently low, the trial may stop early for futility. If the predictive probability of obtaining sufficient evidence to demonstrate treatment efficacy is very high, the trial may stop accrual for expected success, with a decisive analysis performed when all enrolled patients have completed 12 weeks of follow-up (Broglio 2014). Simulations are used to calculate the expected sample size, Type 1 error, and statistical power under a variety of assumed treatment profiles (to be provided in SAP).

It is anticipated that approximately 60% of subjects will enter PART 2 of the study. Given a minimum of 102 patients on active treatment in PART 1, at least 61 patients are expected to enter PART 2. Approximately 17 placebo responders are expected to enter PART 2. It is anticipated that 70% of the placebo responders and approximately 20% of those on active treatment may relapse prior to Week 26. Approximately 82 subjects on active treatment are expected to enter PART 3.

In addition, assuming a 20% dropout rate into PART 3, at least 66 subjects (22 per dose) are expected to be evaluable on the active treatment arms for the assessment of sustained remission at Week 52, and at least 4 patients are expected on control. This provides a minimum expected power of 73% for comparing sustained remission rates of 80% versus 20% for each active dose versus control, and a minimum expected power of 80% for comparing the pooled active treatment remission rates versus control. However, the primary focus of PART 3 will be descriptive in nature.

Statistical Methodology

Summary statistics will be presented in tabular form by dose group and subgroups, as applicable) or each PART of the study including the OL treatment.

The primary analysis population for efficacy is the intent-to-treat (ITT) population, defined as all randomized subjects. The analysis population for safety is the safety population, defined as all subjects who receive at least one dose of study drug. The single-dose PK population will be defined as all subjects in the ITT population of PART 1 who are randomized to one of the three APT-1011 dosing groups, take their first dose of APT-1011, and have at least one PK sample included in the final single-dose population PK analysis. The steady-state PK population will be defined as all subjects in the ITT population of PART 1 who are randomized to one of the three APT-1011 arms, take their dose of APT-1011 that corresponds to the steady-state PK sampling period, and have at least one PK sample included in the final steady-state population PK analysis. Additional per protocol analysis populations who complete PARTs 1, 2, and 3 and OL treatment may be defined in the Statistical Analysis Plan (SAP).

Baseline and demographic information will be summarized using descriptive statistics for continuous and ordinal variables (e.g., age, weight, height) and counts and percentages for categorical variables (e.g., sex, race).

Pharmacokinetics and Pharmacodynamics Analysis

In this study, the 1.5 mg BID and 3.0 mg BID doses will be administered at least 30 minutes AFTER breakfast and at bedtime (at least 2 hours after the evening meal). The 1.5 mg HS dose will be administered at bedtime (at least 2 hours after the evening meal). Subjects receiving 1.5 mg HS daily will also receive placebo at least 30 minutes after breakfast.

Using the PK data from the intensely sampled subjects, PK parameters for FP will be calculated by noncompartmental methods when possible, as follows:

Cmax: Maximum observed concentration, observed by inspection of individual study participant plasma concentration time plots.

Tmax: Time of maximum observed concentration, obtained directly from the observed concentration time data AUC0-12: The area under the plasma concentration time curve, from time 0 to the 12 hours post-dose, calculated by a combination of linear and logarithmic trapezoidal methods (Linear up/log down method).

CLss/F Apparent Clearance at Steady-State

Accumulation Ratio Accumulation ratio calculated from AUC0-12 at steady state and AUC0-12 after single dosing Individual and mean plasma concentration time curves (both linear and semi-log) will be generated. Detailed methodology for summary statistics of the concentration data and the PK parameters will be documented in the SAP.

A Population PK analysis will be performed based on a combination of serial and sparse plasma concentration data. Previous serial PK data for APT-1011 (Studies PR-023 and Food-effect) may be included in this analysis to facilitate development of a base PK model.

Population PK parameters including oral clearance (CL/F) and volume of distribution (V/F) will be estimated, as data permit. Additional parameters will be estimated, as appropriate, based on the final structural PK model.

The output from the final population models including appropriate diagnostic plots, listings, and summaries of PK parameters will be generated. In addition, graphical and tabular presentations of any PK simulations will be produced. A separate PopPK report will be generated and linked to the clinical study report.

As data permit, exploratory analyses assessing the relationship between systemic exposure to FP and changes in cortisol levels also may be performed as described above. Additional exploratory exposure-response analyses may be performed based upon the co-primary endpoint or its components to facilitate selection of safe and effective doses for future studies and clinical use.

TABLE 9

Schedule of Assessments: Screening through PART 1

| Assessments and Procedures | Screening | Baseline Symptoms | Randomization | Week 4 | Week 8 DAY | Week 12 | Week 14 | Unscheduled Visit [c] | Early Withdrawal [b] |
|---|---|---|---|---|---|---|---|---|---|
| | −42 to −14 | −14 to −1 | 1 | 28 ± 3 | 56 ± 3 | 84 ± 3 | 98 + 3 | | |
| Informed consent signed | X | | | | | | | | |
| No exclusion criteria | | X | | | | | | | |
| Global EoE Symptom Score >3 | | | | | | | | | |
| >=3 dysphagia episodes in prior 7 days | | | | | | | | | |
| Inclusion/exclusion criteria | X | X | X[d] | | | | | | |
| Demographics, medical, surgical history, medication history | X | | | | | | | | |
| Concomitant medication(s) | X | X | X | X | X | X | | | |
| Physical examination | X | | X | X | X | X | | X | X |
| Tanner stage if age < 18 | | X | | | | | | | |
| Vital signs | X | X | X | X | X | X | | X | X |
| Chemistry; Hematology | X | | X | X | X | X | | X | X |
| Serum cortisol (AM fasting)[e] | X | | X | X | X | X | Results[f] | Optional | X |
| Urinalysis | X | | X | X | X | X | | X | X |
| Electrocardiogram - Standard 12-lead | X | | X | | | X | | | X |
| Population Pharmacokinetics | | | X[g] Pre-Dose | X[g] | X[g] | X[g] | | | |
| Intensive PK | | | X[h] | X[h] | | | | | |
| EGD with multiple esophageal biopsies[a,i] | X | | Pre-Dose | | | X | | | X[m] |
| Urine pregnancy test for women of CBP Menopausal women FSH at screening only | X | | X | X | X | X | | Optional | X |
| ACTH stimulation test (250 μg)[k] | X | | | | | X | | Optional[K] | X |
| Adverse events | X | X | X | X | X | X | X | X | X |
| Global EoE Score | X | X | X | | | X | | | X |
| 7-day EEsAI | X | X | X | X | X | X | X | | X |
| Daily Diary | | X | X | X | X | X | X | | X |
| Symptoms compared to prior visit | | | | | X | X | | | X |
| EoE-QoL-A | X | | X | | X | X | | | X |
| Bone Age[j] | | X | | | | | | | |
| Study Drug Dispensed | | | X | X | X | X | | | |
| Drug return and accountability (Study Drug compliance assessment) | | | | X | X | X | X | | X |

TABLE 9-continued

Schedule of Assessments: Screening through PART 1

| Assessments and Procedures | Screening | Baseline Symptoms | Randomization | Week 4 | Week 8 DAY | Week 12 | Week 14 | Unscheduled Visit [C] | Early Withdrawal [b] |
|---|---|---|---|---|---|---|---|---|---|
| | −42 to −14 | −14 to −1 | 1 | 28 ± 3 | 56 ± 3 | 84 ± 3 | 98 + 3 | | |
| Daily Diary Compliance Assessment | | | X | | | | | | |

[a] Endoscopy may be performed at a separate visit. Results of histology will be required at randomization and Week 14.

[b] Patient should be seen in the office within 7 days of determination of the need to withdraw the patient. If this is not possible due to an SAE or other unforeseen circumstance, visit may be completed with a phone visit with the patient or family member. Documentation of why the patient could not come to the site should be placed in the patient record.

[C] The reason for an unscheduled visit will guide procedures, at the discretion of the PI.

[d] Confirmation that the patient still meets inclusion/exclusion criteria based upon >3 episodes of dysphagia per week based upon the daily diary for the previous 14 days in addition to other inclusion/exclusion criteria including histology

[e] To be drawn as close as possible to 0800 hours. Patients must be fasting for an eight (8)-hour period prior to the serum cortisol assessments. Blood may be drawn for AM Serum Cortison +/− 2 days of scheduled visit to accommodate accurate timing. Other blood draws scheduled for the visit may be done at the same time.

[f] If abnormal serum cortisol level is reported at Final on treatment Visit; additional monitory and ACTH test may be required. See Safty sEction

[g] Sparse PK samples will be obtained from all subjects excluding those in the intensive PK subset. A baseline, pre-dose sample will be collected on Day 1, prior to the first dose. At Weeks 4, 8, and 12 of repeat dosing the subjects will take their morning dose at home and will have two samples taken during their scheduled visit. One sample will be taken upon arrival to the site and another sample taken 1 to 1.5 hours later, immediately prior to leaving the site. The time of dosing the prior evening (bedtime of preceding night) and the time of the morning dosing (the day of planned visit) will be recorded. The actual PK sampling times also will be documented.

[h] Approximately 8 adult subjects and 5 adolescents per dose group will undergo intensive PK sampling at selected sites. After taking both doses (AM and HS Tablets), Intensive PK samples will be collected on Day 1 and Week 4. At each of these visits, PK samples will be collected predose (no more than 15 minutes prior to AM dose) and at 0.5, 1, 2, 4, 8 and 12 hours post AM dose. The PK samples planned for Week 4 may be collected at the Week 8 or Week 12 visit if the subject cannot stay for 12 hours on Week 4.

[i] Can be done up to 30 days prior to Screening Visit (in absence of systemic or inhaled, intranasal or high-potency dermal topical corticosteroids within these 30 days prior to the Screening Visit). EREFS must be done and 3 biopsies taken from at least 2 levels of the esophagus.

[j] If the patient is withdrawing from the study due to lack of efficacy or other reasons, the Investigator may perform an EGD, if clinically indicated.

[K] All subjects undergo a 250 μg ACTH stimulation test at baseline and EOT or at early withdrawal. An ACTH simulation test will also be performed during the study at an optional visit for subjects whose serum cortisol level is confirmed by two blood draws as ≤5 μg/dL (138 nmol/L) or if they have signs and symptoms of hypercortism to assess for hypothalamic-pituitary-adrenal (IPA) axis suppression of potential clinical concern.

[l] Bone age to be performed on all adolescents (<18 years of age at randomization); exceptions include female subjects who have completed their linear growth or male subject who have not completed their liner growth by 18 years of age, at the discretion of the PI.

TABLE 10

Schedule of Assessments: PART 2

| Assessments and Procedures | Week 14 Randomization | Week 18 | Week 22 | Week 26 DAY | Week 28 | Unscheduled Visit [C] | Early Withdrawal [b] |
|---|---|---|---|---|---|---|---|
| | 98 + 3 | 126 ± 3 | 154 ± 3 | 192 ± 3 | 220 ± 3 | | |
| EoE Responder in PART 1 No contra-indications to continue | X | | | | | | |
| Concomitant medication(s) | Data Transfer | X | X | X | X | X | X |
| Physical examination | Data Transfer | X | | X | | X | X |
| Vital signs | Data Transfer | X | X | X | X | X | X |
| Chemistry; Hematology | Data Transfer | X | X | X | | X | X |
| Serum cortisol (AM fasting)[e] | Data Transfer | X | X | X | Results[f] | Optional | X |
| Urinalysis | Data Transfer | X | X | X | | X | X |
| Electrocardiogram - Standard 12-lead | Data Transfer | | | X | | | X |
| EGD with multiple esophageal biopsies[a, i] | Data Transfer | | | | Results | X | |
| Urine Pregnancy Test for women of CBP | Data Transfer | X | X | X | X | X | Optional |
| ACTH stimulation test (250 μg)[k] | Data Transfer | | | X | Results | Optional[k] | X |
| Adverse events | Data Transfer | X | X | X | X | X | X |
| 7-day EEsAI | Data Transfer | X | X | X | X | X | X |
| Daily Diary | Data Transfer | X | X | X | | | X |
| Global EoE Score | Data Transfer | | | X | | | X |
| Symptoms compared to previous visit | Data Transfer | X | | X | | | |
| EoE-QoL-A | Data Transfer | | | X | | | X |
| Study Drug Dispensed | X | X | X | X | | | |
| Drug return and accountability (Study Drug compliance assessment) | | X | X | X | X | | X |

TABLE 10-continued

Schedule of Assessments: OL Treatment

| Assessments and Procedures | Week 14 98 + 3 | Week 18 126 ± 3 | Week 22 154 ± 3 | Week 26 DAY 192 ± 3 | Week 28 220 ± 3 | Unscheduled Visit [c] | Early Withdrawal [b] |
|---|---|---|---|---|---|---|---|
| EoE Non-Responder in PART 1 | X | | | | | | |
| Concomitant medication(s) | Data Transfer | X | X | X | | X | X |
| Physical examination | Data Transfer | X | X | X | | X | X |
| Vital signs | Data Transfer | X | X | X | | X | X |
| Chemistry; Hematology | Data Transfer | X | X | X | | X | X |
| Serum cortisol (AM fasting)[e] | Data Transfer | X | X | X | Results[f] | Optional | X |
| Urinalysis | Data Transfer | X | X | X | | X | X |
| Electrocardiogram - Standard 12-lead | Data Transfer | | | | X | | X |
| EGD with multiple esophageal biopsies[a, i] | Data Transfer | | | | | X | |
| Urine pregnancy test for women of CBP | Data Transfer | X | X | X | | | X |
| ACTH stimulation test (250 μg)[k] | Data. Transfer | | | | X | Optional[k] | X |
| Adverse events | Data Transfer | X | X | X | X | X | X |
| 7-day EEsAI | Data Transfer | X | X | X | X | X | X |
| Daily Diary | Data Transfer | X | X | X | | | X |
| Global EoE Score | Data Transfer | | | | X | | X |
| Symptoms compared to previous visit | Data Transfer | X | | | X | | X |
| EoE-QoL-A | Data Transfer | | | | X | | |
| Study Drug Dispensed | | X | X | X | X | | |
| Drug return and accountability (Study Drug compliance assessment) | | X | X | X | X | | X |

TABLE 11

Schedule of Assessment: PART 3

| Assessments and Procedures | Week 28 Randomization or assigned dose 220 + 3 | Week 36 126 ± 3 | Week 44 154 ± 3 | Week 52 DAY 192 ± 3 | Week 54 220 ± 3 | Unscheduled Visit [c] | Early Withdrawal [b] | Follow-up Any Subject with Early Withdrawal 2 weeks after last dose |
|---|---|---|---|---|---|---|---|---|
| Inclusion Criteria for PART 3[o] | X | | | | | | | |
| Concomitant medication(s) | Data Transfer | X | X | X | | X | X | X |
| Physical examination | Data Transfer | X | X | X | | X | X | X |
| Vital signs | Data Transfer | X | X | X | | X | X | X |
| Chemistry; Hematology | Data Transfer | X | X | X | | X | X | X |
| Serum cortisol (AM fasting)[e] | Data Transfer | X | X | X | Results[f] | Optional | X | X |
| Urinalysis | Data Transfer | X | X | X | | X | X | X |
| Electrocardiogram - Standard 12-lead | Data Transfer | | | | X | X | X | X |
| EGD with multiple esophageal biopsies[a, i] | Data Transfer | | | | X | Results | X | |
| Urine pregnancy test for women of CBP | Data Transfer | X | X | X | | Optional | X | X |
| ACTH stimulation test (250 μg)[k] | Data. Transfer | | | | X | Results | Optional[k] | X |
| Adverse events | Data Transfer | X | X | X | X | X | X | |
| 7-day EEsAI | Data Transfer | X | X | X | X | X | X | |
| Daily Diary | Data Transfer | X | X | X | X | X | X | X |
| Global EoE Score | Data Transfer | | | | X | | X | |
| Symptoms compared to previous visit | Data Transfer | X | | | X | | | |

TABLE 11-continued

Schedule of Assessment: PART 3

| | VISIT | | | | | | | Follow-up |
|---|---|---|---|---|---|---|---|---|
| | Week 28 Randomization or assigned dose | Week 36 | Week 44 | Week 52 | Week 54 | Unscheduled Visit [C] | Early Withdrawal [b] | Any Subject with Early Withdrawal |
| Assessments and Procedures | DAY | | | | | | | |
| | 220 + 3 | 126 ± 3 | 154 ± 3 | 192 ± 3 | 220 ± 3 | | | 2 weeks after last dose |
| EoE-QoL-A | Data Transfer | | | X | | | X | |
| Study Drug Dispensed | X | X | X | X | | | | |
| Drug return and accountability (Study Drug compliance assessment) | | X | X | X | X | | X | X |

Footnotes: a-m see previous footnotes
[a]Subjects meet Inclusion Criteria for PART 3:
Complete PART 2 as a Responder - continue on same dose; Complete PART 2 as a Non-Responder - Assigned to 3 mg BID; Relapse on Placebo - return to prior dose from PART 1 when entering PART 3; Relapse PART 2 on placebo - Assigned to 3 mg BID in PART 3; Complete OL Treatment as a Responder - Continue 3 mg BID; C Example 4—FLUTicasone in Eosinophilic Esophagitis (FLUTE): A Randomized, Double-Blind, Placebo-Controlled, Dose Ranging, and Maintenance Study of APT-1011 in Subjects with Eosinophilic Esophagitis Primary Objective:
The primary objective of the study is to evaluate the efficacy (histological response) of APT-1011 in adults (≥18 years of age) with eosinophilic esophagitis (EoE).

Secondary Objectives:
The secondary objectives of the study are as follows: To define the dose-response of APT-1011; To select a dose(s) of APT-1011 for Phase 3; To evaluate the effect of APT-1011 on histology and endoscopic appearance; To evaluate maintenance of efficacy and long-term safety of APT-1011; To evaluate the population pharmacokinetics (PopPK) of APT-1011; To evaluate the effect of APT-1011 on dysphagia episodes.

Exploratory Objectives:
The exploratory objectives of the study are as follows:
To evaluate the effect of APT-1011 on dysphagia and other symptoms of EoE; To evaluate quality of life; To evaluate symptomatology over time; To evaluate the pharmacokinetic (PK)/pharmacodynamic (PD) relationship (with cortisol as the primary endpoint); To evaluate the dose-response relationship for the histological response and symptom response; To derive a scoring structure, and various endpoints from the Patient Reported Outcome Symptoms of EoE (PROSE); To evaluate the measurement properties of the PROSE, including reliability, construct validity, sensitivity to change; To produce guidelines for interpreting clinically meaningful change and derive the cut-off for treatment response on the PROSE, or a responder definition.

Study Design
This is a randomized, double-blind, placebo-controlled dose-ranging study of 4 total daily doses of APT-1011 versus placebo in 100 adult subjects (≥18 years of age) diagnosed with EoE.

During the single-blind run-in/baseline symptom assessment, the subjects will receive placebo 30 minutes after breakfast and hora somni (HS; at bedtime). Four doses of study drug will be administered: Placebo 30 minutes after breakfast and 1.5 mg hora somni (HS; at bedtime) APT-1011, 1.5 mg twice daily (BID) (30 minutes after breakfast and at bedtime; total daily dose of 3 mg) APT-1011, Placebo 30 minutes after breakfast and 3 mg HS (at bedtime), and 3 mg BID (30 minutes after breakfast and at bedtime; total daily dose of 6 mg) APT-1011, and matching placebo administered 30 minutes after breakfast and HS (at bedtime).

The 100 subjects will be randomized in a 1:1:1:1:1 to receive placebo or one of the active doses into Part 1 of the study. As described below, the treatment that a subject receives in Part 2 depends on their histologic response status at Week 12.

Randomization will occur in a double-blind manner using an integrated Interactive Web Response System (IWRS), and will be stratified by the presence or absence of a history of or current esophageal strictures at Screening and history of a prior positive steroid response to any corticosteroid treatment previously received to treat the subject's EoE captured with demography.

Efficacy (including sustained EoE response and patient-reported outcomes), safety, and PK of APT-1011 will be examined.

FLUTE will be conducted in several parts (Screening [4 weeks], followed by a 4-week single-blind placebo run-in and Baseline Symptom Assessment, and 2 treatment parts [Part 1 and Part 2]), with a Follow-up Visit to occur 2 weeks after the final dose of study drug. Screening will take up to 28 days. The esophagogastroduodenoscopy (EGD) to determine eligibility (Inclusion Criterion #7: evidence of EOE as defined by ≥15 PEAK eosinophils/high-power field [HPF] with at least 5-6 biopsies including both proximal and distal specimens [3 each]) will be completed during the Screening Period and the biopsies must be received by the central pathologist by the times noted in this inclusion criterion. To enter the 4-weeks Baseline Symptom Assessment, the subject must satisfy all eligibility criteria including the Global EoE score >3 (Inclusion Criterion #5), except those to be confirmed during this phase (Inclusion Criterion #7: evidence of EOE as defined by ≥15 PEAK eosinophils/HPF with at least 5-6 biopsies including both proximal and distal specimens [3 each]; Inclusion Criterion #8: in the daily diary, report episodes of dysphagia ≥3 days per week during the last 2 weeks of the 4-week Baseline Symptom Assessment; Inclusion Criterion #9: completion of episode entries on at least 5 of out of each 7 days during the 4-week Baseline Symptom Assessment; and Exclusion Criterion #23: a serum cortisol level <18 μg/dL (497 nmol/L) at 60 minutes with adrenocorticotropic hormone [ACTH] stimulation test using 250 μg cosyntropin [i.e., a positive result on the ACTH stimulation test]). The subjects will be dispensed placebo along with their electronic diary at the beginning of the 4-week placebo run-in/Baseline Symptom Assessment.

During the 4-week Baseline Symptom Assessment, baseline symptom severity will be determined and the ability of the subject to be compliant with diary entries will be assessed. The subjects must have ≥15 PEAK eosinophils/HPF on their esophageal biopsies to be randomized. In order to ensure that a diagnosis can be made, at least 5-6 biopsies from both the proximal and distal (3 each) should be taken. The presence or absence of a history of or current esophageal stricture on the EGD along with a history of a prior positive response to any corticosteroids treatment previously received to treat the subject's EoE captured with demography will be stratification variables at randomization.

Following confirmation of these eligibility criteria, eligible subjects may be randomized as described above.

During treatment, all subjects will return to the site approximately monthly for scheduled visits and for unscheduled visits due to significant adverse events or worsening of symptoms including food impaction.

Definitions of Histologic Response, Histologic Non-Response, and Treatment Failure.

Response or non-responsive status will be assessed 2 weeks prior to the planned end of treatment for Part 1 (Week 12), and Part 2 (Weeks 26 and 52).

A histologic responder will be defined as a subject who achieves a histologic response of peak eosinophils/HPF number ≤6 (as primary determinant). HPF will be defined as a standard area of 0.235 square millimeters in a microscope with 40× lens and 22 mm ocular.

A histologic non-responder will be defined as a subject who does not have a histologic response (i.e., do not achieve a histologic response of peak eosinophils/HPF number ≤6).

Subjects who develop food impaction with or without esophageal dilatation anytime during the study will be considered treatment failures and complete early termination assessments and exit the study after the 2 week post-treatment follow-up period. Subjects who voluntarily withdraw from the study due to worsening symptoms before the week 12 evaluation or later in the study will also be considered treatment failures. Every effort should be made to perform an EGD in subjects wishing to withdraw due to worsening symptoms. They also must complete the early termination assessments and exit the study after a 2-week post-treatment follow-up period.

Part 1: Induction (Day 1 to Week 14)

Figure 5:
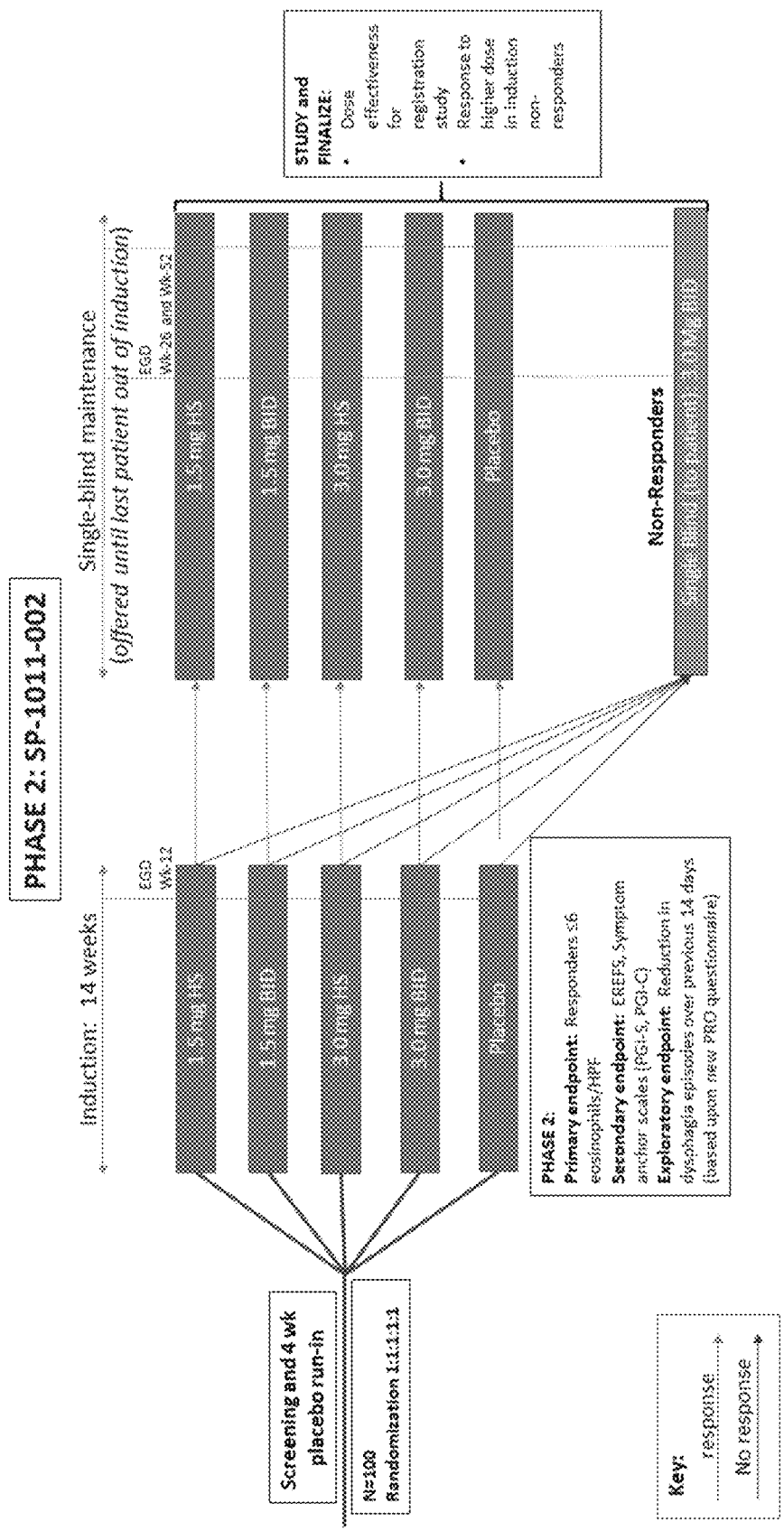
FIG. 5 shows a study schematic providing an overview of the treatment each subject will receive throughout the FLUTE study.

During Part 1, subjects will be treated for 14 weeks with study drug (FIG. 5). At Week 12, the subjects will undergo a response assessment, including EGD to assess endoscopic and histologic status.

Histologic responders and histologic non-responders (at Week 12) will enter Part 2.

Part 2: Maintenance (Week 14 to Week 52)

In Part 2, all subjects classified as histologic responders at Week 12 will continue to be treated according to the dosing group to which they were randomized for Part 1 for an additional 14 weeks, beginning at Week 14 (FIG. 5). Subjects may continue on this dose for up to 9 months after the completion of Part 1.

Subjects who are histologic non-responders at Week 12 will receive single-blind 3 mg BID in Part 2.

At Week 26, subjects will undergo a response assessment, including EGD to assess histologic response. Symptoms will also be assessed. The 14 days prior Week 26 will be compared to the 14 days prior to Randomization. Subjects who are histologic non-responders will stop treatment at Week 28 and enter the 2 week follow-up and exit the study. Histologic responders will continue on the same dose.

Subjects who complete the study at Week 52 will undergo a response assessment, including EGD to assess endoscopic and histologic status. Symptoms will also be assessed. The 14 days prior Week 52 will be compared to the 14 days prior to Randomization.

Subjects will complete a Follow up Visit 2 weeks after the final dose of study drug.

Follow-Up Visit

Subjects will complete a Follow-up Visit for 1 or more of the following reasons: Subject completed treatment at Week 52 (following EGD); Subject experienced an adverse event (AE) requiring early discontinuation, including food impaction requiring EGD; Subject with histologic non-response at week 26 including subjects on single-blind 3 mg BID; Subject with worsening symptoms who voluntarily withdraws during the study. The Follow-up Visit will occur 2 weeks after the subject takes the final dose of study drug. All subjects must have a final EGD within 3 weeks prior to completing the Follow up Visit unless the subject withdraws consent or has a contraindication to EGD.

Pharmacokinetics

Sparse PK sampling will be performed to characterize fluticasone propionate (FP) exposure in the study population. PopPK analysis will be performed on sparse plasma concentration data.

Pharmacokinetic samples will be collected from subjects in all 5 dosing groups to maintain the blind. Samples collected from subjects in the placebo dosing group will not be analyzed. Samples collected from the subjects on active doses will be analyzed for PopPK results.

For this sparse PK sampling, a pre-dose sample will be collected on Day 1. At Week 4, Week 8, and Week 12, subjects will take their "after breakfast" dose as scheduled on the day of the visit (most likely at home) and 2 samples will be taken during their scheduled visit: upon arrival to the site and approximately 1 to 1.5 hours after first sample (immediately prior to leaving the site). Sites will be encouraged to book subject visits throughout the day. Due to this variability, the sparse PK samples are expected to represent a large portion of the 12 hour post-dosing interval.

Planned Number of Subjects

Approximately 100 subjects will be randomized into Part 1 in a 1:1:1:1:1 fashion stratified by presence or absence of a history of or current esophageal stricture and a history of a prior positive steroid response to any corticosteroids treatment previously received to treat the subject's EoE.

While both genders will be encouraged to enroll, it is expected that approximately 25% of subjects enrolled will be female. Although subjects are allowed to be up to 75 years old, it is expected that 5% of enrolled subjects will be geriatric (>65 years).

No interim analyses are planned.

Inclusion Criteria:

Subjects must satisfy all of the following criteria:

Before entering 4-week Baseline Symptom Assessment: Male or female between ≥18 and ≤75 years of age at the time of informed consent; Signed the informed consent form (ICF) and willing and able to adhere to all study procedures; Diagnosis or presumptive diagnosis of EoE; Diagnosis of EoE must be confirmed by symptoms, histology, and historical documentation of failed treatment on ≥8 weeks of high-dose proton pump inhibitors (PPI). For the purposes of FLUTE, high dose PPI is defined as 20 mg BID omeprazole or 20 to 40 BID mg of any marketed PPI; maintenance doses of PPIs are not acceptable. A lack of response to PPI therapy is defined as ≥15 PEAK eosinophils/HPF with at least 5 biopsies including both proximal and distal specimens after 8 weeks of high dose PPI treatment.

Documentation of PPI failure prior to initial diagnosis or by documentation of PPI failure at the time of Screening is required. The subjects may be pre-screened but should not be consented, sign an ICF, or be offered participation in FLUTE if they have not met the diagnostic criteria for EoE that requires that they fail an 8-week trial of high dose PPIs EXCEPT those that have taken PPIs for 8 weeks will use the EGD within the study for this documentation. The Investigator and potential subject must make the decision to complete a PPI trial independent of any considerations of the study. There is insufficient time to do the 8 week trial within the current study. Should a subject be consented in error and screen fails due to this point, they may be rescreened as described in the protocol. Have a subject reported history of ≥3 episodes of dysphagia (difficulty with food going down) in the 7 days prior to Screening; Have a 7-day recall Global EoE Symptom Score >3; at baseline (EoE score must remain >3 at each of Visits 1, 2 and 3 before randomization). This will be performed on paper during the Screening visit; Willing and able to adhere to study related treatment regimens, procedures, and visit schedule;

Before Randomization:

To be determined prior to randomization: have evidence of EoE, as defined by ≥15 PEAK eosinophils/HPF with at least 5-6 biopsies including both proximal and distal specimens (3 each); No EGDs and biopsies performed outside FLUTE are acceptable for meeting eligibility criteria. Optional biopsies may be taken and processed locally for local use if specified in the local ICF. Biopsies are to be obtained PRIOR to the 4-week Baseline Symptom Assessment. Eligibility from a histological perspective will be based solely on the central pathologist's assessment.

To be determined prior to randomization: in the daily diary, report at least 3 episodes of dysphagia (difficulty with food going down) for each of the last 7 days during the last 2 weeks of the 4-week Baseline Symptom Assessment;

To be determined prior to randomization: completion of episode entries on at least 5 out of each 7 days during the last 14 days of the 4-week Baseline Symptom Assessment.

Exclusion Criteria:

Subjects will not be entered in FLUTE for any of the following reasons:

Before entering 4-week Baseline Symptom Assessment: Have known contraindication, hypersensitivity, or intolerance to corticosteroids; Have any physical, mental, or social condition or history of illness or laboratory abnormality that in the Investigator's judgment might interfere with study procedures or the ability of the subject to adhere to and complete the study; Presence of oral or esophageal mucosal infection of any type; Have any mouth or dental condition that prevents normal eating; Have any condition affecting the esophageal mucosa or altering esophageal motility other than EoE, including erosive esophagitis (grade B or higher as per the Los Angeles Classification of Gastroesophageal Reflux Disease), hiatus hernia longer than 3 cm, Barrett's esophagus, and achalasia; Use of systemic (oral or parenteral) corticosteroids within 60 days prior to Screening, use of inhaled/swallowed corticosteroids within 30 days prior to Screening, or extended use of high-potency dermal topical corticosteroids within 30 days prior to Screening; Initiation of an elimination diet or elemental diet within 30 days before Screening; Morning (0700 to 0800 hours, or as close to that window as possible) serum cortisol level ≤5 µg/dL (138 nmol/L); Use of biologic immunomodulators in the 24 weeks prior to Screening; Use of calcineurin inhibitors or purine analogues (azathioprine, 6 mercaptopurine) in the 12 weeks prior to Screening; Use of potent cytochrome P450 (CYP) 3A4 inhibitors (e.g., ritonavir and ketoconazole) in the 12 weeks prior to Screening; Have a contraindication to or factors that substantially increase the risk of EGD or esophageal biopsy or have narrowing of the esophagus that precludes EGD with a standard 9 mm endoscope; Have history of an esophageal stricture requiring dilatation with the previous 12 weeks prior to Screening; Subjects who have initiated, discontinued or changed dosage regimen of PPIs, H2 antagonists, antacids or antihistamines for any condition such as GERD for allergic rhinitis within 4 weeks prior to qualifying endoscopy. These drugs must remain constant throughout the study. Infection with hepatitis B, hepatitis C, or human immunodeficiency virus (to be tested during Screening);

The following parameters will be utilized to determine hepatitis B and hepatitis C infection: positive for hepatitis B surface antigen [HBsAg], total hepatitis B core antibody [anti HBc], or hepatitis C virus antibody. However, subjects who are positive for hepatitis B surface antibody, but negative for HBsAg and anti HBc, will be eligible.

Have gastrointestinal (GI) bleeding within 4 weeks prior to Screening or between the Screening Visit and the Randomization Visit; Have current (>30 days) chronic infection, immunosuppression, or immunodeficiency; Have history or presence of Crohn's disease, celiac disease, or other inflammatory disease of the GI tract, including eosinophilic gastroenteritis; Have current alcohol or drug abuse in the opinion of the Investigator; Female subjects who are pregnant, breastfeeding, or planning to become pregnant during the study; Serum pregnancy test at Screening and urine pregnancy test during 4-week Baseline Symptom Assessment in women of childbearing potential must be negative. Sexually active females of childbearing potential who do not agree to follow highly effective contraceptive methods through the Follow up Visit; For systemic contraceptive, use must be stable for ≥28 days prior to Screening. Female subjects with surgical menopause or menopause confirmed by follicle stimulating hormone/luteinizing hormone do not require contraception or pregnancy testing during the study. Participation in a clinical study involving an investigational product within 30 days (or 5 half-lives, whichever is longer) of Screening;

Before Randomization

A serum cortisol level <18 µg/mL (497 nmol/dL) at 60 minutes with adrenocorticotropic hormone (ACTH) stimulation test using 250 µg cosyntropin (i.e., a positive result on the ACTH stimulation test).

Test Product, Dose and Mode of Administration:

APT-1011 is an orally disintegrating tablet that includes FP as its active ingredient.

For the purposes of this protocol, the term study drug is used to refer to any blinded medication administered (i.e., any dosage of APT-1011 or placebo).

Subjects will be instructed to take the study drug orally, with no water or other liquids. The tablet should be placed in the mouth and manipulated between the tongue and the roof of the mouth and allowed to disintegrate completely on the subject's tongue. It should be swallowed when fully disintegrated, without biting or chewing. No rinsing with water or liquids is to be allowed after administration.

Dosing will occur in the morning ("after breakfast;" ≥30 minutes after breakfast) and at bedtime ("at bedtime;" ≥2 hours after the evening meal). The "at bedtime" dose of study drug will be administered immediately prior to sleep, while lying in bed. All eating, drinking, and tooth brushing should be completed prior to dosing.

Study drug will be administered BID (30 minutes after breakfast and at bedtime) in all parts of the study. During the placebo run-in, the subjects will receive placebo BID. In the HS groups, the subjects will receive placebo in the morning 30 minutes after breakfast and their doses at bedtime. Placebo subjects after randomization will receive placebo BID.

Subjects in the 1.5 mg BID APT-1011, 3 mg BID APT-1011, and placebo dosing groups will take the same study drug for the "after breakfast" and "at bedtime" doses. Subjects in the 1.5 mg HS and 3 mg HS APT 1011 groups will take placebo "after breakfast" and 1.5 mg or 3 mg APT 1011 "at bedtime."

Subjects should refrain from oral intake of solids or liquids for >1 hour after dosing.

Criteria for Evaluation:

Efficacy will be assessed histologically (eosinophils per HPF), endoscopically (Eosinophilic Esophagitis Endoscopic Reference Score [EREFs]), clinically as an exploratory endpoint (via the PROSE completed for each dysphagia episode and at the end of each day), and the following additional patient-reported outcomes: Global EoE Symptom Score, Patient Global Impression of Severity (PGIS) and Patient Global Impression of Change (PGIC), 7-day recall Eosinophilic Esophagitis Activity Index (EEsAI) total and subscores, and subject's assessment of symptoms. Health Related Quality of Life (HRQoL) will be assessed as an exploratory endpoint by the Adult Eosinophilic Esophagitis Quality of Life Questionnaire (EoE-QoL-A).

Primary Efficacy Endpoint:

The following primary efficacy endpoint will be evaluated at Week 12 to assess EoE response:

Histology: percentage of subjects with PEAK eosinophils/HPF number ≤6 after assessing at least 5-6 biopsies from the proximal and distal esophagus (~3 each) where the HPF area is 235 square microns (40 magnification lens with a 22 mm ocular).

Secondary Efficacy Endpoints:

The following secondary efficacy endpoints will be evaluated:

EoE sustained response: percentage of subjects who met the primary endpoint at Week 12 and maintained the primary endpoint at Week 26 and Week 52;

Change from baseline EREFs at Week 12, Week 26, and Week 52;

Endoscopic changes will as per the EREFs evaluation based on the following endoscopic features: edema, rings, exudates, furrows, stricture, and several miscellaneous features (crepe paper esophagus, narrow caliber esophagus, and esophageal erosions).

Percentage of subjects with a peak eosinophils/HPF number <1 and <15 at Week 12, Week 26, and Week 52;

Change from baseline Global EoE Symptom Score accessed prior to randomization, which will be assessed for the 7-day period prior to the following study visits: Week 4, Week 8, Week 12, Week 18, Week 22, Week 26, Week 28, Week 36, Week 44, and Week 52;

Dysphagia: Change in the number of dysphagia episodes at baseline (14-day period prior to randomization) compared with the 14-day period prior to the time point of interest (Week 12, Week 26, and Week 52)

Change from baseline 7-day recall EEsAI total score at Week 12, Week 26, and Week 52;

Change from baseline 7-day recall EEsAI subscores at Week 12, Week 26, and Week 52;

Percentage of subjects with mean 7-day recall EEsAI total score <20 at Week 12, Week 26, and Week 52;

Change from baseline PGIS assessed prior to randomization to those assessed at Weeks 4, 8, 12, 14, 18, 22, 26, 28, 36, 44 and 52;

PGIC at weeks 4, 8, 12, 14, 18, 22, 26, 28, 36, 44, and 52.

Assessment of treatment failure and relapse, including:

Percentage of histologic non-responders by dose at Week 12, Week 26, and Week 52;

Percentage of subjects requiring emergency endoscopic food disimpaction by dose before Week 14, between Week 14 and Week 28, and between Week 28 and Week 52;

Percentage of subjects requiring esophageal dilation by dosing group and part of the study.

Exploratory Efficacy Endpoints:

The following exploratory efficacy endpoints will be evaluated:

Dysphagia: Change in the number of dysphagia episodes at baseline (14-day period prior to randomization) compared with the 14 day period prior to the time point of interest (Weeks 12, 26 and 52).

Change from baseline in dysphagia-free days during the 14 day period prior to the following study visits: Week 12, Week 26, and Week 52;

EoE sustained response (dysphagia): percentage of all subjects who met the dysphagia secondary endpoint at Week 12 and maintained a dysphagia-related response at Week 26 and Week 52;

Evaluation of PK/PD (cortisol) and exposure-response (efficacy) relationships;

Subject's assessment of symptoms compared with the previous visit at Week 4, Week 8, Week 12, Week 14, Week 18, Week 22, Week 26, Week 28, Week 36, Week 44, Week 52, and the Early Termination Visit (if applicable);

Evaluation of HRQoL based on the EoE-QoL-A at randomization, Week 12, Week 26, Week 52 for all subjects by dose and subgroup;

Subjects receiving single-blind (to subject) treatment (in Part 2) will be tabulated separately.

Percentage of subjects who were classified as histologic non-responders at Week 12 and have a peak eosinophils/ HPF number ≤6 at all biopsied esophageal locations at Week 26 and Week 52;

Change from baseline dysphagia episodes during the 14 day period prior to Week 26 and Week 52 for subjects who were classified as non-responders at Week 12;

Percentage of subjects who were classified as histologic non-responders at Week 12 and meet the primary endpoint at Week 26 and Week 52;

A scoring structure, and various endpoints will be derived from the DEDI.

Psychometric measurement properties of the PROSE will be evaluated;

Anchor and distribution analyses to evaluate meaningful changes on the PROSE.

Adverse Events

Any AE or concurrent illness experienced by a subject during any portion of FLUTE must be described in detail and be fully evaluated by the Investigator. The Investigator is responsible for recording all AEs observed or reported during the study, regardless of causality and/or clinical significance.

Safety will be assessed by monitoring and recording all treatment-emergent adverse events (TEAEs), TEAEs leading to discontinuation, and serious adverse events (SAEs). All TEAEs will be coded using the Medical Dictionary for Regulatory Activities version 14.0 classification and classified by severity (mild, moderate, or severe). Relatedness to study drug (related or not related) will be reported for SAEs only by the Investigator. Treatment-emergent adverse events occurring within 3 days of a dose change will be attributed to the previous dose.

APT-1011 (fluticasone proprionate ODT) a minimally absorbed corticosteroid is expected to act topically in the esophagus. Because of this, there is potential for decreased efficacy if the subject swallows water soon after dosing. Since the use of fluticasone has only been rarely associated with oral candidiasis, there will be no need to do swish and spit since this could inadvertently be associated with swallowed water.

Oral and esophageal candidiasis will however be considered AEs of special interest. Subjects may remain in the study during the treatment for these AEs. The investigator may allow swish and spit 30 minutes after dosing for these subjects. Subjects must be instructed not to swallow the rinsing water.

Symptoms of hypercorticism (See below) are also AEs of special interest.

Laboratory Tests

Routine laboratory tests and assessments will be performed throughout the study, including hematology, blood chemistry, urinalysis, and electrocardiograms (ECGs). Clinically significant changes in laboratory tests or ECGs will be summarized.

Physical Examination and Vital Signs

Physical examinations will be performed to document the baseline condition of the subject and to highlight changes related to AEs. Vital signs will also be assessed and clinically significant deviations will be reported.

Cortisol-Related Findings

All subjects will undergo a 250 µg ACTH stimulation test during the 4-week Baseline Symptom Assessment following receipt of the morning serum cortisol level during the Screening period. This test will also be administered at Week 12 (Visit 6), Week 26 (Visit 10), and Week 52 (Visit 14).

At all visits (scheduled or unscheduled), specific attention will be given to potential changes related to corticosteroids, as well as symptoms of hypercorticism. Should a subject undergo surgery or trauma during the study, particular care should be taken in observing subjects for evidence of inadequate adrenal response.

If hypercorticism or adrenal suppression are suspected, an adequate work-up should be performed to confirm or rule out these findings. Specifically, to monitor for hypothalamic pituitary adrenal (HPA) axis suppression of potential clinical concern, a 250 µg ACTH simulation test will also be performed after Screening if any of the following occur:

During routine laboratory testing completed for the study, the subject has a morning serum cortisol level ≤5 µg/dL (138 nmol/L) (confirmed by 2 blood draws), including at the last on-treatment visit for a subject and, if applicable, Early Termination Visit;

The subject reports symptoms of hypercorticism;

The subject discontinues due to HPA axis suppression.

A positive result for the ACTH stimulation test is defined as serum cortisol level <18 µg/dL (497 nmol/L) at 60 minutes after treatment with 250 µg cosyntropin. This result is exclusionary if it occurs at Screening/4 week Baseline Symptom Assessment and requires follow-up through recovery of adrenal function if it occurs thereafter. Treatment for HPA axis suppression is discussion in the full protocol. The Sponsor will provide guidelines for safety follow-up and document of restoration of adrenal function in all subjects demonstrating evidence of hypercorticism or HPA axis suppression during the course of the study.

Electrocardiogram

Electrocardiograms signs will be assessed and clinically significant deviations will be reported.

Safety Endpoints:

The safety endpoints of interest are:

Frequency of TEAEs;

TEAEs leading to discontinuation;

Treatment-emergent SAEs;

Percentage of subjects with serum cortisol level ≤5 µg/dL (≤138 nmol/L) or positive ACTH stimulation test (serum cortisol ≤18 µg/mL [≤497 nmol/L] at 60 minutes);

The number of subjects discontinuing for HPA axis suppression will be recorded.

Frequency of oral and esophageal candidiasis.

Pharmacokinetic Variables:

The following PopPK parameters will be estimated using sparse sampling, as data permit: Oral clearance; Volume of distribution. Additional PopPK parameters will be estimated, as appropriate, based on the final structural PK model.

Statistical Methods:

Sample Size Determination:

Part 1 will include a sample size with a range of 100 subjects, in which 20 patients are randomized to 1.5 mg HS, 1.5 mg BID, 3 mg HS, 3 mg BID, and placebo (1:1:1:1:1). Based on these randomization ratios, approximately 80% of all subjects in Part 1 will be treated with an APT-1011 dosing regimen and approximately 20% of all subjects in Part 1 will be treated with placebo.

Analysis Populations:

The All Enrolled Population includes all subjects who signs an ICF and are enrolled into the study. The Safety Population includes all subjects who receive ≥1 dose of study drug. The Intent-to-treat (ITT) Population includes all subjects who receive ≥1 dose of study drug and have ≥1 efficacy assessment post-dose. A subject who is enrolled in the study and receives study drug, but fails to complete treatment will be considered a dropout. The Sparse PK Subgroup includes all subjects who have ≥1 quantifiable PK sample collected for sparse PK evaluations.

Additional analysis populations (e.g., Per Protocol Populations including subjects who complete Part 1, Part 2 Weeks 26 and 52) may be defined in the Statistical Analysis Plan.

Statistical Methodology:

Subject Characteristics:

Baseline and demographic information will be summarized using descriptive statistics for continuous and ordinal variables (e.g., age and weight) and counts and percentages for categorical variables (presence or absence of strictures, prior response to steroids, sex and race).

Primary Efficacy Analysis for Part 1

Let $p_0$ be the proportion of patients who meet histology response for placebo, and let $p_j$ be the proportion of patients who meet histology response for dose j, with j=1, 2, 3, 4 corresponding to 1.5 mg HS, 1.5 mg BID, 3 mg HS and 3 mg BID doses, respectively. There are 4 hypotheses corresponding to the 4 active doses, which will be tested using a gatekeeping strategy to preserve Type I error for each analysis.

1) Primary Hypothesis #1

$H_0: p_4 \leq p_0$ $H_1: p_4 = p_0$

A Chi-square test of proportions will be used to test primary hypothesis #1, i.e 3 mg BID vs. placebo. If the corresponding p-value is less than or equal to 0.05, the null hypothesis will be rejected, and subsequently the following hypothesis will be tested:

2) Primary Hypothesis #2

$H_0: p_3 \leq p_0$ $H_1: p_3 = p_0$

A Chi-square test of proportions will be used to test primary hypothesis #2, i.e 3 mg HS vs. placebo. If the corresponding p-value is less than or equal to 0.05, the null hypothesis will be rejected, and subsequently the following hypothesis will be tested:

3) Primary Hypothesis #3

$H_0: p_2 \leq p_0$ $H_1: p_2 = p_0$

A Chi-square test of proportions will be used to test primary hypothesis #3, i.e 1.5 mg BID vs. placebo. If the corresponding p-value is less than or equal to 0.05, the null hypothesis will be rejected, and subsequently the following hypothesis will be tested:

4) Primary Hypothesis #4

$H_0: p_1 \leq p_0$ $H_1: p_1 = p_0$

A Chi-square test of proportions will be used to test primary hypothesis #4, i.e 1.5 mg HS vs. placebo. If the corresponding p-value is less than or equal to 0.05, the null hypothesis will be rejected.

Note the gate-keeping strategy only allows formal hypothesis testing of 1.5 mg HS or 1.5 mg BID if the higher doses meet statistical significance.

Efficacy Analysis for Part 2

Sustained EoE response will be assessed in subjects who complete both Part 1 and Part 2 and complete Week 26 and 52 evaluations. This will be assessed by the primary endpoint. Other measures of efficacy will be assessed at Week 26. Efficacy will be summarized for histologic non-responders from Part 1 who are treated in Part 2. Other measures of efficacy will be assessed at Week 52.

Secondary and Exploratory Efficacy Analysis

Statistical tests to compare each APT-1011 dosing group with placebo will be performed for the secondary efficacy endpoints, but the corresponding p-values will be considered as descriptive rather than inferential.

The secondary endpoints will be analyzed via a Cochran-Mantel-Haenzel (CMH) test for categorical endpoints and analysis of covariance for change from baseline endpoints, except for the endpoint of time to relapse after initiation of double-blind treatment in Part 2, which will be analyzed using Kaplan-Meier methods.

No statistical testing of exploratory efficacy endpoints will be performed.

Safety Analyses

The incidence of TEAEs will be summarized by system organ class and preferred term. Separate summaries by maximum severity (all AEs) and relationship to study drug (SAEs only) will be provided. The incidence of TEAEs leading to discontinuation from the study and treatment-emergent SAEs will also be summarized. In subjects who change dosing groups, the TEAEs will be attributed to the previous dose, if they occur within 3 days of the change.

Clinically significant changes of potential clinical interest in clinical tests will be summarized including hematology, chemistry, urinalysis, ECG, cortisol, vital signs, and bone mineral density. No statistical testing of safety endpoints will be performed. Shift tables may be produced, if needed. The number of subjects discontinuing due to HPA axis suppression or positive ACTH stimulation tests will be summarized.

Population Pharmacokinetics

A PopPK analysis will be performed based on sparse plasma concentration data. It will be performed using the nonlinear mixed-effects software, NONMEM, Version 7.2.0 or later (ICON Development Solutions, Ellicott City, Md.) or other appropriate nonlinear mixed-effects modeling software. The structural PK model will include oral clearance and volume of distribution as fixed-effect parameters. Additionally, the intersubject variability in the parameter estimates and the random residual error in the data will be estimated with appropriate error models. The optimal base model will be selected according to the standard criteria such as minimum objective function value and diagnostic plots. A separate PopPK report will be generated as an appendix to the clinical study report.

Exploratory PK/PD Analysis

As data permit, exploratory PK/PD analyses assessing the relationship between systemic exposure to FP and changes in cortisol levels also may be performed as described above. Additional exploratory PK/PD analyses may be performed to facilitate selection of safe and effective doses for future studies and clinical use.

Study Rationale and Risk-Benefit Analysis

The purpose of FLUTicasone in Eosinophilic esophagitis (FLUTE) is to examine 3 total daily doses of APT-1011 to define the exposure-response of APT-1011 and the minimum effective dose while minimizing any clinically significant HPA axis effects. APT-1011 is expected to offer the following advantages for patients with EoE: Oral administration is generally more acceptable and more reliable in terms of accurate dose administration. Currently, the only available formulation of FP is a metered dose inhaler that is sprayed into the mouth and swallowed by the patient. Oral administration of APT-1011 has very low bioavailability even compared with similar compounds such as budesonide, which further reduces its potential for systemic corticosteroid toxicity, while it may be more potent on a mg basis.

The current study represents the first dose ranging study of APT-1011. Given its low bioavailability, it is unlikely that APT-1011 will have any significant systemic corticosteroid effects.

TABLE 12

Schedule of Events (Screening, 4-week Placebo Run-in/Baseline Symptom Assessment, and Part 1)

| Assessments and Procedures | Visit 1 (Screening) | Visit 2 (4-week Baseline Symptom Assessment) | Visit 3 (Randomization) | Visit 4 (Week 4) | Visit 5 (Week 8) | Visit 6 (Week 12) (Response Assessment) [a] | Visit 7 (Week 14 [a]) | Unscheduled Visit [b] | Early Termination Visit [c] |
|---|---|---|---|---|---|---|---|---|---|
| | −56 to −28 | −28 to −1 (Site Visit to Occur Day −28) | 1 | 28 ± 2 | 56 ± 2 | 84 ± 2 | 98 + 2 | | |
| ICF signed | X | | | | | | | | |
| Confirm entry to 4-week Baseline Symptom Assessment [d] | | X | | | | | | | |
| Inclusion/exclusion criteria | X | X | X [e] | | | | | | |
| Demographics; medical, surgical, and medication history | X | | | | | | | | |
| Concomitant medication(s) | X | X | X | X | X | X | X | X | X |
| Physical examination [f] | X | | X | X | X | X | X | X | X |
| Vital signs [g] | X | X | X | X | X | X | X | X | X |
| Chemistry and hematology | X | | X | X | X | X | X | X | X |
| Serum cortisol (morning fasting) [h] | X | | X | X | X | X | X [i] | Optional | X |
| Urinalysis | X | | X | X | X | X | | X | X |
| 12-lead ECG | X | | X | | | X | | | X |
| PopPK [j] | | | X (pre-dose) | X | X | X | | | |
| EGD (with EREFs), including collection of multiple | X | | | | | X | | | X [n] |
| Pregnancy test for women of childbearing potential (menopausal women FSH at Screening only) [o] | X (serum) | X (urine) | X (urine) | X (urine) | X (urine) | X (urine) | X (urine) | Optional | X (urine) |
| ACTH stimulation test (250 μg) | X [p] | | | | | X | | Optional [q] | Optional [r] |
| AEs | X | X | X | X | X | X | X | X | X [s] |
| Global EoE Symptom Score | X [t] | X | X | X | X | X | X | Optional | X |
| 7-day EEsAI | | | X | | | X | | | X |
| PGIC | | | | X | X | X | X | Optional | X |
| PGIS | | X | X | X | X | X | X | Optional [u] | X |
| EoE-QoL-A | | | X | | | X | | | X |
| Training for daily diary | | X [v] | | | | | | | |
| Daily diary | | | X | X | X | X | X | | X |
| Study drug dispensed | | | X | X | X | X | X | | |
| Drug return and accountability and study drug compliance assessment | | | | X | X | X | X | X | X |
| Reason for discontinuation | | | | | | | | | X |

Abbreviations: ACTH = adrenocorticotropic hormone; AE = adverse event; ECG = electrocardiogram; eCRF = electronic case report form; EEsAI = Eosinophilic Esophagitis Activity Index; EGD = esophagogastroduodenoscopy; EoE = eosinophilic esophagitis; EoE-QoL-A = Adult Eosinophilic Esophagitis Quality of Life Questionnaire; EREFs = Eosinophilic Esophagitis Endoscopic Reference Score; FSH = follicle-stimulating hormone; HPA = hypothalamic-pituitary-adrenal; ICF = informed consent form; PGIC = Patient Global Impression of Change; PGIS = Patient Global Impression of Severity; PK = pharmacokinetic(s); popPK = population pharmacokinetic(s); SAE = serious adverse event.
[a] Data and samples collected for Week 14 in the Part 1 Schedule of Events will also apply for this visit in the Part 2 Schedule of Events (as applicable) and procedures will not be repeated. Histologic non-responders at Week 12 will receive single-blind 3 mg BID in Part 2.
[b] The reason for an unscheduled visit will guide procedures, at the discretion of the Investigator.
[c] The subject should be seen at the site within 7 days of determination of the need to discontinue. If this is not possible due to an SAE or other unforeseen circumstance, it may be completed with a phone visit with the subject or a family member. The eCRF should document why the subject was not available for an on-site visit.

TABLE 12-continued

Schedule of Events (Screening, 4-week Placebo Run-in/Baseline Symptom Assessment, and Part 1)

| | | VISIT | | | | | | | |
|---|---|---|---|---|---|---|---|---|---|
| Assessments and Procedures | Visit 1 (Screening) | Visit 2 (4-week Baseline Symptom Assessment) | Visit 3 (Randomization) | Visit 4 (Week 4) | Visit 5 (Week 8) | Visit 6 (Week 12) (Response Assessment)[a] | Visit 7 (Week 14[a]) | Unscheduled Visit[b] | Early Termination Visit[c] |
| | | | | DAY | | | | | |
| | −56 to −28 | −28 to −1 (Site Visit to Occur Day −28) | 1 | 28 ± 2 | 56 ± 2 | 84 ± 2 | 98 + 2 | | |

[d] As described in Section 4.1.4, to enter the 4-week Baseline Symptom Assessment, subjects must meet all inclusion criteria including the Global EoE score >3 (Inclusion Criterion #5) except those to be assessed during the 4-week Baseline Symptom Assessment (Inclusion Criterion #7: evidence of EoE as defined by ≥15 PEAK eosinophils/HPF, Inclusion Criterion #8: in the daily diary, report episodes of dysphagia ≥3 days per 7 days during the last 14 days of the 4-week Baseline Symptom Assessment, Inclusion Criterion #9: completion of the daily diary on at least 5 out of each 7 days during the last 14 days of the Baseline Symptom Assessment, and Exclusion Criterion #23: serum cortisol level <18 μg/dL (497 nmol/L) at 60 minutes with adrenocorticotropic hormone (ACTH) stimulation test using 250 μg cosyntropin [i.e., a positive result on the ACTH stimulation test]).

[e] Confirmation that the subject meets eligibility criteria include the following to be confirmed during the 4-week Baseline Symptom Assessment: Inclusion Criterion #7: evidence of EoE as defined by ≥15 PEAK eosinophils/HPF, Inclusion Criterion #8: in the daily diary, report episodes of dysphagia ≥3 days per 7 days during the last 14 days of the 4-week Baseline Symptom Assessment, Inclusion Criterion #9: completion of the daily diary on at least 5 out of each 7 days during the last 14 days of the Baseline Symptom Assessment, and Exclusion Criterion #23: serum cortisol level <18 μg/dL (497 nmol/L) at 60 minutes with ACTH stimulation test using 250 μg cosyntropin (i.e., a positive result on the ACTH stimulation test).

[f] Physical examination will include assessments of height at screening (Day 1 only), weight, general appearance, head and neck, eyes and ears, nose and throat, chest, lungs, heart, abdomen, extremities and joints, lymph nodes, skin, and neurological examination. Body Mass Index (BMI) will be calculated on Day 1.

[g] Vital signs to be collected include pulse, respiratory rate, temperature (° C.; after a 5-minute rest in sitting position), and blood pressure (measured from the same arm throughout the study).

[h] To be drawn 0700 to 0800 hours, or as close to that window as possible. Subjects must be fasting for an 8-hour period prior to the serum cortisol assessments. Blood may be drawn for serum cortisol (morning fasting) ± 3 days of scheduled visit to accommodate accurate timing. If desired, other blood draws scheduled for the visit may be done at the same time.

[i] If abnormal serum cortisol level is reported at the last on-treatment visit for a subject, additional monitoring and ACTH test may be required (see Section 6.3.4).

[j] Sparse PK samples will be performed in all subjects. A sample will be collected pre-dose on Day 1. At Week 4, Week 8, and Week 12, subjects will take their "after breakfast" dose at home and 2 samples will be taken during their scheduled visit: upon arrival to the site and 1 to 1.5 hours after first sample (immediately prior to leaving the site). Subjects should write down the time they took the morning dose and inform the site staff. The time of the "after breakfast" dose (day of the planned visit) and the time of the immediately preceding "at bedtime" dose (evening prior to planned visit) will be recorded. Actual PK sampling times will be documented.

[k] It is expected that the EGD will typically be performed during a separate time from other procedures for a given time point. Both EGD and any other procedures indicated for a study visit must be completed within the window for that study visit. For Screening, the EGD must be completed after the ICF is signed and ≥2 weeks before the date of expected randomization.

[l] During the EGD, the endoscopist will complete the EREFs and ~3 biopsies will be obtained from both the proximal and the distal esophagus (total of 5-6 biopsies). The pathologist will assess histology.

[m] The EGD to determine eligibility must be performed before entry into the 4-week (28 day) single-blind run-in/Baseline Symptom Assessment. Pathology for EGD biopsies may also be assessed during the 4-week Baseline Symptom Assessment (or earlier if possible).

[n] If the subject discontinues from the study due to lack of efficacy or other reasons, the Investigator may perform an EGD, if clinically indicated.

[o] A serum pregnancy test will be performed at Screening and urine pregnancy tests thereafter. Pregnancy testing in women of childbearing potential must be negative (see Section 6.3.2.1).

[p] All subjects undergo a 250 μg ACTH stimulation test as part of eligibility assessments. This evaluation will be completed following receipt of the morning serum cortisol level during the Screening period. This must be performed before entry into the 4-week (28 day) single-blind run-in/Baseline Symptom Assessment. A positive ACTH stimulation test (serum cortisol level <18 μg/dL (497 nmol/L) at 60 minutes after treatment with 250 μg cosyntropin) will be exclusionary (see Exclusion Criterion #9: use of biologic immunomodulators in the 24 weeks prior to Screening in Section 4.2.2).

[q] A 250 μg ACTH simulation test will be performed (at an unscheduled visit) to assess for HPA axis suppression of potential clinical concern as follows:
1) Any time a subject has a morning serum cortisol level ≤5 μg/dL (138 nmol/L) (confirmed by 2 blood draws)
2) Any time a subject reports symptoms of hypercorticism (Appendix 6)

[r] Subjects who discontinue from the study due to evidence of HPA axis suppression will undergo a 250 μg ACTH stimulation test at the Early Termination Visit.

[s] For the Early Termination Visit, the Investigator should record any occurrence of AEs (14 ± 5 days after discontinuation). Subjects discontinued for HPA issues should be followed until resolution.

[t] Global EoE symptom score at Screening will be completed on paper. EoE score must remain >3 at each of Visits 1, 2 and 3 before randomization, or the subject will be considered a screen failure.

[u] Only if visit is related to EoE change in symptoms.

[v] Recording in the daily diary will not start until 28 days prior to planned date of randomization.

TABLE 13

Schedule of Events Part 2

| | VISIT | | | | | | |
|---|---|---|---|---|---|---|---|
| Assessments and Procedures | Visit 7 (Week 14) | Visit 8 (Week 18) | Visit 9 (Week 22) | Visit 10 (Week 26) (Response Assessment)[a] | Visit 11 (Week 28[a]) | Unscheduled Visit[b] | Early Termination Visit[c] |
| | | | | DAY | | | |
| | 98 + 2 | 126 ± 2 | 154 ± 2 | 182 ± 2 | 196 + 2 | | |
| Histologic Responder/Non-Responders in Part 1 (no contraindications to continue) | X | | | | | | |
| Concomitant medication(s) | X | X | X | X | X | X | X |
| Physical examination[d] | X | X | | X | | X | X |
| Vital signs[e] | X | X | X | X | X | X | X |
| Chemistry and hematology | X | X | X | X | | X | X |
| Serum cortisol (morning fasting)[f] | X | X | X | X | X[g] | Optional | X |
| Urinalysis | | X | X | X | | X | X |
| 12-lead ECG | | | | X | | | X |

TABLE 13-continued

Schedule of Events Part 2

| Assessments and Procedures | Visit 7 (Week 14) 98 + 2 | Visit 8 (Week 18) 126 ± 2 | Visit 9 (Week 22) 154 ± 2 | Visit 10 (Week 26) (Response Assessment) [a] DAY 182 ± 2 | Visit 11 (Week 28 [a]) 196 + 2 | Unscheduled Visit [b] | Early Termination Visit [c] |
|---|---|---|---|---|---|---|---|
| EGD (with EREFs), including collection of multiple | | | | X | | X | X [j] |
| Urine pregnancy test for women of childbearing potential | X | X | X | X | X | Optional | X |
| ACTH stimulation test (250 μg) [k] | | | | X | | Optional [k] | Optional [l] |
| AEs | X | X | X | X | X | X | X [m] |
| Global EoE Symptom Score | X | X | X | X | X | Optional | X |
| 7-day EEsAI | | | | X | | | X |
| PGIC | X | X | X | X | X | Optional | X |
| PGIS | X | X | X | X | X | Optional [n] | X |
| EoE-QoL-A | | | | X | | | X |
| Daily diary | X | X | X | X | | | X |
| Study drug dispensed | X (if needed for dosing group change) | X | X | X | X | | |
| Drug return and accountability and study drug compliance assessment | | X | X | X | X | | X |
| Reason for discontinuation | | | | | | | X |

Abbreviations: ACTH = adrenocorticotropic hormone; AE = adverse event; ECG = electrocardiogram; eCRF = electronic case report form; EEsAI = Eosinophilic Esophagitis Activity Index; EGD = esophagogastroduodenoscopy; EoE = eosinophilic esophagitis; EoE-QoL-A = Adult Eosinophilic Esophagitis Quality of Life Questionnaire; EREFs = Eosinophilic Esophagitis Endoscopic Reference Score; HPA = hypothalamic-pituitary-adrenal; PGIC = Patient Global Impression of Change; PGIS = Patient Global Impression of Severity; SAE = serious adverse event.

[a] Data and samples collected for Week 28 in the Part 1 Schedule of Events will also apply for this visit in the Part 2 Schedule of Events in Table 4-3 (as applicable) and procedures will not be repeated. At Week 26 subjects who are histologic non-responders will stop treatment at Week 28 and enter the 2-week Follow-up period. Histologic responders continue on the same dose.
[b] The reason for an unscheduled visit will guide procedures, at the discretion of the Investigator.
[c] The subject should be seen at the site within 7 days of determination of the need to discontinue. If this is not possible due to an SAE or other unforeseen circumstance, it may be completed with a phone visit with the subject or a family member. The eCRF should document why the subject was not available for an on-site visit.
[d] Physical examination will include assessments of weight, general appearance, head and neck, eyes and ears, nose and throat, chest, lungs, heart, abdomen, extremities and joints, lymph nodes, skin, and neurological examination.
[e] Vital signs to be collected include pulse, respiratory rate, temperature (° C.; after a 5-minute rest in sitting position), and blood pressure (measured from the same arm throughout the study).
[f] To be drawn 0700 to 0800 hours, or as close to that window as possible. Subjects must be fasting for an 8 hour period prior to the serum cortisol assessments. Blood may be drawn for serum cortisol (morning fasting) ±3 days of scheduled visit to accommodate accurate timing. If desired, other blood draws scheduled for the visit may be done at the same time.
[g] If abnormal serum cortisol level is reported at the last on-treatment visit for a subject, additional monitoring and ACTH test may be required (see Section 6.3.4).
[h] It is expected that the EGD will typically be performed during a separate time from other procedures for a given time point. Both EGD and any other procedures indicated for a study visit must be completed within the window for that study visit. For Screening, the EGD must be completed after the ICF is signed and ≥2 weeks before the date of expected randomization.
[i] During the EGD, the endoscopist will complete the EREFs and ~3 biopsies will be obtained from both the proximal and the distal esophagus (total of 5-6 biopsies). The pathologist will assess histology.
[j] If the subject is discontinuation from the study due to lack of efficacy or other reasons, the Investigator may perform an EGD, if clinically indicated.
[k] A 250 μg ACTH simulation test will be performed (at an unscheduled visit) to assess for HPA axis suppression of potential clinical concern as follows:
1) Any time a subject has a morning serum cortisol level ≤5 μg/dL (138 nmol/L) (confirmed by 2 blood draws)
2) Any time a subject reports symptoms of hypercorticism (Appendix 6).
[l] Subjects who discontinue from the study due to evidence of HPA axis suppression will undergo a 250 μg ACTH stimulation test at the Early Termination Visit.
[m] For the Early Termination Visit, the Investigator should record any occurrence of AEs (14 ± 5 days after discontinuation). Subjects discontinued for HPA issues should be followed until resolution.
[n] Only if visit is related to EoE change in symptoms.

TABLE 14

Schedule of Events (Part 2 and follow up visit)

| Assessments and Procedures | Visit 11 (Week 28) 196 + 2 | Visit 12 (Week 36) 252 ± 2 | Visit 13 (Week 44) 308 ± 2 | Visit 14 (Week 52) (Response Assessment) DAY 364 ± 2 | Unscheduled Visit [a] | Early Termination Visit [b] | Follow-up Visit 2 weeks after last dose of study drug |
|---|---|---|---|---|---|---|---|
| Histologic responders at Week 26 [c] | X | | | | | | |
| Responder status | | | | X | | | |
| Concomitant medication(s) | X | X | X | X | X | X | X |
| Physical examination [d] | | X | X | X | X | X | X |
| Vital signs [e] | X | X | X | X | X | X | X |
| Chemistry and hematology | | X | X | X | X | X | X |

TABLE 14-continued

Schedule of Events (Part 2 and follow up visit)

| Assessments and Procedures | Visit 11 (Week 28) 196 + 2 | Visit 12 (Week 36) 252 ± 2 | Visit 13 (Week 44) 308 ± 2 | Visit 14 (Week 52) (Response Assessment) DAY 364 ± 2 | Unscheduled Visit [a] | Early Termination Visit [b] | Follow-up Visit 2 weeks after last dose of study drug |
|---|---|---|---|---|---|---|---|
| Serum cortisol (morning fasting)[f] | X | X | X | X [g] | Optional | X | X |
| Urinalysis | | X | X | X | X | X | X |
| 12-lead ECG | | | | X | | X | X |
| EGD (with EREFs), including collection of multiple esophageal biopsies to be assessed histologically [h,i] | | | | X [k] | X | X [j] | |
| Urine pregnancy test for women of childbearing potential | X | X | X | X | Optional | X | X |
| ACTH stimulation test (250 μg) | | | | X | Optional [k] | Optional [l] | |
| AEs | X | X | X | X | X | X [m] | |
| Global EoE Symptom Score | X | X | X | X | Optional | X | |
| 7-day EEsAI | | | | X | | X | |
| PGIC | X | X | X | X | Optional | X | |
| PGIS | X | X | X | X | Optional [n] | X | |
| EoE-QoL-A | | | | X | | X | |
| Daily diary | | X | X | X | X | X | |
| Study drug dispensed | X (if needed for dosing group change) | X | X | | | | |
| Drug return accountability and study drug compliance assessment | X | X | X | X | | X | X |
| Reason for discontinuation | | | | | | X | |

Abbreviations: ACTH = adrenocorticotropic hormone; AE = adverse event; ECG = electrocardiogram; eCRF = electronic case report form; EEsAI = Eosinophilic Esophagitis Activity Index; EGD = esophagogastroduodenoscopy; EoE = eosinophilic esophagitis; EoE-QoL-A = Adult Eosinophilic Esophagitis Quality of Life Questionnaire; EREFs = Eosinophilic Esophagitis Endoscopic Reference Score; HPA = hypothalamic-pituitary-adrenal; PGIC = Patient Global Impression of Change; PGIS = Patient Global Impression of Severity; SAE = serious adverse event.

[a] The reason for an unscheduled visit will guide procedures, at the discretion of the Investigator.
[b] The subject should be seen at the site within 7 days of determination of the need to discontinue. If this is not possible due to an SAE or other unforeseen circumstance, it may be completed with a phone visit with the subject or a family member. The eCRF should document why the subject was not available for an on-site visit.
[c] Histologic responders will continue on the same dose. Histologic non-responders at Week 26 will stop treatment at Week 28 and enter the 2-week follow-up period.
[d] Physical examination will include assessments of weight, general appearance, head and neck, eyes and ears, nose and throat, chest, lungs, heart, abdomen, extremities and joints, lymph nodes, skin, and neurological examination.
[e] Vital signs to be collected include pulse, respiratory rate, temperature (° C.; after a 5-minute rest in sitting position), and blood pressure (measured from the same arm throughout the study).
[f] To be drawn 0700 to 0800 hours, or as close to that window as possible. Subjects must be fasting for an 8 hour period prior to the serum cortisol assessments. Blood may be drawn for serum cortisol (morning fasting) ±3 days of scheduled visits to accommodate accurate timing. If desired, other blood draws scheduled for the visit may be done at the same time.
[g] If abnormal serum cortisol level is reported at the last on-treatment visit for a subject, additional monitoring and ACTH test may be required (see Section 6.3.4).
[h] It is expected that the EGD will typically be performed during a separate time from other procedures for a given time point. Both EGD and any other procedures indicated for a study visit must be completed within the window for that study visit. For Screening, the EGD must be completed after the ICF is signed and ≥2 weeks before the date of expected randomization.
[i] During the EGD, the endoscopist will complete the EREFs and ~3 biopsies will be obtained from both the proximal and the distal esophagus (total of 5-6 biopsies). The pathologist will assess histology. The subject will be treated with study drug through completion of the EGD associated with the Week 52 visit.
[j] If the subject is discontinued from the study due to lack of efficacy or other reasons, the Investigator may perform an EGD, if clinically indicated.
[k] A 250 μg ACTH simulation test will be performed (at an unscheduled visit) to assess for HPA axis suppression of potential clinical concern as follows:
1) Any time a subject has a morning serum cortisol level ≤5 μg/dL (138 nmol/L) (confirmed by 2 blood draws)
2) Any time a subject reports symptoms of hypercorticism (Appendix 6).
[l] Subjects who discontinue from the study due to evidence of HPA axis suppression will undergo a 250 μg ACTH stimulation test at the Early Termination Visit.
[m] For the Early Termination Visit, the Investigator should record any occurrence of AEs (14 ± 5 days after discontinuation). Subjects discontinued for HPA issues should be followed until resolution.
[n] Only if visit is related to EoE change in symptoms.

Screening

The Screening Period is 4 weeks (28 days). Along with the reports confirming the subject's primary diagnosis of EoE, the Investigator will assess eligibility criteria (see Section 4.2.1 and Section 4.2.2) of the subject based on Screening results. The Global EoE score must be >3 for the subject to continue in the study.

The EGD procedures to determine eligibility (see Inclusion Criterion #7: have evidence of EoE, as defined by ≥15 PEAK eosinophils/HPF. In order to ensure that a diagnosis can be made, at least 5-6 biopsies should be taken including both proximal and distal specimens [~3 each]) will be completed during the Screening Period and the biopsies must be received by the central pathologist by the times noted in this inclusion criterion. EGD must be performed prior to Visit 2 (4-week Baseline Symptom Assessment).

ACTH stimulation test must also be performed prior to Visit 2 (4-week Baseline Symptom Assessment).

With Medical Monitor approval, a subject may be rescreened once if the previous reason for screen failure is no longer present or the subject withdrew due to personal or family reasons that have since resolved. If a subject is rescreened, a new informed consent form (ICF) will be signed and assigned a new number. All tests and assessments must be repeated.

4-Week Baseline Symptom Assessment (Placebo Run-in)

To enter this phase, subjects must:

Meet all inclusion criteria that are possible to assess prior to the 4-week Baseline Symptom Assessment including the Global EoE score >3 (Inclusion Criterion #5; EoE score must remain >3 at each of Visits 1, 2 and 3 before randomization, or the subject will be considered a screen failure) except those to be assessed during the 4-week Baseline Symptom Assessment: Inclusion Criterion #7: evidence of EOE as defined by ≥15 PEAK eosinophils/HPF; Inclusion Criterion #8: in the daily diary, report episodes of dysphagia ≥3 days per 7 days during the last 14 days of the 4-week Baseline Symptom Assessment; Inclusion Criterion #9: completion of the daily diary on at least 5 out of each 7 days during the last 14 days of the Baseline Symptom Assessment;

Meet no exclusion criteria that will be assessed prior to the 4-week Baseline Symptom Assessment (i.e., all except Exclusion Criteria #23: a serum cortisol level <18 µg/dL (497 nmol/L) at 60 minutes with adrenocorticotropic hormone [ACTH] stimulation test using 250 µg cosyntropin [i.e., a positive result on the ACTH stimulation test]).

The subject will complete a site visit at the beginning of the 4-week Baseline Symptom Assessment to complete procedures and assessments noted in Table 4-1.

During the 4-week Baseline Symptom Assessment, baseline symptom severity will be determined and the ability of the subject to be compliant with diary entries will be assessed. Pathology for EGD biopsies may also be assessed (or earlier if possible).

Randomization

Confirmation of Eligibility:

To be eligible for randomization, subjects must satisfy all inclusion/exclusion criteria, including the following inclusion criteria that are expected to be confirmed during the 4-week Baseline Symptom Assessment: Inclusion Criterion #7: evidence of EOE as defined by ≥15 PEAK eosinophils/HPF; Inclusion Criterion #8: in the daily diary, report episodes of dysphagia ≥3 days per 7 days during the last 14 days of the 4-week Baseline Symptom Assessment; Inclusion Criterion #9: completion of the daily diary on at least 5 out of each 7 days during the last 14 days of the Baseline Symptom Assessment and Exclusion Criteria #23: a serum cortisol level <18 µg/dL (497 nmol/L) at 60 minutes with adrenocorticotropic hormone (ACTH) stimulation test using 250 µg cosyntropin (i.e., a positive result on the ACTH stimulation test).

If the Investigator confirms eligibility criteria are met, he or she will randomize the subject using the Interactive Web Response System (IWRS). The IWRS will confirm the eligibility of the subject pertaining to histology (i.e., confirm histological evidence of the EoE diagnosis as per Inclusion Criterion #7: evidence of EOE as defined by ≥15 PEAK eosinophils/HPF), and provide the randomization number to the Investigator and the Sponsor.

Randomization Scheme:

A total of 100 adult subjects will be randomized to 1 of 4 doses of APT-1011 (1.5 mg HS, 1.5 mg BID, 3 mg HS, and 3 mg BID) or placebo. Subjects in the HS treatment groups will receive placebo 30 minutes after breakfast in order to maintain the blind.

Randomization will occur in a double-blind manner using an integrated IWRS, and will be stratified by the presence or absence of a history of or current esophageal stricture at Screening and history of a prior positive steroid response to any corticosteroid treatment previously received to treat the subject's EoE captured with demography. Randomization for subjects in Part 1 will be stratified by use, such that a comparable percentage of subjects during the study will be allocated to each of the 5 dosing groups.

Treatment

FIG. 5 provides an overview of the treatment each subject will receive is determined throughout FLUTE (based on responder status). Symptom improvement or deterioration will be assessed on an ongoing basis.

Induction (Day 1 to Week 14)

During Part 1, subjects will receive their randomized treatment for 14 weeks.

At Week 12, the subjects will undergo a response assessment, including EGD to assess endoscopic and histologic status. The process overview in Section 6.2 will be followed to determine responder status (as defined in Section 4.1.1) and inform the site thereof. Symptoms will also be assessed. The 14 days prior to Week 12 will be compared to the 14 days prior to Randomization.

Histologic responders and non-responders (at Week 12) will enter Part 2 (see Section 4.1.6.2).

Maintenance (Week 14 to Week 52)

In Part 2, all subjects classified as histologic responders at Week 12 will continue to be treated according to the dosing group to which they were randomized for Part 1. Subjects may continue on this dose for up to 9 months after the completion of Part 1.

Subjects who are histologic non-responders (see Section 4.1.1) at Week 12 will receive single-blind 3 mg BID in Part 2.

At Week 26, subjects will undergo an EGD with biopsy, to assess histologic response. The process overview in Section 6.2 will be followed to determine responder status (as defined in Section 4.1.1) and inform the site thereof. Symptoms will also be assessed. All subjects classified as histologic responders will continue to be treated according to the dosing group to which they were randomized for Part 1 up to Week 52. The 14 days prior to Week 26 will be compared to the 14 days prior to Randomization.

Subjects who are histologic non-responders (see Section 4.1.1) at Week 26 will stop treatment at Week 28 and enter the 2-week follow-up period and exit the study.

Subjects who complete the study at Week 52 will undergo a response assessment, including EGD to assess endoscopic and histologic status. The process overview in Section 6.2 will be followed to determine responder status (as defined in Section 4.1.1) and inform the site thereof. Symptoms will also be assessed. The subject will be treated with study drug through completion of the EGD associated with the Week 52 visit. The 14 days prior to Week 52 will be compared to the 14 days prior to Randomization.

Subjects will complete a Follow-up Visit 2 weeks after the final dose of study drug (see Section 4.1.8).

Efficacy, Safety, and Pharmacokinetic Assessments

Baseline and demographic data to be collected include age, gender, weight, race (Caucasian, Black, Asian, Native American, or other), ethnicity (Hispanic, Non-Hispanic, or other), and smoking status.

Efficacy and Patient-Reported Outcome Assessments

Esophagogastroduodenoscopy: For the purposes of the current study, it is expected that the esophagus will be the focus of EGD procedures.

Whenever possible, the same endoscopist should be used for all EGDs performed for the study.

Multiple Esophageal Biopsies

A minimum of 3 biopsies will be obtained from both the proximal and the distal esophagus (total of ≥6 biopsies) during the EGD. Care should be taken to obtain biopsies that are of sufficient size and are opaque. Additional attempts should be made if suboptimal biopsies are taken. It is suggested that biopsies be obtained 1 at a time to achieve optimal results.

All biopsies should be stored at room temperature.

Eosinophilic Esophagitis Histology

A central pathologist will evaluate all esophageal biopsies and count the peak number of eosinophils/HPF. From a histological perspective, the eligibility requirements are described in Inclusion Criterion (e.g. have evidence of EoE, as defined by ≥15 PEAK eosinophils/HPF with at least 5-6 biopsies including both proximal and distal specimens [3 each]).

Eosinophilic Esophagitis Endoscopic Reference Score

The endoscopist will record the observed Eosinophilic Esophagitis Endoscopic Reference Score (EREFs) 27 that assesses edema, furrowing, exudates, rings, strictures, several miscellaneous features, and physician assessment of overall disease activity (absent; mild; moderate; severe) at each EGD. The EREFs has been shown to be a reliable diagnostic tool to both diagnose EoE and to assess the response to treatment.

The endoscopist will complete a worksheet for the EREFs, and data will be transferred to the appropriate eCRF by the site clinical staff/study coordinator. The worksheet should be retained at the site as a source document.

Daily Diary

A daily diary will be completed by the subject to assess the presence of dysphagia and questions related to its severity and associated pain. The diary will be completed by the subject daily throughout the study.

These data will be self-reported electronically by the subject, transferred automatically to the electronic patient-reported outcome (ePRO) vendor, and transmitted thereafter to the clinical database.

Global Eosinophilic Esophagitis Symptom Score

For the Global EoE Symptom Score, the subject will respond to the following:

On a scale from 0 to 10 (0 representing no symptoms and 10 representing most severe symptoms), how severe were your eosinophilic esophagitis symptoms over the past 7 days?

These data will be self-reported electronically by the subject, transferred automatically to the ePRO vendor, and transmitted thereafter to the clinical database.

7-Day Recall Eosinophilic Esophagitis Symptom Assessment Index

Symptoms will be assessed using the 7-day recall EEsAI questionnaire periodically and both total and subscores will be calculated. The subscores will include symptoms such as dysphagia, food avoidance and modification, and painful swallowing (odynophagia).

Additional questions used as anchors for the 7-day recall EEsAI score will also be assessed. These data will be self-reported on paper by the subject and transmitted thereafter to the clinical database by the site.

Subject Assessment of Symptoms

The following Patient Global Impression of Change (PGIC) questions will be asked to examine the subject's assessment of symptoms:

Compared with the beginning of the study, before you started the treatment, your EoE symptoms today are: Much worse; Moderately worse; A little worse; Stayed the same; A little improved; Moderately improved; Much improved. Please think of all your symptoms due to EoE and make an overall statement by choosing 1 of the options above.

Compared with the beginning of the study, before you started the treatment, your difficulty with food or pills going down today is: Much worse; Moderately worse; A little worse; Stayed the same; A little improved; Moderately improved; Much improved. Please think of your difficulty with food or pills going down and make an overall statement by choosing 1 of the options above.

These data will be self-reported electronically by the subject, transferred automatically to the ePRO vendor, and transmitted thereafter to the clinical database.

Subject Assessment of Symptom Severity

The following questions about patient global impression of symptom severity (PGIS) will be asked to examine the subject's assessment of severity:

Please choose the response that best describes the severity of your EoE symptoms over the past week (check one response): None; Mild; Moderate; Severe; Very Severe. Please think of all your symptoms due to EoE and make an overall statement of their severity by choosing 1 of the options above.

Please choose the response that best describes the severity of your difficulty with food or pills going down over the past week (check one response): None; Mild; Moderate; Severe; Very Severe. Please think of your difficulty with food or pills going down and make an overall statement of its severity by choosing 1 of the options above.

These data will be self-reported electronically by the subject, transferred automatically to the ePRO vendor, and transmitted thereafter to the clinical database.

Adult Eosinophilic Esophagitis Quality of Life Questionnaire

The Adult Eosinophilic Esophagitis Quality of Life Questionnaire (EoE-QOL-A) 29 is an assessment that may be administered directly to subjects to determine how EoE impacts their quality of life. It includes 30 questions on a 5-point Likert scale; questions represent 5 factors: eating/diet impact, social impact, emotional impact, disease anxiety, and choking anxiety and has been validated to correlate with established health related quality of life measures. Higher scores indicate better quality of life.

These data will be self-reported electronically by the subject, transferred automatically to the ePRO vendor, and transmitted thereafter to the clinical database.

Efficacy Endpoints

Primary Efficacy Endpoint:

The following primary efficacy endpoint will be evaluated at Week 12 to assess EoE response:

Histology: percentage of subjects with a PEAK eosinophils/HPF number ≤6 after assessing at least 5-6 biopsies from the proximal and distal esophagus where the HPF area is 0.235 square millimeters (40 magnification lens with a 22 mm ocular).

Secondary Efficacy Endpoints

The following secondary efficacy endpoints will be evaluated: EoE sustained response: percentage of subjects who met the primary endpoint (histology) at Week 12 and maintained the primary endpoint at Week 26 and Week 52; Change from baseline EREFs at Week 12, Week 26, and Week 52; Endoscopic changes will as per the EREFs evaluation based on the following endoscopic features: edema, rings, exudates, furrows, stricture, and several miscellaneous features (crepe paper esophagus, narrow caliber esophagus, and esophageal erosions); Percentage of subjects with a peak eosinophils/HPF number <1 and <15 at Week 12, Week 26, and Week 52; Change from baseline Global EoE Symptom Score, which will be assessed for the 7 day period prior to the following study visits: Week 12, Week 26, and Week 52; Dysphagia: Change in the number of dysphagia episodes at baseline (14-day period prior to randomization) compared with the 14-day period prior to the time point of interest (Week 12, Week 26 and Week 52); Change from baseline 7-day recall EEsAI total score at Week 12, Week 26, and Week 52; Change from baseline 7-day recall EEsAI sub scores at Week 12, Week 26, and Week 52; Percentage of subjects with mean 7-day recall EEsAI total score <20 at Week 12, Week 26, and Week 52; Change from baseline PGIS assessed prior to randomization at Weeks 4, 8, 12, 14, 18, 22, 26, 28, 36, 44, and 52; PGIC at Weeks 4, 8, 12, 14, 18, 22, 26, 28, 36, 44, and 52. Assessment of treatment failure and relapse, including: Percentage of non-responders by dose at before Week 14, between Week 14 and 28, and between Week 28 and 52; Percentage of subjects requiring emergency endoscopic food dis-impaction by dose at Week 12, Week 26, and Week 52; Percentage of subjects requiring esophageal dilation by dosing group and part of the study.

Exploratory Efficacy Endpoints

The following exploratory efficacy endpoints will be evaluated:

Dysphagia: Change in the number of dysphagia episodes at baseline (14-day period prior to randomization) compared with the 14 day period prior to the time point of interest (Weeks 12, 26 and 52). Change from baseline in dysphagia-free days during the 14 day period prior to the following study visits: Week 4, Week 8. Week 12, Week 14, Week 18, Week 22, Week 26, Week 28, Week 36, Week 44, and Week 52; EoE sustained response (dysphagia): percentage of all subjects who met the dysphagia secondary endpoint at Week 12 and maintained a dysphagia-related response at Week 26 and Week 52; Evaluation of PK/PD (cortisol) and exposure-response (efficacy) relationships; Subject's assessment of symptoms compared with the previous visit at Week 4, Week 8, Week 12, Week 14, Week 18, Week 22, Week 26, Week 28, Week 36, Week 44, Week 52, and the Early Termination Visit (if applicable); Evaluation of HRQoL based on the EoE-QoL-A at baseline, Week 12, Week 26, Week 52 for all subjects by dose and subgroup; Subjects receiving single-blind (to subject) treatment (Part 2) will be tabulated separately.

Percentage of subjects who were classified as histologic non responders at Week 12 and have a peak eosinophils/HPF number ≤6 at all biopsied esophageal locations at Week 26 and Week 52;

Change from baseline dysphagia episodes during the 14 day period prior to Week 26 and Week 52 for subjects who were classified as non responders at Week 12;

Percentage of subjects who were classified as histologic non-responders at Week 12 and meet the primary endpoint at Week 26 and Week 52.

A scoring structure, and various endpoints will be derived from the DEDI. The populations to be analyzed will be detailed in the Statistical Analysis Plan (SAP). Subgroup analyses may be performed based upon age, gender, PPI status, and other study subpopulations.

Example 5—a Phase 1 Study to Assess the Pharmacokinetics, Safety and Tolerability of a Single Dose of Fluticasone Propionate Administered Under Fed or Fasted Conditions or at Bedtime in a Randomized Three-Way Crossover Design Primary Objective:

The plasma pharmacokinetics (PK) of Fluticasone propionate (FP) after administration under Fed or Fasted conditions in the morning were evaluated.

Secondary Objectives:

The plasma (PK) of FP after administration at bedtime (HS) were evaluated. The safety/tolerability of the administration of a single dose of FP in male and female healthy adult volunteers when administered under fasted, fed, or HS conditions were evaluated.

Primary Endpoint:

FP Cmax, AUClast, and Tmax after administration of FP under fed and fasted conditions for morning dose administration were assessed.

Secondary Endpoints:

FP AUC0-24, AUCinf, AUCext, $\lambda z$, t½, CL/F, and Vz/F after administration of FP under fed and fasted conditions were assessed. FP AUC0-24, AUCinf, AUCext, $\lambda z$, t½, CL/F, and Vz/F after administration of FP under HS administration were assessed. Additional PK parameters were calculated as needed to adequately characterize the pharmacokinetics of FP following morning (fasted and fed) or HS dosing. Incidence of treatment-emergent Adverse Events (AEs), AEs leading to withdrawal, and Serious Adverse Events (SAEs) grouped by system organ class (SOC) were calculated as needed. Clinically significant abnormal values for clinical laboratory, AM cortisol (≤138 nmol/L), urinalysis, vital signs, and electrocardiogram (ECG) findings were measured as needed.

Study Design and Duration:

This study was a randomized, single-dose, three-way crossover study evaluating the effects of 6 mg FP administered in the morning (AM) under fed or fasted conditions or before bedtime (HS), 4 hours after the evening meal. A total of 24 subjects were enrolled and randomized to one of six sequences to receive each of the three treatments over the three periods with a 7-day washout between doses. The three treatments included administration of 6 mg of FP (2×3 mg orally disintegrating tablets) under the following conditions:

A. Fasted: 6.0 mg of APT-1011 (e.g. FP) (Two 3 mg oral dissolving tablets) after an overnight fast (at least 10 hours), with fast continuing 4 hours post-dose B. Fed: 6.0 mg APT-1011 (Two 3 mg oral dissolving tablets) 30 minutes after the start of a high fat breakfast.

C. HS: 6.0 mg APT-1011 (Two 3 mg oral dissolving tablets) at bedtime approximately 4 hours after the standard evening meal.

Subjects on the "Fasted" treatment (Treatment A), were administered 6.0 mg of APT-1011 after an overnight fast of at least 10 hours. These subjects continued fasting for at least 4 hours post-dose.

Subjects on the "Fed" treatment (Treatment B) began a high-fat breakfast 30 minutes after an overnight fast of at least 10 hours. Subjects were administered 6.0 mg of APT-1011, 30 minutes after initiation of the high-fat breakfast.

Subjects on the "HS" treatment (Treatment C) consumed a standard meal approximately 4 hours prior to bedtime. Subjects were administered 6.0 mg of ATP-1011 immediately prior to bedtime (4 hours following the standard meal). Subjects were administered the dose of FP while laying down.

Randomization (Day 1):

Subjects were randomized to one of six sequences (See Table 15) to receive a single dose of each treatment over three periods, with a 7-day washout between doses.

TABLE 15

| Sequence | N | Period 1 | Period 2 | Period 3 |
|---|---|---|---|---|
| 1 | 4 | A | B | C |
| 2 | 4 | B | C | A |
| 3 | 4 | C | A | B |
| 4 | 4 | A | C | B |
| 5 | 4 | C | B | A |
| 6 | 4 | B | A | C |

Treatment Periods:

For each period, subjects were in-patients for 5 days (Days 0-4, Days 7-11, Days 14-18) with PK samples collected over 72 hours following each dose. Subjects were checked-in to the CRU the evening prior to each dosing (Day 0, 7, and 14) and received treatment according to the sequence on which they were randomized on Day 1. APT-1011 was administered as single doses on Days 1, 8, and 15. All meals (AM and 4 hours prior to bedtime) were standardized for all subjects and all periods. Subjects completed these meals within 30 minutes. Serial plasma samples for FP PK were collected pre-dose and at 0.5, 1, 2, 3, 4, 5, 6, 8, 10, 12, 16, 20, 24, 30, 36, 42, 48, 60, and 72 hours following each dose. Subjects dosed HS followed the same PK schedule with PK samples scheduled relative to the bedtime dose.

Subjects were discharged from the CRU following PK sampling and safety assessments for each treatment period (Day 4, Day 11, Day 18).

Follow-Up (Day 25±2 Days):

After Period 3, subjects returned to the clinic within 7 days (±2 days) of discharge from the clinical research unit for follow-up criteria.

Inclusion Criteria:

Female and male subjects were eligible for inclusion in this study only if all of the following criteria applied:

1. Subject was healthy based on evaluation of medical history, physical examination, clinical laboratory tests and 12-lead ECG. Subjects with history of mild acute or chronic medical illness or laboratory parameters outside the normal reference range were included only if the Investigator agree that the finding is unlikely to introduce additional risk and will not interfere with study procedures.

2. An Institutional Review Board (IRB)-approved informed consent was signed and dated prior to any study-related activities.

3. Subject was between the ages of 18 and 55 years, inclusive.

4. Female subject of child-bearing potential had a negative urine pregnancy test or had surgical sterilization, had been diagnosed infertile, or was post-menopausal prior to randomization. Females of childbearing potential must have been willing to practice adequate birth control from at least 28 days prior to the first administration of the study drug, during the study and for at least 30 days after the last dose of the study drug to be eligible.

5. Male subjects who engaged in sexual activity must have agreed to use a condom and spermicide during the study.

6. Body mass index between 19 and 30 kg/m2 (weight/[height]2), inclusive.

7. Normal (or abnormal but clinically insignificant) laboratory values present at Screening.

8. Subject had the ability to understand the requirements of the study and a willingness to comply with all study procedures.

9. Subject had not consumed and agrees to abstain from taking any dietary supplements, herbal therapies, or non-prescription drugs (except as authorized by the Investigator) for 7 days prior to 1st CRU admission (for Period 1) through Follow-Up.

10. Subject had not consumed and agreed to abstain from taking any prescription drugs (except as authorized by the Investigator) for 28 days prior to 1st CRU admission (for Period 1) through Follow-Up.

11. Subject had not consumed alcohol-containing beverages for 3 days prior to 1st CRU admission (for Period 1) through Follow-Up.

12. Subject agreed to abstain from consuming caffeine- or chocolate-containing products from CRU admission to discharge of each period.

13. Subject agreed to abstain from strenuous physical activity from signing of the informed consent form to the final follow up visit.

Key Exclusion Criteria:

A subject was not eligible for inclusion in this study if any of the following criteria applied:

1. Had a history of asthma requiring occasional use of inhaled corticosteroids.

2. Had a recent (within 30 days) history of corticosteroid use, including but not limited to intranasal, inhaled, dermal, ophthalmological, or intra-articular routes of administration.

3. Had a history of illicit drug abuse in the past year or current evidence of such abuse in the opinion of the Investigator based on criteria established in DSM-IV.

4. Used tobacco products within 3 months before Day 1 of this study

5. Had positive findings on urine drug screen or positive cotinine test.

6. Had a history of regular alcohol consumption within 6 months of the study defined as an average weekly intake of >14 drinks/week for men or >10 drinks/week for women. One drink is equivalent to 12 g alcohol-5 ounces (150 mL) of wine or 12 ounces (360 mL) of beer or 1.5 ounces (45 mL) of 80-proof distilled spirits. An ethanol breath test was administered twice and used to document lack of ethanol use at Screening and Day 0 and was exclusionary if positive.

7. Was positive (i.e., evidence of current infection) for human immunodeficiency virus (HIV), hepatitis B and/or hepatitis C on Screening assessments.

8. Female subject who was pregnant or lactating.

9. Male subject whose partner was known to be pregnant.

10. Had an acute illness within 28 days of first CRU admission.

11. Had any history of tuberculosis and/or prophylaxis for tuberculosis

12. Had donated plasma in the previous 7 days before Day 1 of this study

13. Had donated 500 mL or more of blood (Canadian Blood Services, Hema-Quebec, clinical studies, etc.) in the previous 56 days before day 1 of this study 14. Had taken an inducer or inhibitor of Cytochrome P450 3A (CYP3A) enzymes within 28 days of the first dose.

15. Had taken grapefruit juice within 7 days of the first dose.

16. Had participated in an investigational drug study within the 30 days prior to first CRU admission or subject has had less than 5 half-lives washout of any prior investigational drug prior to first CRU admission (whichever is longer).

17. Had any physical, mental, or social condition, history of illness or laboratory abnormality that, in the investigator's judgment, might interfere with study procedures or the ability of the subject to adhere to and complete the study.

18. Clinical laboratory tests indicated the presence of clinically relevant renal or hepatic insufficiency in the opinion of the Investigator.

19. Had a history of any gastrointestinal, renal, or hepatic conditions that could impact absorption or metabolism/elimination of the investigational compound.

20. Could not or would not consume contents of standard high fat meal due to dietary preferences or restrictions 21. Had a history of sensitivity to the study medication (Fluticasone propionate or other corticosteroids) or components thereof, or a history of drug or other allergy (such as eggs) that, in the opinion of the Investigator, contraindicates participation.

Analysis

Pharmacokinetics:

Derived plasma-PK-parameter descriptive statistics were summarized by treatment. To assess the PK of FP in the fasted (reference) and fed (test) states, an analysis of variance (ANOVA) with fixed effect term for treatment (fed or fasted status), fixed effect term for Period (1, 2, 3), fixed effect term for sequence (ABC, BCA, CAB, CBA, ACB, BAC) and subject within sequence as a random effect was performed on log-transformed AUClast, AUC0-24, AUCinf, and Cmax. Relative bioavailability was estimated by exponentiating the difference in least-squares means (test–reference) and the associated 90% confidence interval (CI). Additional comparisons were assessed between HS dosing and Fed and Fasted administration.

TABLE 16

| PK Parameter Description | |
|---|---|
| Cmax | Maximum observed plasma concentration, obtained directly from the observed concentration versus time data |
| Tmax | Time of maximum concentration (h), obtained directly from the observed concentration versus time data |
| AUClast | Area under the plasma concentration-time curve from time 0 to time of last measurable plasma concentration |
| AUCinf | Area under the plasma concentration-time curve from 0-time extrapolated to infinity |
| AUCext | The percentage of the AUC that is extrapolated beyond the last measurable concentration |
| AUC0-24 | Area under the plasma concentration-time curve from time 0 to 24 hours post-dose |
| $\lambda z$ | Apparent plasma terminal-phase elimination rate constant |
| $t\frac{1}{2}$ | Elimination half-life |
| Vz/F | Apparent volume of distribution, terminal phase |
| CL/F | Apparent systemic clearance |

Additional PK parameters may be calculated as necessary to adequately characterize the PK profile of APT-1011.

FP concentrations were summarized using descriptive statistics (including n, mean, SD, coefficient of variation (CV %), median, minimum, and maximum) for each treatment.

The following PK parameters were estimated by noncompartmental methods from plasma samples. Below limit of quantitation concentrations were treated as zero for all PK analyses. All deviations from the scheduled sampling time of 2 minutes or more were taken into consideration for evaluation of the PK parameters. In the case where concentrations of FP could not be determined due to clinical or bioanalytical reasons, these values were set to missing for the pharmacokinetic analysis.

The trapezoidal rule was used to estimate the area under the curve (linear trapezoidal linear interpolation) and the terminal phase were estimated by maximizing the coefficient of determination estimated from the log-linear regression model. However, disposition parameters were not estimated for individual concentration-time profiles where the terminal log-linear phase cannot be reliably characterized.

If a pre-dose concentration of FP was detected, the subject's data was included in the pharmacokinetic analysis without adjustment, if the pre-dose concentration was equal to or less than 5% of the Cmax value of the corresponding period. If the pre-dose concentration was greater than 5% of the Cmax value, the subject was dropped from all pharmacokinetic evaluations.

Given the low expected systemic bioavailability of FP (~1%) it was possible that some PK parameters were not reliably calculated due to low plasma FP concentrations (e.g., concentrations that are BLQ). Whenever possible, PK parameters were calculated.

Derived plasma-PK-parameter descriptive statistics were tabulated by treatment. Descriptive statistics for PK parameters included the arithmetic and geometric mean, CV %, SD of the arithmetic mean, median, minimum, maximum, and n, as appropriate.

To assess the PK of FP, an analysis of variance (ANOVA) with fixed effect term for treatment, fixed effect term for Period (1, 2, 3), fixed effect term for sequence (ABC, BCA, CAB, CBA, ACB, BAC) and subject within sequence as a random effect was performed on loge-transformed AUClast, AUC0-24, AUCinf, and Cmax. Relative bioavailability was estimated by exponentiating the difference in least-squares means (test–reference) and the associated 90% confidence interval (CI).

Food Effect Analysis: The 90% confidence interval for the exponential of the difference in LSmeans between B (fed) and A (fasted) was calculated for the ln-transformed parameters (Test to Reference ratio of geometric LSmeans).

HS vs Fasted Analysis: The 90% confidence interval for the exponential of the difference in LSmeans between C (HS) and A (fasted) was calculated for the ln-transformed parameters (Test to Reference ratio of geometric LSmeans).

HS vs Fed Analysis: The 90% confidence interval for the exponential of the difference in LSmeans between C (HS) and B (fed) was calculated for the ln-transformed parameters (Test to Reference ratio of geometric LSmeans).

Statistical analyses were generated using SAS® (version 9).

Sample Size:

Using an estimate of 54% as determined by using an overall estimate of variability of 60%, and assuming the intra-subject variability is estimated to be about 10% less. Then for a two-sided 90% confidence interval for a normal mean, a sample size of 24 yields a half-width of at most 0.25 with a conditional probability of 0.98.

Rationale for the Current Study:

The approach to treatment of EoE with oral administration of APT-1011 was to provide topical esophageal exposure of FP while minimizing systemic exposure and associated systemic pharmacologic effects. Previous studies demonstrated a significantly decreased exposure when the drug was administered after breakfast; for example administration of APT-1011 after a high-fat meal significantly decreased systemic exposure compared to administration in the fasted state. Additionally, administration of APT-1011 as 6 mg QD resulted in approximately the same dose-normalized, steady-state systemic exposure (AUCtau/Dose) as a 3 mg BID regimen. However, the data were highly variable, with the between-subject variability (CV % Geo mean) of FP AUC (0-24 h) following single-dose administration >55%.

The previous PK study demonstrated significantly lower drug levels with QD administration compared to the same dose divided and administered BID. The reason for this is unclear.

The current study assessed the effect of food on APT-1011 pharmacokinetics. APT-1011 exposures were compared when a morning dose is administered in either the fasted state or 30 minutes after initiating a high fat meal. Additionally, the current study characterized the pharmacokinetics of APT-1001 when administered as a single dose at bedtime (HS).

This study provides guidance on administration of the drug relative to food and time of day of dosing.

Treatments

Treatments Administered:

Study drug was administered by qualified study staff only in accordance with the procedures described in this protocol. All doses of APT-1011 were be 6 mg, administered as two 3 mg orally disintegrating tablets. All subjects were instructed to take the study drug tablet orally without water or other liquids. Subjects placed both study drug tablets on the upper surface of the tongue and gently massaged the study drug tablet between the tongue and the roof of the mouth until it disintegrated sufficiently to allow normal swallowing with saliva over the course of one to five minutes. Subjects were instructed not to chew or crush the study drug tablet and not to swallow any portion of the intact study-drug tablet before it has fully dissolved. Subjects did not drink for at least 1 hour after dosing and did not eat for at least 4 hours after dosing.

Due to the low bioavailability of APT-1011, a dose of 6 mg was selected for this study. Based on previous data, FP concentrations following a 6 mg dose provide detectable plasma levels of FP at most time points using the proposed bioanalytical assay.

Selection and Timing of Dose for Each Subject

All doses of APT-1011 were 6 mg, administered as two 3 mg orally disintegrating tablets simultaneously. For the Fasted treatment (Treatment A), subjects were dosed following an overnight fast of at least 10 hours. A standard meal was provided 4 hours after dosing. For the Fed treatment (Treatment B), subjects started a high-fat, high-calorie meal after an overnight fast of at least 10 hours, and 30 minutes prior to dosing. The meal was consumed within 30 minutes or less.

For the HS treatment, subjects were administered APT-1011 approximately 4 hours after a standard meal with no snacks after dinner. After administering the drug, the subject immediately laid down and did not get up for at least 1 hour.

Pharmacokinetics

Collecting, Processing, and Shipping Pharmacokinetic Samples:

Blood samples (6 mL per sample) were drawn and processed for plasma. The yield of plasma (~3 mL) was subdivided into 2 samples (~1.5 mL each). One of these samples was and the other was stored at $\leq-20°$ C. at the CRU until completion of the study.

Bioanalytical Method for Fluticasone Propionate Quantitation:

Fluticasone propionate concentrations were measured using an LC/MS/MS method validated in accordance with US regulatory guidelines. The method was developed starting from 1 mL of plasma collected from blood containing potassium oxalate/sodium fluoride as anticoagulant/preservative. The method is linear over the nominal concentration range of 1.00 to 500 pg/mL. The limit of quantitation is 1 pg/mL20. Samples from all subjects were analyzed.

Assessment of Safety

Safety assessments included the following: Adverse events, both reported and observed, regardless of severity or seriousness; Body weight; Vital sign measurements (blood pressure, heart rate, temperature, respiration rate); ECG findings; Clinical laboratory tests and urinalysis; Physical examination findings.

Clinical Laboratory Tests:

The clinical laboratories tests were as follows.

Hematology, blood chemistry, coagulation, and urinalysis was performed at Screening, on Day 0 (CRU admission), at 12 hours postdose of each period, before CRU discharge of each period, and at the Follow-up visit.

Hematology:

Red blood cell (RBC) count, hemoglobin, hematocrit, mean corpuscular volume (MCV), mean corpuscular hemoglobin (MCH), mean corpuscular hemoglobin concentration (MCHC), white blood cell (WBC) count and differential, absolute neutrophil count (ANC), and platelet count.

Blood Chemistry/Coagulation:

Alanine aminotransferase (ALT; SGPT) and Aspartate aminotransferase (AST; SGOT), total bilirubin, direct bilirubin, blood urea nitrogen (BUN), creatinine, alkaline phosphatase, sodium, potassium, calcium, chloride, glucose, and albumin Urine Pregnancy Test:

Urine $\beta$-hCG test in women at screening, check-in for each period (i.e. Day 0, Day 7, Day 14) and Follow-up.

Follicle Stimulating Hormone (FSH)/Luteinizing Hormone (LH) Test:

This test was performed in all menopausal women including surgical menopause.

Urinalysis:

Urinalysis included macroscopic analysis and microscopic analysis only when indicated by dipstick. Analyses included: Color, Turbidity, Specific Gravity, pH, Glucose, Protein, Ketones, Urobilinogen, Bilirubin, Blood, Nitrite, and Leukocyte Esterase.

Serology:

HIV Ag/Ab Combo, Hepatitis B (HBsAg (B) (hepatitis B)) and Hepatitis C (HCV (C)) (performed at Screening only).

Urine Drug Screen:

Urine for a drug screening test was collected from all subjects during the screening period and on Day 0, Day 7, and Day 14. The sample was tested for the presence of cotinine, cocaine, tetrahydrocannabinol, barbiturates, amphetamines, benzodiazepines, and opiates. Subjects with positive urine drug screen test results for any of the above substances were excluded from this study.

Ethanol Breath Test:

Alcohol consumption was not permitted within 3 days of first CRU admission through Follow-up. An ethanol breath test was performed at Screening and at CRU admission of each period (i.e., Day 0, Day 7 and Day 14). Subjects with positive ethanol breath test results at Screening were not enrolled in the study to avoid inadvertent enrollment of a subject with chronic alcoholism. Subjects with positive ethanol breath test results on Day 0 (CRU admission) were also excluded from further participation in the study.

Adverse Events

A Serious Adverse Event (SAE) was defined as any untoward medical occurrence that at any dose: Results in death; Is life-threatening; Requires inpatient hospitalization or prolongation of existing hospitalization excepting hospital admissions due to administrative reasons (e.g., the subject has no transportation home) or hospitalization for elective treatment of a pre-existing condition that did not worsen during the study unless a complication occurs during the hospitalization; Results in permanent or significant disability/incapacity; or Results in congenital anomaly/birth defect.

Results

Figure 6:
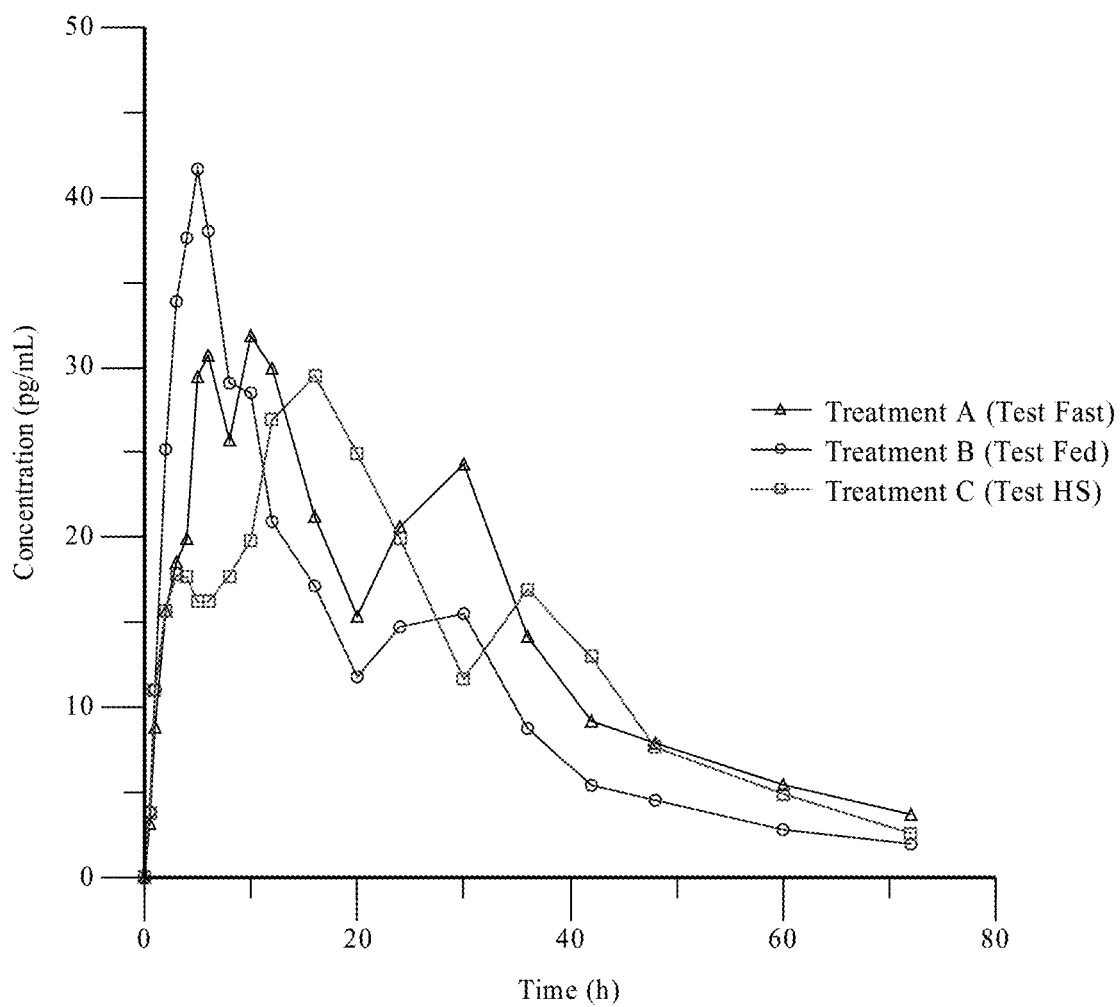
FIG. 6 shows the Mean Linear Plasma Concentration-Time Profile of APT-1011 (Fluticasone Proprionate) for fed, fasted, and HS administration.
Figure 7:
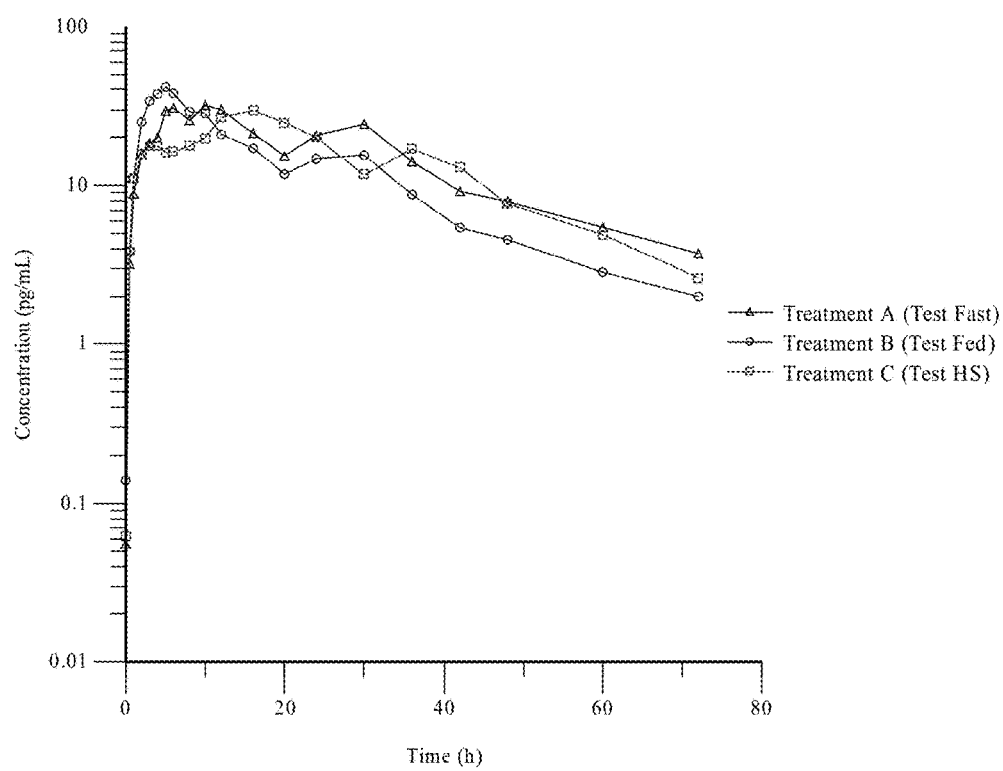
FIG. 7 shows the Mean Logarithmic Plasma Concentration-Time Profile of APT-1011 (Fluticasone Proprionate) for fed, fasted, and HS administration.
Figure 8:
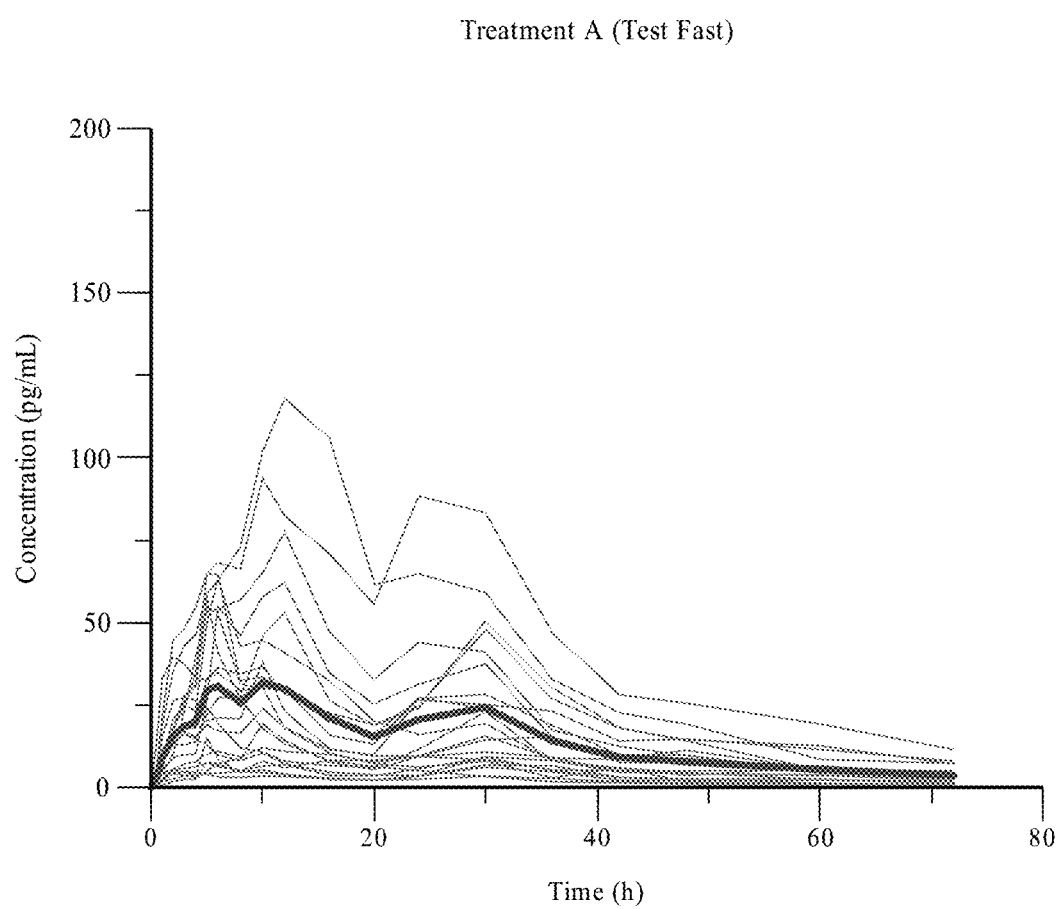
FIG. 8 shows Spaghetti Plots of APT-1011 (Fluticasone Proprionate) (Fasted conditions).
Figure 9:
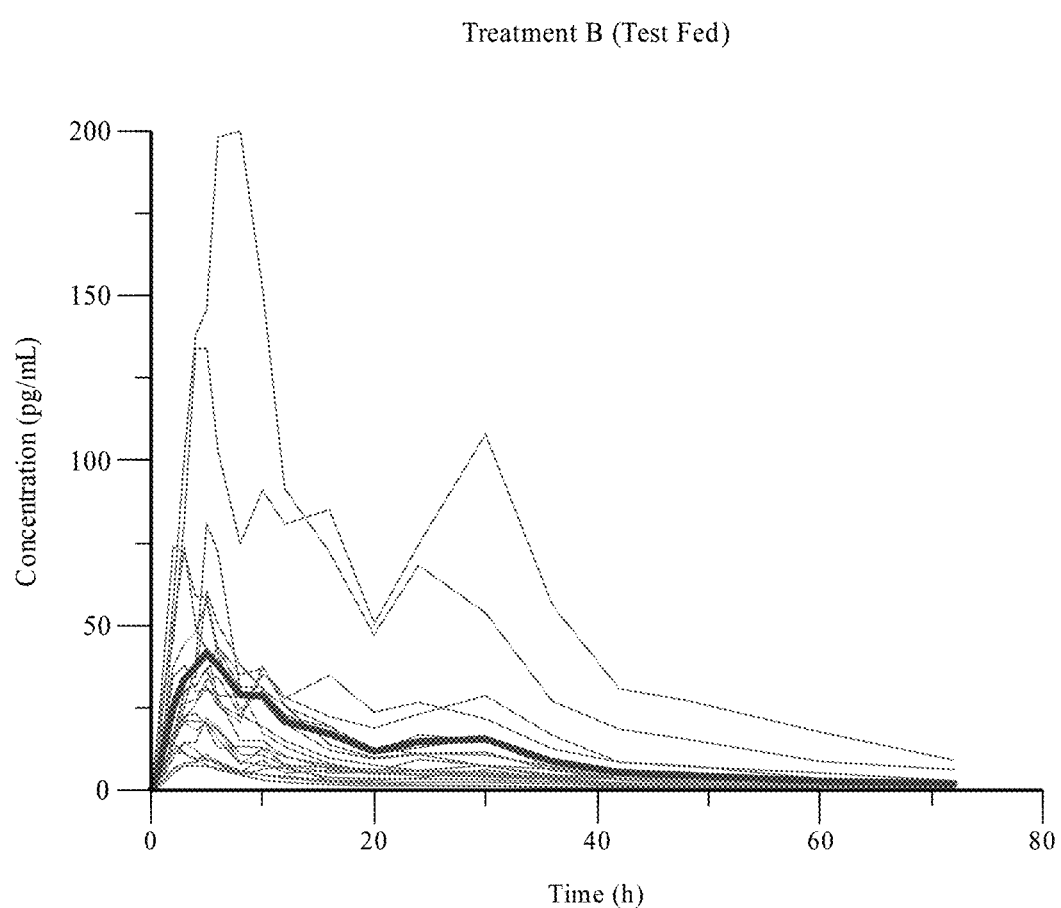
FIG. 9 shows Spaghetti Plots of APT-1011 (Fluticasone Proprionate) (Fed conditions)
Figure 10:
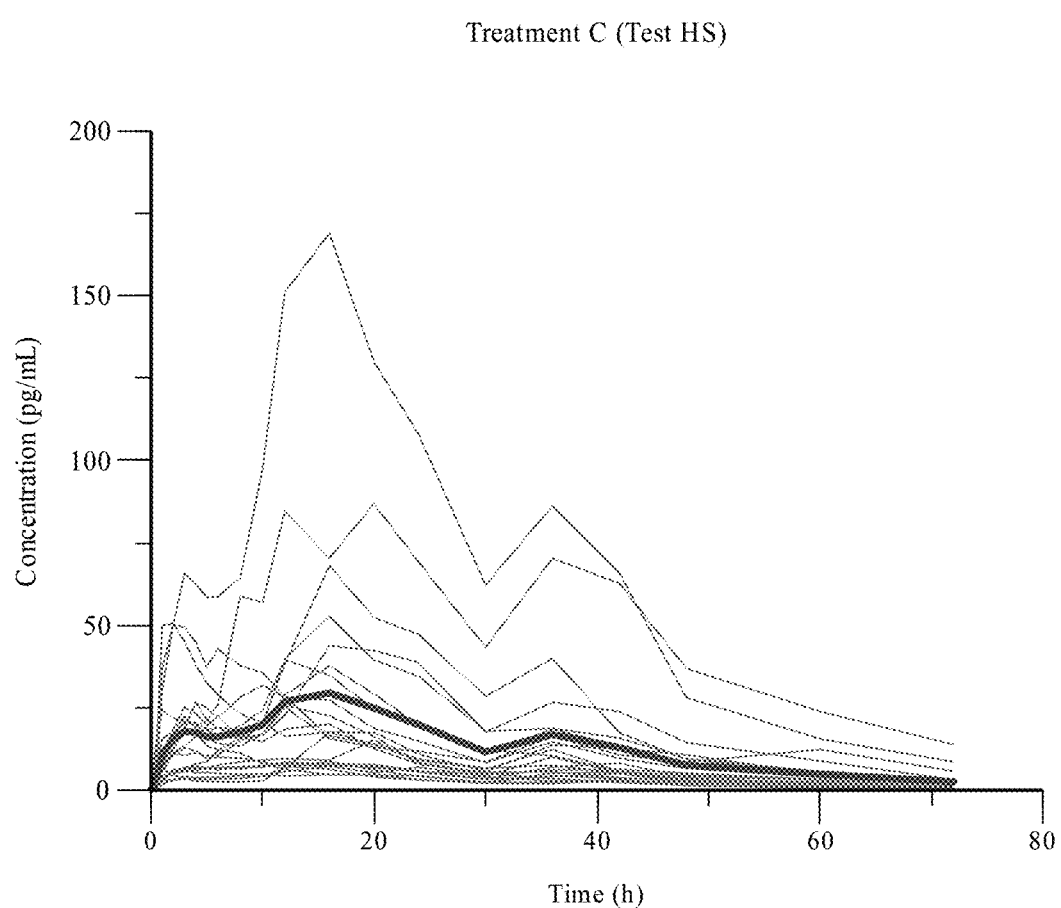
FIG. 10 shows Spaghetti Plots of APT-1011 (Fluticasone Proprionate) (HS conditions).

FIGS. 6 and 7 show the mean plasma concentrations of APT-1011 (Fluticasone Propionate) administration in fasted, fed, and HS treatment regimens. FIGS. 8-10 show spaghetti plots of the plasma concentrations of APT-1011 (Fluticasone Propionate) administration in fasted (FIG. 8), fed (FIG. 9), and HS (FIG. 10) conditions. Surprisingly, HS administration to a patient laying down before sleep shows a sustained level of drug. Instead of a sharp, quick peak as observed in fed and fasted administration, HS administration in a prone position lead to a sustained concentration of APT-1011 in the patient's blood. This may be due to prolonged exposure to the distal esophagus. This long exposure in the distal esophagus has the added advantage of also reducing systemic exposure to APT-1011, which is expected to decrease adverse side effects.

A total of 24 participants enrolled and 22 (92%) completed the study. A summary of the PK parameters by test group is presented in Table 18. AM dosing was associated with a higher rate of absorption under fed compared to fasted conditions. Following a high fat meal, there was a higher peak concentration ($C_{max}$: ratio [90% CI]=120.65% [99.84%-145.79%]), and a faster time to peak concentration, as compared to the fasted state ($T_{max}$: fed=5.00 h; fast=10.00 h). However, lower total exposure in the fed compared to the fasted state ($AUC_{last}$: ratio [90% CI]=76.97% [67.64%-87.59%]) was observed. HS dosing was found to slow the rate of absorption as compared to AM dosing conditions. Specifically, the time to peak concentration with HS ($T_{max}$=14 h) was longer than with AM dosing ($T_{max}$: fast=10 h, fed=5 h). HS dosing was associated with higher overall exposure (AUC: ratio [90% CI]=122.36% [107.02%-139.88%] and lower $C_{max}$ ($C_{max}$: ratio [90% CI]=67.79% [56.29%-81.64%]) as compared to the fed regimen. As compared to the fasted regimen, HS dosing yielded lower overall exposure ($AUC_{inf}$: ratio [90% CI]=87.00% [75.24%-100.59%] and lower $C_{max}$ ($C_{max}$: ratio [90% CI]=81.78% [67.93%-98.47%]). Across all dosing regimens, the $C_{max}$ of fluticasone with APT-1011 ranged from 5.97-200 pg/mL.

No AEs of special interest (AESI), no serious adverse events (SAE), and no deaths were reported for any of the subjects enrolled in this study. No subject was withdrawn by the investigator for safety reasons.

A total of 12 treatment-emergent adverse events (TEAEs) were reported by 7 (29%) of the 24 subjects who participated in this study. Of these events, 4 occurred after administration of Treatment A, 1 after administration of Treatment B, and the other 7 after administration of Treatment C. All TEAEs were deemed mild in severity. Most TEAEs were considered possibly related (92%) to treatment.

The TEAEs reported in this study were experienced with a low incidence, by 1 subject per treatment group (5% for Treatment A, 5% for Treatment B, and 4% for Treatment C). These included: nausea, chest discomfort, upper respiratory tract infection, and headache for Treatment A, chest discomfort for Treatment B, and constipation, oral herpes, dizziness, vessel puncture site bruise, aspartate aminotransferase increased, nasal congestion, and hot flush for Treatment C.

The incidence of TEAEs was of 9% for Treatment A, 5% for Treatment B, and 22% for Treatment C. Drug-related TEAEs were reported with a similar trend as the total TEAE incidence: 9% for Treatment A, 5% for Treatment B, and 17% for Treatment C.

Generally, the abnormal clinical laboratory values were marginally higher or lower than their reference ranges and were mostly considered non-clinically significant by the investigator. However, one subject showed an abnormal aspartate aminotransferase result at poststudy visit, which was considered clinically significant by the investigator and reported as a mild TEAE (increased aspartate aminotransferase). The last treatment administered to this subject was Treatment C. The event outcome was unknown at the end of the study; the subject was lost to follow-up.

Overall, the means of laboratory parameters, vital signs, and ECGs for the different treatments were comparable. In addition, the mean for all subjects at screening and poststudy of evaluated parameters were comparable.

Furthermore, there were no clinically significant abnormalities in the vital signs and ECGs of the subjects in this study.

Overall, the most common answers in the palatability assessments were "Like, a little", and "Neither like not dislike".

Conclusion

Oral APT-1011 was safe and well-tolerated when administered under AM fasted, AM fed, or HS conditions to healthy subjects.

This phase 1 study demonstrated that systemic exposure of FP is confirmed to be very low following oral APT-1011 administration (total dose 6 mg) under fast, fed and at bedtime dosing. PK sampling allowed for accurate estimation of the elimination profile. Therefore, comparison of extent of systemic exposure over 24 hours, 72 hours and infinity was performed.

Peak values were comparable between morning-fast and HS dosing, however maximal concentrations were reached more rapidly when APT-1011 was administered with a high fat meal.

The interindividual variability (CV %) for $C_{max}$ was the highest for the HS regimen followed by the morning-fast and fed regimens. Based on the expected low bioavailability of this formulation (expected minimum systemic exposure), this high level of variability observed was expected.

The food effect and time of day effect are inversely proportional to the peak exposure of FP when compared to the morning-fast dosing. When compared to the morning-fast regimen, maximum peak exposure was 20% higher for the morning-fed regimen and 19% lower for the HS administration. A lower rate of absorption is suggested when APT-1011 is given at bedtime, while a higher rate of absorption is observed when given in the morning with a high fat meal.

While there was faster absorption of APT-1011 under fed conditions and slower absorption at bedtime, overall absorption of fluticasone with this formulation is low (<200 pg/mL). Slower absorption with HS dosing suggests a potential for longer dwell times in the esophagus; the relationship of bedtime dosing with histological efficacy in both the proximal and distal portions of the esophagus will be explored in future studies of APT-1011 in EoE.

Overall, a food effect was observed as $C_{max}$ and AUC ratios and/or 90% CI were not all within the pre-defined standard range of 80.00-125.00%.

Also, complete absence of time of day effect on bioavailability of FP could not be established as lower bounds of the 90% CI for $C_{max}$ and $AUC_{inf}$ were below the pre-defined standard range of 80.00%.

The overall extent of systemic exposure over 72 hours ($AUC_{last}$) was about 24% lower for the fed dosing as compared to a non-statistically significant decrease of 8% when given HS when compared to the morning-fast administration.

The extrapolated extent of systemic exposure to infinity ($AUC_{inf}$) was lower for both regimens (fed; decrease of 29%, and HS; decrease of 13%) when compared the morning-fast dosing.

Finally, HS regimen showed a higher decrease in exposure (33% decreases in $C_{max}$) when compared to the morning-fed regimen than with the morning-fast regimen. Also, the extent of exposure over 72 hours and extrapolated to infinity was around 20% higher at bedtime vs morning-fed suggesting that bedtime administration has a more sustained exposure with lower maximum peaks over time.

Summaries of the pharmacokinetic parameters for the Fast, Fed, and HS studies are provided in Tables 18-21.

TABLE 18

Summary of Plasma FP Pharmacokinetic Parameters

| PARAMETER | Treatment A (Test Fast) N = 22[b,d] | | Treatment B (Test Fed) N = 21[e] | | Treatment C (Test HS) N = 23[c,f] | |
|---|---|---|---|---|---|---|
| | Geometric Mean | (Geometric C.V. %) | Geometric Mean | (Geometric C.V. %) | Geometric Mean | (Geometric C.V. %) |
| $C_{max}$ (pg/mL) | 31.1 | (103.6) | 34.2 | (102.3) | 23.8 | (111.9) |
| $T_{max}$ (hours)[a] | 10.00 | (2.00-30.00) | 5.00 | (1.00-10.00) | 14.00 | (2.00-20.00) |
| $AUC_{last}$ (pg · h/mL) | 775.049 | (94.6) | 548.933 | (111.1) | 669.695 | (98.3) |
| $AUC_{0-24}$ (pg · h/mL) | 366.607 | (115.8) | 361.277 | (105.5) | 359.541 | (100.5) |
| $AUC_{inf}$ (pg · h/mL) | 1044.308 | (90.1) | 587.890 | (107.2) | 726.451 | (100.2) |
| $AUC_{ext}$ (%) | 7.13 | (77.9) | 5.82 | (51.5) | 4.91 | (47.5) |
| $\lambda_Z$ (hours$^{-1}$) | 0.0362 | (32.5) | 0.0370 | (23.7) | 0.0474 | (21.2) |
| $t_{1/2}$ (hours) | 19.14 | (32.5) | 18.72 | (23.7) | 14.61 | (21.2) |
| CL/F (L/hour) | 5745.43 | (90.1) | 10205.99 | (107.2) | 8259.33 | (100.2) |
| $V_z$/F (L) | 158611.12 | (99.9) | 275613.92 | (126.6) | 174108.33 | (106.1) |

[a]Median and range are presented
[b]n = 17 for $AUC_{inf}$, $AUC_{ext}$, CL/F, VZ/F, $\lambda_Z$, and $T_{half}$
[c]n = 21 for $AUC_{inf}$, $AUC_{ext}$, CL/F, VZ/F, $\lambda_Z$, and $T_{half}$
[d]subjects 001, 002, 004-018, and 020-024
[e]subjects 001, 003-007, 009-018, and 020-024
[f]subjects 001, 003-024

TABLE 19

Summary of the Statistical Analysis of FP - Food Effect

| | GEOMETRIC LSMEANS[a] | | | | | |
|---|---|---|---|---|---|---|
| PARAMETER | INTRA-SUBJECT C.V. (%) | Treatment B (Test Fed) (n = 21)[b,d] | Treatment A (Test Fast) (n = 21)[c,e] | RATIO (%) | 90% CONFIDENCE LIMITS (%) | |
| | | | | | LOWER | UPPER |
| $C_{max}$ | 37.1 | 37.7 | 31.3 | 120.65 | 99.84 | 145.79 |
| $AUC_{0-24}$ | 23.1 | 402.404 | 367.351 | 109.54 | 97.12 | 123.55 |
| $AUC_{last}$ | 24.9 | 607.477 | 789.234 | 76.97 | 67.64 | 87.59 |
| $AUC_{inf}$ | 24.9 | 650.820 | 915.302 | 71.10 | 61.46 | 82.26 |

[a]units are pg/mL for $C_{max}$ and pg · h/mL for $AUC_{0-24}$, $AUC_{last}$ and $AUC_{inf}$
[b]n = 20 for $AUC_{inf}$
[c]n = 16 for $AUC_{inf}$
[d]subjects 001, 004-007, 009-018, and 020-024
[e]subjects 001, 004-018, and 020-024

TABLE 20

Summary of the Statistical Analysis of FP - Fast vs HS Regimen

| PARAMETER | INTRA-SUBJECT C.V. (%) | GEOMETRIC LSMEANS[a] | | RATIO (%) | 90% CONFIDENCE LIMITS (%) | |
|---|---|---|---|---|---|---|
| | | Treatment C (Test HS) (n = 22)[b,d] | Treatment A (Test Fast) (n = 21)[c,e] | | LOWER | UPPER |
| $C_{max}$ | 37.1 | 25.6 | 31.3 | 81.78 | 67.93 | 98.47 |
| $AUC_{0-24}$ | 23.1 | 389.137 | 367.351 | 105.93 | 94.14 | 119.19 |
| $AUC_{last}$ | 24.9 | 729.171 | 789.234 | 92.39 | 81.39 | 104.87 |
| $AUC_{inf}$ | 24.9 | 796.317 | 915.302 | 87.00 | 75.24 | 100.59 |

[a] units are pg/mL for $C_{max}$ and pg · h/mL for $AUC_{0-24}$, $AUC_{last}$ and $AUC_{inf}$
[b] n = 20 for $AUC_{inf}$
[c] n = 16 for $AUC_{inf}$
[d] subjects 001, 003-018, and 020-024
[e] subjects 001, 004-018, and 020-024

TABLE 21

Summary of the Statistical Analysis of FP- Fed vs HS Regimen

| PARAMETER | INTRA-SUBJECT C.V. (%) | GEOMETRIC LSMEANS[a] | | RATIO (%) | 90% CONFIDENCE LIMITS (%) | |
|---|---|---|---|---|---|---|
| | | Treatment C (Test HS) (n = 22)[b,c] | Treatment B (Test Fed) (n = 21)[b,d] | | LOWER | UPPER |
| $C_{max}$ | 37.1 | 25.6 | 37.7 | 67.79 | 56.29 | 81.64 |
| $AUC_{0-24}$ | 23.1 | 389.137 | 402.404 | 96.70 | 85.93 | 108.83 |
| $AUC_{last}$ | 24.9 | 729.171 | 607.477 | 120.03 | 105.72 | 136.28 |
| $AUC_{inf}$ | 24.9 | 796.317 | 650.820 | 122.36 | 107.02 | 139.88 |

[a] units are pg/mL for $C_{max}$ and pg · h/mL for $AUC_{0-24}$, $AUC_{last}$ and $AUC_{inf}$
[b] n = 20 for $AUC_{inf}$
[c] subjects 001, 003-018, and 020-024
[d] subjects 001, 004-007, 009-018, and 020-024

Example 6—Scintigraphy Study of Anatomical Contact of Oral Corticosteroid Following Oral Administration to a Lying Down Patient Compared to an Upright Patient The oral corticosteroid (e.g., fluticasone propionate) will be radiolabeled by attaching radioisotopes, and the corticosteroid will be formulated in a pharmaceutical composition, such as an orally disintegrating tablet. The radiolabeled oral corticosteroid will be administered to the patient while the patient is lying down. Independently, radiolabeled oral corticosteroid will be administered to the patient while the patient is upright.

The radioisotopes emit gamma radiation. External detectors (gamma cameras) capture the gamma radiation emitted from the radiolabeled corticosteroid as it traverses the esophagus which are converted to images. The location and relative amount of the corticosteroid in the distal and proximal esophagus for the lying down patient versus the upright patient can measured from said images.

The results of the scintigraphy study will indicate that similar amounts of the corticosteroid contact the proximal and distal esophagus when the oral corticosteroid is administered to a lying down patient, whereas an upright patient has a higher amount of corticosteroid in the proximal esophagus compared to the distal esophagus.

The invention claimed is:

1. A method of topically treating eosinophilic esophagitis (EoE) in a patient in need thereof with an oral corticosteroid, comprising:
   a. administering the oral corticosteroid while the patient is lying down or immediately prior to the patient lying down,
   wherein a therapeutically effective amount of the oral corticosteroid contacts the esophagus, thereby topically treating EoE.

2. The method of claim 1, wherein the lying down is in a supine, prone, or laterally recumbent position.

3. The method of claim 1, wherein the oral corticosteroid is administered about 30 minutes or less before target sleep time.

4. The method of claim 1, wherein the oral corticosteroid is administered at least about 30 minutes after a meal.

5. The method of claim 1, wherein the patient does not eat or drink for at least about 30 minutes after administering the oral corticosteroid.

6. The method of claim 1, wherein the oral corticosteroid is administered:
   (i) once daily; or
   (ii) twice daily, wherein the first daily dose is administered while the subject remains upright.

7. The method of claim 1, wherein the oral corticosteroid has a systemic bioavailability of less than or equal to about 20% of its dose.

8. The method of claim 1, wherein the oral corticosteroid provides an average maximum blood plasma concentration (Cmax) of less than or equal to about 500 pg/mL after oral administration of about 0.01 mg to about 20 mg of the oral corticosteroid.

9. The method of claim 1, wherein the oral corticosteroid provides an average $AUC_{0-24}$ of less than or equal to about 3,000 pg*h/mL after oral administration of about 0.01 mg to about 20 mg of the oral corticosteroid.

10. The method of claim 1, wherein the oral corticosteroid is budesonide, fluticasone, flunisolide, ciclesonide, mometasone or beclomethasone, or a pharmaceutically acceptable salt, solvent, ester, polymorph or prodrug thereof.

11. The method of claim 1, wherein the oral corticosteroid is formulated:
   (i) as a liquid composition;
   (ii) as a solid composition;
   (iii) to form a solution or suspension prior to oral administration; or
   (iv) to form a solution, suspension or gel after oral administration,
   wherein (i)-(iv) delivers a therapeutically effective amount of the oral corticosteroid to the esophagus.

12. The method of claim 11, wherein
   (i) the liquid composition is in the form of a solution, suspension or slurry;
   (ii) the solid composition is in the form of a gel, lozenge, lollipop, effervescent tablet, powder, granules or an orally disintegrating composition.

13. The method of claim 12, wherein the orally disintegrating composition is a tablet, wafer, film, or lyophilized matrix.

14. The method of claim 13, wherein the orally disintegrating composition is a tablet comprising:
   a. the oral corticosteroid in an amount of from about 1.5 mg to about 7.5 mg;
   b. a pharmaceutically acceptable carrier combined with the corticosteroid; and
   c. rapidly dispersing microgranules,
   wherein the orally disintegrating tablet disintegrates within 60 seconds when tested using the USP <701> method for disintegration time.

15. The method of claim 1, wherein the patient has a Cmax of the oral corticosteroid of less than or equal to about 200 pg/mL following oral administration of about 1.5 mg to about 7.5 mg of the oral corticosteroid.

16. The method of claim 1, wherein the oral corticosteroid is fluticasone propionate, and the patient has a Cmax within the range of about 80% to about 125% of about 15 pg/mL to about 45 pg/mL following oral administration of 6 mg fluticasone propionate or 3 mg of fluticasone propionate.

17. The method of claim 1, wherein the Cmax of the corticosteroid for the patient is lower than the Cmax of the oral corticosteroid for a fed patient that is upright and does not lay down immediately after administration of the oral corticosteroid.

18. The method of claim 16, wherein the Cmax of the oral corticosteroid for the patient is lowered by about 10% to about 30% compared to the Cmax of the oral corticosteroid for a fed patient that is upright and does not lay down immediately after administration of the oral corticosteroid.

19. The method of claim 1, wherein the average time to reach a maximum blood plasma concentration (Tmax) is in the range of about 80% to about 125% of about 12 h to about 15 h.

20. The method of claim 1, wherein the Tmax of the corticosteroid for the patient is delayed compared to the Tmax of the oral corticosteroid for a patient that is upright and does not lay down immediately after administration of the oral corticosteroid.

21. The method of claim 20, wherein the Tmax of the corticosteroid for the patient is delayed by at least about 1 hour compared to the average Tmax of the oral corticosteroid for a patient that is upright and does not lay down immediately after administration of the oral corticosteroid.

22. The method of claim 21, wherein the Tmax of the corticosteroid for the patient is delayed by an amount of time in the range of about 4 h to about 9 h compared to the Tmax of the oral corticosteroid for a patient that is upright and does not lay down immediately after administration of the oral corticosteroid.

23. The method of claim 1, wherein after 12 weeks of daily administration of the oral corticosteroid, esophageal inflammation is reduced as measured by a reduction in eosinophil count, an increase in dysphagia-free days, a reduction in episodes of dysphagia, improvement in EREFS score, EndoFLIP documentation of improved esophageal compliance, evaluation of biomarkers, a decrease in episodes of food impaction, an improvement in EEsAI scores (patient, physician, endoscopy, pathology scores), EoE-QOL-A, Visual Dysphagia Questionnaire (VDQ), Avoidance Modification and Slow Eating (AMS) scores, or histology.

24. The method of claim 23, wherein the patient's eosinophil count is reduced by at least about 50%.

25. The method of claim 1, wherein the patient has a lactose allergy or a starch allergy.

26. The method of claim 1, wherein the oral corticosteroid is administered within about 5 minutes prior to the patient lying down.

27. The method of claim 1, wherein the oral corticosteroid is administered within about 4 minutes prior to the patient lying down.

28. The method of claim 1, wherein the oral corticosteroid is administered within about 3 minutes prior to the patient lying down.

29. The method of claim 1, wherein the oral corticosteroid is administered within about 2 minutes prior to the patient lying down.

30. The method of claim 1, wherein the oral corticosteroid is administered within about 1 minute prior to the patient lying down.

* * * * *